United States Patent
Van Der Plas et al.

(10) Patent No.: US 9,351,955 B2
(45) Date of Patent: May 31, 2016

(54) COMPOUNDS AND PHARMACEUTICAL COMPOSITIONS THEREOF FOR THE TREATMENT OF CYSTIC FIBROSIS

(71) Applicant: Galapagos NV, Mechelen (BE)

(72) Inventors: Steven Emiel Van Der Plas, Mechelen (BE); Hans Kelgtermans, Mechelen (BE); Sébastien Jean Jacques Cédric Dropsit Montovert, Mechelen (BE); Sébastien Laurent Xavier Martina, Mechelen (BE); Martin James Inglis Andrews, Mechelen (BE)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 14/808,200

(22) Filed: Jul. 24, 2015

(65) Prior Publication Data

US 2016/0022633 A1 Jan. 28, 2016

Related U.S. Application Data

(62) Division of application No. 14/451,619, filed on Aug. 5, 2014, now Pat. No. 9,133,210.

(30) Foreign Application Priority Data

Aug. 8, 2013 (EP) .................................... 13179671
Oct. 10, 2013 (GB) ................................... 1317935.3

(51) Int. Cl.
| | |
|---|---|
| *A61K 31/675* | (2006.01) |
| *A61K 31/381* | (2006.01) |
| *A61K 31/4155* | (2006.01) |
| *A61K 31/4196* | (2006.01) |
| *A61K 31/4436* | (2006.01) |
| *A61K 31/4178* | (2006.01) |
| *A61K 31/437* | (2006.01) |
| *A61K 31/4162* | (2006.01) |
| *A61K 31/4025* | (2006.01) |
| *A61K 31/422* | (2006.01) |
| *A61K 31/427* | (2006.01) |
| *A61K 31/497* | (2006.01) |
| *A61K 31/519* | (2006.01) |
| *A61K 31/53* | (2006.01) |

(52) U.S. Cl.
CPC ............ *A61K 31/381* (2013.01); *A61K 31/4025* (2013.01); *A61K 31/4155* (2013.01); *A61K 31/4162* (2013.01); *A61K 31/4178* (2013.01); *A61K 31/4196* (2013.01); *A61K 31/422* (2013.01); *A61K 31/427* (2013.01); *A61K 31/437* (2013.01); *A61K 31/4436* (2013.01); *A61K 31/497* (2013.01); *A61K 31/519* (2013.01); *A61K 31/53* (2013.01); *A61K 31/675* (2013.01)

(58) Field of Classification Search
CPC ...................................................... C07D 495/04
USPC .............................................................. 514/94
See application file for complete search history.

(56) References Cited

PUBLICATIONS

Arzneimitteltherapie, 2013, 31(4), 80-88.*

* cited by examiner

*Primary Examiner* — Nizal Chandrakumar
(74) *Attorney, Agent, or Firm* — Quarles & Brady LLP

(57) ABSTRACT

The present invention discloses compounds according to Formula I:

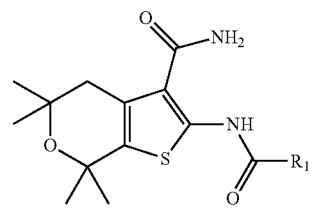

wherein $R^1$ is as defined herein. The present invention relates to compounds and their use in the treatment of cystic fibrosis, methods for their production, pharmaceutical compositions comprising the same, and methods of treatment cystic fibrosis by administering a compound of the invention.

14 Claims, 1 Drawing Sheet

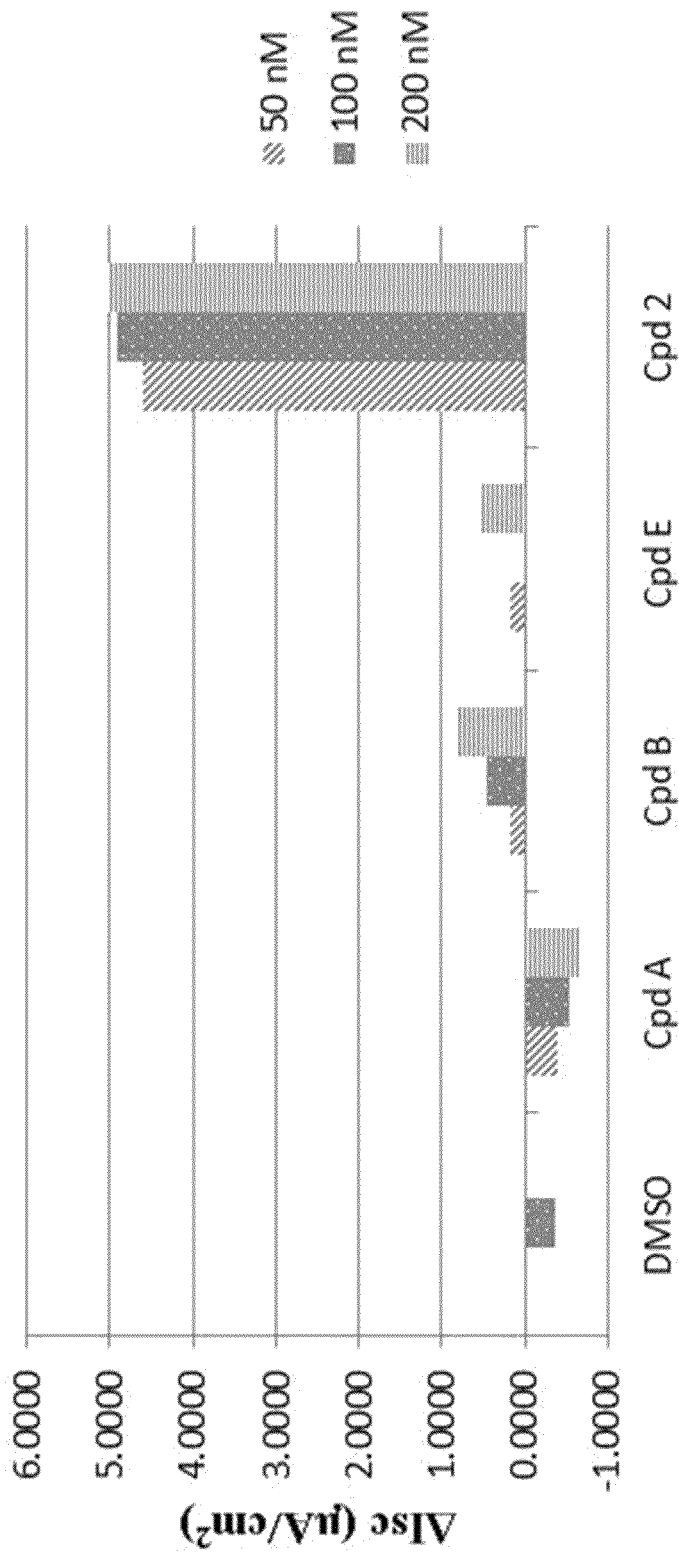

COMPOUNDS AND PHARMACEUTICAL COMPOSITIONS THEREOF FOR THE TREATMENT OF CYSTIC FIBROSIS

CROSS-REFERENCE TO RELATED APPLICATIONS

This application is a divisional of U.S. patent application Ser. No. 14/451,619 filed Aug. 5, 2014, which claims priority to European Patent Application No. EP13179671.6 filed Aug. 8, 2013; and United Kingdom Application No. GB1317935.3 filed Oct. 10, 2013. The contents of each of these applications are incorporated by reference.

FIELD OF THE INVENTION

The present invention relates to compounds that are modulators of cystic fibrosis Transmembrane Conductance regulator (CFTR), and their use in the treatment of cystic fibrosis. The present invention also provides methods for the production of a compound of the invention, pharmaceutical compositions comprising a compound of the invention, and methods for the treatment of cystic fibrosis by administering a compound of the invention.

BACKGROUND OF THE INVENTION

ABC transporters are a family of homologous membrane transporter proteins regulating the transport of a wide variety of pharmacological agents (for example drugs, xenobiotics, anions, etc. . . . ) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cells types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue. (Quinton, 1990)

The gene encoding CFTR has been identified and sequenced (Kerem et al., 1989). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis is caused by a defect in this gene which induces mutations in CFTR. Cystic fibrosis is the most common fatal genetic disease in humans, and affects ~0.04% of white individuals (Bobadilla et al., 2002), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with are infertile.

A variety of disease causing mutations has been identified through sequence analysis of the CFTR gene of CF chromosomes (Kerem et al., 1989). ΔF508-CFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyk and Foskett, 1995).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, G1349D. Mutations affecting chloride conductance have a CFTR protein that is correctly trafficked to the cell membrane but that generates reduced chloride-flow (e.g. missense mutations located within the membrane-spanning domain), examples of these mutations are R117H, R334W.

In addition to cystic fibrosis, CFTR activity modulation may be beneficial for other diseases not directly caused by mutations in CFTR, such as, for example, chronic obstructive pulmonary disease (COPD), dry eye disease, and Sjogren's Syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjogrens's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjogrens's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjogrens's syndrome is also associated with rheumatoid arthritis, systemic lupus, systemic sclerosis, and polymyposits/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the ΔF508-CFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello et al., 2000; Shastry, 2003; Zhang et al., 2012).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormoneN2-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear plasy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal a-galactosidase A), Straussler-Scheinker syndrome, chronic obstructive pulmonary disease (COPD), dry eye disease, and Sjogren's Syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrheas, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition Accordingly, there is a need for novel compounds able to modulate CFTR. In particular, the present invention discloses compounds that may act as CFTR modulators for the treatment of cystic fibrosis. The present invention also provides methods for the production of these compounds, pharmaceutical compositions comprising these compounds and methods for the treatment of cystic fibrosis by administering the compounds of the invention.

BRIEF DESCRIPTION OF THE FIGURES

FIG. 1 shows the current increase measured in the TECC assay for a comparative compound and a compound of the invention at various concentrations of test compound (50, 100, and 200 nM).

SUMMARY OF THE INVENTION

The present invention is based on the identification of novel compounds, and their ability to act as CFTR modulators and that they may be useful for the treatment of cystic fibrosis. The present invention also provides methods for the production of these compounds, pharmaceutical compositions comprising these compounds and methods for the treatment of cystic fibrosis by administering compounds of the invention.

Accordingly, in a first aspect of the invention, compounds of the invention are provided having a Formula (I):

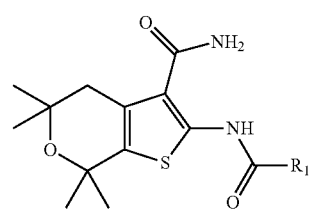

I wherein
$R^1$ is
  $C_{3-7}$ mono or spirocyclic cycloalkyl, optionally substituted with one or more independently selected $R^2$ groups,
  4-7 membered mono or spirocyclic heterocycloalkyl comprising one or more heteroatoms independently selected from O, N, and S, substituted with one or more independently selected $R^2$ groups,
  $C_{6-10}$ monocyclic or bicyclic aryl optionally substituted with one or more independently selected $R^3$ groups,
  5-10 membered monocyclic or fused bicyclic heteroaryl comprising one or more heteroatoms independently selected from N, O, and S, and optionally substituted with one or more independently selected $R^3$ groups, or
  $C_{1-6}$ alkyl optionally substituted with one or more independently selected $R^4$ groups, each $R^2$ is selected from
halo,
OH,
—CN,
—OC(=O)$C_{1-4}$ alkyl.
—C(=O)—$C_{1-4}$ alkoxy,
oxo,
$C_{1-4}$ alkyl (optionally substituted with one or more independently selected $R^{5a}$), and $C_{1-4}$ alkoxy (optionally substituted with one or more independently selected $R^{5a}$),
each $R^3$ is selected from
halo,
—OH,
—CN,
$C_{1-4}$ alkyl (optionally substituted with one or more independently selected $R^{5b}$),
$C_{1-4}$ alkoxy (optionally substituted with one or more independently selected $R^{5b}$),
$C_{2-4}$ alkenyl (optionally substituted with one or more independently selected $R^{5b}$),
$C_{3-7}$ monocyclic cycloalkyl,
4-7 membered monocyclic heterocycloalkyl comprising one or more heteroatoms independently selected from N, O, and S,
4-7 membered monocyclic heterocycloalkenyl comprising one or more heteroatoms independently selected from N, O, and S,
5-10 membered monocyclic or fused bicyclic heteroaryl comprising one or more heteroatoms independently selected from N, O, and S, and
—NHSO$_2$—C$_{1-4}$ alkyl;
each $R^4$ is selected from
halo,
OH,
$C_{3-7}$ monocyclic cycloalkyl,
—CN, and
$C_{1-4}$ alkoxy (optionally substituted with one or more independently selected $R^{5c}$),
each $R^{5a}$, $R^{5b}$, and $R^{5c}$ is independently selected from
halo,
OH,
—OP(=O)$_2$OH,
—CN,
—NR$^{6a}$R$^{6b}$, and
$C_{1-4}$ alkoxy; and
each R$^{6a}$, or R$^{6b}$ is independently selected from H, and C$_{1-4}$ alkyl.

In another aspect of the invention, compounds of the invention are provided having a Formula (I):

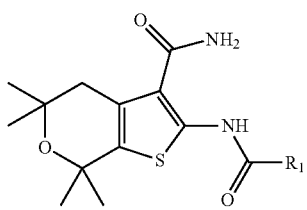

I wherein
$R^1$ is
$C_{3-7}$ cycloalkyl optionally substituted with one or more independently selected $R^2$ groups,
4-7 membered monocyclic heterocycloalkyl comprising one or more heteroatoms independently selected from O, N, and S, substituted with one or more independently selected $R^2$ groups,
$C_{6-10}$ mono or bicyclic aryl optionally substituted with one or more independently selected $R^3$ groups,
5-10 membered mono or fused bicyclic heteroaryl comprising one or more heteroatoms independently selected from N, O, and S, and optionally substituted with one or more independently selected $R^3$ groups, or $C_{1-6}$ alkyl optionally substituted with one or more independently selected $R^4$ groups,
each $R^2$ is selected from
halo,
OH,
—CN,
—OC(=O)C$_{1-4}$ alkyl,
—C(=O)—C$_{1-4}$ alkoxy,
oxo,
$C_{1-4}$ alkyl (optionally substituted with one or more independently selected $R^{5a}$), and
$C_{1-4}$ alkoxy (optionally substituted with one or more independently selected $R^{5a}$),
each $R^3$ is selected from
halo,
—OH,
—CN,
$C_{1-4}$ alkyl (optionally substituted with one or more independently selected $R^{5b}$),
$C_{1-4}$ alkoxy (optionally substituted with one or more independently selected $R^{5b}$),
$C_{3-7}$ cycloalkyl,
5-10 membered mono or fused bicyclic heteroaryl comprising one or more heteroatoms independently selected from N, O, and S, and
—NHSO$_2$—C$_{1-4}$ alkyl;
each $R^4$ is selected from
halo,
OH,
—CN, and
$C_{1-4}$ alkoxy (optionally substituted with one or more independently selected $R^{5c}$),
each $R^{5a}$, $R^{5b}$, and $R^{5c}$ is independently selected from
halo,
OH,
—CN,
NR$^{6a}$R$^{6b}$, and
$C_{1-4}$ alkoxy; and
each R$^{ha}$, or R$^{6b}$ is independently selected from H, and C$_{1-4}$ alkyl.

In a particular aspect, the compounds of the invention are provided for use in the treatment of cystic fibrosis. In a particular aspect, the compounds of the invention are provided for use in the treatment of cystic fibrosis caused by class I, II, III, IV, and/or VI mutations.

In an alternative embodiment, the compounds of the invention have a potentiator activity.

In another particular aspect, the compounds of the invention exhibit low activity on CYP enzymes, which may result in low drug-drug interaction potential, and accordingly may be advantageous for patients under multiple therapies.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, with a condition selected from among those listed herein, and particularly cystic fibrosis, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the treatment of cystic fibrosis.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —$OR^{26}$ where $R^{26}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—$CH_2$—), ethylene (—$CH_2$—$CH_2$—), or —$CH(CH_3)$— and the like.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—$CH=CH_2$), n-propenyl ($CH_2CH=CH_2$), isopropenyl (—$C(CH_3)=CH_2$) and the like.

'Amino' refers to the radical —$NH_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, naphthyl, indenyl, and tetrahydronaphthyl.

'Cycloalkyl' refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or polycyclic, that includes one or more heteroatoms independently selected from O, N and S and the number of ring atoms specified. In particular, the aromatic ring structure may have from 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g. adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

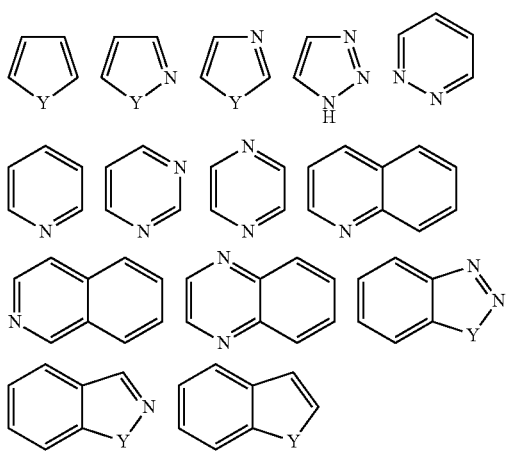

wherein each Y is selected from >C(=O), NH, O and S.

As used herein, the term 'heterocycloalkyl' means a stable non-aromatic ring structure, monocyclic or polycyclic, that includes one or more heteroatoms independently selected from O, N and S and the number of ring atoms specified. The non-aromatic ring structure may have from 4 to 10 ring members, and in particular from 4 to 7 ring members. A fused heterocyclic ring system may include carbocyclic rings and need only to include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

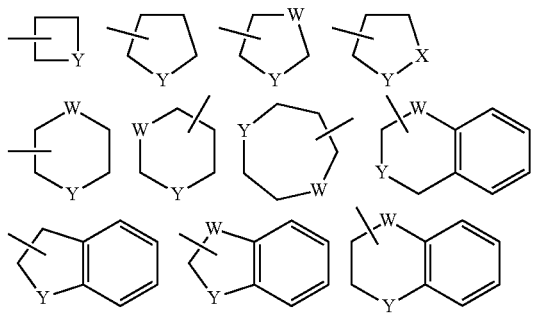

wherein each W is selected from $CH_2$, NH, O and S; and each Y is selected from NH, O, C(=O), $SO_2$, and S.

As used herein, the term 'heterocycloalkenyl' means a 'heterocycloalkyl, wherein one bond of the ring is reduced, thus the ring comprises a double bond. Particular examples of heterocycloalkenyl groups are shown in the following illustrative examples:

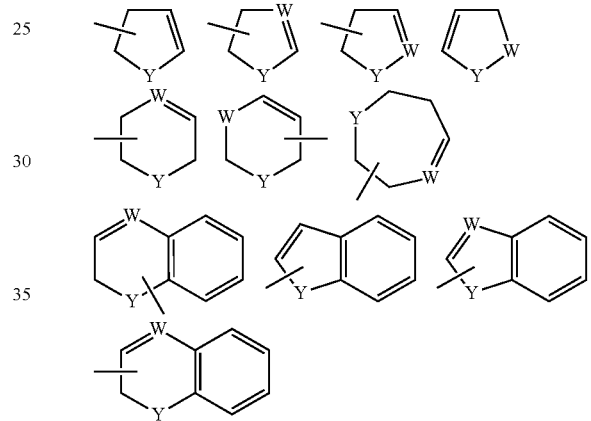

wherein each W is selected from $CH_2$, NH, O and S; and each Y is selected from NH, O, C(=O), $SO_2$, and S.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —$SO_3H$.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —$SR^{26}$ where $R^{26}$ has the number of carbon atoms specified and particularly $C_1$-$C_8$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc. . . . , of the subject to be treated.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; 51251N, G178R, S549N mutations. More particularly, Class III mutation(s) refers to G551D, R553G, G1349D, 51251N, G178R, or S549N mutations.

As used herein, "Class IV mutation(s)" refers to mutations which affect chloride conductance. The CFTR protein is correctly trafficked to the cell membrane but generates reduced Cl— flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.3140-26A>G (3272-26A>G), c.3850-2477C>T (3849+10 kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326dellTC, or 4279insA mutations. More particularly, Class VI mutation(s) refers to Rescued F508del mutations.

When ranges are referred to herein, for example but without limitation, C1-8 alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

All tautomeric forms of the compounds provided herein are intended to be encompassed within the scope of the invention. 'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Still another example of tautomerism is illustrated below:

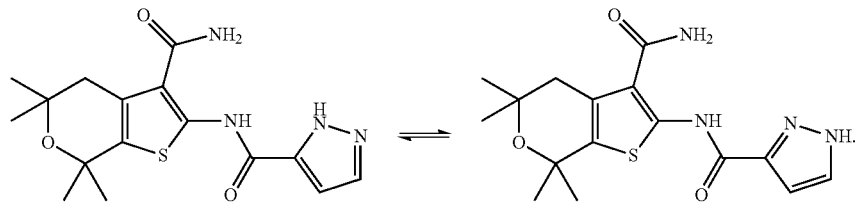 [SMILES: CC1(C)Cc2c(sc(NC(=O)c3ccn[nH]3)c2C(N)=O)C(C)(C)O1 ; CC1(C)Cc2c(sc(NC(=O)c3cc[nH]n3)c2C(N)=O)C(C)(C)O1]

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel compounds, that may be useful for the treatment of cystic fibrosis.

The present invention also provides methods for the production of these compounds, pharmaceutical compositions comprising these compounds and methods for the treatment of cystic fibrosis by administering the compounds of the invention.

Accordingly, in a one aspect of the invention, compounds of the invention are provided having a Formula (I):

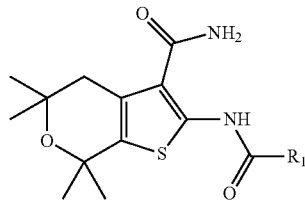

I wherein
$R^1$ is
$C_{3-7}$ mono or spirocyclic cycloalkyl, optionally substituted with one or more independently selected $R^2$ groups,
4-7 membered mono or spirocyclic heterocycloalkyl comprising one or more heteroatoms independently selected from O, N, and S, substituted with one or more independently selected $R^2$ groups,
$C_{6-10}$ monocyclic or fused bicyclic aryl optionally substituted with one or more independently selected $R^3$ groups,
5-10 membered monocyclic or fused bicyclic heteroaryl comprising one or more heteroatoms independently selected from N, O, and S, and optionally substituted with one or more independently selected $R^3$ groups, or
$C_{1-6}$ alkyl optionally substituted with one or more independently selected $R^4$ groups,
each $R^2$ is selected from
halo,
OH,
—CN,
—OC(=O)$C_{1-4}$ alkyl,
—C(=O)—$C_{1-4}$ alkoxy,
oxo,
$C_{1-4}$ alkyl (optionally substituted with one or more independently selected $R^{5a}$), and
$C_{1-4}$ alkoxy (optionally substituted with one or more independently selected $R^{5a}$),
each $R^3$ is selected from
halo,
—OH,
—CN,
$C_1$ alkyl (optionally substituted with one or more independently selected $R^{5b}$),
$C_1$ alkoxy (optionally substituted with one or more independently selected $R^{5b}$),
$C_2$ alkenyl (optionally substituted with one or more independently selected $R^{5b}$),
$C_{3-7}$ monocyclic cycloalkyl,
4-7 membered monocyclic heterocycloalkyl comprising one or more heteroatoms independently selected from N, O, and S,
4-7 membered monocyclic heterocycloalkenyl comprising one or more heteroatoms independently selected from N, O, and S,
5-10 membered monocyclic or fused bicyclic heteroaryl comprising one or more heteroatoms independently selected from N, O, and S, and
—NHSO$_2$—$C_{1-4}$ alkyl;
each $R^4$ is selected from
halo,
OH,
$C_{3-7}$ monocyclic cycloalkyl,
—CN, and
$C_1$ alkoxy (optionally substituted with one or more independently selected $R^{5c}$),
each $R^{5a}$, $R^{5b}$, and $R^{5c}$ is independently selected from
halo,
OH,
—OP(=O)$_2$OH,
—CN,
—NR$^{6a}$R$^{6b}$, and
$C_{1-4}$ alkoxy; and
each $R^{6a}$, or $R^{6b}$ is independently selected from H, and $C_{1-4}$ alkyl.

In another aspect of the invention, compounds of the invention are provided having a Formula (I):

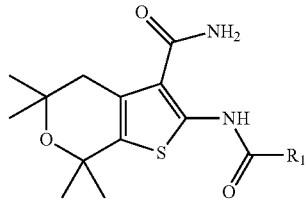

I wherein
$R^1$ is
$C_{3-7}$ cycloalkyl optionally substituted with one or more independently selected $R^2$ groups,
4-7 membered monocyclic heterocycloalkyl comprising one or more heteroatoms independently selected from O, N, and S, substituted with one or more independently selected $R^2$ groups,
$C_{6-10}$ mono or bicyclic aryl optionally substituted with one or more independently selected $R^3$ groups,
5-10 membered mono or fused bicyclic heteroaryl comprising one or more heteroatoms independently selected from N, O, and S, and optionally substituted with one or more independently selected $R^3$ groups, or
$C_{1-6}$ alkyl optionally substituted with one or more independently selected $R^4$ groups;
each $R^2$ is selected from
halo,
OH,
—CN,
—OC(=O)$C_{1-4}$ alkyl.
—C(=O)—$C_{1-4}$ alkoxy,
oxo, $C_{1-4}$ alkyl (optionally substituted with one or more independently selected $R^{5a}$), and $C_{1-4}$ alkoxy (optionally substituted with one or more independently selected $R^{5a}$), each $R^3$ is selected from halo,

—OH,

—CN, $C_{1-4}$ alkyl (optionally substituted with one or more independently selected $R^{5b}$), $C_{1-4}$ alkoxy (optionally substituted with one or more independently selected $R^{5b}$), $C_{3-7}$ cycloalkyl, 5-10 membered mono or fused bicyclic heteroaryl comprising one or more heteroatoms independently selected from N, O, or S, and —NHSO$_2$—C$_{1-4}$ alkyl;

each $R^4$ is selected from halo,

OH,

—CN, and $C_{1-4}$ alkoxy (optionally substituted with one or more independently selected $R^{5c}$), each $R^{5a}$, $R^{5b}$, and $R^{5'}$ is independently selected from halo,

OH,

—CN,

—NR$^{6a}$R$^{6b}$, and $C_{1-4}$ alkoxy; and each $R^{6a}$, or $R^{6b}$ is independently selected from H, and $C_{1-4}$ alkyl.

In one embodiment, a compound of the invention is according to Formula I, wherein $R^1$ is $C_{3-7}$ mono or spirocyclic cycloalkyl. In a particular embodiment, $R^1$ is spiro[3.3]heptane, cyclopropyl, cyclobutyl, cyclopentyl, or cyclohexyl. In a more particular embodiment, $R^1$ is cyclopropyl, cyclobutyl, cyclopentyl, or cyclohexyl.

In one embodiment, a compound of the invention is according to Formula I, wherein $R^1$ is $C_{3-7}$ cycloalkyl. In a particular embodiment, $R^1$ is cyclopropyl, cyclobutyl, cyclopentyl, or cyclohexyl.

In one embodiment, a compound of the invention is according to Formula I, wherein $R^1$ is $C_{3-7}$ mono or spirocyclic cycloalkyl substituted with one or more independently selected $R^2$ groups, and $R^2$ is as described above. In another embodiment, $R^1$ is spiro[3.3]heptane, cyclopropyl, cyclobutyl, cyclopentyl, or cyclohexyl, each of which is substituted with one or more independently selected $R^2$ groups. In a particular embodiment, $R^1$ is $C_{3-7}$ mono or spirocyclic cycloalkyl substituted with one or two independently selected $R^2$ groups. In another particular embodiment, $R^1$ is spiro[3.3]heptane, cyclopropyl, cyclobutyl, cyclopentyl, or cyclohexyl, each of which is substituted with one or two independently selected $R^2$ groups. In a more particular embodiment, $R^1$ is $C_{3-7}$ mono or spirocyclic cycloalkyl substituted with one $R^2$ group. In another particular embodiment, $R^1$ is spiro[3.3]heptane, cyclopropyl, cyclobutyl, cyclopentyl, or cyclohexyl, each of which is substituted with one $R^2$ group.

In one embodiment, a compound of the invention is according to Formula I, wherein $R^1$ is $C_{3-7}$ cycloalkyl substituted with one or more independently selected $R^2$ groups, and $R^2$ is as described above. In another embodiment, $R^1$ is cyclopropyl, cyclobutyl, cyclopentyl, or cyclohexyl, each of which is substituted with one or more independently selected $R^2$ groups. In a particular embodiment, $R^1$ is $C_{3-7}$ cycloalkyl substituted with one or two independently selected $R^2$ groups. In another particular embodiment, $R^1$ is cyclopropyl, cyclobutyl, cyclopentyl, or cyclohexyl, each of which is substituted with one or two independently selected $R^2$ groups. In a more particular embodiment, $R^1$ is $C_{3-7}$ cycloalkyl substituted with one $R^2$ group. In another particular embodiment, $R^1$ is cyclopropyl, cyclobutyl, cyclopentyl, or cyclohexyl, each of which is substituted with one $R^2$ group.

In one embodiment, a compound of the invention is according to Formula I, wherein $R^1$ is $C_{3-7}$ cycloalkyl substituted with one or more independently selected $R^2$ groups, and $R^2$ is as described above. In a particular embodiment, $R^1$ is cyclopropyl, cyclobutyl, cyclopentyl, or cyclohexyl, each of which is substituted with one or more independently selected $R^2$ groups. In a particular embodiment, $R^2$ is selected from halo, CN, oxo, and OH. In a more particular embodiment, $R^2$ is selected from F, Cl, CN, oxo, and OH.

In one embodiment, a compound of the invention is according to Formula I, wherein $R^1$ is $C_{3-7}$ cycloalkyl substituted with one or more independently selected $R^2$ groups, and $R^2$ is as described above. In a particular embodiment, $R^1$ is cyclopropyl, cyclobutyl, cyclopentyl, or cyclohexyl, each of which is substituted with one or more independently selected $R^2$ groups. In a particular embodiment, $R^2$ is $C_{1-4}$ alkyl, optionally substituted with one or more independently selected $R^{5a}$, wherein $R^{5a}$ is as defined above. In a more particular embodiment, $R^2$ is —CH$_3$, —CH$_2$CH$_3$, —CH(CH$_3$)$_2$, or —C(CH$_3$)$_3$. In another more particular embodiment, $R^2$ is —CH$_3$, —CH$_2$CH$_3$, —CH(CH$_3$)$_2$, or —C(CH$_3$)$_3$, each of which is optionally substituted with one or more independently selected $R^{5'}$. In yet another more particular embodiment, $R^2$ is $C_{1-4}$ alkyl, optionally substituted with one or more independently selected $R^{5a}$, wherein $R^{5a}$ is F, Cl, OH, —CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a further more particular embodiment, $R^2$ is —CH$_3$, —CH$_2$CH$_3$, —CH(CH$_3$)$_2$, or —C(CH$_3$)$_3$, each of which is optionally substituted with one or more independently selected $R^{5a}$, wherein $R^{5a}$ is F, Cl, OH, —CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, $R^2$ is —CH$_3$, —CH$_2$CH$_3$, —CH(CH$_3$)$_2$, —C(CH$_3$)$_3$, —CH$_2$—O, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

In one embodiment, a compound of the invention is according to Formula I, wherein $R^1$ is $C_{3-7}$ cycloalkyl substituted with one or more independently selected $R^2$ groups, and $R^2$ is as described above. In another embodiment, $R^1$ is cyclopropyl, cyclobutyl, cyclopentyl, or cyclohexyl, each of which is substituted with one or more independently selected $R^2$ groups. In a particular embodiment, $R^2$ is $C_{1-4}$ alkoxy, optionally substituted with one or more independently selected $R^{5a}$, wherein $R^{5a}$ is as defined above. In a particular embodiment, $R^2$ is —OCH$_3$, —OCH$_2$CH$_3$, or —OCH(CH$_3$)$_2$. In a particular embodiment, $R^2$ is —OCH$_3$, —OCH$_2$CH$_3$, or —OCH(CH$_3$)$_2$, each of which is optionally substituted with one or more independently selected $R^{5a}$. In another particular embodiment, $R^2$ is $C_{1-4}$ alkoxy, optionally substituted with one or more independently selected $R^{5a}$, wherein $R^{5a}$ is F, Cl, OH, —CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a more particular embodiment, $R^2$ is —OCH$_3$, —OCH$_2$CH$_3$, or —OCH(CH$_3$)$_2$, each of which is optionally substituted with one or more independently selected $R^{5a}$, wherein $R^{5a}$ is F, Cl, OH, —CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, $R^2$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to Formula I, wherein $R^1$ is 4-7 membered mono or spirocyclic heterocycloalkyl comprising one or more heteroatoms independently selected from O, N, and S, substituted with one or more independently selected $R^2$ groups, and $R^2$ is as described above. In another embodiment, $R^1$ is oxa-spiro[3.3]heptane, aza-spiro[3.3]heptane, oxa-6-aza-spiro[3.3]heptane, diaza-spiro[3.3]heptane, pyrrolidinyl, tetrahydrofuranyl, tetrahydropyranyl, piperidinyl, piperazinyl, morpholinyl, or thiomorpholinyl, each of which is substituted with one or more independently selected $R^2$ groups. In a particular embodiment, $R^1$ is 4-7 membered mono or spirocyclic heterocycloalkyl comprising one or more heteroatoms independently selected from O, N, and S, substituted with one or two independently selected $R^2$ groups. In another particular embodiment, $R^1$ is oxa-spiro[3.3]heptane, aza-spiro[3.3]heptane, oxa-6-aza-spiro[3.3]heptane, diaza-spiro[3.3]heptane, pyrrolidinyl, tetrahydrofuranyl, tetrahydropyranyl, piperidinyl, piperazinyl, morpholinyl, or thiomorpholinyl, each of which is substituted with one or two independently selected $R^2$ groups. In a more particular embodiment, $R^1$ is 4-7 membered mono or spirocyclic heterocycloalkyl comprising one or more heteroatoms independently selected from O, N, and S, substituted with one $R^2$ group. In another particular embodiment, $R^1$ is oxa-spiro[3.3]heptane, aza-spiro[3.3]heptane, oxa-6-aza-spiro[3.3]heptane, diaza-spiro[3.3]heptane, pyrrolidinyl, tetrahydrofuranyl, tetrahydropyranyl, piperidinyl, piperazinyl, morpholinyl, or thiomorpholinyl, each of which is substituted with one $R^2$ group.

In one embodiment, a compound of the invention is according to Formula I, wherein $R^1$ is 4-7 membered monocyclic heterocycloalkyl comprising one or more heteroatoms independently selected from O, N, and S, substituted with one or more independently selected $R^2$ groups, and $R^2$ is as described above. In another embodiment, $R^1$ is pyrrolidinyl, tetrahydrofuranyl, tetrahydropyranyl, piperidinyl, piperazinyl, morpholinyl, or thiomorpholinyl, each of which is substituted with one or more independently selected $R^2$ groups. In a particular embodiment, $R^1$ is 4-7 membered monocyclic heterocycloalkyl comprising one or more heteroatoms independently selected from O, N, and S, substituted with one or two independently selected $R^2$ groups. In another particular embodiment, $R^1$ is pyrrolidinyl, tetrahydrofuranyl, tetrahydropyranyl, piperidinyl, piperazinyl, morpholinyl, or thiomorpholinyl, each of which is substituted with one or two independently selected $R^2$ groups. In a more particular embodiment, $R^1$ is 4-7 membered monocyclic heterocycloalkyl comprising one or more heteroatoms independently selected from O, N, and S, substituted with one $R^2$ group. In another particular embodiment, $R^1$ is pyrrolidinyl, tetrahydrofuranyl, tetrahydropyranyl, piperidinyl, piperazinyl, morpholinyl, or thiomorpholinyl, each of which is substituted with one $R^2$ group.

In one embodiment, a compound of the invention is according to Formula I, wherein $R^1$ is 4-7 membered monocyclic heterocycloalkyl comprising one or more heteroatoms independently selected from O, N, and S, substituted with one or more independently selected $R^2$ groups, and $R^2$ is as described above. In a particular embodiment, $R^1$ is pyrrolidinyl, tetrahydrofuranyl, tetrahydropyranyl, piperidinyl, piperazinyl, morpholinyl, or thiomorpholinyl, each of which is substituted with one or more independently selected $R^2$ groups. In a particular embodiment, $R^2$ is selected from halo, CN, oxo, and OH. In a more particular embodiment, $R^2$ is selected from F, Cl, CN, oxo, and OH.

In one embodiment, a compound of the invention is according to Formula I, wherein $R^1$ is 4-7 membered monocyclic heterocycloalkyl comprising one or more heteroatoms independently selected from O, N, and S, substituted with one or more independently selected $R^2$ groups, and $R^2$ is as described above. In a particular embodiment, $R^1$ is pyrrolidinyl, tetrahydrofuranyl, tetrahydropyranyl, piperidinyl, piperazinyl, morpholinyl, or thiomorpholinyl, each of which is substituted with one or more independently selected $R^2$ groups. In a particular embodiment, $R^2$ is selected from —OC(=O)CH$_3$, —OC(=O)CH$_2$CH$_3$, and —OC(=O)CH(CH$_3$)$_2$.

In one embodiment, a compound of the invention is according to Formula I, wherein $R^1$ is 4-7 membered monocyclic heterocycloalkyl comprising one or more heteroatoms independently selected from O, N, and S, substituted with one or more independently selected $R^2$ groups, and $R^2$ is as described above. In a particular embodiment, $R^1$ is pyrrolidinyl, tetrahydrofuranyl, tetrahydropyranyl, piperidinyl, piperazinyl, morpholinyl, or thiomorpholinyl, each of which is substituted with one or more independently selected $R^2$ groups. In a particular embodiment, $R^2$ is —CH$_3$, —CH$_2$CH$_3$, CH(CH$_3$)$_2$, or —C(CH$_3$)$_3$. In another more particular embodiment, $R^2$ is —CH$_3$, —CH$_2$CH$_3$, CH(CH$_3$)$_2$, or —C(CH$_3$)$_3$, each of which is optionally substituted with one or more independently selected $R^{5a}$. In yet another more particular embodiment, $R^2$ is $C_{1-4}$ alkyl, optionally substituted with one or more independently selected $R^{5a}$, wherein $R^{5a}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a further more particular embodiment, $R^2$ is —CH$_3$, —CH$_2$CH$_3$, —CH(CH$_3$)$_2$, or, —C(CH$_3$)$_3$, each of which is optionally substituted with one or more independently selected $R^{5a}$, wherein $R^{5a}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, $R^2$ is —CH$_3$, —CH$_2$CH$_3$, —CH(CH$_3$)$_2$, —C(CH$_3$)$_3$, —CH$_2$—OH, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

In one embodiment, a compound of the invention is according to Formula I, wherein $R^1$ is 4-7 membered monocyclic heterocycloalkyl comprising one or more heteroatoms independently selected from O, N, and S, substituted with one or more independently selected $R^2$ groups, and $R^2$ is as described above. In a particular embodiment, $R^1$ is pyrrolidinyl, tetrahydrofuranyl, tetrahydropyranyl, piperidinyl, piperazinyl, morpholinyl, or thiomorpholinyl, each of which is substituted with one or more independently selected $R^2$ groups. In a particular embodiment, $R^2$ is $C_{1-4}$ alkoxy, optionally substituted with one or more independently selected $R^{5a}$, wherein $R^{5a}$ is as defined above. In a more particular embodiment, $R^2$ is —OCH$_3$, —OCH$_2$CH$_3$, or —OCH(CH$_3$)$_2$, each of which is optionally substituted with one or more independently selected $R^{5'}$. In another more particular embodiment, $R^2$ is $C_{1-4}$ alkoxy, optionally substituted with one or more independently selected $R^{5a}$, wherein $R^{5a}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^2$ is —OCH$_3$, —OCH$_2$CH$_3$, or —OCH(CH$_3$)$_2$, each of which is optionally substituted with one or more independently selected $R^{5a}$, wherein $R^{5a}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to Formula I, wherein $R^1$ is $C_{6-10}$ mono or bicyclic aryl. In a particular embodiment, $R^1$ is phenyl.

In one embodiment, a compound of the invention is according to Formula I, wherein $R^1$ is $C_{6-10}$ mono or bicyclic aryl optionally substituted with one or more independently selected $R^3$ groups, and $R^3$ is as described above. In another embodiment, $R^1$ is phenyl is substituted with one or more independently selected $R^3$ groups. In a particular embodiment, $R^1$ is $C_{6-10}$ mono or bicyclic aryl, substituted with one or two independently selected $R^3$ groups. In another particular embodiment, $R^1$ is phenyl substituted with one or two independently selected $R^3$ groups. In a more particular embodiment, $R^1$ is $C_{6-10}$ mono or bicyclic aryl, substituted with one $R^3$ group. In another particular embodiment, $R^1$ is phenyl substituted with one $R^3$ group.

In one embodiment, a compound of the invention is according to Formula I, wherein $R^1$ is $C_{6-10}$ mono or bicyclic aryl, substituted with one or more independently selected $R^3$ groups, and $R^3$ is as described above. In a particular embodiment, $R^1$ is phenyl substituted with one or more independently selected $R^3$ groups. In a particular embodiment, $R^3$ is selected from halo, CN, and OH. In a more particular embodiment, $R^3$ is selected from F, Cl, CN, and OH.

In one embodiment, a compound of the invention is according to Formula I, wherein $R^1$ is $C_{6-10}$ monocyclic or bicyclic aryl, substituted with one or more independently selected $R^3$ groups, and $R^3$ is as described above. In a particular embodiment, $R^1$ is phenyl substituted with one or more independently selected $R^3$ groups. In a particular embodiment, $R^3$ is $C_{1-4}$ alkyl, optionally substituted with one or more independently selected $R^{5b}$, wherein $R^{5b}$ is as defined above. In a more particular embodiment, $R^3$ is —$CH_3$, —$CH_2CH_3$, —$CH(CH_3)_2$, or —$C(CH_3)_3$, each of which is optionally substituted with one or more independently selected $R^{5b}$. In another more particular embodiment, $R^3$ is $C_{1-4}$ alkyl, optionally substituted with one or more independently selected $R^{5b}$, wherein $R^{5b}$ is F, Cl, OH, —$OP(=O)_2OH$, CN, —$OCH_3$, —$OCH_2CH_3$, —$NHCH_3$, —$N(CH_3)_2$, —$NH(CH_2-CH_3)$, —$N(CH_2-CH_3)CH_3$, or —$N(CH_2-CH_3)_2$. In yet another more particular embodiment, $R^3$ is —$CH_3$, —$CH_2CH_3$, —$CH(CH_3)_2$, or —$C(CH_3)_3$, each of which is optionally substituted with one or more independently selected $R^{5b}$, wherein $R^{5b}$ is F, Cl, OH, —$OP(=O)_2OH$, CN, or —$OCH_3$. In a further more particular embodiment, $R^3$ is $C_{1-4}$ alkyl, optionally substituted with one or more independently selected $R^{5b}$, wherein $R^{5b}$ is F, Cl, OH, —$OP(=O)_2OH$, CN, or —$OCH_3$. In yet a further more particular embodiment, $R^3$ is —$CH_3$, —$CH_2CH_3$, —$CH(CH_3)_2$, or —$C(CH_3)_3$, each of which is optionally substituted with one or more independently selected $R^{5b}$, wherein $R^{5b}$ is F, Cl, OH, —$OP(=O)_2OH$, CN, or —$OCH_3$. In a most particular embodiment, $R^3$ is —$CH_3$, —$CH_2CH_3$, $CH(CH_3)_2$, —$C(CH_3)_3$. —$CH_2$—OH, —$CH_2$—$OP(=O)_2OH$, —$C(OH)(CH_3)_2$, —$CF_3$, —$CH_2$—$CHF_2$, —$CH_2CH_2OCH_3$, or —$CH_2CH_2N(CH_3)_2$.

In one embodiment, a compound of the invention is according to Formula I, wherein $R^1$ is $C_{6-10}$ mono or bicyclic aryl, substituted with one or more independently selected $R^3$ groups, and $R^3$ is as described above. In a particular embodiment, $R^1$ is phenyl substituted with one or more independently selected $R^3$ groups. In a particular embodiment, $R^3$ is $C_{1-4}$ alkyl, optionally substituted with one or more independently selected $R^{5b}$, wherein $R^{5b}$ is as defined above. In a more particular embodiment, $R^3$ is —$CH_3$, —$CH_2CH_3$, —$CH(CH_3)_2$, or —$C(CH_3)_3$, each of which is optionally substituted with one or more independently selected $R^{5b}$. In another more particular embodiment, $R^3$ is $C_{1-4}$ alkyl, optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2-CH_3)$, —$N(CH_2-CH_3)CH_3$, or —$N(CH_2-CH_3)_2$. In yet another more particular embodiment, $R^3$ is —$CH_3$, —$CH_2CH_3$, $CH(CH_3)_2$, —$C(CH_3)_3$. —$CH_2$—OH, —$C(OH)(CH_3)_2$, —$CF_3$, —$CH_2$—$CHF_2$, —$CH_2CH_2OCH_3$, or —$CH_2CH_2N(CH_3)_2$.

In one embodiment, a compound of the invention is according to Formula I, wherein $R^1$ is $C_{6-10}$ monocyclic or bicyclic aryl, substituted with one or more independently selected $R^3$ groups, and $R^3$ is as described above. In a particular embodiment, $R^1$ is phenyl substituted with one or more independently selected $R^3$ groups. In a particular embodiment, $R^3$ is $C_{1-4}$ alkoxy, optionally substituted with one or more independently selected $R^{5b}$, wherein $R^{5b}$ is as defined above. In a more particular embodiment, $R^3$ is —$OCH_3$, —$OCH_2CH_3$, or —$OCH(CH_3)_2$, each of which is optionally substituted with one or more independently selected $R^{5b}$. In another more particular embodiment, $R^3$ is $C_{1-4}$ alkoxy, optionally substituted with one or more independently selected $R^{5b}$, wherein $R^{5b}$ is F, Cl, OH, —$OP(=O)_2OH$, CN, —$OCH_3$, —$OCH_2CH_3$, —$NHCH_3$, —$N(CH_3)_2$, —$NH(CH_2-CH_3)$, —$N(CH_2-CH_3)CH_3$, or —$N(CH_2-CH_3)_2$. In yet another more particular embodiment, $R^3$ is —$OCH_3$, —$OCH_2CH_3$, or —$OCH(CH_3)_2$, each of which is optionally substituted with one or more independently selected $R^{5b}$, wherein $R^{5b}$ is F, Cl, OH, —$OP(=O)_2OH$, CN, —$OCH_3$, —$OCH_2CH_3$, —$NHCH_3$, —$N(CH_3)_2$, —$NH(CH_2-CH_3)$, —$N(CH_2-CH_3)CH_3$, or —$N(CH_2-CH_3)_2$. In a further more particular embodiment, $R^3$ is $C_{1-4}$ alkoxy, optionally substituted with one or more independently selected $R^{5b}$, wherein $R^{5b}$ is F, Cl, OH, —$OP(=O)_2OH$, CN, or —$OCH_3$. In yet a further more particular embodiment, $R^3$ is —$OCH_3$, —$OCH_2CH_3$, or —$OCH(CH_3)_2$, each of which is optionally substituted with one or more independently selected $R^{5b}$, wherein $R^{5b}$ is F, Cl, OH, —$OP(=O)_2OH$, CN, or —$OCH_3$.

In one embodiment, a compound of the invention is according to Formula I, wherein $R^1$ is $C_{6-10}$ mono or bicyclic aryl, substituted with one or more independently selected $R^3$ groups, and $R^3$ is as described above. In a particular embodiment, $R^1$ is phenyl substituted with one or more independently selected $R^3$ groups. In a particular embodiment, $R^3$ is $C_{1-4}$ alkoxy, optionally substituted with one or more independently selected $R^{5b}$, wherein $R^{5b}$ is as defined above. In a more particular embodiment, $R^3$ is —$OCH_3$, —$OCH_2CH_3$, or —$OCH(CH_3)_2$, each of which is optionally substituted with one or more independently selected $R^{5b}$. In another more particular embodiment, $R^3$ is $C_{1-4}$ alkoxy, optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2-CH_3)$, —$N(CH_2-CH_3)CH_3$, or —$N(CH_2-CH_3)_2$. In yet another more particular embodiment, $R^3$ is —$OCH_3$, —$OCH_2CH_3$, or —$OCH(CH_3)_2$, each of which is optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2-CH_3)$, —$N(CH_2-CH_3)CH_3$, or —$N(CH_2-CH_3)_2$.

In one embodiment, a compound of the invention is according to Formula I, wherein $R^1$ is $C_{6-10}$ monocyclic or bicyclic aryl, substituted with one or more independently selected $R^3$ groups, and $R^3$ is as described above. In a particular embodiment, $R^1$ is phenyl substituted with one or more independently selected $R^3$ groups. In a particular embodiment, $R^3$ is $C_{2-4}$ alkenyl, optionally substituted with one or more independently selected $R^{5b}$, wherein $R^{5b}$ is as defined above. In a more particular embodiment, $R^3$ is —$CH=CH_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$), each of which is optionally substituted with one or more independently selected R$^{5b}$. In another more particular embodiment, R$^3$ is C$_{2-4}$ alkenyl, optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$), each of which is optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or N(CH$_2$—CH$_3$)$_2$. In a most particular embodiment, R$^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$). In another most particular embodiment, R$^3$ is —CH=CH—CH$_2$—OCH$_3$, —CH=CH—CH$_2$—OCH$_2$CH$_3$, —OCH$_3$=CH—CH$_2$—OCH$_3$, or —CH=CCH$_3$—CH$_2$—OCH$_2$CH$_3$.

In one embodiment, a compound of the invention is according to Formula I, wherein R$^1$ is C$_{6-10}$ mono or bicyclic aryl, substituted with one or more independently selected R$^3$ groups, and R$^3$ is as described above. In a particular embodiment, R$^1$ is phenyl substituted with one or more independently selected R$^3$ groups. In a particular embodiment, R$^3$ is C$_{3-7}$ cycloalkyl. In a more particular embodiment, R$^3$ is cyclopropyl, cyclobutyl, cylopentyl, or cyclohexyl. In a most particular embodiment, R$^3$ is cyclopropyl.

In one embodiment, a compound of the invention is according to Formula I, wherein R$^1$ is C$_{6-10}$ monocyclic or bicyclic aryl, substituted with one or more independently selected R$^3$ groups, and R$^3$ is as described above. In a particular embodiment, R$^1$ is phenyl substituted with one or more independently selected R$^3$ groups. In a particular embodiment, R$^3$ is 4-7 membered monocyclic heterocycloalkyl comprising one or more heteroatoms independently selected from N, O, and S. In a more particular embodiment, R$^3$ is tetrahydropyranyl, piperidinyl, piperazinyl, morpholinyl, or thiomorpholinyl In one embodiment, a compound of the invention is according to Formula I, wherein R$^1$ is C$_{6-10}$ mono or bicyclic aryl, substituted with one or more independently selected R$^3$ groups, and R$^3$ is as described above. In a particular embodiment, R$^1$ is phenyl substituted with one or more independently selected R$^3$ groups. In a particular embodiment, R$^3$ is 4-7 membered monocyclic heterocycloalkenyl comprising one or more heteroatoms independently selected from N, O, and S. In a more particular embodiment, R$^3$ is dihydropyranyl, or tetrahydropyridinyl.

In one embodiment, a compound of the invention is according to Formula I, wherein R$^1$ is C$_{6-10}$ mono or bicyclic aryl, substituted with one or more independently selected R$^3$ groups, and R$^3$ is as described above. In a particular embodiment, R$^1$ is phenyl substituted with one or more independently selected R$^3$ groups. In a particular embodiment, R$^3$ is 5-10 membered mono or fused bicyclic heteroaryl comprising one or more heteroatoms independently selected from N, O, and S. In a more particular embodiment, R$^3$ is furanyl, thiophenyl, pyrazolyl, imidazolyl, thiazolyl, oxazolyl, pyridinyl, pyridazinyl, pyrimidyl, or pyrazinyl.

In one embodiment, a compound of the invention is according to Formula I, wherein R$^1$ is C$_{6-10}$ mono or bicyclic aryl, substituted with one or more independently selected R$^3$ groups, and R$^3$ is as described above. In a particular embodiment, R$^1$ is phenyl substituted with one or more independently selected R$^3$ groups. In a particular embodiment, R$^3$ is —NHSO$_2$—CH$_3$, or —NHSO$_2$—CH$_2$CH$_3$.

In one embodiment, a compound of the invention is according to Formula I, wherein R$^1$ is 5-10 membered mono or fused bicyclic heteroaryl comprising one or more heteroatoms independently selected from N, O, and S. In a particular embodiment, R$^1$ is furanyl, thiophenyl, pyrazolyl, imidazolyl, thiazolyl, oxazolyl, pyridinyl, pyridazinyl, pyrimidyl, or pyrazinyl. In a more particular embodiment, R$^1$ is pyrazolyl, thiazolyl, or thiophenyl.

In one embodiment, a compound of the invention is according to Formula I, wherein R$^1$ is 5-10 membered mono or fused bicyclic heteroaryl comprising one or more heteroatoms independently selected from N, O, and S, optionally substituted with one or more independently selected R$^3$ groups, and R$^3$ is as described above. In another embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^1$ is 5-10 membered mono or fused bicyclic heteroaryl comprising one or more heteroatoms independently selected from N, O, and S, substituted with one or two independently selected R$^3$ groups. In another particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or two independently selected R$^3$ groups. In a more particular embodiment, R$^1$ is 5-10 membered mono or fused bicyclic heteroaryl comprising one or more heteroatoms independently selected from N, O, and S, substituted with one R$^3$ group. In another particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one R$^3$ group.

In one embodiment, a compound of the invention is according to Formula I, wherein R$^1$ is 5-10 membered mono or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is selected from halo, CN, and OH. In a more particular embodiment, R$^3$ is selected from F, Cl, CN, and OH.

In one embodiment, a compound of the invention is according to Formula I, wherein R$^1$ is 5-10 membered monocyclic or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is C$_{1-4}$ alkyl, optionally substituted with one or more independently selected R$^{5b}$, wherein R$^{5b}$ is as defined above. In a more particular embodiment, R$^3$ is —CH$_3$, —CH$_2$CH$_3$, or —CH(CH$_3$)$_2$, each of which is optionally substituted with one or more independently selected R$^{5b}$. In another more particular embodiment, R$^3$ is C$_{1-4}$ alkyl, optionally substituted with one or more independently selected R$^{5b}$, wherein R$^{5b}$ is F, Cl, OH, —OP(=O)$_2$OH, CN, —OCH$_3$, —OCH$_2$CH$_3$, —NHCH$_3$, —N(CH$_3$)$_2$, —NH(CH$_2$—CH$_3$), N(CH$_2$—CH$_3$)CH$_3$, or —N(CH$_2$—CH$_3$)$_2$. In yet another more particular embodiment, R$^3$ is —CH$_3$, —CH$_2$CH$_3$, —CH(CH$_3$)$_2$, or —C(CH$_3$)$_3$, each of which is optionally substituted with one or more independently selected R$^{5b}$, wherein R$^{5a}$ is F, Cl, OH, —OP(=O)$_2$OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a further more particular embodiment, R$^3$ is C$_{1-4}$ alkyl, optionally substituted with one or more independently selected R$^{5b}$, wherein R$^{5b}$ is F, Cl, OH, —OP(=O)$_2$OH, CN, or —OCH$_3$. In yet a further more particular embodiment, R$^3$ is —CH$_3$, —CH$_2$CH$_3$, —CH(CH$_3$)$_2$, or —C(CH$_3$)$_3$, each of which is optionally substituted with one or more independently selected R$^{5b}$, wherein R$^{5a}$ is F, Cl, OH, —OP(=O)$_2$OH, CN, or —OCH$_3$. In a most particular embodiment, each R$^3$ is independently selected from —CH$_3$, —CH$_2$CH$_3$, —CH(CH$_3$)$_2$, —C(CH$_3$)$_3$. —CH$_2$—OH, —CH$_2$—OP(=O)$_2$OH, —C(OH)(CH$_3$)$_2$, —CF$_3$, —CH$_2$—CHF$_2$, —CH$_2$CH$_2$OCH$_3$, and —CH$_2$CH$_2$N(CH$_3$)$_2$.

In one embodiment, a compound of the invention is according to Formula I, wherein R$^1$ is 5-10 membered mono or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is C$_{1-4}$ alkyl, optionally substituted with one or more independently selected R$^{5b}$, wherein R$^{5b}$ is as defined above. In a more particular embodiment, R$^3$ is —CH$_3$, —CH$_2$CH$_3$, or —CH(CH$_3$)$_2$, each of which is optionally substituted with one or more independently selected R$^{5b}$. In another more particular embodiment, R$^3$ is C$_{1-4}$ alkyl, optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —CH$_3$, —CH$_2$CH$_3$, —CH(CH$_3$)$_2$, or —C(CH$_3$)$_3$, each of which is optionally substituted with one or more independently selected R$^{5b}$, wherein R$^{5a}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, R$^3$ is —CH$_3$, —CH$_2$CH$_3$, —CH(CH$_3$)$_2$, or —C(CH$_3$)$_3$.

In one embodiment, a compound of the invention is according to Formula I, wherein R$^1$ is 5-10 membered monocyclic or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In another more particular embodiment, R$^3$ is C$_{1-4}$ alkoxy, optionally substituted with one or more independently selected R$^{5b}$, wherein R$^{5b}$ is F, Cl, OH, —OP(=O)$_2$OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —OCH$_3$, —OCH$_2$CH$_3$, or —OCH(CH$_3$)$_2$, each of which is optionally substituted with one or more independently selected R$^{5b}$, wherein R$^{5b}$ is F, Cl, OH, —OP(=O)$_2$OH, CN, or —OCH$_3$. In a further more particular embodiment, R$^3$ is C$_{1-4}$ alkoxy, optionally substituted with one or more independently selected R$^{5b}$, wherein R$^{5b}$ is F, Cl, OH, —OP(=O)$_2$OH, CN, or —OCH$_3$. In yet a further more particular embodiment, R$^3$ is —OCH$_3$, —OCH$_2$CH$_3$, or —OCH(CH$_3$)$_2$, each of which is optionally substituted with one or more independently selected R$^{5b}$, wherein R$^{5b}$ is F, Cl, OH, —OP(=O)$_2$OH, CN, or —OCH$_3$.

In one embodiment, a compound of the invention is according to Formula I, wherein R$^1$ is 5-10 membered mono or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is C$_{1-4}$ alkoxy, optionally substituted with one or more independently selected R$^{5b}$, wherein R$^{5b}$ is as defined above. In a more particular embodiment, R$^3$ is —OCH$_3$, —OCH$_2$CH$_3$, or —OCH(CH$_3$)$_2$, each of which is optionally substituted with one or more independently selected R$^{5b}$. In another more particular embodiment, R$^3$ is C$_{1-4}$ alkoxy, optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —OCH$_3$, —OCH$_2$CH$_3$, or —OCH(CH$_3$)$_2$, each of which is optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to Formula I, wherein R$^1$ is 5-10 membered monocyclic or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is C$_{2-4}$ alkenyl, optionally substituted with one or more independently selected R$^{5b}$, wherein R$^{5b}$ is as defined above. In a more particular embodiment, R$^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$), each of which is optionally substituted with one or more independently selected R$^{5b}$. In another more particular embodiment, R$^3$ is C$_{2-4}$ alkenyl, optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$), each of which is optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, R$^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$). In another most particular embodiment, R$^3$ is —CH=CH—CH$_2$—OCH$_3$, —CH=CH—CH$_2$—OCH$_2$CH$_3$, —CCH$_3$=CH—CH$_2$—OCH$_3$, or —CH=CCH$_3$—CH$_2$—OCH$_2$CH$_3$.

In one embodiment, a compound of the invention is according to Formula I, wherein R$^1$ is 5-10 membered mono or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is C$_{3-7}$ cycloalkyl. In a more particular embodiment, R$^3$ is cyclopropyl, cyclobutyl, cylopentyl, or cyclohexyl. In a most particular embodiment, R$^3$ is cyclopropyl.

In one embodiment, a compound of the invention is according to Formula I, wherein R$^1$ is 5-10 membered monocyclic or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is 4-7 membered monocyclic heterocycloalkyl comprising one or more heteroatoms independently selected from N, O, and S. In a more particular embodiment, R$^3$ is tetrahydropyranyl, piperidinyl, piperazinyl, morpholinyl, or thiomorpholinyl.

In one embodiment, a compound of the invention is according to Formula I, wherein R$^1$ is 5-10 membered monocyclic or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is 4-7 membered monocyclic heterocycloalkenyl comprising one or more heteroatoms independently selected from N, O, and S. In a more particular embodiment, R$^3$ is dihydropyranyl, or tetrahydropyridinyl.

In one embodiment, a compound of the invention is according to Formula I, wherein R$^1$ is 5-10 membered mono or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is 5-10 membered mono or fused bicyclic heteroaryl comprising one or more heteroatoms independently selected from N, O, or S. In a more particular embodiment, R$^3$ is furanyl, thiophenyl, pyrazolyl, imidazolyl, thiazolyl, oxazolyl, pyridinyl, pyridazinyl, pyrimidyl, or pyrazinyl.

In one embodiment, a compound of the invention is according to any one of Formula I, wherein R$^1$ is 5-10 membered mono or fused bicyclic heteroaryl comprising one or more heteroatoms independently selected from N, O, and S, substituted with one or more independently selected R$^3$ groups, and R$^3$ is as described above. In a particular embodiment, R$^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^3$ groups. In a particular embodiment, R$^3$ is —NHSO$_2$—CH$_3$, or —NHSO$_2$—CH$_2$CH$_3$.

In one embodiment, a compound of the invention is according to Formula I, wherein R$^1$ is 5-6 membered monocyclic heteroaryl comprising one or more heteroatoms independently selected from N, O, and S, substituted with one or more independently selected R$^3$ groups, wherein two adjacent R$^3$ groups together with the carbon they are linked to form together a 8-10 membered fused bicycle. In a particular embodiment, R$^1$ is

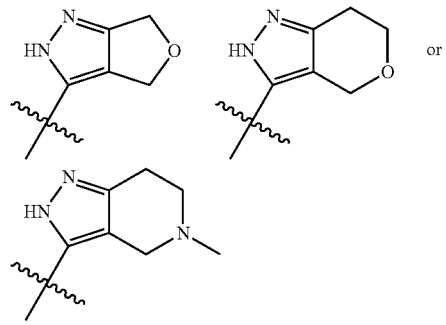

In one embodiment, a compound of the invention is according to Formula I, wherein R$^1$ is C$_{1-6}$ alkyl. In a particular embodiment, R$^1$ is —CH$_3$, —CH$_2$—CH$_3$, —CH(CH$_3$)$_2$, —C(CH$_3$)$_3$, —C(CH$_3$)$_2$—CH$_3$, or —C(CH$_3$)H—C(CH$_3$)$_2$H. In a more particular embodiment, R$^1$ is —C(CH$_3$)$_3$, or —CH$_2$CH(CH$_3$)$_2$. In a most particular embodiment, R$^1$ is —C(CH$_3$)$_3$.

In one embodiment, a compound of the invention is according to Formula I, wherein R$^1$ is C$_{1-6}$ alkyl substituted with one or more independently selected R$^4$ groups. In a particular embodiment, R$^1$ is C$_{1-6}$ alkyl substituted with one, two or three independently selected R$^4$ groups. In a more particular embodiment, R$^1$ is C$_{1-6}$ alkyl substituted with one R$^4$ group.

In one embodiment, a compound of the invention is according to Formula I, wherein R$^1$ is C$_{1-6}$ alkyl substituted with one or more independently selected R$^4$ groups. In a particular embodiment, R$^1$ is —CH$_3$, —CH$_2$—CH$_3$, —CH(CH$_3$)$_2$, —C(CH$_3$)$_3$, —C(CH$_3$)$_2$—CH$_3$, or —CH(CH$_3$)—CH(CH$_3$)$_2$, each of which is substituted with one or more independently selected R$^4$ groups. In another particular embodiment, R$^1$ is C$_{1-6}$ alkyl substituted with one or more independently selected R$^4$ groups selected from F, Cl, OH, and CN. In a particular embodiment, R$^1$ is —CH$_3$, —CH$_2$—CH$_3$, —CH(CH$_3$)$_2$, —C(CH$_3$)$_3$, —C(CH$_3$)$_2$—CH$_3$, or —CH(CH$_3$)—CH(CH$_3$)$_2$, each of which is substituted with one or more independently selected R$^4$ groups selected from F, Cl, OH, and CN. In a most particular embodiment, R$^1$ is —CF$_3$, —CH$_2$CF$_3$, —CH(OH)CF$_3$, —CH$_2$—OH, —CH$_2$—CH$_2$—OH, —C(CH$_3$)$_2$—CH$_2$—OH, —CH$_2$—CN, or —CH$_2$—CH$_2$—CN.

In one embodiment, a compound of the invention is according to Formula I, wherein R$^1$ is C$_{1-6}$ alkyl substituted with one or more independently selected R$^4$ groups. In a particular embodiment, R$^1$ is —CH$_3$, —CH$_2$—CH$_3$, —CH(CH$_3$)$_2$, —C(CH$_3$)$_3$, —C(CH$_3$)$_2$—CH$_3$, or —CH(CH$_3$)—CH(CH$_3$)$_2$, each of which is substituted with one or more independently selected R$^4$ groups, and R$^4$ is C$_{3-7}$ cycloalkyl. In another particular embodiment, R$^1$ is C$_{1-6}$ alkyl substituted with one or more independently selected R$^4$ groups selected from cyclopropyl, cyclobutyl, cyclopentyl, and cyclohexyl. In a particular embodiment, R$^1$ is —CH$_3$, —CH$_2$—CH$_3$, —CH (CH$_3$)$_2$, —C(CH$_3$)$_3$, —C(CH$_3$)$_2$—CH$_3$, or —CH(CH$_3$)—CH(CH$_3$)$_2$, each of which is substituted with one or more independently selected R$^4$ groups selected from cyclopropyl, cyclobutyl, cyclopentyl, and cyclohexyl. In a most particular embodiment, R$^1$ is —CH$_2$-cyclopropyl, or —CH(CH$_3$)-cyclopropyl.

In one embodiment, a compound of the invention is according to Formula I, wherein R$^1$ is C$_{1-6}$ alkyl substituted with one or more independently selected R$^4$ groups, wherein R$^4$ is C$_{1-4}$ alkoxy optionally substituted with one or more independently selected R$^{5c}$. In a particular embodiment, R$^1$ is —CH$_3$, —CH$_2$—CH$_3$, —CH(CH$_3$)$_2$, —C(CH$_3$)$_3$, —C(CH$_3$)$_2$—CH$_3$, or —CH(CH$_3$)—CH(CH$_3$)$_2$, each of which is substituted with one or more independently selected R$^4$ groups, wherein R$^4$ is C$_{1-4}$ alkoxy optionally substituted with one or more independently selected R$^{5c}$. In a more particular embodiment, R$^4$ —OCH$_3$, —OCH$_2$CH$_3$, or —OCH(CH$_3$)$_2$, each of which is optionally substituted with one or more independently selected R$^{5c}$. In another more particular embodiment, R$^4$ is C$_{1-4}$ alkoxy optionally substituted with one or more independently selected R$^{5c}$, wherein R$^{5c}$ is selected from F, Cl, OH, —CN, —OCH$_3$, —OCH$_2$CH$_3$, —NH(CH$_3$) or —N(CH$_3$)$_2$. In a further more particular embodiment, R$^4$ is —OCH$_3$, —OCH$_2$—CH$_3$, or —OCH(CH$_3$)$_2$, each of which is substituted with one or more independently selected R$^{5c}$, and each R$^{5c}$ is F, Cl, OH, —CN, —OCH$_3$, —OCH$_2$CH$_3$, —NH(CH$_3$) or —N(CH$_3$)$_2$. In a most particular embodiment, R$^4$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to Formula I, wherein R$^1$ is

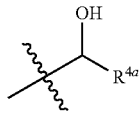

wherein R$^{4a}$ is C$_{1-5}$ alkyl optionally substituted with one or more independently selected halo, CN, C$_{1-4}$ alkoxy, or C$_{3-7}$ monocyclic cycloalkyl. In a particular embodiment, R$^{4a}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$, each of which is optionally substituted with one or more independently selected halo, CN, C$_{1-4}$ alkoxy, or C$_{3-7}$ monocyclic cycloalkyl. In a particular embodiment, R$^{4a}$ is C$_{1-5}$ alkyl optionally substituted with one or more independently selected F, Cl, OH, CN, —OCH$_3$, —OCH$_2$CH$_3$, cyclopropyl, cyclobutyl, or cyclopentyl. In another particular embodiment, R$^{4a}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$, each of which is optionally substituted with one or more independently selected F, Cl, OH, CN, —OCH$_3$, —OCH$_2$CH$_3$, cyclopropyl, cyclobutyl, or cyclopentyl. In a most particular embodiment, R$^{4a}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$. In another most particular embodiment, R$^{4a}$ is —CF$_3$, —CH$_2$CF$_3$, or —CH$_2$CN.

In one embodiment, a compound of the invention is according to Formula I, wherein R$^1$ is

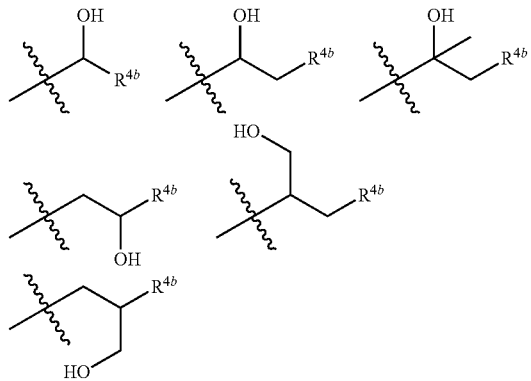

wherein R$^{4b}$ is C$_{3-7}$ monocyclic cycloalkyl. In a particular embodiment, R$^{4b}$ is cyclopropyl, cyclobutyl, or cyclopentyl. In a more particular embodiment, R$^{4b}$ is cyclopropyl.

In one embodiment, a compound of the invention is according to Formula IIa

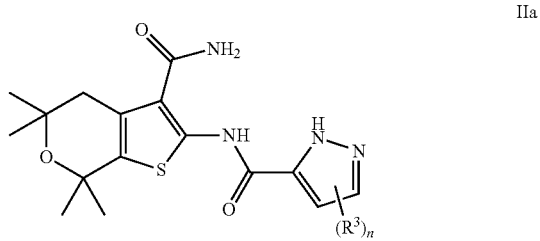

wherein R$^3$ is as described above, and the subscript n is 0, 1 or 2.

In another embodiment, a compound of the invention is according to Formula IIb

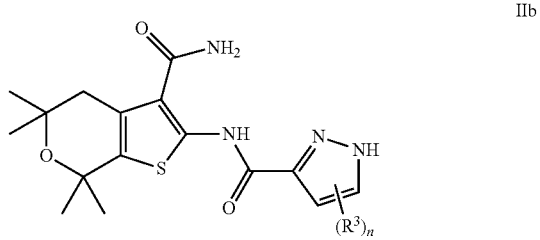

wherein R$^3$ is as described above, and the subscript n is 0, 1 or 2.

In one embodiment, a compound of the invention is according to Formula IIa wherein the subscript n is 0.

one embodiment, a compound of the invention is according to Formula IIb wherein the subscript n is 0.

In one embodiment, a compound of the invention is according to Formula IIa wherein the subscript n is 1 or 2, wherein each R$^3$ is independently selected from halo, CN, and OH. In a more particular embodiment, each R$^3$ is independently selected from F, Cl, CN, and OH.

In one embodiment, a compound of the invention is according to Formula IIb wherein the subscript n is 1 or 2, wherein each R$^3$ is independently selected from halo, CN, and OH. In a more particular embodiment, each R$^3$ is independently selected from F, Cl, CN, and OH.

In one embodiment, a compound of the invention is according to Formula IIa wherein the subscript n is 1 or 2, wherein each $R^3$ is independently selected from $C_{1-4}$ alkyl, optionally substituted with one or more independently selected $R^{5b}$, wherein $R^{5b}$ is as defined above. In a more particular embodiment, $R^3$ is independently selected from —$CH_3$, —$CH_2CH_3$, —$CH(CH_3)_2$, and —$C(CH_3)_3$, each of which is optionally substituted with one or more independently selected $R^{5b}$. In another more particular embodiment, each $R^3$ is independently selected from $C_{1-4}$ alkyl, optionally substituted with one or more independently selected $R^{5b}$, wherein $R^{5b}$ is F, Cl, OH, —OP(=O)$_2$OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In yet another more particular embodiment, each $R^3$ is independently selected from —$CH_3$, —$CH_2CH_3$, $CH(CH_3)_2$, and —$C(CH_3)_3$, each of which is optionally substituted with one or more independently selected $R^{5b}$, wherein $R^{5b}$ is F, Cl, OH, —OP(=O)$_2$OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In a most particular embodiment, each $R^3$ is independently selected from —$CH_3$, —$CH_2CH_3$, —$CH(CH_3)_2$, —$C(CH_3)_3$. —$CH_2$—OH, —$CH_2$—OP(=O)$_2$OH, —$C(OH)(CH_3)_2$, —$CF_3$, —$CH_2$—$CHF_2$, —$CH_2CH_2OCH_3$, and —$CH_2CH_2N(CH_3)_2$.

In one embodiment, a compound of the invention is according to Formula IIb wherein the subscript n is 1 or 2, wherein each $R^3$ is independently selected from $C_{1-4}$ alkyl, optionally substituted with one or more independently selected $R^{5b}$, wherein $R^{5b}$ is as defined above. In a more particular embodiment, $R^3$ is independently selected from —$CH_3$, —$CH_2CH_3$, —$CH(CH_3)_2$, and —$C(CH_3)_3$, each of which is optionally substituted with one or more independently selected $R^{5b}$. In another more particular embodiment, each $R^3$ is independently selected from $C_{1-4}$ alkyl, optionally substituted with one or more independently selected $R^{5b}$, wherein $R^{5b}$ is F, Cl, OH, —OP(=O)$_2$OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In yet another more particular embodiment, each $R^3$ is independently selected from —$CH_3$, —$CH_2CH_3$, $CH(CH_3)_2$, and —$C(CH_3)_3$, each of which is optionally substituted with one or more independently selected $R^{5b}$, wherein $R^{5b}$ is F, Cl, OH, —OP(=O)$_2$OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In a most particular embodiment, each $R^3$ is independently selected from —$CH_3$, —$CH_2CH_3$, —$CH(CH_3)_2$, —$C(CH_3)_3$. —$CH_2$—OH, —$CH_2$—OP(=O)$_2$OH, —$C(OH)(CH_3)_2$, —$CF_3$, —$CH_2$—$CHF_2$, —$CH_2CH_2OCH_3$, and —$CH_2CH_2N(CH_3)_2$.

In one embodiment, a compound of the invention is according to Formula IIa wherein the subscript n is 1 or 2, wherein each $R^3$ is independently selected from $C_{1-4}$ alkyl, optionally substituted with one or more independently selected $R^{5b}$, wherein $R^{5b}$ is as defined above. In a more particular embodiment, $R^3$ is independently selected from —$CH_3$, —$CH_2CH_3$, —$CH(CH_3)_2$, and —$C(CH_3)_3$, each of which is optionally substituted with one or more independently selected $R^{5b}$. In another more particular embodiment, each $R^3$ is independently selected from $C_{1-4}$ alkyl, optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In yet another more particular embodiment, each $R^3$ is independently selected from —$CH_3$, —$CH_2CH_3$, —$CH(CH_3)_2$, and —$C(CH_3)_3$, each of which is optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In a most particular embodiment, each $R^3$ is independently selected from —$CH_3$, —$CH_2CH_3$, —$CH(CH_3)_2$, —$C(CH_3)_3$. —$CH_2$—OH, —$C(OH)(CH_3)_2$, —$CF_3$, —$CH_2$—$CHF_2$, —$CH_2CH_2OCH_3$, and —$CH_2CH_2N(CH_3)_2$.

In one embodiment, a compound of the invention is according to Formula IIb wherein the subscript n is 1 or 2, wherein each $R^3$ is independently selected from $C_{1-4}$ alkyl, optionally substituted with one or more independently selected $R^{5b}$, wherein $R^{5b}$ is as defined above. In a more particular embodiment, $R^3$ is independently selected from —$CH_3$, —$CH_2CH_3$, —$CH(CH_3)_2$, and —$C(CH_3)_3$, each of which is optionally substituted with one or more independently selected $R^{5b}$. In another more particular embodiment, each $R^3$ is independently selected from $C_{1-4}$ alkyl, optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In yet another more particular embodiment, each $R^3$ is independently selected from —$CH_3$, —$CH_2CH_3$, $CH(CH_3)_2$, and —$C(CH_3)_3$, each of which is optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In a most particular embodiment, each $R^3$ is independently selected from —$CH_3$, —$CH_2CH_3$, —$CH(CH_3)_2$, —$C(CH_3)_3$. —$CH_2$—OH, —$C(OH)(CH_3)_2$, —$CF_3$, —$CH_2$—$CHF_2$, —$CH_2CH_2OCH_3$, and —$CH_2CH_2N(CH_3)_2$.

In one embodiment, a compound of the invention is according to Formula IIa wherein the subscript n is 1 or 2, wherein each $R^3$ is independently selected from $C_{1-4}$ alkoxy, optionally substituted with one or more independently selected $R^{5b}$, wherein $R^{5b}$ is as defined above. In a more particular embodiment, each $R^3$ is independently selected from —$OCH_3$, —$OCH_2CH_3$, and —$OCH(CH_3)_2$, each of which is optionally substituted with one or more independently selected $R^{5b}$. In another more particular embodiment, each $R^3$ is independently selected from $C_{1-4}$ alkoxy, optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In yet another more particular embodiment, each $R^3$ is independently selected from —$OCH_3$, —$OCH_2CH_3$, and —$OCH(CH_3)_2$, each of which is optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$.

In one embodiment, a compound of the invention is according to Formula IIb wherein the subscript n is 1 or 2, wherein each $R^3$ is independently selected from $C_{1-4}$ alkoxy, optionally substituted with one or more independently selected $R^{5b}$, wherein $R^{5b}$ is as defined above. In a more particular embodiment, each $R^3$ is independently selected from —$OCH_3$, —$OCH_2CH_3$, and —$OCH(CH_3)_2$, each of which is optionally substituted with one or more independently selected $R^{5b}$. In another more particular embodiment, each $R^3$ is independently selected from $C_{1-4}$ alkoxy, optionally substituted with one or more independently selected $R^{5b}$, wherein $R^{5b}$ is F, Cl, OH, CN, —$OCH_3$, —$OCH_2CH_3$, —$NHCH_3$, —$N(CH_3)_2$, —$NH(CH_2—CH_3)$, —$N(CH_2—CH_3)CH_3$, or —$N(CH_2—CH_3)_2$. In yet another more particular embodiment, each $R^3$ is independently selected from —$OCH_3$, —$OCH_2CH_3$, and —$OCH(CH_3)_2$, each of which is optionally substituted with one or more independently selected $R^{5b}$, wherein $R^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to Formula IIa wherein the subscript n is 1 or 2, wherein each R$^3$ is independently selected from C$_{2-4}$ alkenyl, optionally substituted with one or more independently selected R$^{5b}$, wherein R$^{5b}$ is as defined above. In a more particular embodiment, R$^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$), each of which is optionally substituted with one or more independently selected R$^{5b}$. In another more particular embodiment, R$^3$ is C$_{2-4}$ alkenyl, optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$), each of which is optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), N(CH$_2$—CH$_3$)CH$_3$, or —N(CH$_2$—CH$_3$)$_2$. In a most particular embodiment, R$^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$). In another most particular embodiment, R$^3$ is —CH═CH—CH$_2$—OCH$_3$, —CH═CH—CH$_2$—OCH$_2$CH$_3$, —CCH$_3$═CH—CH$_2$—OCH$_3$, or —CH═CCH$_3$—CH$_2$—OCH$_2$CH$_3$.

In one embodiment, a compound of the invention is according to Formula IIb wherein the subscript n is 1 or 2, wherein each R$^3$ is independently selected from C$_{2-4}$ alkenyl, optionally substituted with one or more independently selected R$^{5b}$, wherein R$^{5b}$ is as defined above. In a more particular embodiment, R$^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$), each of which is optionally substituted with one or more independently selected R$^{5b}$. In another more particular embodiment, R$^3$ is C$_{2-4}$ alkenyl, optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, R$^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$), each of which is optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, R$^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$). In another most particular embodiment, R$^3$ is —CH═CH—CH$_2$—OCH$_3$, —CH═CH—CH$_2$—OCH$_2$CH$_3$, —CCH$_3$═CH—CH$_2$—OCH$_3$, or —CH═CCH$_3$—CH$_2$—OCH$_2$CH$_3$.

In one embodiment, a compound of the invention is according to Formula IIa wherein the subscript n is 1 or 2, wherein each R$^3$ is independently selected from C$_{3-7}$ cycloalkyl. In a more particular embodiment, each R$^3$ is independently selected from cyclopropyl, cyclobutyl, cylopentyl, and cyclohexyl. In a most particular embodiment, R$^3$ is cyclopropyl.

In one embodiment, a compound of the invention is according to Formula IIb wherein the subscript n is 1 or 2, wherein each R$^3$ is independently selected from C$_{3-7}$ cycloalkyl. In a more particular embodiment, each R$^3$ is independently selected from cyclopropyl, cyclobutyl, cylopentyl, and cyclohexyl. In a most particular embodiment, R$^3$ is cyclopropyl.

In one embodiment, a compound of the invention is according to Formula IIa wherein the subscript n is 1 or 2, wherein each R$^3$ is independently selected from 4-7 membered monocyclic heterocycloalkyl comprising one or more heteroatoms independently selected from N, O, or S. In a particular embodiment, each R$^3$ is independently selected from tetrahydropyranyl, piperidinyl, piperazinyl, morpholinyl, and thiomorpholinyl.

In one embodiment, a compound of the invention is according to Formula IIb wherein the subscript n is 1 or 2, wherein each R$^3$ is independently selected from 4-7 membered monocyclic heterocycloalkyl comprising one or more heteroatoms independently selected from N, O, or S. In a particular embodiment, each R$^3$ is independently selected from tetrahydropyranyl, piperidinyl, piperazinyl, morpholinyl, and thiomorpholinyl.

In one embodiment, a compound of the invention is according to Formula IIa wherein the subscript n is 1 or 2, wherein each R$^3$ is independently selected from 4-7 membered monocyclic heterocycloalkenyl comprising one or more heteroatoms independently selected from N, O, or S. In a particular embodiment, each R$^3$ is independently selected from dihydropyranyl, and tetrahydropyridinyl.

In one embodiment, a compound of the invention is according to Formula IIb wherein the subscript n is 1 or 2, wherein each R$^3$ is independently selected from 4-7 membered monocyclic heterocycloalkenyl comprising one or more heteroatoms independently selected from N, O, or S. In a particular embodiment, each R$^3$ is independently selected from dihydropyranyl, and tetrahydropyridinyl.

In one embodiment, a compound of the invention is according to Formula Ma or Mb:

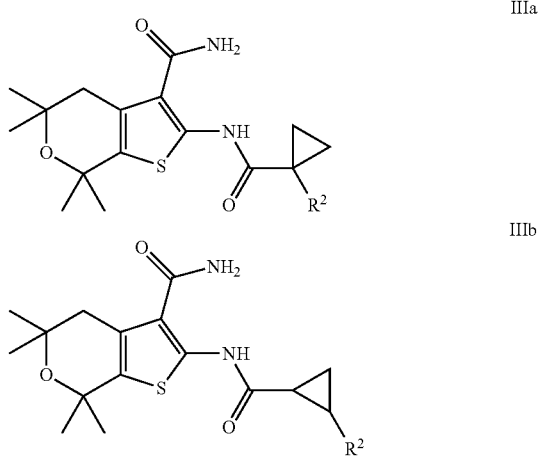

wherein R$^2$ is as described above.

In one embodiment, a compound of the invention is according to Formula Ma or Mb, wherein R$^2$ is selected from halo, CN, oxo, and OH. In a more particular embodiment, R$^2$ is selected from F, Cl, CN, oxo, and OH.

In one embodiment, a compound of the invention is according to Formula Ma or Mb, wherein $R^2$ is $C_{1-4}$ alkyl, optionally substituted with one or more independently selected $R^{5a}$, wherein $R^{5a}$ is as defined above. In a more particular embodiment, $R^2$ is —$CH_3$, —$CH_2CH_3$, $CH(CH_3)_2$, or —$C(CH_3)_3$. In another more particular embodiment, $R^2$ is —$CH_3$, —$CH_2CH_3$, $CH(CH_3)_2$, or —$C(CH_3)_3$, each of which is optionally substituted with one or more independently selected $R^{5a}$. In yet another more particular embodiment, $R^2$ is $C_{1-4}$ alkyl, optionally substituted with one or more independently selected $R^{5a}$, wherein $R^{5a}$ is F, Cl, OH, CN, —$OCH_3$, —$OCH_2CH_3$, —$NHCH_3$, —$N(CH_3)_2$, —$NH(CH_2$—$CH_3)$, —$N(CH_2$—$CH_3)CH_3$, or —$N(CH_2$—$CH_3)_2$. In a further more particular embodiment, $R^2$ is —$CH_3$, —$CH_2CH_3$, $CH(CH_3)_2$, or —$C(CH_3)_3$, each of which is optionally substituted with one or more independently selected $R^{5a}$, wherein $R^{5a}$ is F, Cl, OH, CN, —$OCH_3$, —$OCH_2CH_3$, —$NHCH_3$, —$N(CH_3)_2$, —$NH(CH_2$—$CH_3)$, —$N(CH_2$—$CH_3)CH_3$, or —$N(CH_2$—$CH_3)_2$. In a most particular embodiment, $R^2$ is —$CH_3$, —$CH_2CH_3$, —$CH(CH_3)_2$, —$C(CH_3)_3$, —$CH_2$—OH, —$C(OH)(CH_3)_2$, —$CF_3$, —$CH_2$—$CHF_2$, —$CH_2CH_2OCH_3$, or —$CH_2CH_2N(CH_3)_2$.

In one embodiment, a compound of the invention is according to Formula Ma or Mb, wherein $R^2$ is $C_{1-4}$ alkoxy, optionally substituted with one or more independently selected $R^{5a}$, wherein $R^{5a}$ is as defined above. In a particular embodiment, $R^2$ is —$OCH_3$, —$OCH_2CH_3$, or —$OCH(CH_3)_2$. In a particular embodiment, $R^2$ is —$OCH_3$, —$OCH_2CH_3$, or —$OCH(CH_3)_2$, each of which is optionally substituted with one or more independently selected $R^{5a}$. In another particular embodiment, $R^2$ is $C_{1-4}$ alkoxy, optionally substituted with one or more independently selected $R^{5a}$, wherein $R^{5a}$ is F, Cl, OH, CN, —$OCH_3$, —$OCH_2CH_3$, —$NHCH_3$, —$N(CH_3)_2$, —$NH(CH_2$—$CH_3)$, —$N(CH_2$—$CH_3)CH_3$, or —$N(CH_2$—$CH_3)_2$. In a more particular embodiment, $R^2$ is —$OCH_3$, —$OCH_2CH_3$, or —$OCH(CH_3)_2$, each of which is optionally substituted with one or more independently selected $R^{5a}$, wherein $R^{5a}$ is F, Cl, OH, CN, —$OCH_3$, —$OCH_2CH_3$, —$NHCH_3$, —$N(CH_3)_2$, —$NH(CH_2$—$CH_3)$, —$N(CH_2$—$CH_3)CH_3$, or —$N(CH_2$—$CH_3)_2$. In a most particular embodiment, $R^2$ is —$OCH_3$, —$OCH_2$—$CH_3$, O—$CF_3$, —$OCH_2$—$CHF_2$, —$OCH_2CH_2OCH_3$, or —$OCH_2CH_2N(CH_3)_2$.

In one embodiment, a compound of the invention is selected from:
2-(2-fluorobenzamido)-5,5,7,7-tetramethyl-5,7-dihydro-4H-thieno[2,3-c]pyran-3-carboxamide,
N-(3-carbamoyl-5,5,7,7-tetramethyl-5,7-dihydro-4H-thieno[2,3-c]pyran-2-yl)-1H-pyrazole-5-carboxamide,
2-(2-hydroxybenzamido)-5,5,7,7-tetramethyl-5,7-dihydro-4H-thieno[2,3-c]pyran-3-carboxamide,
2-(1-hydroxycyclopropanecarboxamido)-5,5,7,7-tetramethyl-5,7-dihydro-4H-thieno[2,3-c]pyran-3-carboxamide,
5,5,7,7-tetramethyl-2-(2-(trifluoromethyl)benzamido)-5,7-dihydro-4H-thieno[2,3-c]pyran-3-carboxamide,
2-(2-hydroxy-2-methylpropanamido)-5,5,7,7-tetramethyl-5,7-dihydro-4H-thieno[2,3-c]pyran-3-carboxamide,
2-(4-fluoro-2-(trifluoromethyl)benzamido)-5,5,7,7-tetramethyl-5,7-dihydro-4H-thieno[2,3-c]pyran-3-carboxamide,
2-(2,4-difluorobenzamido)-5,5,7,7-tetramethyl-5,7-dihydro-4H-thieno[2,3-c]pyran-3-carboxamide,
2-(1-(hydroxymethyl)cyclopropanecarboxamido)-5,5,7,7-tetramethyl-5,7-dihydro-4H-thieno[2,3-c]pyran-3-carboxamide,
2-(3-hydroxy-2,2-dimethylpropanamido)-5,5,7,7-tetramethyl-5,7-dihydro-4H-thieno[2,3-c]pyran-3-carboxamide,
N-(3-carbamoyl-5,5,7,7-tetramethyl-5,7-dihydro-4H-thieno[2,3-c]pyran-2-yl)-5-methyl-1H-pyrazole-3-carboxamide,
methyl 1-(3-carbamoyl-5,5,7,7-tetramethyl-5,7-dihydro-4H-thieno[2,3-c]pyran-2-ylcarbamoyl)cyclopropanecarboxylate,
N-(3-carbamoyl-5,5,7,7-tetramethyl-5,7-dihydro-4H-thieno[2,3-c]pyran-2-yl)-5-cyclopropyl-1H-pyrazole-3-carboxamide,
N-(3-carbamoyl-5,5,7,7-tetramethyl-5,7-dihydro-4H-thieno[2,3-c]pyran-2-yl)-5-isopropyl-1H-pyrazole-3-carboxamide,
N-(3-carbamoyl-5,5,7,7-tetramethyl-5,7-dihydro-4H-thieno[2,3-c]pyran-2-yl)-5-(trifluoromethyl)-1H-pyrazole-3-carboxamide,
5-tert-butyl-N-(3-carbamoyl-5,5,7,7-tetramethyl-5,7-dihydro-4H-thieno[2,3-c]pyran-2-yl)-1H-pyrazole-3-carboxamide,
N-(3-carbamoyl-5,5,7,7-tetramethyl-5,7-dihydro-4H-thieno[2,3-c]pyran-2-yl)-5-ethyl-1H-pyrazole-3-carboxamide,
N-(3-carbamoyl-5,5,7,7-tetramethyl-5,7-dihydro-4H-thieno[2,3-c]pyran-2-yl)-1H-1,2,4-triazole-3-carboxamide,
N-(3-carbamoyl-5,5,7,7-tetramethyl-5,7-dihydro-4H-thieno[2,3-c]pyran-2-yl)-3-ethyl-4-methyl-1H-pyrazole-5-carboxamide,
N-(3-carbamoyl-5,5,7,7-tetramethyl-5,7-dihydro-4H-thieno[2,3-c]pyran-2-yl)-2-fluoronicotinamide,
2-(4-fluoro-2-hydroxybenzamido)-5,5,7,7-tetramethyl-5,7-dihydro-4H-thieno[2,3-c]pyran-3-carboxamide,
2-(2-hydroxypropanamido)-5,5,7,7-tetramethyl-5,7-dihydro-4H-thieno[2,3-c]pyran-3-carboxamide,
N-(3-carbamoyl-5,5,7,7-tetramethyl-5,7-dihydro-4H-thieno[2,3-c]pyran-2-yl)-2-oxo-1,2-dihydropyridine-3-carboxamide,
N-(3-carbamoyl-5,5,7,7-tetramethyl-5,7-dihydro-4H-thieno[2,3-c]pyran-2-yl)-6-fluoropicolinamide,
N-(3-carbamoyl-5,5,7,7-tetramethyl-5,7-dihydro-4H-thieno[2,3-c]pyran-2-yl)-4-chloro-1H-pyrazole-3-carboxamide,
2-(2-(1H-1,2,4-triazol-5-yl)benzamido)-5,5,7,7-tetramethyl-5,7-dihydro-4H-thieno[2,3-c]pyran-3-carboxamide,
2-(2-(1H-imidazol-2-yl)benzamido)-5,5,7,7-tetramethyl-5,7-dihydro-4H-thieno[2,3-c]pyran-3-carboxamide,
5,5,7,7-tetramethyl-2-(2-(methylsulfonamido)benzamido)-5,7-dihydro-4H-thieno[2,3-c]pyran-3-carboxamide,
N-(3-carbamoyl-5,5,7,7-tetramethyl-5,7-dihydro-4H-thieno[2,3-c]pyran-2-yl)-5-oxopyrrolidine-3-carboxamide,
N-(3-carbamoyl-5,5,7,7-tetramethyl-5,7-dihydro-4H-thieno[2,3-c]pyran-2-yl)-2-oxopyrrolidine-3-carboxamide,
N-(3-carbamoyl-5,5,7,7-tetramethyl-5,7-dihydro-4H-thieno[2,3-c]pyran-2-yl)-5-methyl-4,5,6,7-tetrahydro-1H-pyrazolo[4,3-c]pyridine-3-carboxamide,
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide,
4-bromo-N-(3-carbamoyl-5,5,7,7-tetramethyl-5,7-dihydro-4H-thieno[2,3-c]pyran-2-yl)-1H-pyrazole-3-carboxamide,
N-(3-carbamoyl-5,5,7,7-tetramethyl-5,7-dihydro-4H-thieno[2,3-c]pyran-2-yl)-4-chloro-5-methyl-1H-pyrazole-3-carboxamide,
N-(3-carbamoyl-5,5,7,7-tetramethyl-5,7-dihydro-4H-thieno[2,3-c]pyran-2-yl)-4-methyl-1H-pyrazole-3-carboxamide,
N-(3-carbamoyl-5,5,7,7-tetramethyl-5,7-dihydro-4H-thieno[2,3-c]pyran-2-yl)-4-chloro-5-ethyl-1H-pyrazole-3-carboxamide, N-(3-carbamoyl-5,5,7,7-tetramethyl-5,7-dihydro-4H-thieno [2,3-c]pyran-2-yl)-4,6-dihydro-1H-furo[3,4-c]pyrazole-3-carboxamide,
2-(2-hydroxy-3,3-dimethylbutanamido)-5,5,7,7-tetramethyl-5,7-dihydro-4H-thieno[2,3-c]pyran-3-carboxamide,
2-(2-hydroxy-3-methylbutanamido)-5,5,7,7-tetramethyl-5,7-dihydro-4H-thieno[2,3-c]pyran-3-carboxamide,
2-(1-(hydroxymethyl)cyclobutanecarboxamido)-5,5,7,7-tetramethyl-5,7-dihydro-4H-thieno[2,3-c]pyran-3-carboxamide,
4-(3-carbamoyl-5,5,7,7-tetramethyl-5,7-dihydro-4H-thieno [2,3-c]pyran-2-ylcarbamoyl)tetrahydro-2H-pyran-4-yl acetate, and
N-(3-carbamoyl-5,5,7,7-tetramethyl-5,7-dihydro-4H-thieno [2,3-c]pyran-2-yl)-5-(methoxymethyl)-1H-pyrazole-3-carboxamide.

In another embodiment, a compound of the invention is selected from Cis-2-[[2-fluorocyclopropanecarbonyl] amino]-5,5,7,7-tetramethyl-4H-thieno[2,3-c]pyran-3-carboxamide, Enantiomer 1,
Cis-2-[[2-fluorocyclopropanecarbonyl]amino]-5,5,7,7-tetramethyl-4H-thieno[2,3-c]pyran-3-carboxamide, Enantiomer 2,
N-(3-carbamoyl-5,5,7,7-tetramethyl-4H-thieno[2,3-c]pyran-2-yl)-4-(3,6-dihydro-2H-pyran-4-yl)-1H-pyrazole-3-carboxamide,
2-[(2-hydroxy-4-methyl-pentanoyl)amino]-5,5,7,7-tetramethyl-4H-thieno[2,3-c]pyran-3-carboxamide,
2-[(3,3-difluorocyclobutanecarbonyl)amino]-5,5,7,7-tetramethyl-4H-thieno[2,3-c]pyran-3-carboxamide,
2-[(2,2-difluorocyclopropanecarbonyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-1H-pyrazole-4-carboxamide,
N-(3-carbamoyl-5,5,7,7-tetramethyl-4H-thieno[2,3-c]pyran-2-yl)-4-chloro-5-(methoxymethyl)-1H-pyrazole-3-carboxamide,
2-[[2-hydroxy-3-methyl-butanoyl]amino]-5,5,7,7-tetramethyl-4H-thieno[2,3-c]pyran-3-carboxamide, Enantiomer 1,
2-[[2-hydroxy-3-methyl-butanoyl]amino]-5,5,7,7-tetramethyl-4H-thieno[2,3-c]pyran-3-carboxamide, Enantiomer 2,
2-(2-hydroxybutanoylamino)-5,5,7,7-tetramethyl-4H-thieno [2,3-c]pyran-3-carboxamide,
5-Ethoxy-1H-pyrazole-3-carboxylic acid (3-carbamoyl-5,5, 7,7-tetramethyl-4,7-dihydro-5H-thieno[2,3-c]pyran-2-yl)-amide,
5-(2-Methoxy-ethoxy)-1H-pyrazole-3-carboxylic acid (3-carbamoyl-5,5,7,7-tetramethyl-4,7-dihydro-5H-thieno [2,3-c]pyran-2-yl)-amide,
2-[(3-hydroxy-3-methyl-butanoyl)amino]-5,5,7,7-tetramethyl-4H-thieno[2,3-c]pyran-3-carboxamide,
5,5,7,7-tetramethyl-2-[[3,3,3-trifluoro-2-(hydroxymethyl) propanoyl]amino]-4H-thieno[2,3-c]pyran-3-carboxamide,
2-(3-hydroxybutanoylamino)-5,5,7,7-tetramethyl-4H-thieno [2,3-c]pyran-3-carboxamide,
2-[[1-(1-hydroxyethyl)cyclopropanecarbonyl]amino]-5,5,7, 7-tetramethyl-4H-thieno[2,3-c]pyran-3-carboxamide,
2-[(2-cyclopropyl-2-hydroxy-acetyl)amino]-5,5,7,7-tetramethyl-4H-thieno[2,3-c]pyran-3-carboxamide,
5-(1-Hydroxy-ethyl)-1H-pyrazole-3-carboxylic acid (3-carbamoyl-5,5,7,7-tetramethyl-4,7-dihydro-5H-thieno[2,3-c]pyran-2-yl)-amide,
2-(3-Carbamoyl-5,5,7,7-tetramethyl-4,7-dihydro-5H-thieno [2,3-c]pyran-2-ylcarbamoyl)-cyclopropanecarboxylic acid ethyl ester,
N-(3-carbamoyl-5,5,7,7-tetramethyl-4H-thieno[2,3-c]pyran-2-yl)-4-[(E)-3-methoxyprop-1-enyl]-1H-pyrazole-3-carboxamide,
N-(3-carbamoyl-5,5,7,7-tetramethyl-4H-thieno[2,3-c]pyran-2-yl)-5-(1-hydroxy-1-methyl-ethyl)-1H-pyrazole-3-carboxamide,
N-(3-carbamoyl-5,5,7,7-tetramethyl-4H-thieno[2,3-c]pyran-2-yl)-4-(3-methoxypropyl)-1H-pyrazole-3-carboxamide,
2-[(2-hydroxyacetyl)amino]-5,5,7,7-tetramethyl-4H-thieno [2,3-c]pyran-3-carboxamide,
2-[(3-hydroxy-4-methyl-pentanoyl)amino]-5,5,7,7-tetramethyl-4H-thieno[2,3-c]pyran-3-carboxamide,
2-[(3-cyclopropyl-3-hydroxy-propanoyl)amino]-5,5,7,7-tetramethyl-4H-thieno[2,3-c]pyran-3-carboxamide,
5,5,7,7-tetramethyl-2-[(4,4,4-trifluoro-3-hydroxy-butanoyl) amino]-4H-thieno[2,3-c]pyran-3-carboxamide,
2-[(3-hydroxy-2-methyl-propanoyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-4-propyl-1H-pyrazole-3-carboxamide,
N-(3-carbamoyl-5,5,7,7-tetramethyl-4H-thieno[2,3-c]pyran-2-yl)-4-(2-ethoxyethyl)-1H-pyrazole-3-carboxamide,
N-(3-carbamoyl-5,5,7,7-tetramethyl-4H-thieno[2,3-c]pyran-2-yl)-4-cyano-1H-pyrazole-3-carboxamide,
2-[[2-(hydroxymethyl)-3-methyl-butanoyl]amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-4-(1,2-dihydroxyethyl)-1H-pyrazole-3-carboxamide,
2-[[(2S)-2-hydroxy-3,3-dimethyl-butanoyl]amino]-5,5,7,7-tetramethyl-4H-thieno[2,3-c]pyran-3-carboxamide,
2-[[(2R)-2-hydroxy-3,3-dimethyl-butanoyl]amino]-5,5,7,7-tetramethyl-4H-thieno[2,3-c]pyran-3-carboxamide,
2-[[1-[1-hydroxyethyl]cyclopropanecarbonyl]amino]-5,5,7, 7-tetramethyl-4H-thieno[2,3-c]pyran-3-carboxamide,
2-[[1-[1-hydroxyethyl]cyclopropanecarbonyl]amino]-5,5,7, 7-tetramethyl-4H-thieno[2,3-c]pyran-3-carboxamide,
N-(3-carbamoyl-5,5,7,7-tetramethyl-4H-thieno[2,3-c]pyran-2-yl)-5-(hydroxymethyl)-1-methyl-pyrazole-3-carboxamide,
2-[(2-hydroxy-2,3,3-trimethyl-butanoyl)amino]-5,5,7,7-tetramethyl-4H-thieno[2,3-c]pyran-3-carboxamide,
2-[[2-(hydroxymethyl)cyclopropanecarbonyl]amino]-5,5,7, 7-tetramethyl-4H-thieno[2,3-c]pyran-3-carboxamide,
2-[[(1S,2S)-2-(hydroxymethyl)cyclopropanecarbonyl] amino]-5,5,7,7-tetramethyl-4H-thieno[2,3-c]pyran-3-carboxamide,
2-[[2-(cyclopropylmethyl)-3-hydroxy-propanoyl]amino]-5, 5,7,7-tetramethyl-4H-thieno[2,3-c]pyran-3-carboxamide,
2-[[2-(hydroxymethyl)-3,3-dimethyl-butanoyl]amino]-5,5, 7,7-tetramethyl-4H-thieno[2,3-c]pyran-3-carboxamide,
2-[2-(hydroxymethyl)butanoylamino]-5,5,7,7-tetramethyl-4H-thieno[2,3-c]pyran-3-carboxamide,
2-[[(1R,3R)-3-(hydroxymethyl)-2,2-dimethyl-cyclopropanecarbonyl]amino]-5,5,7,7-tetramethyl-4H-thieno[2,3-c] pyran-3-carboxamide,
N-(3-carbamoyl-5,5,7,7-tetramethyl-4H-thieno[2,3-c]pyran-2-yl)-4-(hydroxymethyl)-1H-pyrazole-3-carboxamide,
2-[[2-(hydroxymethyl)-3,3-dimethyl-butanoyl]amino]-5,5, 7,7-tetramethyl-4H-thieno[2,3-c]pyran-3-carboxamide,
2-[[2-(hydroxymethyl)-3,3-dimethyl-butanoyl]amino]-5,5, 7,7-tetramethyl-4H-thieno[2,3-c]pyran-3-carboxamide, 2-[[1-(hydroxymethyl)-2,2-dimethyl-cyclopropanecarbonyl]amino]-5,5,7,7-tetramethyl-4H-thieno[2,3-c]pyran-3-carboxamide,

[5-[(3-carbamoyl-5,5,7,7-tetramethyl-4H-thieno[2,3-c]pyran-2-yl)carbamoyl]pyrazol-1-yl]methyl dihydrogen phosphate,

[3-[(3-carbamoyl-5,5,7,7-tetramethyl-4H-thieno[2,3-c]pyran-2-yl)carbamoyl]pyrazol-1-yl]methyl dihydrogen phosphate, N-(3-carbamoyl-5,5,7,7-tetramethyl-4H-thieno[2,3-c]pyran-2-yl)-4-(2,3-dihydro-1,4-dioxin-5-yl)-1H-pyrazole-3-carboxamide, and N-(3-carbamoyl-5,5,7,7-tetramethyl-4H-thieno[2,3-c]pyran-2-yl)-4-(1,4-dioxan-2-yl)-1H-pyrazole-3-carboxamide.

In yet another embodiment, the compound of the invention is selected from:

2-[[2-(cyclopropylmethyl)-3-hydroxy-propanoyl]amino]-5,5,7,7-tetramethyl-4H-thieno[2,3-c]pyran-3-carboxamide, enantiomer 1, 2-[[2-(cyclopropylmethyl)-3-hydroxy-propanoyl]amino]-5,5,7,7-tetramethyl-4H-thieno[2,3-c]pyran-3-carboxamide, enantiomer 2, 2-[[(2S)-3-cyclopropyl-2-hydroxy-propanoyl]amino]-5,5,7,7-tetramethyl-4H-thieno[2,3-c]pyran-3-carboxamide, 2-[[(1R)-1-(hydroxymethyl)-2,2-dimethyl-cyclopropanecarbonyl]amino]-5,5,7,7-tetramethyl-4H-thieno[2,3-c]pyran-3-carboxamide, N-(3-carbamoyl-5,5,7,7-tetramethyl-4H-thieno[2,3-c]pyran-2-yl)-4-(2-methoxyethoxy)-1H-pyrazole-3-carboxamide, N-(3-carbamoyl-5,5,7,7-tetramethyl-4H-thieno[2,3-c]pyran-2-yl)-4-(2-isopropoxyethoxy)-1H-pyrazole-3-carboxamide,

[3-[(3-carbamoyl-5,5,7,7-tetramethyl-4H-thieno[2,3-c]pyran-2-yl)carbamoyl]-4-methyl-pyrazol-1-yl]methyl dihydrogen phosphate,

[5-[(3-carbamoyl-5,5,7,7-tetramethyl-4H-thieno[2,3-c]pyran-2-yl)carbamoyl]-4-methyl-pyrazol-1-yl]methyl dihydrogen phosphate, N-(3-carbamoyl-5,5,7,7-tetramethyl-4H-thieno[2,3-c]pyran-2-yl)-2-oxo-1,3-dihydroimidazole-4-carboxamide, N-(3-carbamoyl-5,5,7,7-tetramethyl-4H-thieno[2,3-c]pyran-2-yl)-4-(methoxymethyl)-1H-pyrazole-3-carboxamide, 2-[(2-hydroxy-4,4-dimethyl-pentanoyl)amino]-5,5,7,7-tetramethyl-4H-thieno[2,3-c]pyran-3-carboxamide, N-(3-carbamoyl-5,5,7,7-tetramethyl-4H-thieno[2,3-c]pyran-2-yl)-5-oxo-pyrrolidine-2-carboxamide, (2R)—N-(3-carbamoyl-5,5,7,7-tetramethyl-4H-thieno[2,3-c]pyran-2-yl)-5-oxo-pyrrolidine-2-carboxamide, 2-[[2-hydroxy-4,4-dimethyl-pentanoyl]amino]-5,5,7,7-tetramethyl-4H-thieno[2,3-c]pyran-3-carboxamide, enantiomer 1, 2-[[2-hydroxy-4,4-dimethyl-pentanoyl]amino]-5,5,7,7-tetramethyl-4H-thieno[2,3-c]pyran-3-carboxamide, enantiomer 2, N-(3-carbamoyl-5,5,7,7-tetramethyl-4H-thieno[2,3-c]pyran-2-yl)-4-[1,4-dioxan-2-yl]-1H-pyrazole-3-carboxamide, enantiomer 1, N-(3-carbamoyl-5,5,7,7-tetramethyl-4H-thieno[2,3-c]pyran-2-yl)-4-[1,4-dioxan-2-yl]-1H-pyrazole-3-carboxamide, enantiomer 2, 2-[[2-(difluoromethoxy)benzoyl]amino]-5,5,7,7-tetramethyl-4H-thieno[2,3-c]pyran-3-carboxamide, N-(3-carbamoyl-5,5,7,7-tetramethyl-4H-thieno[2,3-c]pyran-2-yl)-1-(difluoromethyl)pyrazole-3-carboxamide, N-(3-carbamoyl-5,5,7,7-tetramethyl-4H-thieno[2,3-c]pyran-2-yl)-2-(difluoromethyl)pyrazole-3-carboxamide, N-(3-carbamoyl-5,5,7,7-tetramethyl-4H-thieno[2,3-c]pyran-2-yl)-4-chloro-1-(difluoromethyl)pyrazole-3-carboxamide, N-(3-carbamoyl-5,5,7,7-tetramethyl-4H-thieno[2,3-c]pyran-2-yl)-3-(difluoromethyl)-1-methyl-pyrazole-4-carboxamide, N-(3-carbamoyl-5,5,7,7-tetramethyl-4H-thieno[2,3-c]pyran-2-yl)-5-(difluoromethyl)-1-methyl-pyrazole-4-carboxamide, N-(3-carbamoyl-5,5,7,7-tetramethyl-4H-thieno[2,3-c]pyran-2-yl)-1-methyl-pyrazole-3-carboxamide, N-(3-carbamoyl-5,5,7,7-tetramethyl-4H-thieno[2,3-c]pyran-2-yl)-2-methyl-pyrazole-3-carboxamide, N-(3-carbamoyl-5,5,7,7-tetramethyl-4H-thieno[2,3-c]pyran-2-yl)-1-(2,2,2-trifluoroethyl)pyrazole-3-carboxamide, 2-[[3-(difluoromethyl)benzoyl]amino]-5,5,7,7-tetramethyl-4H-thieno[2,3-c]pyran-3-carboxamide, 2-[[2-(difluoromethyl)benzoyl]amino]-5,5,7,7-tetramethyl-4H-thieno[2,3-c]pyran-3-carboxamide, 2-[(3,3-difluoro-1-methyl-cyclobutanecarbonyl)amino]-5,5,7,7-tetramethyl-4H-thieno[2,3-c]pyran-3-carboxamide, N-(3-carbamoyl-5,5,7,7-tetramethyl-4H-thieno[2,3-c]pyran-2-yl)-2-methyl-oxazole-4-carboxamide, N-(3-carbamoyl-5,5,7,7-tetramethyl-4H-thieno[2,3-c]pyran-2-yl)-1-(2,2-difluoroethyl)pyrazole-3-carboxamide, N-(3-carbamoyl-5,5,7,7-tetramethyl-4H-thieno[2,3-c]pyran-2-yl)-2-(trifluoromethyl)thiazole-4-carboxamide, N-(3-carbamoyl-5,5,7,7-tetramethyl-4H-thieno[2,3-c]pyran-2-yl)thiazole-4-carboxamide, N-(3-carbamoyl-5,5,7,7-tetramethyl-4H-thieno[2,3-c]pyran-2-yl)oxazole-4-carboxamide, N-(3-carbamoyl-5,5,7,7-tetramethyl-4H-thieno[2,3-c]pyran-2-yl)-2-(trifluoromethyl)-1H-imidazole-4-carboxamide, N-(3-carbamoyl-5,5,7,7-tetramethyl-4H-thieno[2,3-c]pyran-2-yl)-4-methyl-thiazole-2-carboxamide, N-(3-carbamoyl-5,5,7,7-tetramethyl-4H-thieno[2,3-c]pyran-2-yl)-2,4-dimethyl-oxazole-5-carboxamide, N-(3-carbamoyl-5,5,7,7-tetramethyl-4H-thieno[2,3-c]pyran-2-yl)isoxazole-5-carboxamide, N-(3-carbamoyl-5,5,7,7-tetramethyl-4H-thieno[2,3-c]pyran-2-yl)thiazole-5-carboxamide, N-(3-carbamoyl-5,5,7,7-tetramethyl-4H-thieno[2,3-c]pyran-2-yl)-4-methyl-oxazole-5-carboxamide, N-(3-carbamoyl-5,5,7,7-tetramethyl-4H-thieno[2,3-c]pyran-2-yl)oxazole-5-carboxamide, N-(3-carbamoyl-5,5,7,7-tetramethyl-4H-thieno[2,3-c]pyran-2-yl)-1-methyl-5-(trifluoromethyl)pyrazole-4-carboxamide, N-(3-carbamoyl-5,5,7,7-tetramethyl-4H-thieno[2,3-c]pyran-2-yl)pyrazine-2-carboxamide, 6-butyl-N-(3-carbamoyl-5,5,7,7-tetramethyl-4H-thieno[2,3-c]pyran-2-yl)-2-oxo-1H-pyridine-3-carboxamide, N-(3-carbamoyl-5,5,7,7-tetramethyl-4H-thieno[2,3-c]pyran-2-yl)-3,5-dimethyl-isoxazole-4-carboxamide, N-(3-carbamoyl-5,5,7,7-tetramethyl-4H-thieno[2,3-c]pyran-2-yl)-5-methyl-pyrazine-2-carboxamide, N-(3-carbamoyl-5,5,7,7-tetramethyl-4H-thieno[2,3-c]pyran-2-yl)-1H-pyrrole-2-carboxamide, N-(3-carbamoyl-5,5,7,7-tetramethyl-4H-thieno[2,3-c]pyran-2-yl)-6-methyl-pyridine-3-carboxamide, N-(3-carbamoyl-5,5,7,7-tetramethyl-4H-thieno[2,3-c]pyran-2-yl)-8-methyl-4-oxo-pyrido[1,2-a]pyrimidine-3-carboxamide, N-(3-carbamoyl-5,5,7,7-tetramethyl-4H-thieno[2,3-c]pyran-2-yl)-2,3-dihydro-[1,4]dioxino[2,3-b]pyridine-7-carboxamide, N-(3-carbamoyl-5,5,7,7-tetramethyl-4H-thieno[2,3-c]pyran-2-yl)-5-methyl-isoxazole-4-carboxamide, 5,5,7,7-tetramethyl-2-[(3-methyloxetane-3-carbonyl)amino]-4H-thieno[2,3-c]pyran-3-carboxamide, N-(3-carbamoyl-5,5,7,7-tetramethyl-4H-thieno[2,3-c]pyran-2-yl)-2-methyl-4-oxo-3H-quinazoline-5-carboxamide, N-(3-carbamoyl-5,5,7,7-tetramethyl-4H-thieno[2,3-c]pyran-2-yl)-4,7-dimethyl-pyrazolo[5,1-c][1,2,4]triazine-3-carboxamide, N-(3-carbamoyl-5,5,7,7-tetramethyl-4H-thieno[2,3-c]pyran-2-yl)-2-methyl-4-oxo-3H-quinazoline-7-carboxamide, N-(3-carbamoyl-5,5,7,7-tetramethyl-4H-thieno[2,3-c]pyran-2-yl)-2-(2,2,2-trifluoroethyl)pyrazole-3-carboxamide, 5,5,7,7-tetramethyl-2-[[(2S)-3,3,3-trifluoro-2-hydroxy-2-methyl-propanoyl]amino]-4H-thieno[2,3-c]pyran-3-carboxamide, 2-[[(2S)-2-hydroxypropanoyl]amino]-5,5,7,7-tetramethyl-4H-thieno[2,3-c]pyran-3-carboxamide, 2-[(4-hydroxytetrahydropyran-4-carbonyl)amino]-5,5,7,7-tetramethyl-4H-thieno[2,3-c]pyran-3-carboxamide, 2-[(2-hydroxy-3-methoxy-2-methyl-propanoyl)amino]-5,5,7,7-tetramethyl-4H-thieno[2,3-c]pyran-3-carboxamide, 2-[(2-hydroxy-3-methoxy-propanoyl)amino]-5,5,7,7-tetramethyl-4H-thieno[2,3-c]pyran-3-carboxamide, N-(3-carbamoyl-5,5,7,7-tetramethyl-4H-thieno[2,3-c]pyran-2-yl)-1H-pyrazolo[3,4-b]pyridine-3-carboxamide, 5,5,7,7-tetramethyl-2-(tetrahydropyran-4-carbonylamino)-4H-thieno[2,3-c]pyran-3-carboxamide, 2-[(2-ethoxyacetyl)amino]-5,5,7,7-tetramethyl-4H-thieno[2,3-c]pyran-3-carboxamide, 2-[(2-methoxyacetyl)amino]-5,5,7,7-tetramethyl-4H-thieno[2,3-c]pyran-3-carboxamide, 2-[[2-(2-methoxyethoxy)acetyl]amino]-5,5,7,7-tetramethyl-4H-thieno[2,3-c]pyran-3-carboxamide, 5,5,7,7-tetramethyl-2-(tetrahydrofuran-2-carbonylamino)-4H-thieno[2,3-c]pyran-3-carboxamide, 5,5,7,7-tetramethyl-2-(tetrahydrofuran-3-carbonylamino)-4H-thieno[2,3-c]pyran-3-carboxamide, 2-[(2-methoxy-2-methyl-propanoyl)amino]-5,5,7,7-tetramethyl-4H-thieno[2,3-c]pyran-3-carboxamide, 2-[[2-hydroxy-3-methoxy-2-methyl-propanoyl]amino]-5,5,7,7-tetramethyl-4H-thieno[2,3-c]pyran-3-carboxamide, enantiomer 1, 2-[[(2S)-2-hydroxy-3-methoxy-2-methyl-propanoyl]amino]-5,5,7,7-tetramethyl-4H-thieno[2,3-c]pyran-3-carboxamide, enantiomer 2, 5,5,7,7-tetramethyl-2-[(3,3,3-trifluoro-2-hydroxy-propanoyl)amino]-4H-thieno[2,3-c]pyran-3-carboxamide, 6-Oxo-1,6-dihydro-pyridazine-3-carboxylic acid (3-carbamoyl-5,5,7,7-tetramethyl-4,7-dihydro-5H-thieno[2,3-c]pyran-2-yl)-amide, and N-(3-carbamoyl-5,7-dihydro-4H-thieno[2,3-c]pyran-2-yl)-1H-pyrazole-3-carboxamide.

In one embodiment, the compound of the invention is N-(3-carbamoyl-5,5,7,7-tetramethyl-5,7-dihydro-4H-thieno[2,3-c]pyran-2-yl)-1H-pyrazole-5-carboxamide.

In another embodiment, the compound of the invention is not N-(3-carbamoyl-5,5,7,7-tetramethyl-5,7-dihydro-4H-thieno[2,3-c]pyran-2-yl)-1H-pyrazole-5-carboxamide.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Clauses

1) A compound according to Formula I

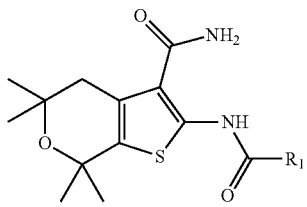

wherein
R$^1$ is
C$_{3-7}$ mono or spirocyclic cycloalkyl, optionally substituted with one or more independently selected R$^2$ groups,
4-7 membered mono or spirocyclic heterocycloalkyl comprising one or more heteroatoms independently selected from O, N, and S, substituted with one or more independently selected R$^2$ groups,
C$_{6-10}$ monocyclic or bicyclic aryl optionally substituted with one or more independently selected R$^3$ groups,
5-10 membered monocyclic or fused bicyclic heteroaryl comprising one or more heteroatoms independently selected from N, O, and S, and optionally substituted with one or more independently selected R$^3$ groups, or
C$_{1-6}$ alkyl optionally substituted with one or more independently selected R$^4$ groups,
each R$^2$ is selected from
halo,
OH,
—CN,
—OC(=O)C$_{1-4}$ alkyl,
—C(=O)—C$_{1-4}$ alkoxy,
oxo,
C$_{1-4}$ alkyl (optionally substituted with one or more independently selected R$^{5a}$), and
C$_{1-4}$ alkoxy (optionally substituted with one or more independently selected R$^{5a}$),
each R$^3$ is selected from
halo,
—OH,
—CN,
C$_{1-4}$ alkyl (optionally substituted with one or more independently selected R$^{5b}$),
C$_{1-4}$ alkoxy (optionally substituted with one or more independently selected R$^{5b}$),
C$_{1-4}$ alkenyl (optionally substituted with one or more independently selected R$^{5b}$),
C$_{3-7}$ cycloalkyl,
4-7 membered monocyclic heterocycloalkyl comprising one or more heteroatoms independently selected from N, O, and S,
4-7 membered monocyclic heterocycloalkenyl comprising one or more heteroatoms independently selected from N, O, and S,
5-10 membered monocyclic or fused bicyclic heteroaryl comprising one or more heteroatoms independently selected from N, O, and S, and
—NHSO$_2$—C$_{1-4}$ alkyl;
each R$^4$ is selected from
halo,
OH,
C$_{3-7}$ cycloalkyl,
—CN, and
C$_{1-4}$ alkoxy (optionally substituted with one or more independently selected R$^{5c}$),
each R$^{5a}$, R$^{5b}$, and R$^{5c}$ is independently selected from
halo,
OH,
—OP(=O)$_2$OH,
—CN,
—NR$^{6a}$R$^{6b}$, and
C$_{1-4}$ alkoxy; and
each R$^{6a}$, or R$^{6b}$ is independently selected from H, and C$_{1-4}$ alkyl;
or a pharmaceutically acceptable salt, or a solvate, or a pharmaceutically acceptable salt of a solvate thereof 2) A compound according to Formula I:

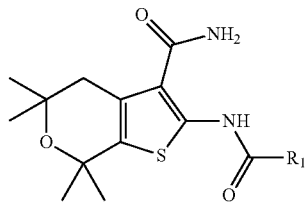

wherein
R$^1$ is
C$_{3-7}$ cycloalkyl optionally substituted with one or more independently selected R$^2$ groups,
4-7 membered monocyclic heterocycloalkyl comprising one or more heteroatoms independently selected from O, N, and S, substituted with one or more independently selected R$^2$ groups, or
C$_{6-10}$ mono or bicyclic aryl optionally substituted with one or more independently selected R$^3$ groups,
5-10 membered mono or fused bicyclic heteroaryl comprising one or more heteroatoms independently selected from N, O, and S, and optionally substituted with one or more independently selected R$^3$ groups,
C$_{1-6}$ alkyl optionally substituted with one or more independently selected R$^4$ groups,
each R$^2$ is selected from
halo,
OH,
—CN,
—OC(=O)C$_{1-4}$ alkyl,
—C(=O)—C$_{1-4}$ alkoxy,
oxo,
C$_{1-4}$ alkyl (optionally substituted with one or more independently selected R$^{5a}$), and
C$_{1-4}$ alkoxy (optionally substituted with one or more independently selected R$^{5a}$),
each R$^3$ is selected from
halo,
—OH,
—CN,
C$_{1-4}$ alkyl (optionally substituted with one or more independently selected R$^{5b}$),
C$_{1-4}$ alkoxy (optionally substituted with one or more independently selected R$^{5b}$),
C$_{3-7}$ cycloalkyl,
5-10 membered mono or fused bicyclic heteroaryl comprising one or more heteroatoms independently selected from N, O, and S, and
—NHSO$_2$—C$_{1-4}$ alkyl;

each $R^4$ is selected from
halo,
OH,
—CN, and
$C_{1-4}$ alkoxy (optionally substituted with one or more independently selected $R^{5c}$),
each $R^{5a}$, $R^{5b}$, and $R^{5c}$ is independently selected from
halo,
OH,
—CN,
—$NR^{6a}R^{6b}$, and
$C_{1-4}$ alkoxy;
each $R^{ha}$, or $R^{6b}$ is independently selected from H, and $C_{1-4}$ alkyl;
or a pharmaceutically acceptable salt, or a solvate, or a pharmaceutically acceptable salt of a solvate thereof 3) A compound or pharmaceutically acceptable salt thereof, according to clause 1 or 2, wherein $R^1$ is $C_{3-7}$ mono or spirocyclic cycloalkyl.
4) A compound or pharmaceutically acceptable salt thereof, according to clause 1 or 2, wherein $R^1$ is $C_{3-7}$ mono or spirocyclic cycloalkyl substituted with one or more independently selected $R^2$ groups.
5) A compound or pharmaceutically acceptable salt thereof, according to clause 3 or 4, wherein $R^1$ is cyclopropyl, cyclobutyl, cyclopentyl, or cyclohexyl.
6) A compound or pharmaceutically acceptable salt thereof, according to clause 4, wherein $R^2$ is selected from F, Cl, CN, oxo, and OH.
7) A compound or pharmaceutically acceptable salt thereof, according to clause 4, wherein $R^2$ is $C_{1-4}$ alkyl or $C_{1-4}$ alkoxy, each of which is optionally substituted with one or more independently selected $R^{5a}$.
8) A compound or pharmaceutically acceptable salt thereof, according to clause 7, wherein $R^2$ is —$CH_3$, —$CH_2CH_3$, —$CH(CH_3)_2$, —$C(CH_3)_3$, —$OCH_3$, or —$OCH_2$—$CH_3$, each of which is optionally substituted with one or more independently selected $R^{5a}$.
9) A compound or pharmaceutically acceptable salt thereof, according to clause 7, or 8, wherein $R^{5a}$ is F, Cl, OH, CN, or —$OCH_3$.
10) A compound or pharmaceutically acceptable salt thereof, according to clause 1 or 2, wherein $R^1$ is 4-7 membered mono or spirocyclic heterocycloalkyl comprising one or more heteroatoms independently selected from O, N, and S, substituted with one or more independently selected $R^2$ groups.
11) A compound or pharmaceutically acceptable salt thereof, according to clause 10, wherein $R^1$ is pyrrolidinyl, tetrahydrofuranyl, tetrahydropyranyl, piperidinyl, piperazinyl, morpholinyl, or thiomorpholinyl.
12) A compound or pharmaceutically acceptable salt thereof, according to clause 10, wherein $R^2$ is F, Cl, CN, oxo, or OH.
13) A compound or pharmaceutically acceptable salt thereof, according to clause 10, wherein $R^2$ is —OC(=O)$CH_3$.
14) A compound or pharmaceutically acceptable salt thereof, according to clause 10, wherein $R^2$ is $C_{1-4}$ alkyl or $C_{1-4}$ alkoxy, each of which is optionally substituted with one or more independently selected $R^{5a}$.
15) A compound or pharmaceutically acceptable salt thereof, according to clause 10, wherein $R^2$ is —$CH_3$, —$CH_2CH_3$, —$CH(CH_3)_2$, —$C(CH_3)_3$, —$OCH_3$, or —$OCH_2$—$CH_3$, each of which is optionally substituted with one or more independently selected $R^{5a}$.
16) A compound or pharmaceutically acceptable salt thereof, according to clause 14, or 15, wherein Rya is F, Cl, OH, CN, or —$OCH_3$.
17) A compound or pharmaceutically acceptable salt thereof, according to clause 1 or 2, wherein $R^1$ is $C_{6-10}$ monocyclic or bicyclic aryl.
18) A compound or pharmaceutically acceptable salt thereof, according to clause 1 or 2, wherein $R^1$ is $C_{6-10}$ monocyclic or bicyclic aryl, substituted with one or more independently selected $R^3$ groups.
19) A compound or pharmaceutically acceptable salt thereof, according to clause 17 or 18, wherein $R^1$ is phenyl.
20) A compound or pharmaceutically acceptable salt thereof, according to clause 18, wherein $R^3$ is F, Cl, OH, or CN.
21) A compound or pharmaceutically acceptable salt thereof, according to clause 18, wherein $R^3$ is $C_{1-4}$ alkyl or $C_{1-4}$ alkoxy, each of which is optionally substituted with one or more independently selected $R^{5b}$.
22) A compound or pharmaceutically acceptable salt thereof, according to clause 18, wherein $R^3$ is —$CH_3$, —$CH_2CH_3$, —$CH(CH_3)_2$, —$C(CH_3)_3$, —$OCH_3$, or —$OCH_2$—$CH_3$, each of which is optionally substituted with one or more independently selected $R^{5b}$.
23) A compound or pharmaceutically acceptable salt thereof, according to clause 21, or 22, wherein $R^{5b}$ is F, Cl, OH, —OP(=O)$_2$OH, CN, or —$OCH_3$.
24) A compound or pharmaceutically acceptable salt thereof, according to clause 18, wherein $R^3$ is $C_{2-4}$ alkenyl, optionally substituted with one or more independently selected $R^{5b}$.
25) A compound or pharmaceutically acceptable salt thereof, according to clause 18, wherein $R^3$ is —CH=$CH_2$, —CH=CH—$CH_3$, —CH=CH—$CH_2CH_3$, —$CH_2$—CH=CH—$CH_3$, —$CH_2$—$CH_2$—CH=$CH_2$, —C($CH_3$)=$CH_2$, —CH=CH($CH_3$), —C($CH_3$)=CH($CH_3$), each of which is optionally substituted with one or more independently selected $R^{5b}$.
26) A compound or pharmaceutically acceptable salt thereof, according to clause 21, or 22, wherein $R^{5b}$ is F, Cl, OH, CN, or —$OCH_3$.
27) A compound or pharmaceutically acceptable salt thereof, according to clause 18, wherein $R^3$ is cyclopropyl, cyclobutyl, cyclopentyl, or cyclohexyl.
28) A compound or pharmaceutically acceptable salt thereof, according to clause 18, wherein $R^3$ is 5-6 membered monocyclic, or fused bicyclic heteroaryl comprising one or more heteroatoms independently selected from N, O, or S.
29) A compound or pharmaceutically acceptable salt thereof, according to clause 25, wherein $R^3$ is pyrrazolyl, imidazolyl, thiazolyl, oxazolyl, pyridinyl, pyrimidyl, or pyrazinyl.
30) A compound or pharmaceutically acceptable salt thereof, according to clause 25, wherein $R^3$ is 4-7 membered monocyclic heterocycloalkyl comprising one or more heteroatoms independently selected from N, O, or S.
31) A compound or pharmaceutically acceptable salt thereof, according to clause 25, wherein $R^3$ is tetrahydropyranyl, piperidinyl, piperazinyl, morpholinyl, or thiomorpholinyl.
32) A compound or pharmaceutically acceptable salt thereof, according to clause 25, wherein $R^3$ is 4-7 membered monocyclic heterocycloalkenyl comprising one or more heteroatoms independently selected from N, O, or S.
33) A compound or pharmaceutically acceptable salt thereof, according to clause 25, wherein $R^3$ is dihydropyranyl, or tetrahydropyridinyl 34) A compound or pharmaceutically acceptable salt thereof, according to clause 25, wherein $R^3$ is —NHSO$_2$—C$_{1-4}$ alkyl.
35) A compound or pharmaceutically acceptable salt thereof, according to clause 1 or 2, wherein $R^1$ is 5-10 membered monocyclic or fused bicyclic heteroaryl comprising one or more heteroatoms independently selected from N, O, and S.
36) A compound or pharmaceutically acceptable salt thereof, according to clause 1 or 2, wherein $R^1$ is 5-10 membered monocyclic or fused bicyclic heteroaryl comprising one or more heteroatoms independently selected from N, O, and S, substituted with one or more independently selected $R^3$ groups.
37) A compound or pharmaceutically acceptable salt thereof, according to clause 35 or 36, wherein $R^1$ is furanyl, thiophenyl, pyrazolyl, imidazolyl, thiazolyl, oxazolyl, pyridinyl, pyridazinyl, pyrimidyl, or pyrazinyl.
38) A compound or pharmaceutically acceptable salt thereof, according to clause 36, wherein $R^3$ is F, Cl, OH, or CN.
39) A compound or pharmaceutically acceptable salt thereof, according to clause 36, wherein $R^3$ is C$_{1-4}$ alkyl or C$_{1-4}$ alkoxy, each of which is optionally substituted with one or more independently selected $R^{5b}$.
40) A compound or pharmaceutically acceptable salt thereof, according to clause 36, wherein $R^3$ is —CH$_3$, —CH$_2$CH$_3$, —CH(CH$_3$)$_2$, —C(CH$_3$)$_3$, —OCH$_3$, or —OCH$_2$—CH$_3$, each of which is optionally substituted with one or more independently selected $R^{5b}$, and $R^{5b}$ is as described in clause 1.
41) A compound or pharmaceutically acceptable salt thereof, according to clause 39, or 40, wherein $R^{5b}$ is F, Cl, OH, —OP(=O)$_2$OH, CN, or —OCH$_3$.
42) A compound or pharmaceutically acceptable salt thereof, according to clause 36, wherein $R^3$ is C$_{2-4}$ alkenyl, optionally substituted with one or more independently selected $R^{5b}$.
43) A compound or pharmaceutically acceptable salt thereof, according to clause 36, wherein $R^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$), each of which is optionally substituted with one or more independently selected $R^{5b}$.
44) A compound or pharmaceutically acceptable salt thereof, according to clause 42, or 43, wherein $R^{5b}$ is F, Cl, OH, —CN, or —OCH$_3$.
45) A compound or pharmaceutically acceptable salt thereof, according to clause 36, wherein $R^3$ is cyclopropyl, cyclobutyl, cyclopentyl, or cyclohexyl.
46) A compound or pharmaceutically acceptable salt thereof, according to clause 45, wherein $R^3$ is 4-7 membered monocyclic heterocycloalkyl comprising one or more heteroatoms independently selected from N, O, or S.
47) A compound or pharmaceutically acceptable salt thereof, according to clause 46, wherein $R^3$ is tetrahydropyranyl, piperidinyl, piperazinyl, morpholinyl, or thiomorpholinyl.
48) A compound or pharmaceutically acceptable salt thereof, according to clause 45, wherein $R^3$ is 4-7 membered monocyclic heterocycloalkenyl comprising one or more heteroatoms independently selected from N, O, and S.
49) A compound or pharmaceutically acceptable salt thereof, according to clause 48, wherein $R^3$ is dihydropyranyl, or tetrahydropyridinyl.
50) A compound or pharmaceutically acceptable salt thereof, according to clause 36, wherein $R^3$ is 5-6 membered monocyclic, or fused bicyclic heteroaryl comprising one or more heteroatoms independently selected from N, O, and S.
51) A compound or pharmaceutically acceptable salt thereof, according to clause 46, wherein $R^3$ is pyrrazolyl, imidazolyl, thiazolyl, oxazolyl, pyridinyl, pyrimidyl, or pyrazinyl.
52) A compound or pharmaceutically acceptable salt thereof, according to clause 1 or 2, wherein $R^1$ is C$_{1-6}$ alkyl.
53) A compound or pharmaceutically acceptable salt thereof, according to clause 1 or 2, wherein $R^1$ is C$_{1-6}$ alkyl substituted with one or more independently selected $R^4$ groups.
54) A compound or pharmaceutically acceptable salt thereof, according to clauses 52 or 53, wherein $R^1$ is —CH$_3$, —CH$_2$—CH$_3$, —CH(CH$_3$)$_2$, —C(CH$_3$)$_3$, —C(CH$_3$)$_2$—CH$_3$, or —CH(CH$_3$)—CH(CH$_3$)$_2$.
55) A compound or pharmaceutically acceptable salt thereof, according to clause 53, wherein $R^4$ is F, Cl, OH, or CN.
56) A compound or pharmaceutically acceptable salt thereof, according to clause 53, wherein $R^4$ is C$_{3-7}$ monocyclic cycloalkyl.
57) A compound or pharmaceutically acceptable salt thereof, according to clause 56, wherein $R^4$ is cyclopropyl, cyclobutyl, cyclopentyl, or cyclohexyl.
58) A compound or pharmaceutically acceptable salt thereof, according to clause 53, wherein $R^4$ is C$_{1-4}$ alkoxy, each of which is optionally substituted with one or more independently selected $R^{5'}$.
59) A compound or pharmaceutically acceptable salt thereof, according to clause 58, wherein $R^4$ is —OCH$_3$, —OCH$_2$—CH$_3$, or —OCH(CH$_3$)$_2$, each of which is optionally substituted with one or more independently selected $R^{5'}$.
60) A compound or pharmaceutically acceptable salt thereof, according to clause 58, or 59, wherein $R^{5'}$ is F, Cl, OH, —CN, —OCH$_3$, —OCH$_2$CH$_3$, —NH(CH$_3$) or —N(CH$_3$)$_2$.
61) A compound or pharmaceutically acceptable salt thereof, according to clause 1 or 2, wherein $R^1$ is

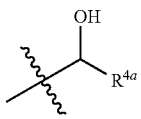

wherein $R^{4a}$ is C$_{1-5}$ alkyl optionally substituted with one or more independently selected halo, CN, C$_{1-4}$ alkoxy, or C$_{3-7}$ monocyclic cycloalkyl.
62) A compound or pharmaceutically acceptable salt thereof, according to clause 61, wherein $R^{4a}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$, each of which is optionally substituted with one or more independently selected F, Cl, OH, CN, —OCH$_3$, —OCH$_2$CH$_3$, cyclopropyl, cyclobutyl, or cyclopentyl.
63) A compound or pharmaceutically acceptable salt thereof, according to clause 1 or 2, wherein $R^1$ is

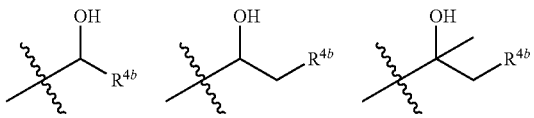

-continued

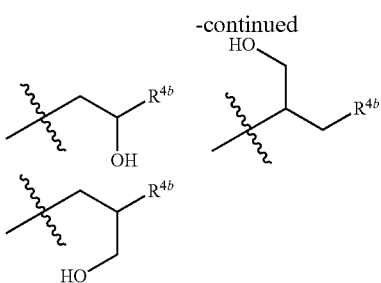

wherein R$^{4b}$ is C$_{3-7}$ monocyclic cycloalkyl. In a particular embodiment, R$^{4b}$ is cyclopropyl, cyclobutyl, or cyclopentyl. In a more particular embodiment, R$^{4b}$ is cyclopropyl.

64) A compound or pharmaceutically acceptable salt thereof, according to clause 1 or 2, wherein the compound is according to Formula IIa or IIb:

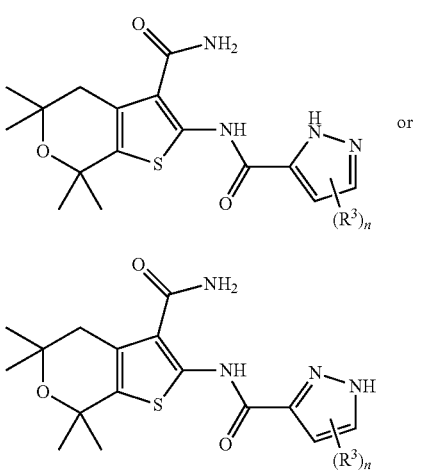

wherein R$^3$ is as described in clause 1, and the subscript n is 0, 1 or 2.

65) A compound or pharmaceutically acceptable salt thereof, according to clause 64, wherein the subscript n is 0.
66) A compound or pharmaceutically acceptable salt thereof, according to clause 64, wherein the subscript n is 1 or 2, wherein R$^3$ is selected from halo, CN, and OH.
67) A compound or pharmaceutically acceptable salt thereof, according to clause 64, wherein the subscript n is 1 or 2, wherein R$^3$ is —CH$_3$, —CH$_2$CH$_3$, —CH(CH$_3$)$_2$, —C(CH$_3$)$_3$, —CH$_2$—OH, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.
68) A compound or pharmaceutically acceptable salt thereof, according to clause 64, wherein the subscript n is 1 or 2, wherein R$^3$ is —OCH$_3$, —OCH$_2$CH$_3$, —OCH(CH$_3$)$_2$, each of which is optionally substituted with one or more independently selected R$^{5b}$, wherein R$^{5b}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.
69) A compound or pharmaceutically acceptable salt thereof, according to clause 64, wherein R$^3$ is C$_{2-4}$ alkenyl, optionally substituted with one or more independently selected R$^{5b}$.
70) A compound or pharmaceutically acceptable salt thereof, according to clause 64, wherein R$^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$), each of which is optionally substituted with one or more independently selected R$^{5b}$.
71) A compound or pharmaceutically acceptable salt thereof, according to clause 69, or 70, wherein R$^{5b}$ is F, Cl, OH, CN, or —OCH$_3$.
72) A compound or pharmaceutically acceptable salt thereof, according to clause 69, wherein R$^3$ is —CH=CH—CH$_2$—OCH$_3$, —CH=CH—CH$_2$—OCH$_2$CH$_3$, —CCH$_3$=CH—CH$_2$—OCH$_3$, or —CH=CCH$_3$—CH$_2$—OCH$_2$CH$_3$.
73) A compound or pharmaceutically acceptable salt thereof, according to clause 64, wherein the subscript n is 1 or 2, wherein R$^3$ is cyclopropyl, cyclobutyl, cylopentyl, or cyclohexyl.
74) A compound or pharmaceutically acceptable salt thereof, according to clause 1 or 2, wherein the compound is according to Formula IIIa or IIIb:

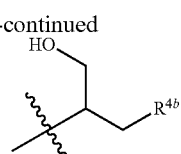

wherein R$^2$ is as described in clause 1.
75) A compound or pharmaceutically acceptable salt thereof, according to clause 74, wherein R$^2$ is selected from F, Cl, CN, oxo, and OH.
76) A compound or pharmaceutically acceptable salt thereof, according to clause 74, wherein R$^2$ is —CH$_3$, —CH$_2$CH$_3$, —CH(CH$_3$)$_2$, —C(CH$_3$)$_3$, —CH$_2$—OH, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.
77) A compound or pharmaceutically acceptable salt thereof, according to clause 74, wherein R$^2$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.
78) A pharmaceutical composition comprising a pharmaceutically acceptable carrier and a pharmaceutically effective amount of a compound according to any one of clauses 1-77.
79) A pharmaceutical composition according to clause 54 comprising a further therapeutic agent.
80) A compound or pharmaceutically acceptable salt thereof, according to any one of clauses 1-77, or a pharmaceutical composition according to clause 78 or 79, for use in medicine.
81) A compound or pharmaceutically acceptable salt thereof, according to any one of clauses 1-77, or a pharmaceutical composition according to clause 78 or 79, for use in the treatment of cystic fibrosis.

82) A method for the treatment of cystic fibrosis, comprising administering an amount of the compound according to any one of clauses 1-77, or the pharmaceutical composition according to clause 78 or 79, sufficient to effect said treatment.
83) The use according to clause 81, or the method according to clause 80, wherein the cystic fibrosis is caused by a Class I, II, III, IV and/or VI mutation.
84) The use or method according to clause 83, wherein the Class I mutation is G452X; and/or W1282X.
85) The use or method according to clause 83, wherein the Class II mutation is F508del and/or N1303K.
86) The use or method according to clause 83, wherein the Class III mutation is G551D, R553G, G1349D, S1251N, G178R, and/or S549N.
87) The use or method according to clause 83, wherein the Class IV mutation is R117H, and/or R334W.
88) The use or method according to clause 83, wherein the Class VI mutation is Rescued F508del.
89) The method according to clause 82, wherein the compound according to any one of clauses 1-75, or the pharmaceutical composition according to clause 78 or 79, is administered in combination with a further therapeutic agent.
90) The pharmaceutical composition according to clause 79, or the method according to claim 89, wherein the further therapeutic agent is an agent for the treatment of cystic fibrosis.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, a compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences (Remington, 1985).

The following formulation examples illustrate representative pharmaceutical compositions that may be prepared in accordance with this invention. The present invention, however, is not limited to the following pharmaceutical compositions.

Formulation 1

Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2

Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3

Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4

Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5

Injection

A compound of the invention according to Formula I may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in treatment of cystic fibrosis. In a more particular embodiment, the cystic fibrosis is caused by a Class I, II, III, IV and/or VI mutation.

In another embodiment, the present invention provides compounds of the invention, or pharmaceutical compositions comprising a compound of the invention for use in the manufacture of a medicament for use in the treatment of cystic fibrosis. In a more particular embodiment, the cystic fibrosis is caused by a Class I, II, III, IV and/or VI mutation.

In one embodiment, the present invention provides pharmaceutical compositions comprising a compound of the invention, and another therapeutic agent. In a particular embodiment, the other therapeutic agent is a cystic fibrosis treatment agent. In a more particular embodiment, the cystic fibrosis is caused by a Class I, II, III, IV and/or VI mutation.

In additional method of treatment aspects, this invention provides methods of treatment of a mammal afflicted with cystic fibrosis, which methods comprise the administration of an effective amount of a compound of the invention or one or more of the pharmaceutical compositions herein described to a patient in need thereof. In a more particular embodiment, the cystic fibrosis is caused by a Class I, II, III, IV and/or VI mutation.

A compound of the invention can be administered as the sole active agent or it can be administered in combination with other therapeutic agents, including other compounds that demonstrate the same or a similar therapeutic activity and that are determined to safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment of cystic fibrosis, particular agents include but are not limited to antibiotics (for example aminoglycosides, colistin, aztreonam, ciprofloxacin azithromycin), expectorants (for example hypertonic saline, acetylcysteine, dornase alfa, denufosol), CFTR correctors (for example VX-809, VX-661, VX-983), pancreatic enzyme supplements (for example pancreatin, pancrelipase).

By co-administration is included any means of delivering two or more therapeutic agents to the patient as part of the same treatment regime, as will be apparent to the skilled person. Whilst the two or more agents may be administered simultaneously in a single formulation this is not essential. The agents may be administered in different formulations and at different times.

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts and Greene, 2012).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm). $^1$H NMR spectra were recorded on a Bruker DPX 400 NMR spectrometer (400 MHz or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity H—Class UPLC coupled to a Waters Mass detector 3100 spectrometer. Columns used: Waters Acquity UPLC BEH C18 1.7 µm, 2.1 mm ID×50 mm L, Waters Acquity UPLC BEH C18 1.7 µm, 2.1 mm ID×30 mm L, or Waters Xterra MS 5 µm C18, 100×4.6 mm. The methods are using either MeCN/$H_2O$ gradients ($H_2O$ contains either 0.1% TFA or 0.1% $NH_3$) or MeOH/$H_2O$ gradients ($H_2O$ contains 0.05% TFA). Microwave heating was performed with a Biotage Initiator.

Racemic mixtures were separated on a Agilent HP1100 system with UV detection. Column used: Chiralpak 1A (10× 250 mm, 5 µm). Solvents used: iPrOH and tBME. Alternatively, separation was done using a SFC2 system. Column used: Lux Cellulose-4. Solvents used: $CO_2$ and MeOH. Enantiomeric purity was determined on a Agilent HP1100 system with UV detection. Column used: Chiralpak IA (4.6×250 mm, 5 µm). Solvents used: iPrOH and tBME.

List of abbreviations used in the experimental section:

| Abbreviation | Definition |
| --- | --- |
| DCM | Dichloromethane |
| DIEA | N,N-diisopropylethylamine |
| MeCN | Acetonitrile |
| DMF | N,N-dimethylformamide |
| Cat. | Catalytic amount |
| TFA | Trifluoroacetic acid |
| THF | Tetrahydrofuran |
| NMR | Nuclear Magnetic Resonnance |
| DMSO | Dimethylsulfoxide |
| LC-MS | Liquid Chromatography-Mass Spectrometry |
| EtOAc | ethyl acetate |

-continued

| Abbreviation | Definition |
| --- | --- |
| APCI | atmospheric pressure chemical ionization |
| Rt | retention time |
| s | singlet |
| br s | broad singlet |
| m | multiplet |
| min | minute |
| Cpd | Compound |
| Mtd | Method |
| Int | Intermediate |
| MW | Molecular weight |
| Mes | Molecular weight measured |
| NA | Not active |
| Pd(dppf)$Cl_2$.DCM | 1,1'-Bis(diphenylphosphino) ferrocene-palladium(II) dichloride dichloromethane |
| µm | micrometer |
| mL | milliliter |
| µL | microliter |
| g | gram |
| mg | milligram |
| PS-CDI | polymer-supported carbodiimide |
| PS-trisamine | polymer-supported trisamine |
| TEA | Triethylamine |
| mmol | millimoles |
| HPLC | High pressure liquid chromatography |
| NMP | N-Methylpyrrolidone |
| AcCl | Acetyl Chloride |
| ppm | parts per million |
| HOBt | N-hydroxy benzotriazole |
| EDC | 1-Ethyl-3-(3-dimethylaminopropyl) carbodiimide |
| $Pd_2(dba)_3$ | Tris(dibenzylideneacetone) dipalladium(0) |
| XPhos | 2-Dicyclohexylphosphino-2',4',6'-triisopropylbiphenyl |
| tBME | tent-Butylmethylether |
| iPrOH | iso-Propanol |
| SEM-Cl | 2-(Trimethylsilyl) ethoxymethy 1 chloride |
| DIBAL-H | Diisobutylaluminium hydride |
| DMA | dimethylacetamide |
| NaOEt | sodium ethoxide |
| chir sep | Chiral separation |
| tBuOLi | lithium tert-butoxide |

Synthetic Preparation of the Compound of the Invention

Example 1

General synthetic methods

The compounds of the invention and the comparative examples can be produced according to the following schemes.

Scheme 1: synthesis of the core and subsequent amide coupling
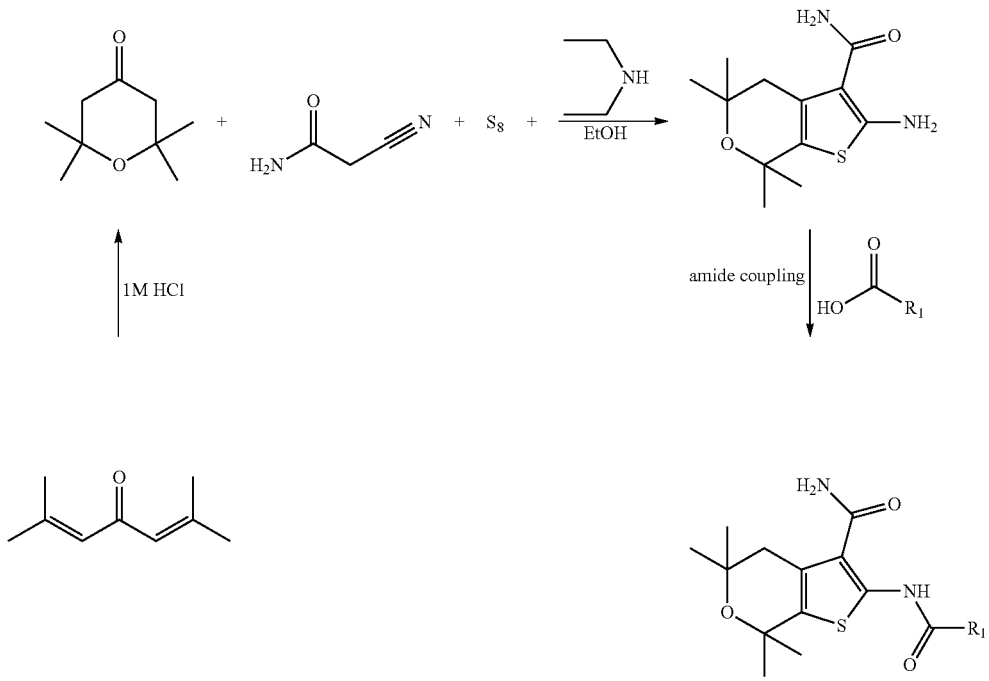
Scheme 2: synthesis of 4-substituted pyrazole derivatives
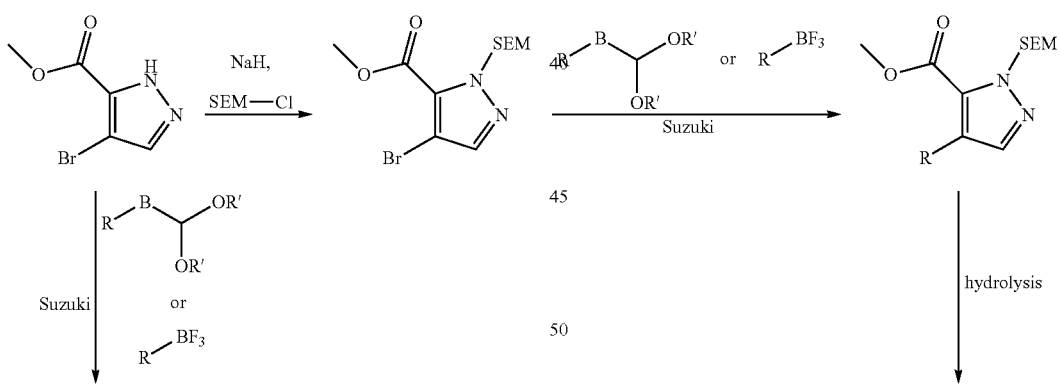
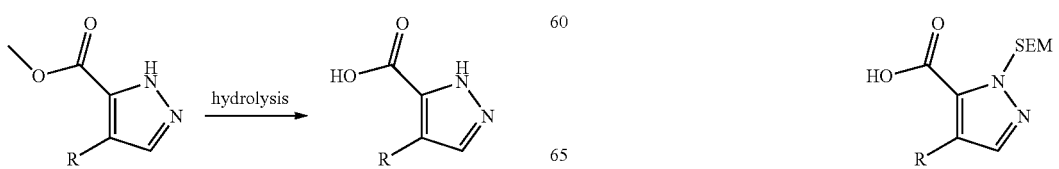

Scheme 3: synthesis of 3-substituted payrazole derivatives

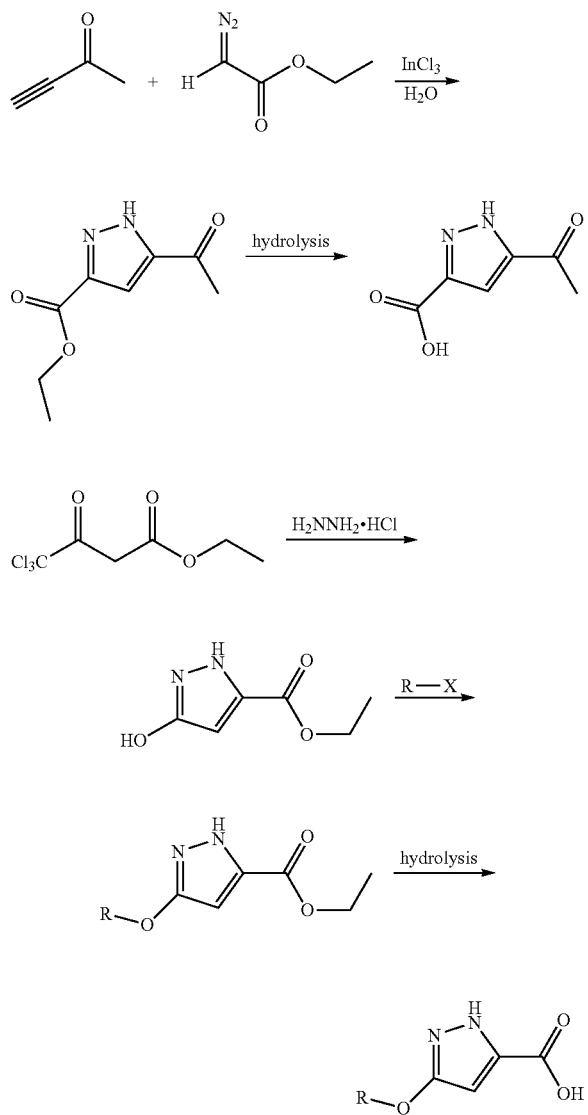

Example 2

Synthesis of intermediates

Intermediate 2:
2,2,6,6-tetramethyltetrahydro-4H-pyran-4-one

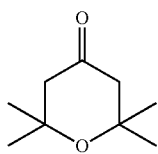

Phorone or 2,6-dimethyl-2,5-heptadien-4-one (1 eq) is mixed with an aqueous 1 M HCl solution and the obtained emulsion is stirred at 40° C. for 6 days. The water phase is extracted with DCM, and the organic phase is concentrated and purified by distillation to afford the desired product.

Alternative Synthesis of Intermediate 2

A 20 L reactor is charged with aqueous 6M HCl and is warmed up to 30° C. Molten Phorone is added while stirring vigorously at 40° C. for up to 3 h until completion. The resulting solution is then cooled to 30° C. and extracted with 4×1 L DCM. The combined organic phases are washed with saturated NaHCO$_3$ solution (400 mL) and are dried over Na$_2$SO$_4$. The resulting crude mixture is then concentrated under vacuo, and finally purified by distillation.

Intermediate 3: 2-Amino-5,5,7,7-tetramethyl-4,7-dihydro-5H-thieno[2,3-c]pyran-3-carboxylic acid amide

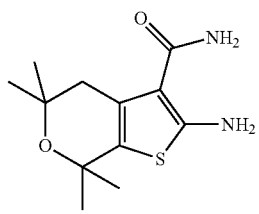 [SMILES: CC1(C)Cc2c(sc(N)c2C(N)=O)C(C)(C)O1]

Route 1:

To a flask containing 2,2,6,6-tetramethyltetrahydro-4H-pyran-4-one (Int 2, 1 eq), cyanoacetamide (1 eq), sulfur (0.9 eq) and diethylamine (1.1 eq) are added. EtOH is then added and the resulting mixture is stirred at 40° C. overnight. The reaction is diluted with water and partially concentrated by evaporation causing the precipitation of a solid that is separated by filtration. The cake is then washed with water and hexane to afford the desired product.

Alternative Synthesis 1 of Intermediate 3

Starting from 2,2,6,6-tetramethyltetrahydro-4H-pyran-4-one (Int 2, 1 eq), cyanoacetamide (1.1 eq) and morpholine (1.5 eq) are heated in EtOH at 80° C. under inert atmosphere. After 6 h of heating, the mixture is cooled down, and sulfur (1.1 eq) is added. Next, the mixture is heated at 80° C. overnight, then concentrated in vacuo and extracted with saturated NH$_4$Cl and NaHCO$_3$. The organic phase is subsequently dried over MgSO$_4$, filtered and concentrated in vacuo. The residue obtained can finally be purified by column chromatography.

Alternative Synthesis 2 of Intermediate 3

A 20 L glass reactor with a mechanical stirrer (400 rpm) and a reflux condenser is charged with 2,2,6,6-tetramethyltetrahydro-4H-pyran-4-one (Int 2) (1.466 kg, 9.01 mol, 1 eq) and 2-cyanoacetamide (1.363 kg, 1.8 eq.) followed by absolute EtOH (4.5 L) and morpholine (0.706 kg, 0.9 eq.). The resulting suspension is heated for 23 h at 75° C. (internal temperature). After 23 h, sulfur (0.26 kg, 0.9 eq.) is added in one portion at 75° C. and the resulting suspension is stirred further for 90 min after which the resulting solution is cooled to 20° C. Then, the entire solution is concentrated in vacuo (50 mbar/45° C.) to yield a solid residue. Water (13.5 L) is added in one portion at 75° C. and the mixture is cooled to 22° C. Stirring (700 rpm at 22° C.) is continued for 2.5 h. The solids are separated by filtration, dried under vacuum suction, and subsequently in the vacuum oven at 40° C. over 3 d to obtain yield the desired product.

Intermediate 7: 5-Acetyl-1H-pyrazole-3-carboxylic acid ethyl ester

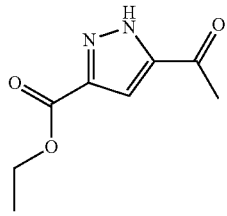

But-3-yn-2-one (Int 5, 1 eq) and diazo-acetic acid ethyl ester (Int 6, 1.1 eq) are added to a solution of InCl₃ (0.2 eq) in water and stirred for 30 min at room temperature. After overnight stirring at room temperature, the mixture is diluted with water and extracted with EtOAc. The resulting organic phase is dried and evaporated to give the desired product.

Intermediate 9: 5-Hydroxy-2H-pyrazole-3-carboxylic acid ethyl ester

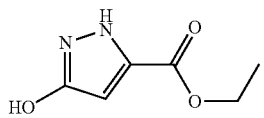

4,4,4-Trichloro-3-oxo-butyric acid ethyl ester (Int 8, 1 eq) and H₂NNH₂.HCl (1.1 eq) are mixed in EtOH. The resulting mixture is refluxed overnight. The mixture is then evaporated and the obtained crude is purified by chromatography to give Int 9 and 5-ethoxy-2H-pyrazole-3-carboxylic acid ethyl ester (Int 10).

Intermediate 11: Dipyrazolo[1,5-a;1',5'-d]pyrazine-4,9-dione

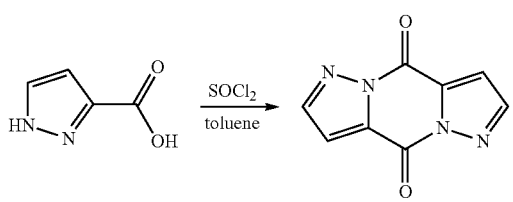

10 g (89 mmol) of pyrrazole carboxylic acid is suspended in toluene 100 mL at room temperature. Then, 2 equivalents of thionyl chloride are added, followed by a catalytic amount of DMF (0.5 ml). The mixture was stirred for 1 h at 75° C. After 1 h at 70° C., the reaction was cooled to room temperature, the solid material was collected by filtration, washed with toluene and resuspended in DCM. Triethylamine (2 equivalents) was added and the suspension was stirred for 2 h at room temperature. The product was collected by filtration, washed with DCM and dried at 40° C. under vacuum to afford the desired product.

TABLE I

Illustrative intermediates towards the compounds of the invention

| Int | Structure | SM | MW | Mes |
|---|---|---|---|---|
| 1 | ![structure] | Commercially available | 138 | 139 |
| 2 | ![structure] | Commercially available or Int1 | 156 | 157 |
| 3 | ![structure] | Int 2 | 254 | 238 |
| 4 | ![structure] | Commercially available | 205 | 205-207 |
| 5 | ![structure] | Commercially available | 68 | NA |
| 6 | ![structure] | Commercially available | 114 | NA |
| 7 | ![structure] | Int 5, Int 6 | 182 | 183 |
| 8 | ![structure] | Commercially available | 69 | NA |
| 9 | ![structure] | Int 8 | 156 | 157 |
| 10 | ![structure] | Int 8 | 184 | 185 |

TABLE I-continued

Illustrative intermediates towards the compounds of the invention

| Int | Structure | SM | MW | Mes |
|---|---|---|---|---|
| 11 | 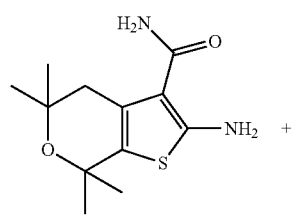 | Commercially available | 188 | — |

Example 3

General Synthetic Methods for Preparation of the Compounds of Invention

Method A1: Amide Coupling with Acid Chlorides

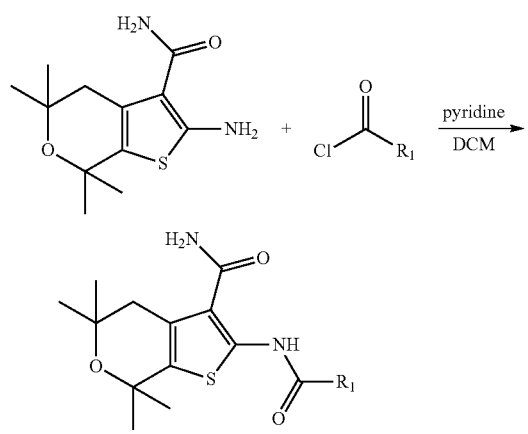

The amino-thiophene (1 eq) is mixed with DCM and pyridine (1.5 eq). This mixture is cooled in an ice bath. The acid chloride (1.15 eq) as obtained by Method B or from a commercial source is dissolved in DCM and added to this mixture. When the addition is complete, the ice bath is removed and the resulting mixture is stirred at room temperature 1-2 hours. The mixture is then evaporated, and the residue is purified by preparative chromatography to yield the desired product.

Method A2: Mukaiyama Coupling

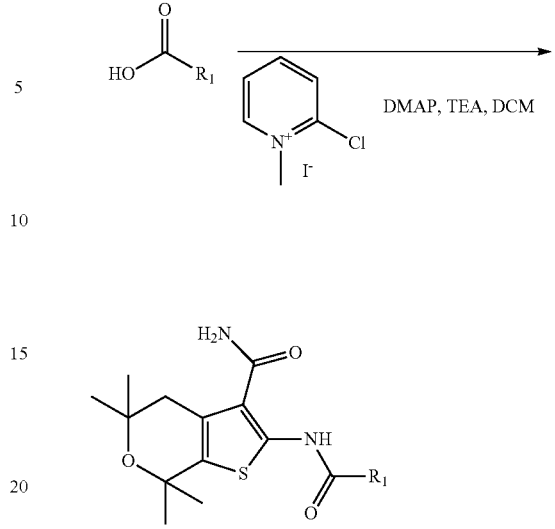

A reaction vessel is charged with the amino-thiophene (1 eq), carboxylic acid (2 eq), DMAP (0.5 eq), TEA (4 eq) and 2-chloro-1-methylpyridinium iodide (2 eq) in DCM. After stirring the mixture at 50° C. for 2 h, the mixture is cooled, diluted with DCM and washed with aqueous $NaHCO_3$. Organic phase is dried over $MgSO_4$. Evaporation gives a crude residue that is purified by preparative chromatography to yield the desired product.

Method A3: Primary Amide Formation

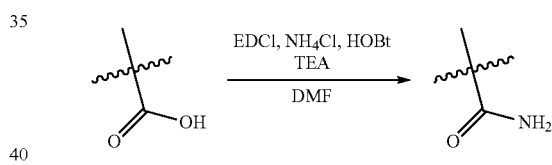

The acid (1 eq) is dissolved in DMF and $NH_4Cl$ (2 eq), TEA (2 eq), HOBt (1.5 eq) and EDC (1.5 eq) are added. Resulting mixture is stirred at room temperature overnight. The mixture is diluted with EtOAc and washed with brine. The organic phase is evaporated and the obtained crude is purified by preparative chromatography to give the desired product.

Method A4: Amide Coupling with Esters

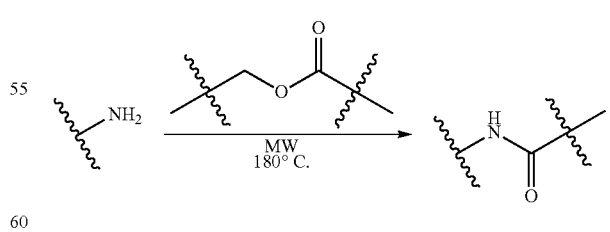

The amine (1 eq) is mixed with the ester (10 eq) and the resulting mixture is heated at high temperature (180° C. or more) in a microwave oven. After 30 min, the mixture is diluted with EtOAc and washed with brine. Evaporation of the organic phase gives a residue that is used as such in the next step.

Illustrative Example 2-(3-Carbamoyl-5,5,7,7-tetramethyl-4,7-dihydro-5H-thieno[2,3-c]pyran-2-ylcarbamoyl)-butyric acid methyl ester

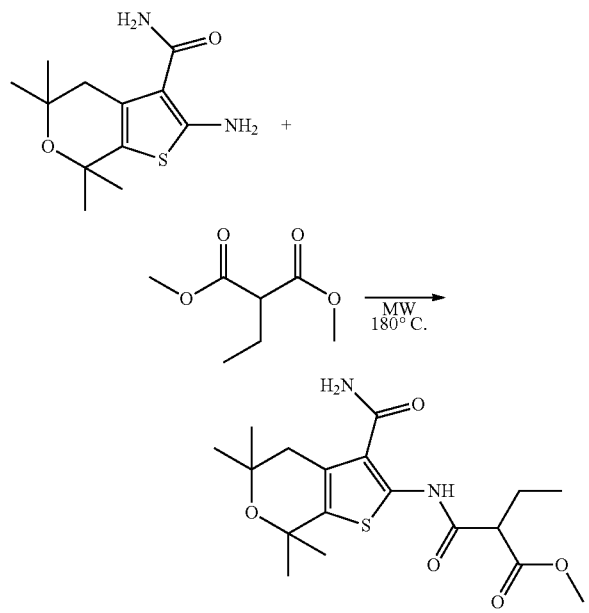

The amine (100 mg, 0.39 mmol) is mixed with 2-Ethyl-malonic acid dimethyl ester (0.6 mL, 3.99 mmol) and the resulting mixture is heated 180° C. in the microwave oven. After 30 min, the mixture is diluted with EtOAc and washed with brine. Evaporation of the organic phase gives a residue that is used as such.

Method A5: Amide Formation

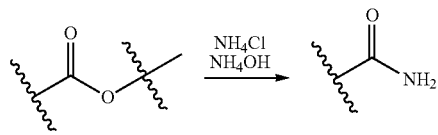

The ester (1 eq) is mixed with $NH_4Cl$ (spatula) and a solution of $NH_4OH$. The resulting mixture is stirred at room temperature until the reaction is finished. Mixture is diluted with water and extracted with EtOAc. Organic layer is then dried and evaporated. Desired product is obtained by chromatographic purification.

Method B: Acid Chloride Formation.

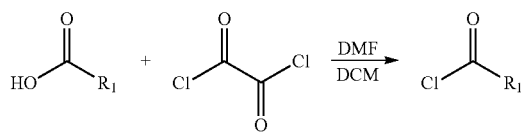

The acid (1 eq) is dissolved in DCM and treated with oxalyl chloride (10 eq) and a few drops of DMF. The mixture is stirred at 45° C. in a sealed tube for 1.5 h. The mixture is then evaporated, and the crude is used as such.

Illustrative Example

Acetic acid 1-chlorocarbonyl-cyclopropyl ester

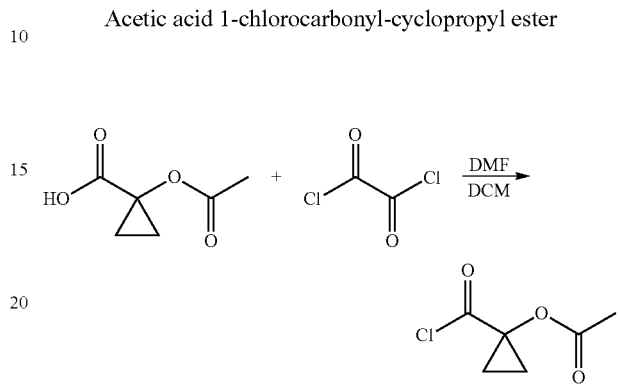

A solution of 1-acetoxy-cyclopropanecarboxylic acid (100 mg, 0.69 mmol) in DCM (1 mL) is treated with oxalyl chloride (0.59 mL, 6.9 mmol) and one drop of DMF and then stirred at 45° C. in a sealed tube for 1 h. Solvent and excess of oxalyl chloride are evaporated (several times by washing with DCM) to give the acid chloride (72.7 mg), which is used in the next step as such.

Method B2: Acid Chloride Formation.

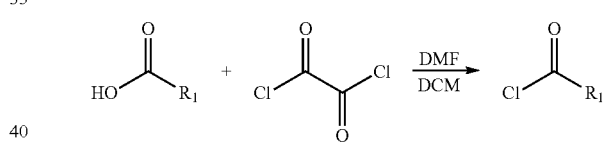

The acid (1 eq) is dissolved in DCM and treated with oxalyl chloride (10 eq) and a few drops of DMF. The mixture is stirred at 45° C. in a sealed tube for 1.5 h. The mixture is then evaporated, and the crude is used as such.

Method C1: Acetyl Protection of Hydroxy-Acids

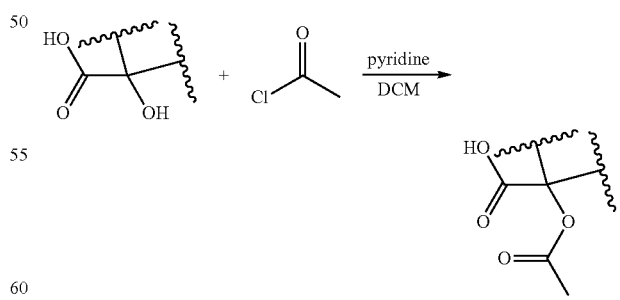

The alcohol (1 eq) is mixed with pyridine (1.2 eq) and DCM and the resulting solution is cooled at 0° C. After the dropwise addition of AcCl (1 eq), the mixture is stirred at room temperature for 3 h, the mixture is then washed with aqueous $NH_4Cl$ and the aqueous phase is extracted twice with DCM. The combined organic phases are dried over MgSO$_4$, filtered and evaporated to give a residue that is used as such.

Illustrative Example

1-Acetoxy-cyclopropanecarboxylic acid

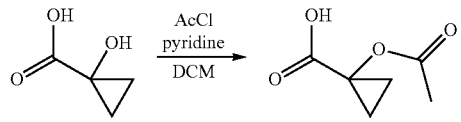

A solution of 1-hydroxy-cyclopropanecarboxylic acid (100 mg, 0.98 mmol) and pyridine (100 µL) in 3 mL of DCM is cooled to 0° C. A solution of acetyl chloride (80 µL, 1.18 mmol) in 3 mL of DCM is then added dropwise to the ice cold mixture. After the addition, the resulting mixture is stirred at room temperature for 3 h. Next, the mixture is washed with saturated NH$_4$Cl. The aqueous phase is extracted twice with DCM. The combined organic phases are combined, dried over MgSO$_4$, filtered, and evaporated to afford the desired product that is used as such.

Method C2: TBS Protection of Hydroxyl Groups

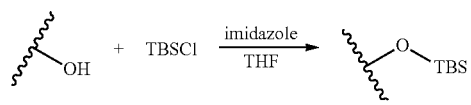

The alcohol (1 eq) is dissolved in dry THF at 0° C. After the addition of imidazole (1.4 eq) and TBSCl (1.2 eq), the solution was stirred at 0° C. for 30 min. Mixture is then stirred at room temperature overnight. Evaporation gives a residue that is dissolved in EtOAc. This organic phase is extracted with NH$_4$Cl. The organic phase is then dried over Na$_2$SO$_4$, filtered and evaporated to give a residue that is used as such.

Illustrative Example 1-(tert-Butyl-dimethyl-silanyloxymethyl)-cyclobutanecarboxylic acid ethyl ester)

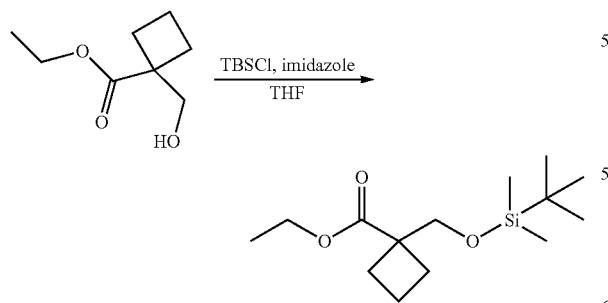

The alcohol (400 mg, 2.5 mmol) is dissolved in dry THF (4 mL). Solution is cooled till 0° C. and imidazole (238 mg, 3.5 mmol) and TBSCl (457 mg, 3.0 mmol) are added. After 30 min, the mixture is stirred at room temperature overnight. The reaction mixture is then concentrated under vacuo, and the residue is redissolved in EtOAc. This organic phase is extracted with NH$_4$Cl. The organic phase is then dried over Na$_2$SO$_4$, filtered and evaporated to give a residue that is used as such.

Illustrative Example 3-(tert-Butyl-dimethyl-silanyloxy)-butyric acid

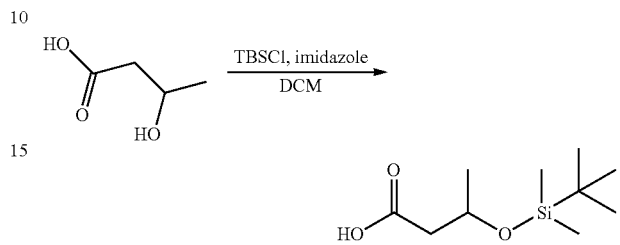

3-Hydroxy-butyric acid (500 mg, 4.8 mmol) is dissolved in a mixture of TBSCl (1.5 g, 10.1 mmol) in dry DCM (48 mL). The resulting mixture is stirred overnight at room temperature. The resulting suspension is then filtered and the obtained residues are washed with DCM, then stirred in Et$_2$O and filtered. The obtained filtrate is evaporated to give the desired product that is used as such.

Method C3: SEM Protection of Pyrazoles

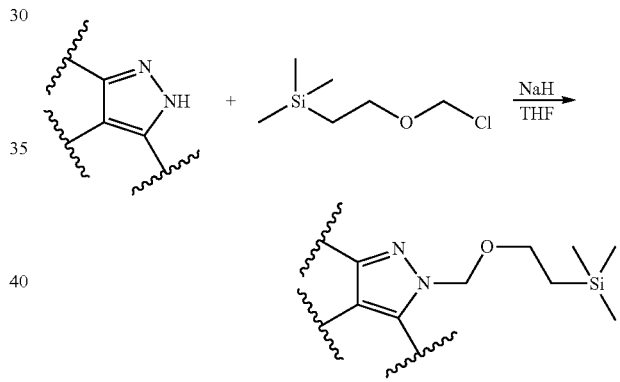

The pyrazole (1 eq) is dissolved in dry THF at 0° C. After addition of NaH (1.5 eq), the mixture is stirred at 0° C. under N$_2$ atmosphere for 30 min. Next, SEM-Cl (1.5 eq) is slowly added and the resulting mixture is stirred at room temperature overnight. Subsequently, the mixture is quenched with water and extracted with EtOAc. The organic phase is isolated, dried over Na$_2$SO$_4$, filtered and evaporated to give a residue that is used as such.

Illustrative Example

4-Bromo-1-(2-trimethylsilanyl-ethoxymethyl)-1H-pyrazole-3-carboxylic acid methyl ester

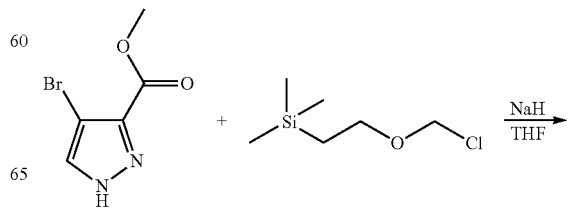

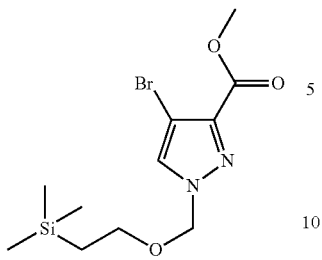

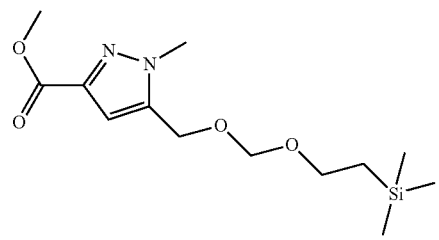

The pyrazole (Int 4, 2 g, 9.76 mmol) is dissolved in dry THF (20 mL) at 0° C. After addition of NaH (60 w %, 584 mg, 14.6 mmol), the mixture is stirred at 0° C. under $N_2$ atmosphere for 30 min. Next, SEM-Cl (2.58 mL, 14.6 mmol) is slowly added and the resulting mixture is stirred at room temperature overnight. Subsequently, the mixture is quenched with water and extracted with EtOAc. The organic phase is isolated, dried over $Na_2SO_4$, filtered and evaporated to give a residue that is used as such.

Method C4: SEM Protection of Alcohols

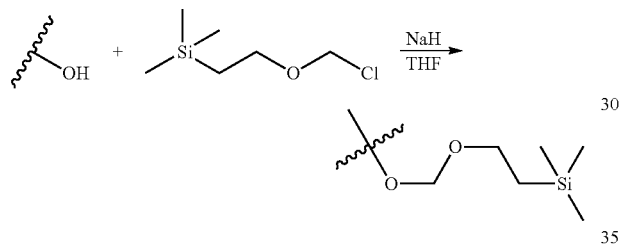

The alcohol (1 eq) is dissolved in dry THF at 0° C. After the addition of NaH (1.3 eq), the mixture is stirred at 0° C. under $N_2$ atmosphere for 30 min. Next, SEM-Cl (1.2 eq) is slowly added and the resulting mixture is stirred at room temperature overnight. If any starting material remains, additional NaH and SEM-Cl is added. Finally, the mixture is quenched with water and extracted with EtOAc. The organic phase is isolated, dried over $Na_2SO_4$, filtered and evaporated to give a residue that is used as such.

Illustrative Example

1-Methyl-5-(2-trimethylsilanyl-ethoxymethoxymethyl)-1H-pyrazole-3-carboxylic acid methyl ester

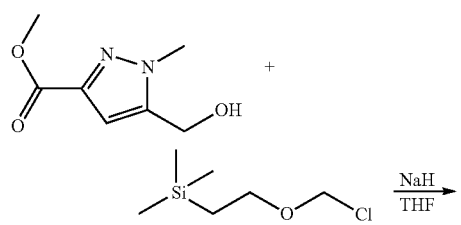

Starting from the commercially available alcohol (170 mg, 1 mmol), a solution in dry THF (2 mL) at 0° C. is prepared. After the addition of NaH (60% by weight, 44 mg, 1.3 mmol), the mixture is stirred at 0° C. under $N_2$ atmosphere for 30 min. Next, SEM-Cl (0.212 mL, 1.2 mmol) is slowly added and the resulting mixture is stirred at room temperature overnight. Another amount of NaH (22 mg, 0.65 mmol) and SEM-Cl (0.1 mL, 0.6 eq) are added and the reaction is now stirred at 80° C. for 4 h. Finally, the mixture is quenched with water and extracted with EtOAc. The organic phase is isolated, dried over $Na_2SO_4$, filtered and evaporated to give a residue that is used as such.

Method D1: Acetyl Deprotection

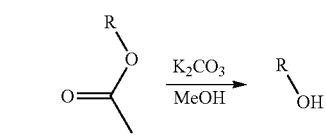

The acetyl ester (1 eq) is dissolved in MeOH and treated with $K_2CO_3$ (2 eq) and is stirred at room temperature overnight. Additional $K_2CO_3$ (2 eq) is added and the obtained mixture is heated at 60° C. for a further 5 h. Evaporation gives a residue that is purified by preparative chromatography.

Instead of using $K_2CO_3$ in MeOH, alternatively, LiOH (3 eq) in a MeOH-water mixture can be used.

Method D2: Ester Hydrolysis

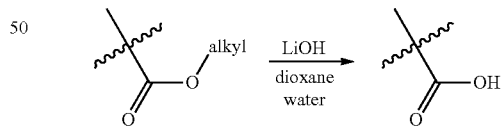

The ester (1 eq) is mixed with LiOH (3 eq) in a dioxane: water mixture (2:1). The mixture is stirred at 40° C. for 3 h. Evaporation gives an aqueous phase that is acidified to pH=1. A suspension is formed which is filtered to gives the desired product as a solid.

The desired acid can also be isolated by extraction with EtOAc or DCM. Drying and evaporation of the organic solvent then gives the acid that can be used as such. Instead of LiOH, NaOH can also be used. Dioxane can be replaced with other organic solvents that are miscible with water like MeOH or EtOH.

Illustrative Example

2-tert-Butyl-malonic acid monoethyl ester

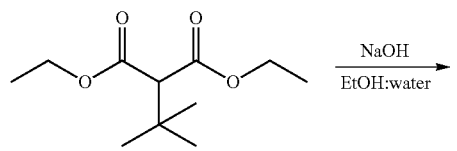

The commercially available 2-tert-butyl-malonic acid diethyl ester (1 g, 4.6 mmol) is dissolved in EtOH (7 mL). A 1N NaOH solution (5.06 mL, 5.06 mmol) is added and the resulting mixture is stirred at 40° C. overnight. Next, the mixture is acidified to pH=1 with HCl. Extraction with EtOAc gives an organic phase that is dried over $MgSO_4$, filtered and evaporated to give the desired product.

Method D3: Hydrolysis to Pyridone

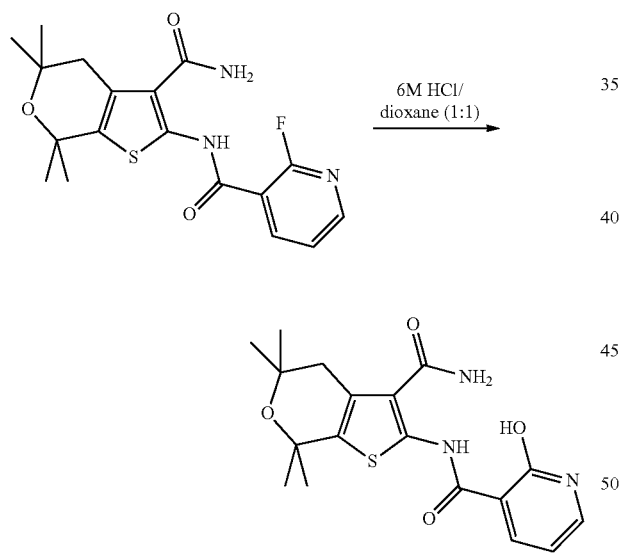

The 2-fluoropyridine is dissolved in a mixture of 6 M $HCl_{aq}$ and dioxane. The mixture is heated for 6 h at 70° C. Evaporation gives an aqueous phase that is quenched with a saturated $K_2CO_3$ solution. The obtained suspension is filtered to give a solid that is washed with water. Trituration of this solid with MeOH gives the desired product.

Method D4: TBS Deprotection

The silyl-ether (1 eq) is dissolved in dry THF and this solution is cooled at 0° C. TBAF (1.1 eq) is added and the mixture is stirred at room temperature overnight. The solution is diluted with a saturated $NH_4Cl$ solution and extracted with EtOAc. The organic phase is evaporated to give a residue that is purified by preparative chromatography.

Illustrative Example

2-(1-(hydroxymethyl)cyclobutanecarboxamido)-5,5,7,7-tetramethyl-5,7-dihydro-4H-thieno[2,3-c]pyran-3-carboxamide

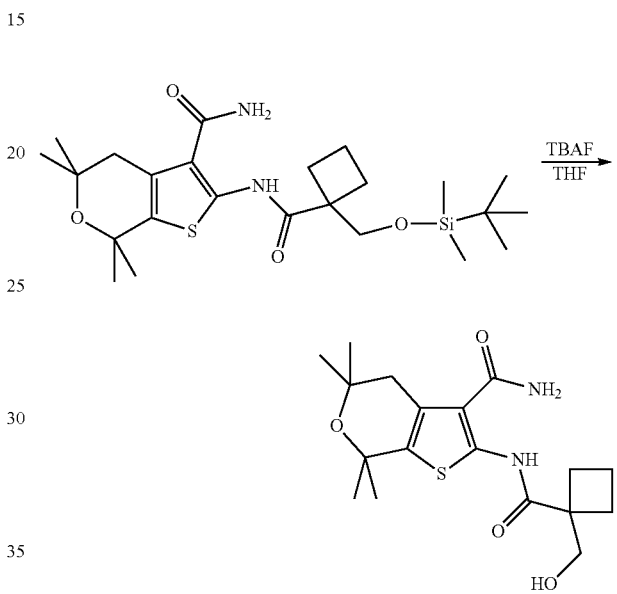

The silyl-ether (474 mg, 0.99 mmol) is dissolved dry THF (1.5 mL) and this solution is cooled at 0° C. TBAF (1.09 mL of 1 M solution in THF, 1.08 mmol) is added and the mixture is stirred at room temperature overnight. The solution is diluted with a saturated $NH_4Cl$ solution and extracted with EtOAc. The organic phase is evaporated to give a residue that is purified by preparative chromatography to yield the desired product.

Method D5: SEM Deprotection of Pyrazoles

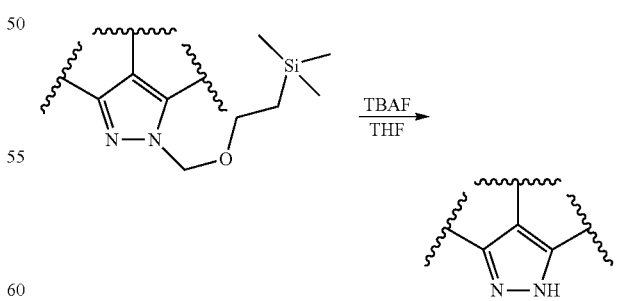

The SEM protected pyrazole (1 eq) is dissolved in THF together with TBAF (1 M solution in THF, 3 eq). The resulting solution is heated at 70° C. overnight in a sealed microwave tube under inert atmosphere. Next, the reaction mixture is evaporated and the obtained crude is diluted with EtOAc.

The organic phase is extracted with brine and evaporated to give a residue that is purified by preparative chromatography.

Illustrative Example

N-(3-carbamoyl-5,5,7,7-tetramethyl-4H-thieno[2,3-c]pyran-2-yl)-4-(3-methoxypropyl)-1H-pyrazole-3-carboxamide

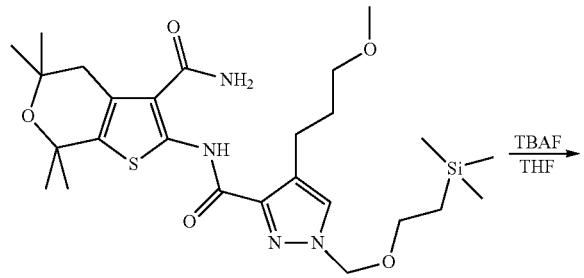

extracted with brine and evaporated to give a residue that is purified by preparative chromatography to yield the desired product.

Method D6: SEM Deprotection of Alcohols

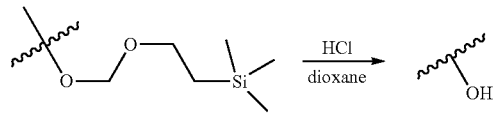

The SEM protected alcohol (1 eq) is dissolved in dioxane and a 4M HCl in dioxane solution (1 eq) is added to this mixture. After stirring at 50° C. for 1 h, the mixture is diluted with water and extracted with EtOAc. The organic phase is dried over Na₂SO₄, filtered and evaporated to give a crude that is purified by preparative chromatography.

Illustrative Example

N-(3-carbamoyl-5,5,7,7-tetramethyl-4H-thieno[2,3-c]pyran-2-yl)-5-(hydroxymethyl)-1-methyl-pyrazole-3-carboxamide

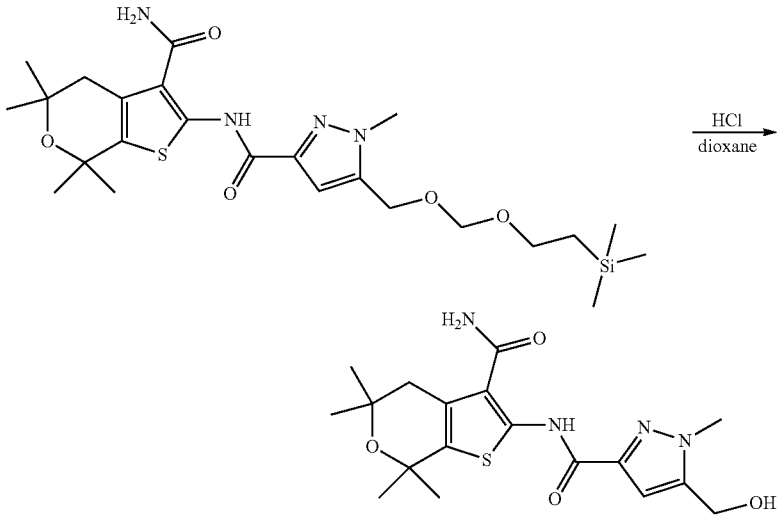

-continued

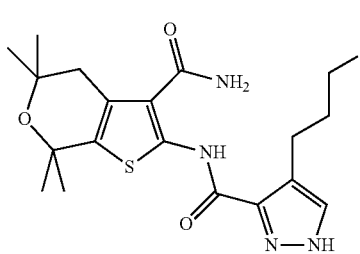

The SEM protected pyrazole (25 mg, 0.046 mmol) is dissolved in THF (1 mL) together with TBAF (1 M solution in THF, 136 μL, 0.438 mmol). The resulting solution is heated at 70° C. overnight in a sealed microwave tube under inert atmosphere. Next, the reaction mixture is evaporated and the obtained crude is diluted with EtOAc. The organic phase is The SEM protected alcohol (523 mg, 1 mmol) is dissolved in dioxane (10 mL) and a 4 M HCl in dioxane solution (0.25 mL, 1 mmol) is added to this mixture. After stirring at 50° C. for 1 h, the mixture is diluted with water and extracted with EtOAc. The organic phase is dried over Na2SO4, filtered and evaporated to give a crude that is purified by preparative chromatography.

Method D7: Ester Hydrolysis

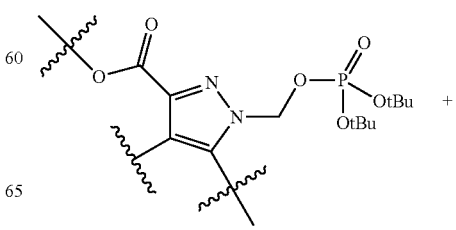

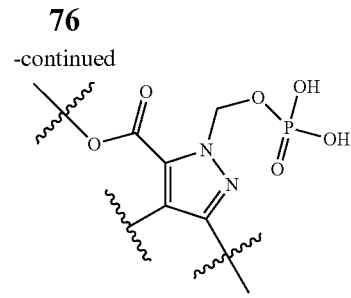

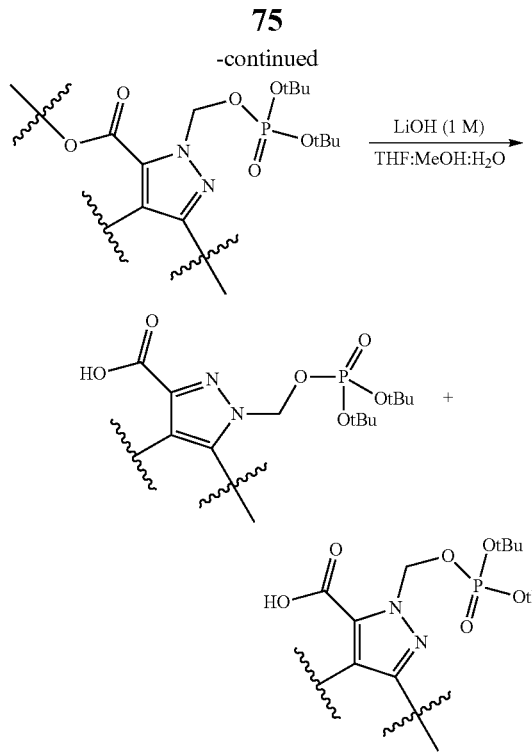

To a solution of the ester (1 eq) in THF:MeOH:H2O, LiOH (1 eq) is added. The resulting mixture is stirred at 45° C. Next, the reaction mixture is diluted with water and LiOH (1M solution) is added until pH=10. The aqueous layer is extracted with CH2Cl2 after which the aqueous phase is acidified until pH=3 using 1M HCl solution. Extraction with EtOAc gives an organic phase that dried and evaporated to give a crude that is used as such.

Method D8: Phosphate Ester Hydrolysis

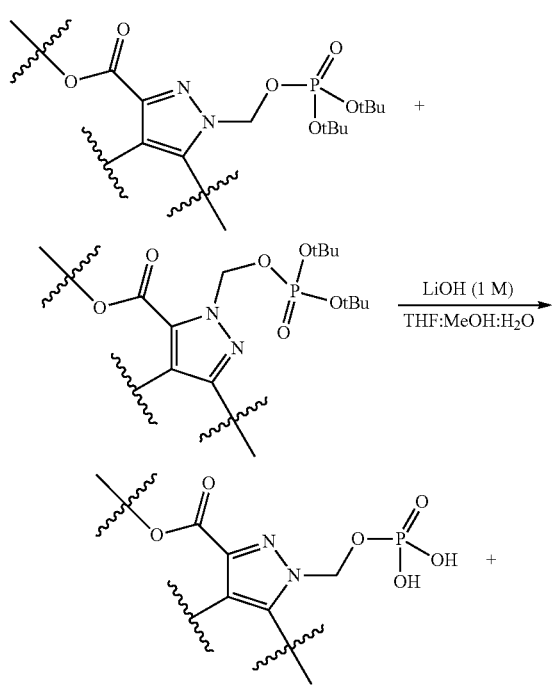

The phosphate ester (1 eq) is dissolved in a mixture of acetone and H$_2$O (1:1) and stirred at 40° C. overnight. The mixture is then partially evaporated and the obtained aqueous phase made basic with an aqueous NH$_4$OH solution. This solution is extracted with DCM. The aqueous solution is next acidified using 12 M HCl in H$_2$O. Extraction with EtOAc gives an organic phase that is dried and evaporated. Obtained crude is purified by preparative chromatography to give the desired product. Using preparative chromatography, the 2 regio-isomers can be separated.

Method D9: Ester Hydrolysis

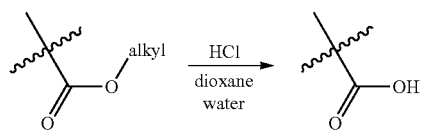

The ester is added to a mixture of 2 M HClaq:dioxane (1:1). The resulting mixture is heated at 70° C. overnight. The desired product can be obtained by extraction with organic solvents like EtOAc or DCM. Alternatively, the desired product can be obtained by evaporating the reaction mixture and purifying the obtained crude by chromatography.

Method D10: SEM Deprotection of Pyrazoles Using HCl

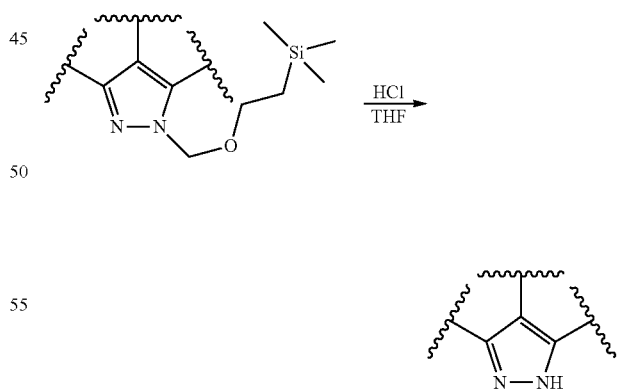

The SEM protected pyrazole (1 eq) is dissolved in THF and a 4M HCl in dioxane solution (3 eq) is added to this mixture. The mixture is stirred at 50° C. When the reaction is finished, the mixture is diluted with water and extracted with EtOAc. The organic phase is dried over Na$_2$SO$_4$, filtered and evaporated to give a crude that is purified by chromatography to give the desired product.

Method E₁: Ester Reduction with LiBH₄

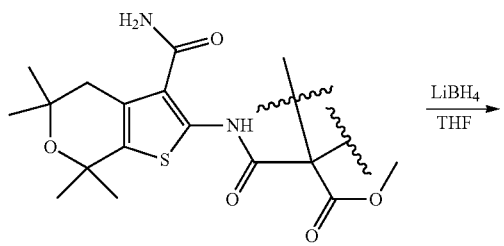

The ester (1 eq) is weighed in a flask together with LiBH₄ (3 eq). The flask is placed in an ice bath followed by the addition of dry THF. When the solvent is added, the mixture is stirred at room temperature. After 4 h, another 3 eq of LiBH₄ are added and the reaction mixture is stirred at room temperature overnight. Next, the reaction is quenched with 2 M HCl. The organic solvent is evaporated and obtained mixture is extracted with DCM. The organic phase is concentrated under vacuo, and the residue is purified by preparative chromatography.

Illustrative Example 2-(1-(hydroxymethyl)cyclopropanecarboxamido)-5,5,7,7-tetramethyl-5,7-dihydro-4H-thieno[2,3-c]pyran-3-carboxamide

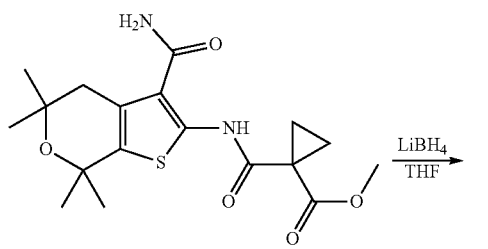

The ester (900 mg, 2.34 mmol) is weighed together with LiBH₄ (153 mg, 7.02 mmol) in a flask. The flask is put in an ice bath and dry THF (20 mL) is slowly added. After stirring for 5 min, the ice bath is removed and the mixture is stirred at room temperature. After 4 h, another portion of LiBH₄ (153 mg, 7.02 mmol) is added to the mixture at room temperature. Mixture is then stirred overnight. Reaction is subsequently quenched with 2 M HCl. Evaporation of the THF gives an aqueous phase that is extracted with DCM. The organic phase is concentrated under vacuo, and the residue is purified by preparative chromatography.

Method E₂: Keton Reduction with NaBH₄

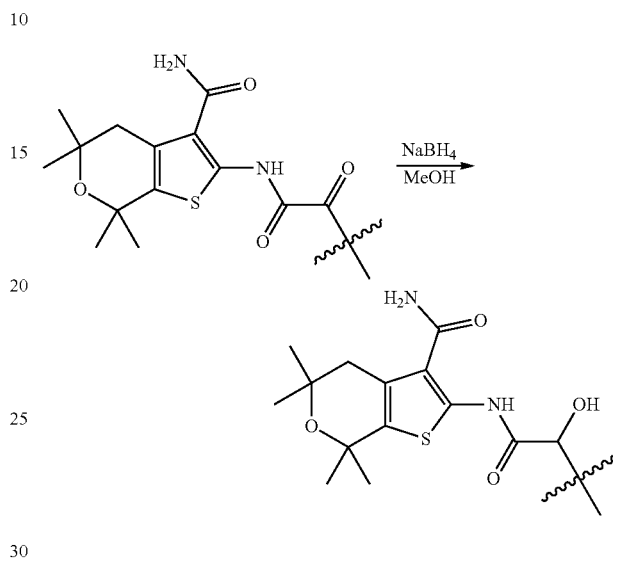

The ketone (1 eq) is dissolved in MeOH and the resulting solution is cooled at 0° C. NaBH₄ (2 eq) is added and the mixture is stirred at room temperature overnight. The reaction is quenched with water and extracted with EtOAc. The organic phase is evaporated and the obtained residue is purified by preparative chromatography to give desired compound.

The same method may be applied to aldehyde reduction

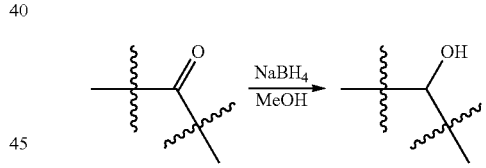

Illustrative Example 2-(2-hydroxy-3-methylbutanamido)-5,5,7,7-tetramethyl-5,7-dihydro-4H-thieno[2,3-c]pyran-3-carboxamide

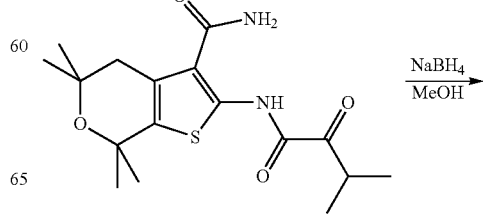

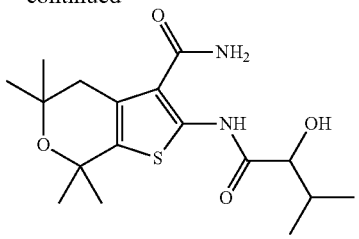

The ketone (338 mg, 0.96 mmol) is dissolved in MeOH (3.3 mL) and the resulting solution is cooled at 0° C. NaBH$_4$ (67 mg, 1.92 mmol) is added and the mixture is stirred at room temperature overnight. The reaction is quenched with water and extracted with EtOAc. The organic phase is evaporated and the obtained residue is purified by preparative chromatography to give desired compound.

The enantiomerically pure compounds are obtained by purification on a chiral column.

Method E$_3$: Alkene Reduction with H$_2$ and Pd/C

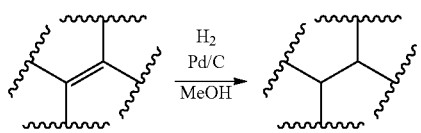 [SMILES: "MeOH" ; *C(*)=C(*)* ; *C(*)C(*)*]

The alkene (1 eq) is dissolved in MeOH together with Pd/C (10% by weight, 0.1 eq) and a balloon of H$_2$ is applied. The mixture is stirred at room temperature until the reaction is finished. The mixture is then filtered over celite and the resulting liquid is concentrated to give a residue that is used as such or purified by preparative chromatography.

Method E$_4$: Nitrile Reduction with DIBAL-H

The nitrile (1 eq) is dissolved in DCM and the resulting solution is cooled at −78° C. under N$_2$ atmosphere. To this mixture, a solution of DIBAL-H in hexane (1 M, 4 eq) is added. The reaction is stirred at −78° C. for 15 min, after which it is let to warm to room temperature. After overnight stirring, extra DIBAL-H is added depending on the conversion of the starting nitrile. Next, the mixture is quenched with water and Rochelle's salt. Extraction with DCM gives an organic phase that is dried and filtered over silica. After evaporation, a residue is obtained that is used as such.

Illustrative Example

4-Formyl-1H-pyrazole-3-carboxylic acid (3-carbamoyl-5,5,7,7-tetramethyl-4,7-dihydro-5H-thieno[2,3-c]pyran-2-yl)-amide

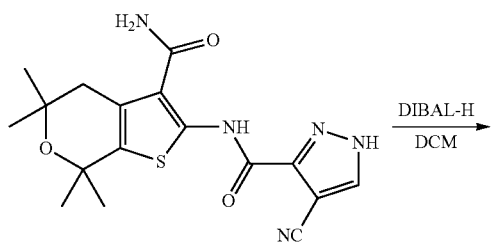

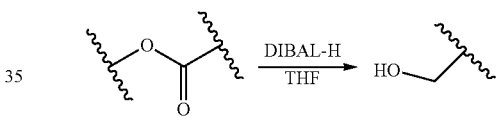

The nitrile (250 mg, 0.67 mmol) is dissolved in DCM (4 mL) and the resulting solution is cooled at −78° C. under N$_2$ atmosphere. To this mixture, a solution of DIBAL-H in hexane (1 M, 2.68 mL, 2.68 mmol) is added. The reaction is stirred at −78° C. for 15 min, after which it is allowed to warm to room temperature. After overnight stirring, additional DIBAL-H (2 mL, 2 mmol) is added at −78° C. The solution is allowed to reach room temperature and stirred for another 1 h. Next, the mixture is quenched with water and Rochelle's salt. Extraction with DCM gives an organic phase that is dried and filtered over silica. After evaporation, a residue is obtained that is used as such.

Method E$_5$: Ester Reduction with DIBAL-H

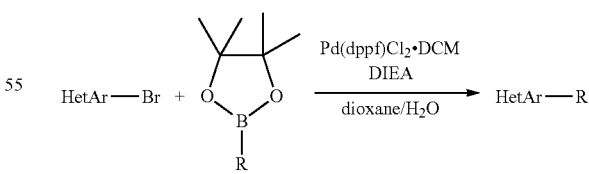

The ester (1 eq) is dissolved in dry THF at −78° C. A mixture of DIBAL-H in hexanes (2.2 eq) is added dropwise to the mixture under inert atmosphere. The mixture is stirred for 10 min at −78° C. after which the mixture is allowed to reach room temperature. If the reaction is incomplete, extra eq of DIBAL-H can be added. Next, the mixture is diluted with aqueous HCl (2M) and extracted with EtOAc. Combined organic fractions are dried and evaporated. Obtained crude can be used as such or purified by chromatography to give the desired product.

Method F$_1$: Suzuki Coupling

HetAr—Br + [boronic ester with R] →(Pd(dppf)Cl$_2$·DCM, DIEA, dioxane/H$_2$O) HetAr—R The heteroaryl bromide (1 eq) is mixed with the boronic ester (1.25 eq), Pd(dppf)Cl$_2$.DCM (0.07 eq) and DIEA (2.5 eq) in a dioxane:water mixture (2:1). The reaction mixture is heated at 110° C. until the reaction is finished. Dilution with DCM gives an organic phase that is washed with water. Next, the organic phase is dried and evaporated to give a residue that is used as such or purified by preparative chromatography.

Illustrative Example

4-(3,6-Dihydro-2H-pyran-4-yl)-1H-pyrazole-3-carboxylic acid methyl ester

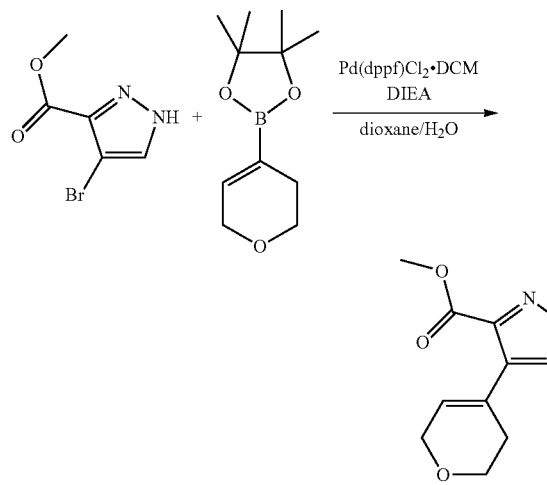

The pyrazole (Int 4, 200 mg, 0.976 mmol) is mixed with the boronic ester (256 mg, 1.22 mmol), Pd(dppf)Cl₂.DCM (56 mg, 0.068 mmol) and DIEA (425 µL, 2.43 mmol) in a dioxane:water mixture (2:1, 3 mL). The reaction mixture is heated at 110° C. in the microwave for 2 h. Dilution with DCM gives an organic phase that is washed with water. Next, the organic phase is dried and evaporated to give a crude that is used as such or purified by preparative chromatography.

Method F₂: Cu Catalyzed Coupling of Alcohols

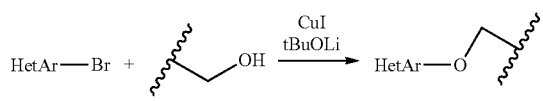

The heteroaryl bromide (1 eq) is mixed with CuI (0.05 eq) and tBuOLi (3.0 eq). The alcohol is used as solvent. The reaction mixture is heated at 120° C. in the microwave until the reaction is finished. The mixture is diluted with water and extracted with EtOAc. Organic layer is dried and evaporated to give a crude that is used such or that is purified by chromatography.

Illustrative Example

4-(2-Methoxy-ethoxy)-1-(2-trimethylsilanyl-ethoxymethyl)-1H-pyrazole-3-carboxylic acid

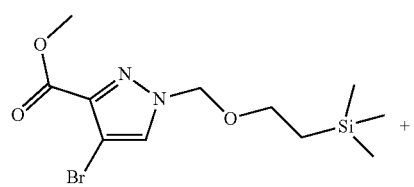

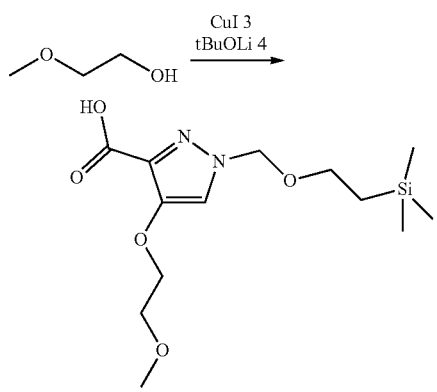

The pyrazole (1.10 g, 3.28 mmol) is mixed with ethylene glycol (6 mL). CuI (31 mg, 0.164 mmol) and tBuOLi (789 mg, 9.85 mmol) are added. Mixture is heated in the microwave at 120° C. until the reaction is finished. During the reaction, the ester is hydrolysed. Next, the mixture is diluted with a saturated solution of NaHCO₃ and extracted with EtOAc. Aqueous layer is acidified till pH=7 and extracted with EtOAc. This organic phase is dried and evaporated to give a crude that is used as such.

Method F₃: Carboxylation

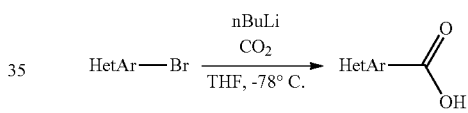

The heteroaryl bromide (1 eq) is dissolved in dry THF at −78° C. A mixture of nBuLi in hexanes (1.2 eq) is added dropwise to this mixture. After stirring for 10 min, CO₂ gas is bubbled through the mixture. The mixture is allowed to reach room temperature and quenched with water. The aqueous mixture is brought to pH-10 and extracted with EtOAc. Aqueous layer is than acidified till pH ~3 and extracted with EtOAc. The resulting organic fraction is dried and evaporated to give a crude that is used as such.

Illustrative Example

4-Methoxymethyl-1-(2-trimethylsilanyl-ethoxymethyl)-1H-pyrazole-3-carboxylic acid

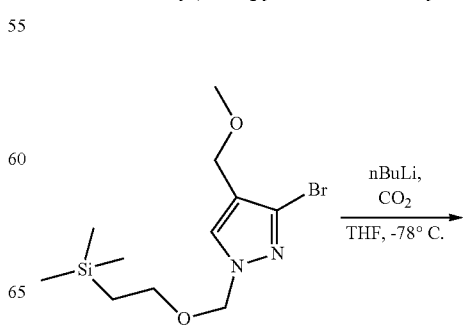

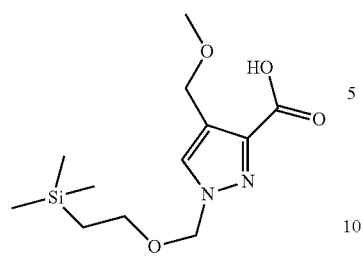

The pyrazole (161 mg, 0.5 mmol) is dissolved in dry THF (3 mL) at −78° C. A mixture of nBuLi in hexanes (2.5 M in hexanes, 240 μL, 0.6 mmol) is added dropwise to this mixture. After stirring for 10 min, CO₂ gas is bubbled through the mixture. The mixture is allowed to reach room temperature and quenched with water. The aqueous mixture is brought to pH~10 and extracted with EtOAc. Aqueous layer is than acidified to pH ~3 and extracted with EtOAc. The resulting organic fraction is dried and evaporated to give a crude that is used as such.

Method G₁: Grignard

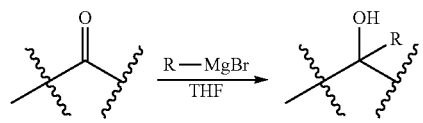

The carbonyl (1 eq) is dissolved in dry THF under N₂ atmosphere. This solution is cooled at −78° C., upon which the organomagnesium bromide solution (4 eq) is added. After the addition, the reaction is allowed to reach room temperature. Next, the mixture is quenched with water and diluted with a saturated NH₄Cl solution. Extraction with EtOAc gives an organic phase that is dried, filtered and evaporated.

Illustrative Example

N-(3-carbamoyl-5,5,7,7-tetramethyl-4H-thieno[2,3-c]pyran-2-yl)-5-(1-hydroxy-1-methyl-ethyl)-1H-pyrazole-3-carboxamide

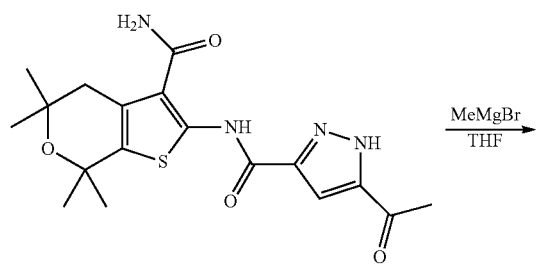

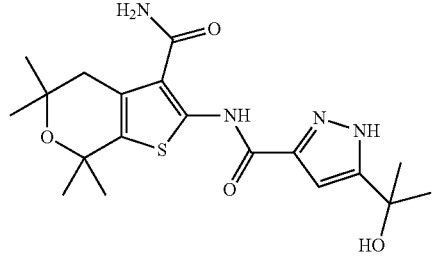

The carbonyl (98 mg, 0.25 mmol) is dissolved in dry THF under N₂ atmosphere. This solution is cooled at −78° C., upon which the MeMgBr (3 M in ether, 0.33 mL, 1 mmol) is added. After the addition, the reaction is allowed to reach room temperature. Next, the mixture is quenched with water and diluted with a saturated NH₄Cl solution. Extraction with EtOAc gives an organic phase that is dried, filtered and evaporated. The obtained crude is purified by preparative chromatography to yield the desired product.

Method H₁: Alkylation of Alcohols

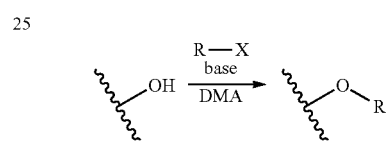

A mixture of the alcohol (1 eq), alkylating agent (1 eq) and base (1.2 eq) is mixed in DMA. The resulting mixture is stirred at room temperature overnight. Next, the mixture is quenched with water and diluted with brine. Extraction with EtOAc gives an organic phase that is dried, filtered and evaporated. The obtained crude is used as such.

Illustrative Example 5-(2-Methoxy-ethoxy)-2H-pyrazole-3-carboxylic acid ethyl ester

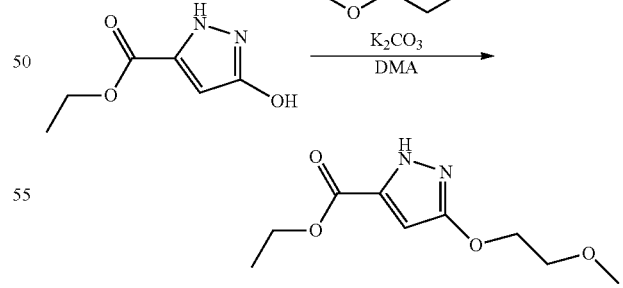

A mixture of the alcohol (79 mg, 0.5 mmol), 1-bromo-2-methoxy-ethane (47 pt, 0.5 mmol) and K₂CO₃ (83 mg, 0.6 mmol) is mixed in DMA (1 mL). Resulting mixture is stirred at room temperature overnight. Next, the mixture is quenched with water and diluted with brine. Extraction with EtOAc gives an organic phase that is dried, filtered and evaporated. The obtained residue is used as such.

Method H₂: Alkylation of Malonic Esters

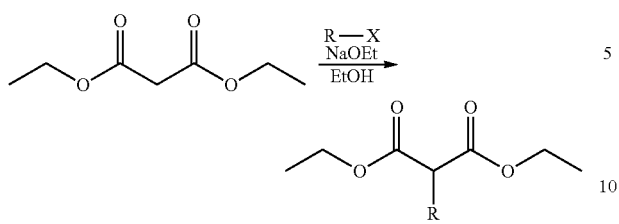

A solution of NaOEt (1.1 eq) in EtOH is stirred at 0° C. The diethyl malonate (1 eq) is added to this mixture together with the desired alkylating agent (1.1 eq). The ice bath is allowed to melt and the mixture is stirred at room temperature overnight. Next, the mixture is quenched with water and extracted with ether. The organic phase is dried and evaporated to give the desired product that is used as such.

Illustrative Example

2-Cyclopropylmethyl-malonic acid diethyl ester

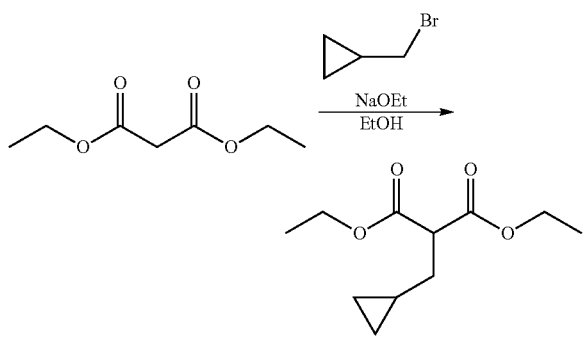

A solution of NaOEt in EtOH (2.7 M, 2.6 mL, 6.9 mmol) is cooled at 0° C. and diethylmalonate (0.95 mL, 6.2 mmol) is added with another 1.5 mL of EtOH. Bromo methyl cyclopropane (0.67 mL, 6.9 mmol) is subsequently added. The resulting mixture is allowed to reach room temperature and stirred overnight. The mixture is then quenched with water and extracted with ether. The organic phase is dried and evaporated to give the desired product that is used as such.

Method H3: Alkylation of Pyrazole Ring

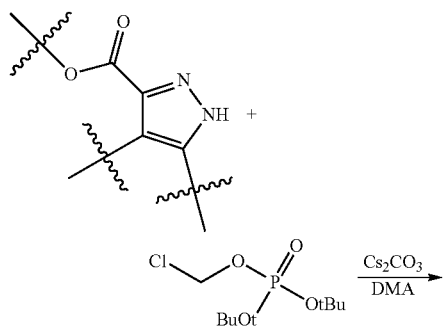

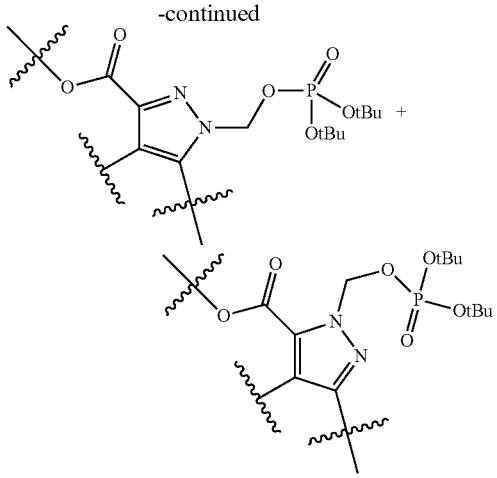

Phosphoric acid di-tert-butyl ester chloromethyl ester (1 eq) is dissolved in DMA together with the pyrazole (1 eq) and Cs₂CO₃ (1.25 eq). The resulting mixture is stirred at room temperature overnight. Dilution with water gives an aqueous phase that is extracted with EtOAc. Obtained organic phase is dried and evaporated to give the desired product that is used as such.

Method H₄: Methylation of Alcohols

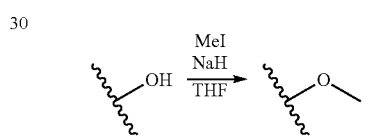

A mixture of the alcohol (1 eq) is dissolved in dry THF and cooled at 0° C. NaH (1.2 eq) is added in portions. The resulting mixture is stirred for 10 min at 0° C. after which MeI (1.2 eq) is added. Finally, the ice bath is removed and the mixture is stirred at room temperature. After dilution with water, the mixture is extracted with EtOAc. Combined organic fractions are dried and evaporated. Obtained crude is used such or purified by chromatography to give the desired product.

Method I₁: Halogenation Using NXS

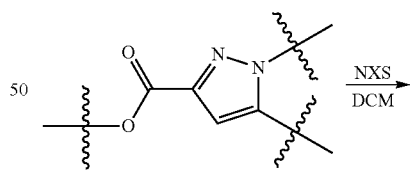

X = ―Cl, ―Br or ―I

A solution of the pyrazole (1 eq) and N-halo succinimide (NXS) (1.2 eq) is stirred at 55° C. overnight. Depending on the conversion, extra eq of NXS can be added after overnight stirring. The mixture is worked up by portioning between an aqueous phase and an organic phase. The organic phase is then dried and evaporated to give a residue that is either purified by chromatography or used as such.

Illustrative Example

4-Chloro-5-methoxymethyl-1H-pyrazole-3-carboxylic acid

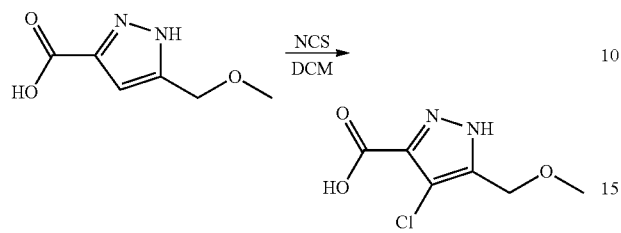

A solution of the commercially available pyrazole (156 mg, 1 mmol) and NCS (160 mg, 1.2 eq) is stirred at 55° C. overnight. An additional 31 mg (0.2 mmol) of NCS is added and the mixture is kept at 55° C. for another 4 h. The mixture is then diluted with 1M LiOH solution and washed with EtOAc. Next, the aqueous phase is acidified with 2 M HCl solution to pH=1. Extraction with EtOAc gives an organic phase that is dried and evaporated to give a residue that is used as such.

Method $J_1$: Oxidation of an Alkene to the Diol

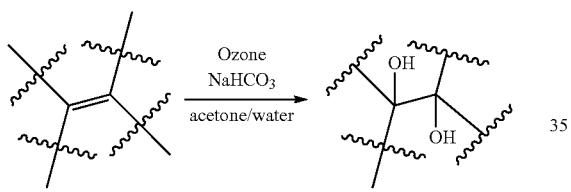

Oxone (2 eq) and $NaHCO_3$ (4 eq) are added to a solution of the alkene (1 eq) in a acetone:water mixture (4:1). The resulting mixture is stirred at room temperature overnight. Depending on the conversion, additional oxone and $NaHCO_3$ can be added to the mixture after overnight stirring. The mixture is then concentrated, diluted with EtOAc and washed with a solution of $Na_2SO_3$ and water. The organic phase is dried and evaporated to give a residue that is either purified by preparative chromatography or used as such.

Illustrative Example

N-(3-carbamoyl-5,5,7,7-tetramethyl-4H-thieno[2,3-c]pyran-2-yl)-4-(1,2-dihydroxyethyl)-1H-pyrazole-3-carboxamide

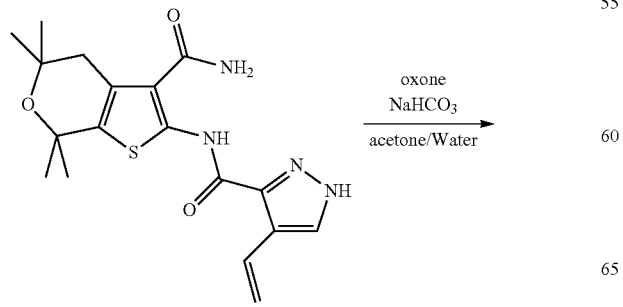

-continued

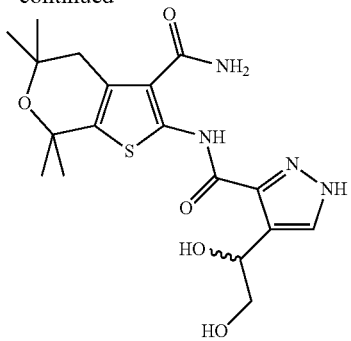

Oxone (395 mg, 0.64 mmol) and $NaHCO_3$ (108 mg, 1.28 mmol) are added to a solution of the alkene (120 mg, 0.32 mmol) in a acetone:water mixture (4:1, 3 mL). After stirring the resulting mixture at room temperature overnight, additional oxone and $NaHCO_3$ are added to the mixture. The mixture is stirred for another 4 h at room temperature. The mixture is then concentrated, diluted with EtOAc and washed with a solution of $Na_2SO_3$ and water. The organic phase is dried and evaporated to give a residue that is purified by preparative chromatography to yield the desired product.

Example 4

Illustrative examples for the Preparation of the Compounds of Invention

Compound 2: N-(3-carbamoyl-5,5,7,7-tetramethyl-5,7-dihydro-4H-thieno[2,3-c]pyran-2-yl)-1H-pyrazole-5-carboxamide

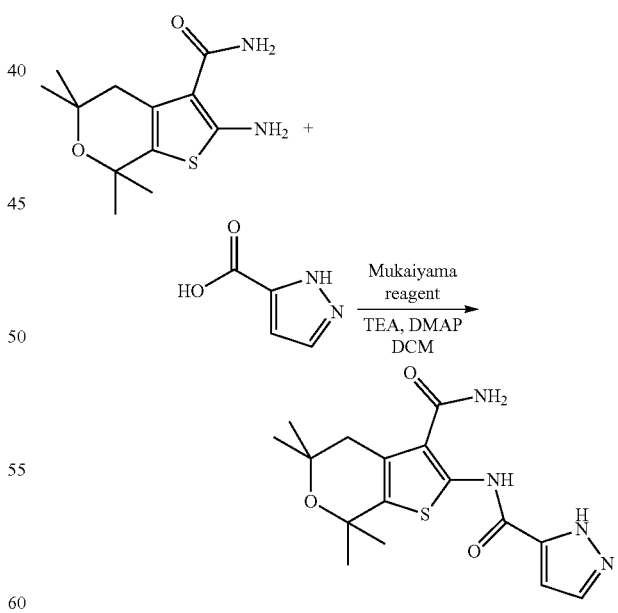

Intermediate 3 (15 g, 59 mmol) and 2H-pyrazole-3-carboxylic acid (9.9 g, 88 mmol) are suspended in DCM (250 mL). Mukaiyama reagent (2-chloro-1-methylpyridinium iodide) (18.1 g, 71 mmol), TEA (24.7 mL, 177 mmol) and DMAP (3.6 g, 29 mmol) are added. The reaction mixture is stirred at 40° C. overnight and then cooled. The mixture is evaporated and the obtained crude is suspended in a 1 M HCl solution. After stirring for 10 min, the suspension is filtered and obtained precipitate is isolated. This precipitate is resuspended in a 0.1 M citric acid solution. Again, filtration gives a precipitate. A third trituration is done using ether as a solvent to give a precipitate after filtration. Finally, the precipitate (13.6 g) is suspended in EtOH (816 mL) and heated at reflux. To this suspension, 65 mL of DMF is added and a clear solution is obtained. The solution is concentrated to 275 mL and cooled at 0° C. A suspension is obtained, the solid is separated by filtration, and the cake is dried affording the desired product.

Alternative Route

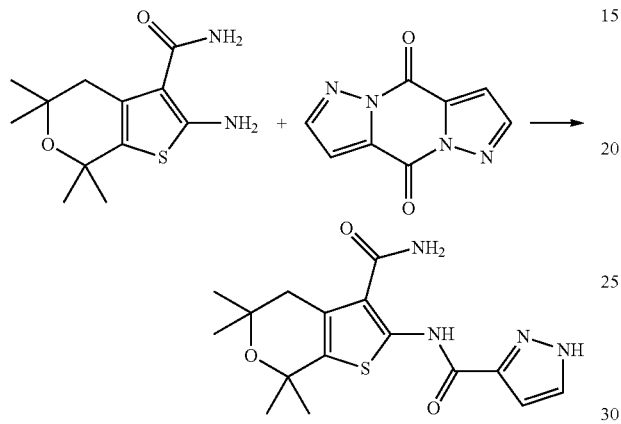

To a stirred (400 rpm) solution of 600 g (2.36 mol) of Intermediate 3 in DMAc (6 L), is added at ambient temperature 1.3 equivalents of Intermediate 11. To this resulting suspension, at room temperature, DIPEA (618 mL, 1.5 eq.) is added in small portions over a period of 5 min. The resulting suspension is heated to 80° C. and stirred for 18 h at this temperature. The resulting mixture is cooled to 15° C. and an aqueous saturated $NH_4Cl$ solution (7.5 L) is added over 30 minutes thus maintaining the internal temperature between 15-24° C. The resulting solid product is collected by filtration, and triturated with water (7.5 L) under mechanical stirring (600 rpm) for 30 min. The resulting suspension is filtered and the resulting solid is triturated in MTBE (8 L) under mechanical stirring for 45 minutes. The resulting solid is separated by filtration, and dried in a vacuum stove.

Finally, the solid is purified by hot trituration in ethanol. Therefore, the crude solid is suspended in absolute EtOH (16 L) for 1.5 h at 78° C. The suspension is cooled to 20° C. and subsequently stirred for another hour. The solid product was collected by filtration, washed with 500 mL and again with 200 ml absolute EtOH, then dried to yield the desired product.

Compound 3: 2-(2-hydroxybenzamido)-5,5,7,7-tetramethyl-5,7-dihydro-4H-thieno[2,3-c]pyran-3-carboxamide

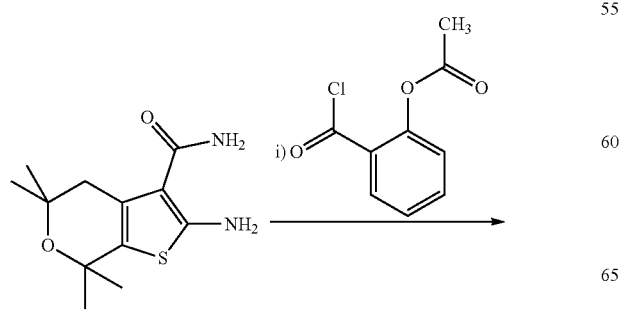

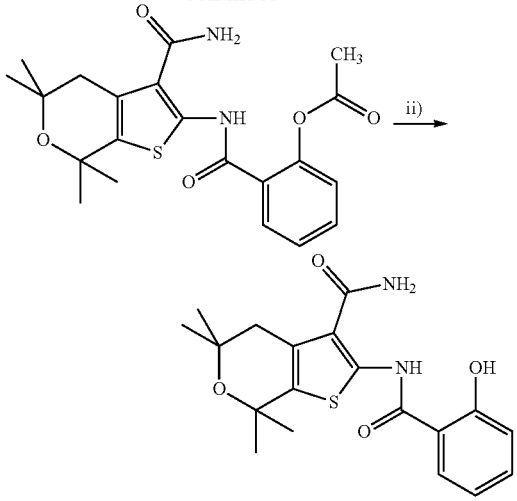

Step i): synthesis of 2-(2-acetoxybenzamido)-5,5,7,7-tetramethyl-5,7-dihydro-4H-thieno[2,3-c]pyran-3-carboxamide

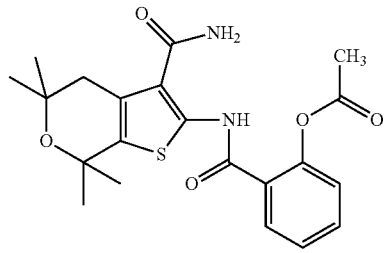 [SMILES: CC(=O)Oc1ccccc1C(=O)Nc1sc2c(c1C(N)=O)CC(C)(C)OC2(C)C]

A solution of Int 2 (112 mg, 0.44 mmol) and pyridine (53 µL, 0.66 mmol) in 5 mL of DCM, cooled to 0° C., is treated dropwise with a solution of the acid chloride (114 mg, 0.57 mmol) in 5 mL of DCM. The resulting mixture is stirred at room temperature for 1 h. Mixture is washed with saturated $NaHCO_3$ and aqueous phase is extracted twice with DCM. Organic phases are combined, dried and evaporated to afford the crude product that is used as such.

Step ii) synthesis of 2-(2-hydroxybenzamido)-5,5,7,7-tetramethyl-5,7-dihydro-4H-thieno[2,3-c]pyran-3-carboxamide

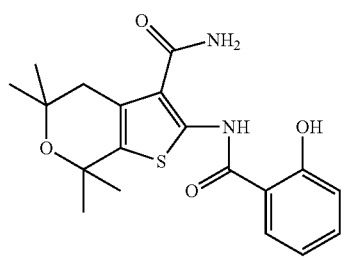 [SMILES: CC1(C)Cc2c(sc(NC(=O)c3ccccc3O)c2C(N)=O)C(C)(C)O1]

To a solution of 2-(2-acetoxybenzamido)-5,5,7,7-tetramethyl-5,7-dihydro-4H-thieno[2,3-c]pyran-3-carboxamide (200 mg, 0.48 mmol) in 4 mL of MeOH/dioxane=1:1, cooled to 0° C., is added potassium carbonate (66 mg, 0.52 mmol). The reaction mixture is stirred at room temperature for 90 min, filtered off and filtrate is then acidified with 1M HCl. A precipitate is formed which is separated by filtration to afford the desired compound which is used as such.

Compound 8: 2-(4-fluoro-2-(trifluoromethyl)benzamido)-5,5,7,7-tetramethyl-5,7-dihydro-4H-thieno[2,3-c]pyran-3-carboxamide

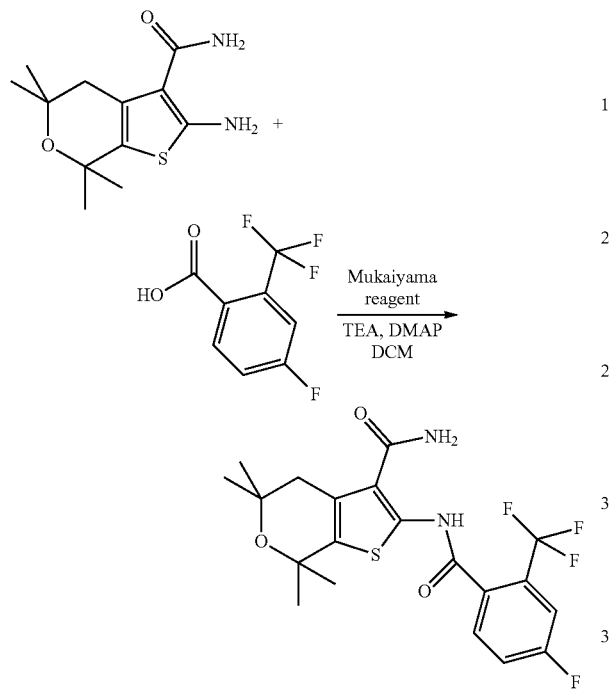

Intermediate 2 (69 mg, 0.27 mmol) and 4-fluoro-2-trifluoro-benzoic acid (114 mg, 0.55 mmol) are suspended in DCM (5 mL). Mukaiyama reagent (2-chloro-1-methylpyridinium iodide) (140 mg, 0.55 mmol), TEA (0.170 mL, 1.1 mmol) and DMAP (17 mg, 0.14 mmol) are added. The reaction mixture is stirred at 50° C. for 2 hours and then cooled, diluted with DCM and washed with saturated NaHCO$_3$. Organic phases are combined, dried and evaporated to afford the crude product, which is purified by preparative chromatography to give the desired product.

Example 5

Illustrative examples for the Preparation of the Comparative Compounds

Compound D: 2-(2-hydroxybenzamido)-5,7-dihydro-4H-thieno[2,3-c]pyran-3-carboxamide

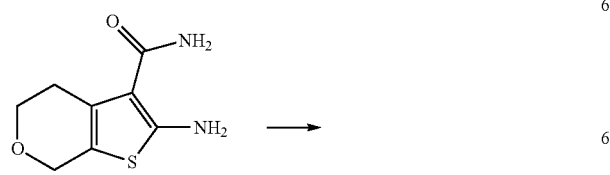

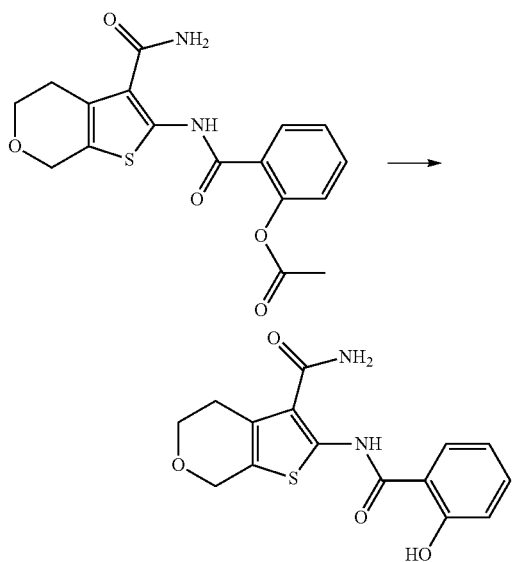

Synthesised using commercially available intermediate 2-Amino-4,7-dihydro-5H-thieno[2,3-c]pyran-3-carboxamide in method A1 and D1.

Compound C: 2-(2-hydroxybenzamido)-4,5,6,7-tetrahydrothieno[2,3-c]pyridine-3-carboxamide

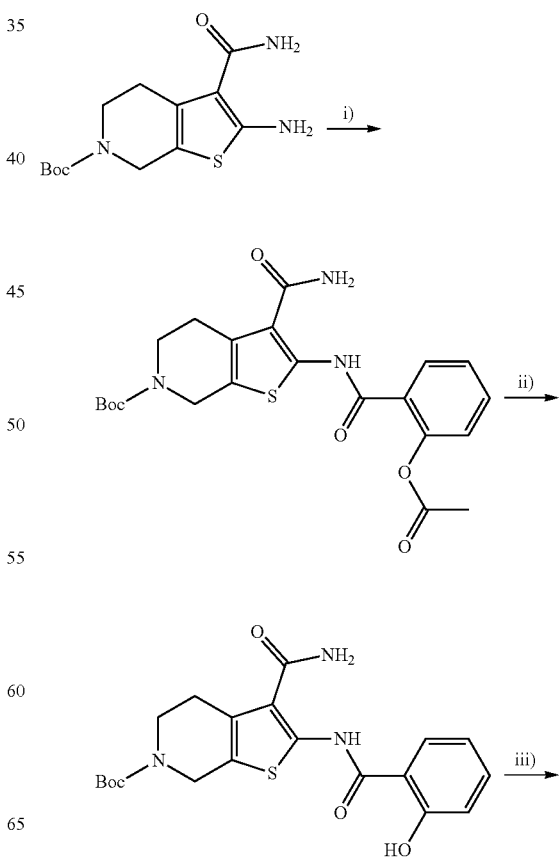

-continued

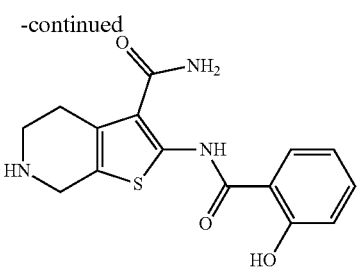

Step i)
2-Amino-3-carbamoyl-4,7-dihydro-5H-thieno[2,3-c]pyridine-6-carboxylic acid tert-butyl ester is subjected to Method A1 to obtain the desired compound.

Step ii)
The product of step i described above is subjected to Method D1 to obtain the desired compound.

Step iii)
The product of step ii described above is (1 eq) is dissolved in a mixture of TFA and DCM at 0° C. The ice bath is allowed to melt and resulting mixture is stirred overnight at room temperature. The mixture is then diluted with DCM and extracted with a saturated NaHCO$_3$ solution. Trituration with di-isopropylether gives the desired compound.

Similarly, Comparative compound A, can be prepared following the same method as disclosed for Comparative Compound C, starting from commercially available 2-Amino-6-methyl-4,5,6,7-tetrahydro-thieno[2,3-c]pyridine-3-carboxylic acid amide.

TABLE II

List of final compounds

| Cpd # | Structure | Name | Mtd | Int | MW | Mes |
|---|---|---|---|---|---|---|
| 1 | 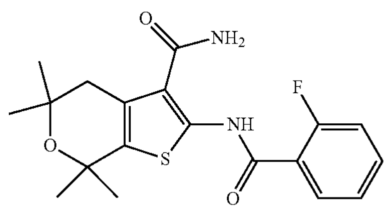 [SMILES: CC1(C)Cc2c(sc(NC(=O)c3ccccc3F)c2C(N)=O)C(C)(C)O1] | 2-(2-fluorobenzamido)-5,5,7,7-tetramethyl-5,7-dihydro-4H-thieno[2,3-c]pyran-3-carboxamide | A2 | Int 3 | 376 | 377 |
| 2 | 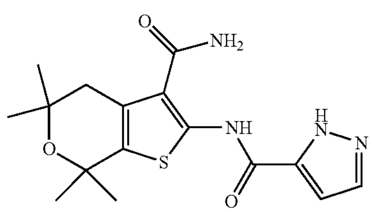 [SMILES: CC1(C)Cc2c(sc(NC(=O)c3ccn[nH]3)c2C(N)=O)C(C)(C)O1] | N-(3-carbamoyl-5,5,7,7-tetramethyl-5,7-dihydro-4H-thieno[2,3-c]pyran-2-yl)-1H-pyrazole-5-carboxamide | A2 | Int 3 | 348 | 371 |
| 3 | 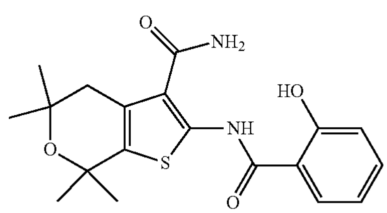 | 2-(2-hydroxybenzamido)-5,5,7,7-tetramethyl-5,7-dihydro-4H-thieno[2,3-c]pyran-3-carboxamide | A1, D1 | Int 3 | 374 | 375 |
| 4 | 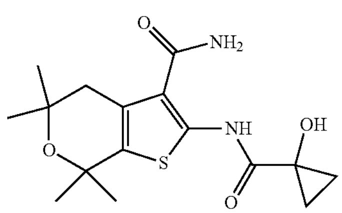 [SMILES: CC1(C)Cc2c(sc(NC(=O)C3(O)CC3)c2C(N)=O)C(C)(C)O1] | 2-(1-hydroxycyclopropanecarboxamido)-5,5,7,7-tetramethyl-5,7-dihydro-4H-thieno[2,3-c]pyran-3-carboxamide | C1, A2, D1 | Int 3 | 338 | 339 |
| 5 | 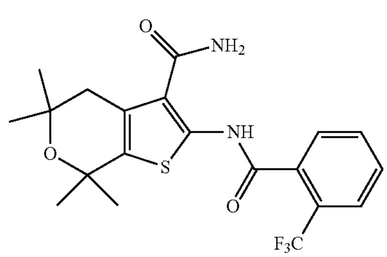 [SMILES: CC1(C)Cc2c(sc(NC(=O)c3ccccc3C(F)(F)F)c2C(N)=O)C(C)(C)O1] | 5,5,7,7-tetramethyl-2-(2-(trifluoromethyl)benzamido)-5,7-dihydro-4H-thieno[2,3-c]pyran-3-carboxamide | A2 | Int 3 | 426 | 427 |

TABLE II-continued

List of final compounds

| Cpd # | Structure | Name | Mtd | Int | MW | Mes |
|---|---|---|---|---|---|---|
| 6 | 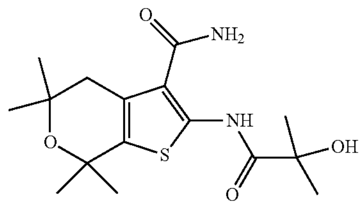 [SMILES: CC1(C)Cc2c(sc(NC(=O)C(C)(C)O)c2C(N)=O)C(C)(C)O1] | 2-(2-hydroxy-2-methylpropanamido)-5,5,7,7-tetramethyl-5,7-dihydro-4H-thieno[2,3-c]pyran-3-carboxamide | C1, A2, D1 | Int 3 | 340 | 341 |
| 7 | 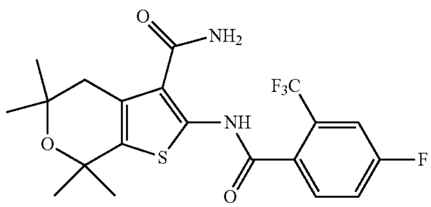 [SMILES: CC1(C)Cc2c(sc(NC(=O)c3ccc(F)cc3C(F)(F)F)c2C(N)=O)C(C)(C)O1] | 2-(4-fluoro-2-(trifluoromethyl)benzamido)-5,5,7,7-tetramethyl-5,7-dihydro-4H-thieno[2,3-c]pyran-3-carboxamide | A2 | Int 3 | 444 | 445 |
| 8 | 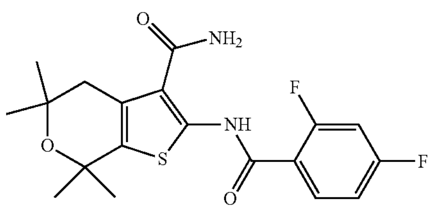 [SMILES: CC1(C)Cc2c(sc(NC(=O)c3ccc(F)cc3F)c2C(N)=O)C(C)(C)O1] | 2-(2,4-difluorobenzamido)-5,5,7,7-tetramethyl-5,7-dihydro-4H-thieno[2,3-c]pyran-3-carboxamide | A2 | Int 3 | 394 | 378 |
| 9 | 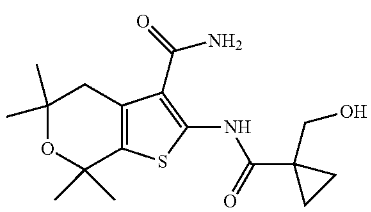 [SMILES: CC1(C)Cc2c(sc(NC(=O)C3(CO)CC3)c2C(N)=O)C(C)(C)O1] | 2-(1-(hydroxymethyl)cyclopropanecarboxamido)-5,5,7,7-tetramethyl-5,7-dihydro-4H-thieno[2,3-c]pyran-3-carboxamide | C1, B, A1, D1 | Int 3 | 352 | 353 |
| 10 | 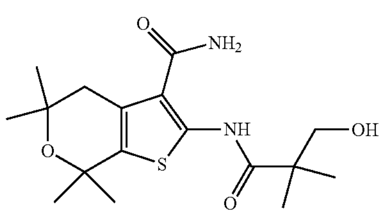 [SMILES: CC1(C)Cc2c(sc(NC(=O)C(C)(C)CO)c2C(N)=O)C(C)(C)O1] | 2-(3-hydroxy-2,2-dimethylpropanamido)-5,5,7,7-tetramethyl-5,7-dihydro-4H-thieno[2,3-c]pyran-3-carboxamide | C1, B, A1, D1 | Int 3 | 354 | 355 |
| 11 | 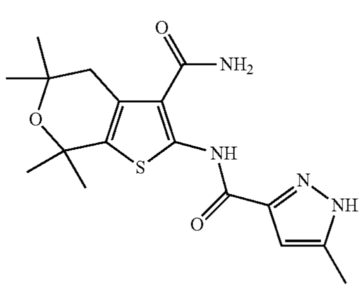 | N-(3-carbamoyl-5,5,7,7-tetramethyl-5,7-dihydro-4H-thieno[2,3-c]pyran-2-yl)-5-methyl-1H-pyrazole-3-carboxamide | A2 | Int 3 | 362 | 363 |

TABLE II-continued

List of final compounds

| Cpd # | Structure | Name | Mtd | Int | MW | Mes |
|---|---|---|---|---|---|---|
| 12 | 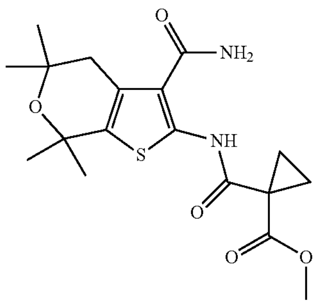 [SMILES: COC(=O)C1(C(=O)Nc2sc3c(c2C(N)=O)CC(C)(C)OC3(C)C)CC1] | methyl 1-(3-carbamoyl-5,5,7,7-tetramethyl-5,7-dihydro-4H-thieno[2,3-c]pyran-2-ylcarbamoyl)cyclopropanecarboxylate | A2 | Int 3 | 380 | 381 |
| 13 | 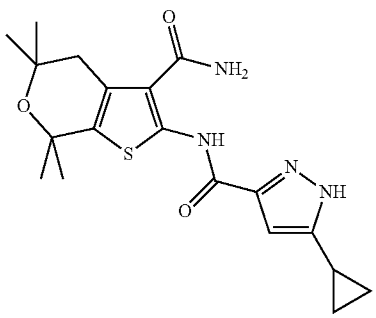 [SMILES: CC1(C)Cc2c(sc(NC(=O)c3cc(C4CC4)[nH]n3)c2C(N)=O)C(C)(C)O1] | N-(3-carbamoyl-5,5,7,7-tetramethyl-5,7-dihydro-4H-thieno[2,3-c]pyran-2-yl)-5-cyclopropyl-1H-pyrazole-3-carboxamide | A2 | Int 3 | 388 | 389 |
| 14 | 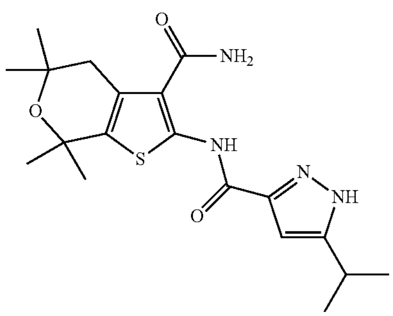 [SMILES: CC(C)c1cc(C(=O)Nc2sc3c(c2C(N)=O)CC(C)(C)OC3(C)C)n[nH]1] | N-(3-carbamoyl-5,5,7,7-tetramethyl-5,7-dihydro-4H-thieno[2,3-c]pyran-2-yl)-5-isopropyl-1H-pyrazole-3-carboxamide | A2 | Int 3 | 390 | 391 |
| 15 | 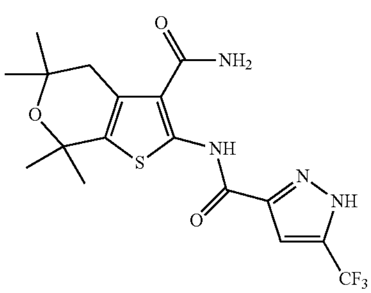 [SMILES: CC1(C)Cc2c(sc(NC(=O)c3cc(C(F)(F)F)[nH]n3)c2C(N)=O)C(C)(C)O1] | N-(3-carbamoyl-5,5,7,7-tetramethyl-5,7-dihydro-4H-thieno[2,3-c]pyran-2-yl)-5-(trifluoromethyl)-1H-pyrazole-3-carboxamide | A2 | Int 3 | 416 | 417 |
| 16 | 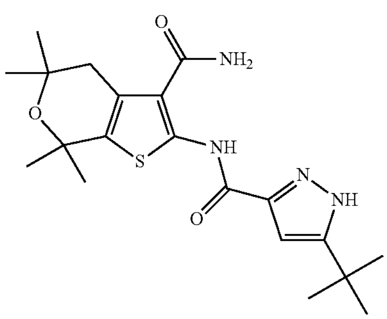 [SMILES: CC1(C)Cc2c(sc(NC(=O)c3cc(C(C)(C)C)[nH]n3)c2C(N)=O)C(C)(C)O1] | 5-tert-butyl-N-(3-carbamoyl-5,5,7,7-tetramethyl-5,7-dihydro-4H-thieno[2,3-c]pyran-2-yl)-1H-pyrazole-3-carboxamide | A2 | Int 3 | 404 | 405 |

TABLE II-continued

List of final compounds

| Cpd # | Structure | Name | Mtd | Int | MW | Mes |
|---|---|---|---|---|---|---|
| 17 | 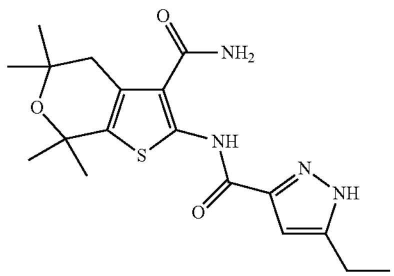 [SMILES: CCc1cc(C(=O)Nc2sc3c(c2C(N)=O)CC(C)(C)OC3(C)C)n[nH]1] | N-(3-carbamoyl-5,5,7,7-tetramethyl-5,7-dihydro-4H-thieno[2,3-c]pyran-2-yl)-5-ethyl-1H-pyrazole-3-carboxamide | A2 | Int 3 | 376 | 377 |
| 18 | 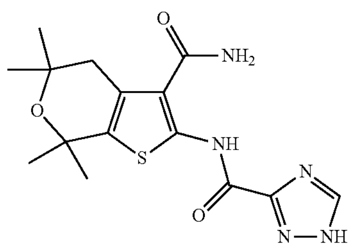 [SMILES: CC1(C)Cc2c(sc(NC(=O)c3nc[nH]n3)c2C(N)=O)C(C)(C)O1] | N-(3-carbamoyl-5,5,7,7-tetramethyl-5,7-dihydro-4H-thieno[2,3-c]pyran-2-yl)-1H-1,2,4-triazole-3-carboxamide | A2 | Int 3 | 349 | 350 |
| 19 | 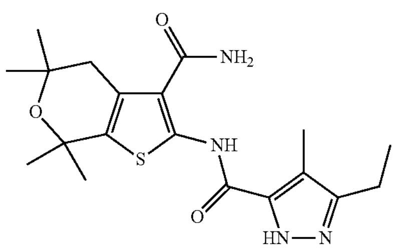 [SMILES: CCc1n[nH]c(C(=O)Nc2sc3c(c2C(N)=O)CC(C)(C)OC3(C)C)c1C] | N-(3-carbamoyl-5,5,7,7-tetramethyl-5,7-dihydro-4H-thieno[2,3-c]pyran-2-yl)-3-ethyl-4-methyl-1H-pyrazole-5-carboxamide | A2 | Int 3 | 390 | 391 |
| 20 | 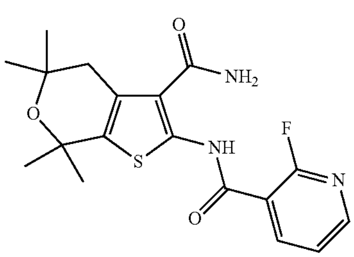 [SMILES: CC1(C)Cc2c(sc(NC(=O)c3cccnc3F)c2C(N)=O)C(C)(C)O1] | N-(3-carbamoyl-5,5,7,7-tetramethyl-5,7-dihydro-4H-thieno[2,3-c]pyran-2-yl)-2-fluoronicotinamide | A2 | Int 3 | 377 | 378 |
| 21 | 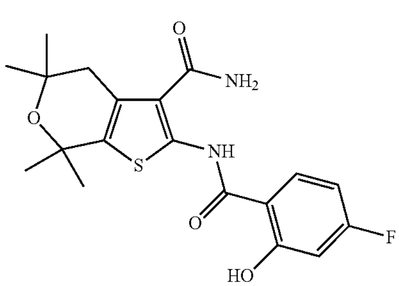 [SMILES: CC1(C)Cc2c(sc(NC(=O)c3ccc(F)cc3O)c2C(N)=O)C(C)(C)O1] | 2-(4-fluoro-2-hydroxybenzamido)-5,5,7,7-tetramethyl-5,7-dihydro-4H-thieno[2,3-c]pyran-3-carboxamide | A2 | Int 3 | 392 | 393 |

TABLE II-continued

List of final compounds

| Cpd # | Structure | Name | Mtd | Int | MW | Mes |
|---|---|---|---|---|---|---|
| 22 | 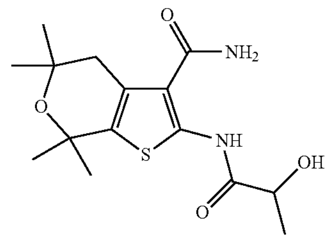 [SMILES: CC(O)C(=O)Nc1sc2c(c1C(N)=O)CC(C)(C)OC2(C)C] | 2-(2-hydroxypropanamido)-5,5,7,7-tetramethyl-5,7-dihydro-4H-thieno[2,3-c]pyran-3-carboxamide | A2, D1 | Int 3 | 326 | 327 |
| 23 | 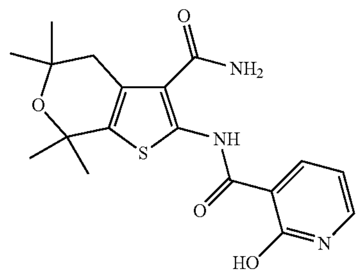 [SMILES: CC1(C)Cc2c(sc(NC(=O)c3cccnc3O)c2C(N)=O)C(C)(C)O1] | N-(3-carbamoyl-5,5,7,7-tetramethyl-5,7-dihydro-4H-thieno[2,3-c]pyran-2-yl)-2-oxo-1,2-dihydropyridine-3-carboxamide | A2, D3 | Int 3 | 375 | 376 |
| 24 | 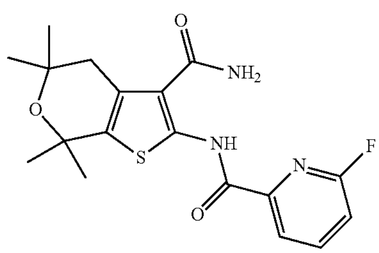 [SMILES: CC1(C)Cc2c(sc(NC(=O)c3cccc(F)n3)c2C(N)=O)C(C)(C)O1] | N-(3-carbamoyl-5,5,7,7-tetramethyl-5,7-dihydro-4H-thieno[2,3-c]pyran-2-yl)-6-fluoropicolinamide | A2 | Int 3 | 377 | 378 |
| 25 | 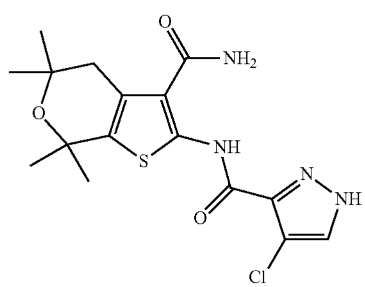 [SMILES: CC1(C)Cc2c(sc(NC(=O)c3n[nH]cc3Cl)c2C(N)=O)C(C)(C)O1] | N-(3-carbamoyl-5,5,7,7-tetramethyl-5,7-dihydro-4H-thieno[2,3-c]pyran-2-yl)-4-chloro-1H-pyrazole-3-carboxamide | A2 | Int 3 | 382 | 383 |
| 26 | 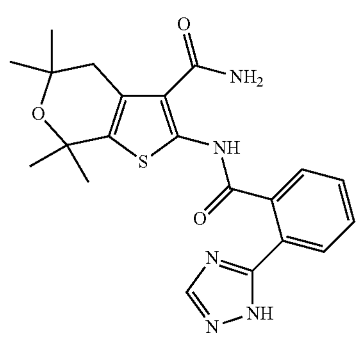 [SMILES: CC1(C)Cc2c(sc(NC(=O)c3ccccc3-c3ncn[nH]3)c2C(N)=O)C(C)(C)O1] | 2-(2-(1H-1,2,4-triazol-5-yl)benzamido)-5,5,7,7-tetramethyl-5,7-dihydro-4H-thieno[2,3-c]pyran-3-carboxamide | A2 | Int 3 | 425 | 426 |

TABLE II-continued

List of final compounds

| Cpd # | Structure | Name | Mtd | Int | MW | Mes |
|---|---|---|---|---|---|---|
| 27 | 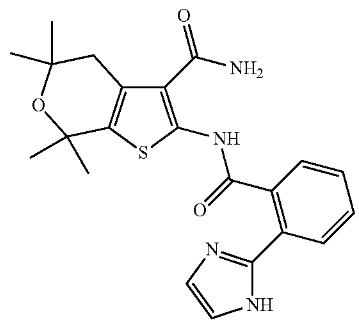 [SMILES: CC1(C)Cc2c(sc(NC(=O)c3ccccc3-c3ncc[nH]3)c2C(N)=O)C(C)(C)O1] | 2-(2-(1H-imidazol-2-yl)benzamido)-5,5,7,7-tetramethyl-5,7-dihydro-4H-thieno[2,3-c]pyran-3-carboxamide | A2 | Int 3 | 424 | 425 |
| 28 | 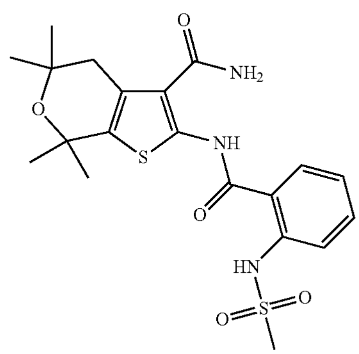 [SMILES: CC1(C)Cc2c(sc(NC(=O)c3ccccc3NS(C)(=O)=O)c2C(N)=O)C(C)(C)O1] | 5,5,7,7-tetramethyl-2-(2-(methylsulfonamido)benzamido)-5,7-dihydro-4H-thieno[2,3-c]pyran-3-carboxamide | A2 | Int 3 | 451 | 452 |
| 29 | 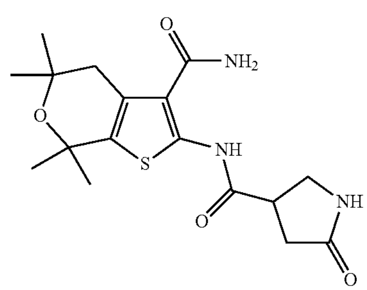 [SMILES: CC1(C)Cc2c(sc(NC(=O)C3CNC(=O)C3)c2C(N)=O)C(C)(C)O1] | N-(3-carbamoyl-5,5,7,7-tetramethyl-5,7-dihydro-4H-thieno[2,3-c]pyran-2-yl)-5-oxopyrrolidine-3-carboxamide | A2 | Int 3 | 365 | 366 |
| 30 | 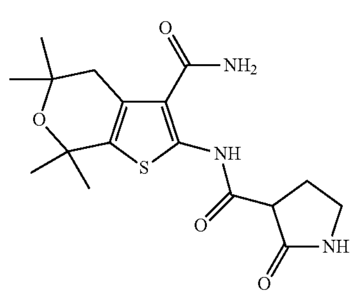 [SMILES: CC1(C)Cc2c(sc(NC(=O)C3CCNC3=O)c2C(N)=O)C(C)(C)O1] | N-(3-carbamoyl-5,5,7,7-tetramethyl-5,7-dihydro-4H-thieno[2,3-c]pyran-2-yl)-2-oxopyrrolidine-3-carboxamide | A2 | Int 3 | 365 | 366 |

TABLE II-continued

List of final compounds

| Cpd # | Structure | Name | Mtd | Int | MW | Mes |
|---|---|---|---|---|---|---|
| 31 | 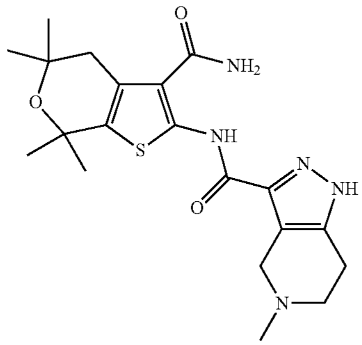 [SMILES: CN1CCc2[nH]nc(C(=O)Nc3sc4c(c3C(N)=O)CC(C)(C)OC4(C)C)c2C1] | N-(3-carbamoyl-5,5,7,7-tetramethyl-5,7-dihydro-4H-thieno[2,3-c]pyran-2-yl)-5-methyl-4,5,6,7-tetrahydro-1H-pyrazolo[4,3-c]pyridine-3-carboxamide | A2 | Int 3 | 418 | 419 |
| 32 | 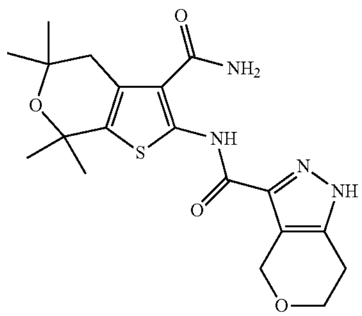 [SMILES: CC1(C)Cc2c(sc(NC(=O)c3n[nH]c4c3COCC4)c2C(N)=O)C(C)(C)O1] | N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide | A2 | Int 3 | 404 | 405 |
| 33 | 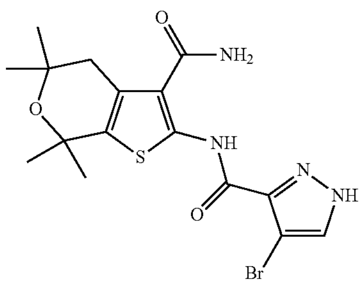 [SMILES: CC1(C)Cc2c(sc(NC(=O)c3n[nH]cc3Br)c2C(N)=O)C(C)(C)O1] | 4-bromo-N-(3-carbamoyl-5,5,7,7-tetramethyl-5,7-dihydro-4H-thieno[2,3-c]pyran-2-yl)-1H-pyrazole-3-carboxamide | A2 | Int 3 | 427 | 428 |
| 34 | 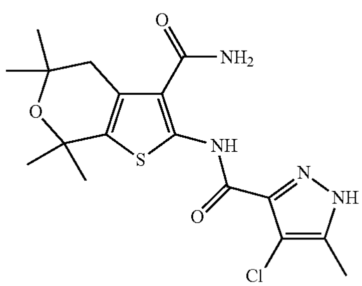 | N-(3-carbamoyl-5,5,7,7-tetramethyl-5,7-dihydro-4H-thieno[2,3-c]pyran-2-yl)-4-chloro-5-methyl-1H-pyrazole-3-carboxamide | A2 | Int 3 | 397 | 398 |
| 35 | 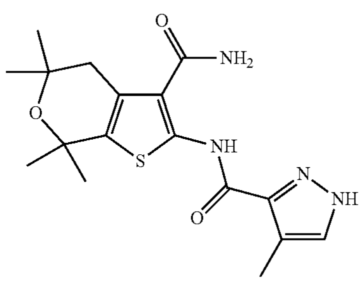 [SMILES: Cc1c[nH]nc1C(=O)Nc1sc2c(c1C(N)=O)CC(C)(C)OC2(C)C] | N-(3-carbamoyl-5,5,7,7-tetramethyl-5,7-dihydro-4H-thieno[2,3-c]pyran-2-yl)-4-methyl-1H-pyrazole-3-carboxamide | A2 | Int 3 | 362 | 363 |

TABLE II-continued

List of final compounds

| Cpd # | Structure | Name | Mtd | Int | MW | Mes |
|---|---|---|---|---|---|---|
| 36 | 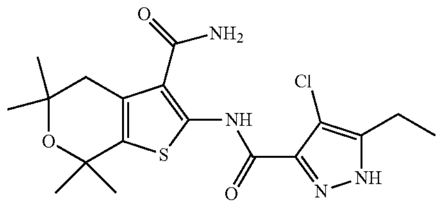 [SMILES: CCc1[nH]nc(C(=O)Nc2sc3c(c2C(N)=O)CC(C)(C)OC3(C)C)c1Cl] | N-(3-carbamoyl-5,5,7,7-tetramethyl-5,7-dihydro-4H-thieno[2,3-c]pyran-2-yl)-4-chloro-5-ethyl-1H-pyrazole-3-carboxamide | A2 | Int 3 | 411 | 412 |
| 37 | 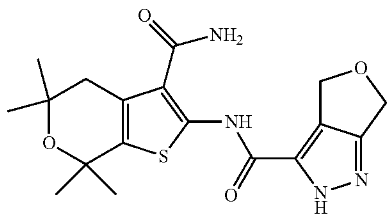 [SMILES: CC1(C)Cc2c(sc(NC(=O)c3[nH]nc4c3COC4)c2C(N)=O)C(C)(C)O1] | N-(3-carbamoyl-5,5,7,7-tetramethyl-5,7-dihydro-4H-thieno[2,3-c]pyran-2-yl)-4,6-dihydro-1H-furo[3,4-c]pyrazole-3-carboxamide | A2 | Int 3 | 390 | 391 |
| 38 | 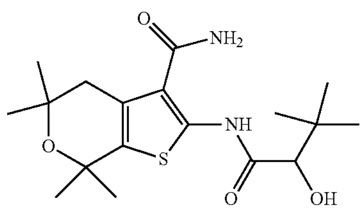 [SMILES: CC1(C)Cc2c(sc(NC(=O)C(O)C(C)(C)C)c2C(N)=O)C(C)(C)O1] | 2-(2-hydroxy-3,3-dimethylbutanamido)-5,5,7,7-tetramethyl-5,7-dihydro-4H-thieno[2,3-c]pyran-3-carboxamide | A2, E2 | Int 3 | 369 | 369 |
| 39 | 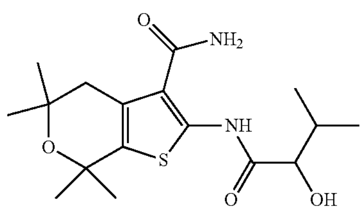 [SMILES: CC(C)C(O)C(=O)Nc1sc2c(c1C(N)=O)CC(C)(C)OC2(C)C] | 2-(2-hydroxy-3-methylbutanamido)-5,5,7,7-tetramethyl-5,7-dihydro-4H-thieno[2,3-c]pyran-3-carboxamide | A2, E2 | Int 3 | 354 | 355 |
| 40 | 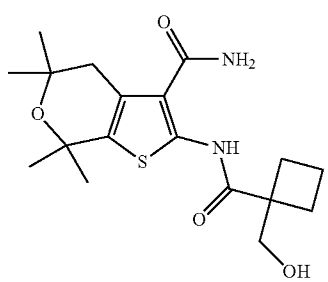 [SMILES: CC1(C)Cc2c(sc(NC(=O)C3(CO)CCC3)c2C(N)=O)C(C)(C)O1] | 2-(1-(hydroxymethyl)cyclobutanecarboxamido)-5,5,7,7-tetramethyl-5,7-dihydro-4H-thieno[2,3-c]pyran-3-carboxamide | C2, D2, A2, D4 | Int 3 | 366 | 367 |
| 41 | 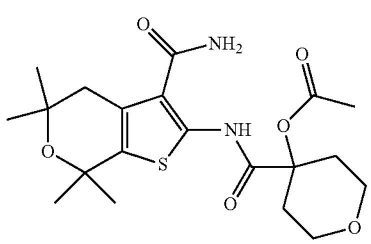 [SMILES: CC(=O)OC1(C(=O)Nc2sc3c(c2C(N)=O)CC(C)(C)OC3(C)C)CCOCC1] | 4-(3-carbamoyl-5,5,7,7-tetramethyl-5,7-dihydro-4H-thieno[2,3-c]pyran-2-ylcarbamoyl)tetrahydro-2H-pyran-4-yl acetate | C1, B, A2 | Int 3 | 424 | 425 |

TABLE II-continued

List of final compounds

| Cpd # | Structure | Name | Mtd | Int | MW | Mes |
|---|---|---|---|---|---|---|
| 42 | 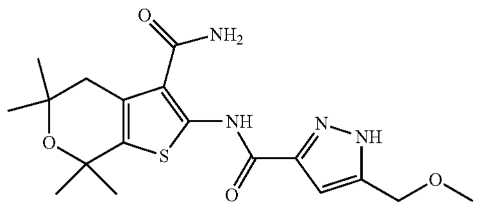 | N-(3-carbamoyl-5,5,7,7-tetramethyl-5,7-dihydro-4H-thieno[2,3-c]pyran-2-yl)-5-(methoxymethyl)-1H-pyrazole-3-carboxamide | D2, A2 | Int 3 | 392 | 393 |
| 43 | 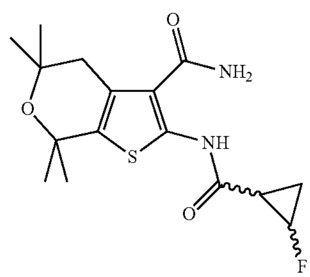 [SMILES: CC1(C)Cc2c(sc(NC(=O)C3CC3F)c2C(N)=O)C(C)(C)O1] | Cis-2-[[2-fluorocyclopropanecarbonyl]amino]-5,5,7,7-tetramethyl-4H-thieno[2,3-c]pyran-3-carboxamide Enantiomer 1 | A2 | Int 3 | 340 | 341 |
| 44 | 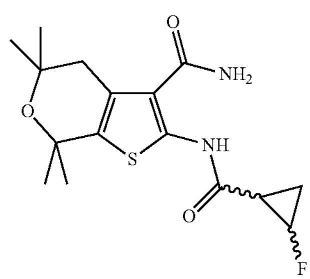 [SMILES: CC1(C)Cc2c(sc(NC(=O)C3CC3F)c2C(N)=O)C(C)(C)O1] | Cis-2-[[2-fluorocyclopropanecarbonyl]amino]-5,5,7,7-tetramethyl-4H-thieno[2,3-c]pyran-3-carboxamide Enantiomer 2 | A2 | Int 3 | 340 | 341 |
| 45 | 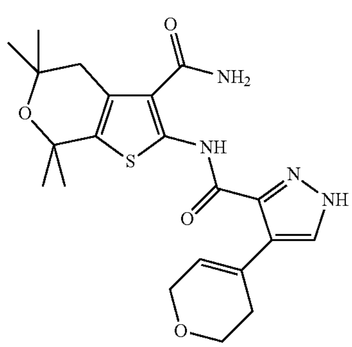 [SMILES: CC1(C)Cc2c(sc(NC(=O)c3n[nH]cc3C3=CCOCC3)c2C(N)=O)C(C)(C)O1] | N-(3-carbamoyl-5,5,7,7-tetramethyl-4H-thieno[2,3-c]pyran-2-yl)-4-(3,6-dihydro-2H-pyran-4-yl)-1H-pyrazole-3-carboxamide | A2, D2, F1 | Int 3, Int 4 | 431 | 431 |
| 46 | 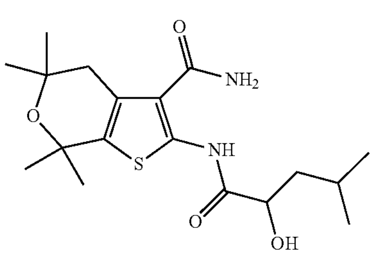 [SMILES: CC(C)CC(O)C(=O)Nc1sc2c(c1C(N)=O)CC(C)(C)OC2(C)C] | 2-[(2-hydroxy-4-methyl-pentanoyl)amino]-5,5,7,7-tetramethyl-4H-thieno[2,3-c]pyran-3-carboxamide | A2, E2 | Int 3 | 369 | 369 |

TABLE II-continued

List of final compounds

| Cpd # | Structure | Name | Mtd | Int | MW | Mes |
|---|---|---|---|---|---|---|
| 47 | 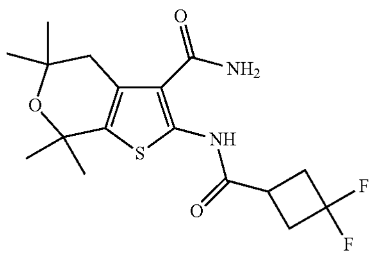 [SMILES: CC1(C)Cc2c(sc(NC(=O)C3CC(F)(F)C3)c2C(N)=O)C(C)(C)O1] | 2-[(3,3-difluorocyclobutanecarbonyl)amino]-5,5,7,7-tetramethyl-4H-thieno[2,3-c]pyran-3-carboxamide | A2 | Int 3 | 372 | 373 |
| 48 | 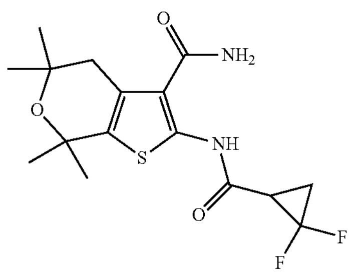 [SMILES: CC1(C)Cc2c(sc(NC(=O)C3CC3(F)F)c2C(N)=O)C(C)(C)O1] | 2-[(2,2-difluorocyclopropanecarbonyl)amino]-5,5,7,7-tetramethyl-4H-thieno[2,3-c]pyran-3-carboxamide | A2 | Int 3 | 358 | 359 |
| 49 | 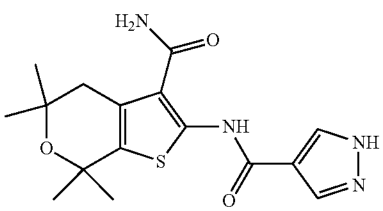 [SMILES: CC1(C)Cc2c(sc(NC(=O)c3cn[nH]c3)c2C(N)=O)C(C)(C)O1] | N-(3-carbamoyl-5,5,7,7-tetramethyl-4H-thieno[2,3-c]pyran-2-yl)-1H-pyrazole-4-carboxamide | D5, A2, D2, C3 | Int 3 | 348 | 349 |
| 50 | 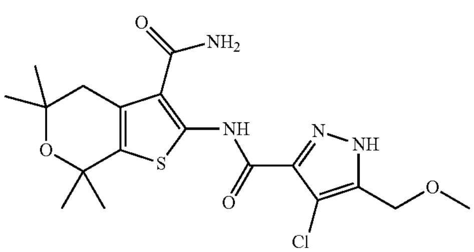 | N-(3-carbamoyl-5,5,7,7-tetramethyl-4H-thieno[2,3-c]pyran-2-yl)-4-chloro-5-(methoxymethyl)-1H-pyrazole-3-carboxamide | I1, A2 | Int 3 | 427 | 427 |
| 51 | 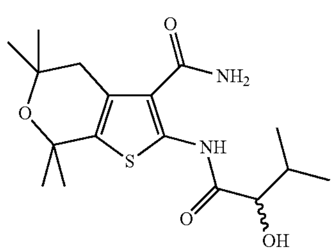 [SMILES: CC(C)C(O)C(=O)Nc1sc2c(c1C(N)=O)CC(C)(C)OC2(C)C] | 2-[[2-hydroxy-3-methyl-butanoyl]amino]-5,5,7,7-tetramethyl-4H-thieno[2,3-c]pyran-3-carboxamide Enantiomer 1 | A2, E2 | Int 3 | 354 | 338 |
| 52 | 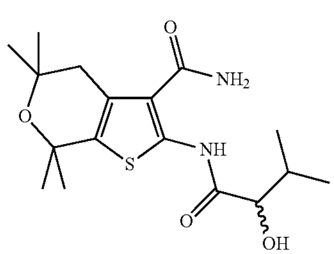 [SMILES: CC(C)C(O)C(=O)Nc1sc2c(c1C(N)=O)CC(C)(C)OC2(C)C] | 2-[[2-hydroxy-3-methyl-butanoyl]amino]-5,5,7,7-tetramethyl-4H-thieno[2,3-c]pyran-3-carboxamide Enantiomer 2 | A2, E2 | Int 3 | 354 | 338 |

TABLE II-continued

List of final compounds

| Cpd # | Structure | Name | Mtd | Int | MW | Mes |
|---|---|---|---|---|---|---|
| 53 | 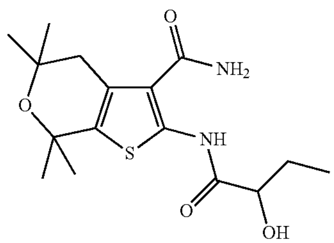 [SMILES: CCC(O)C(=O)Nc1sc2c(c1C(N)=O)CC(C)(C)OC2(C)C] | 2-(2-hydroxybutanoylamino)-5,5,7,7-tetramethyl-4H-thieno[2,3-c]pyran-3-carboxamide | A2, E2 | Int 3 | 340 | 324 |
| 54 | 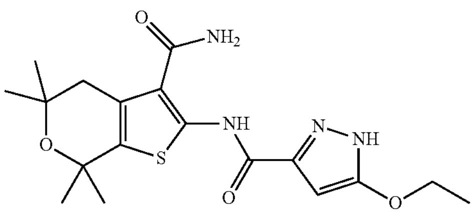 [SMILES: CCOc1cc(C(=O)Nc2sc3c(c2C(N)=O)CC(C)(C)OC3(C)C)n[nH]1] | 5-Ethoxy-1H-pyrazole-3-carboxylic acid (3-carbamoyl-5,5,7,7-tetramethyl-4,7-dihydro-5H-thieno[2,3-c]pyran-2-yl)-amide | D2, A2 | Int 3, Int 10 | 392 | 393 |
| 55 | 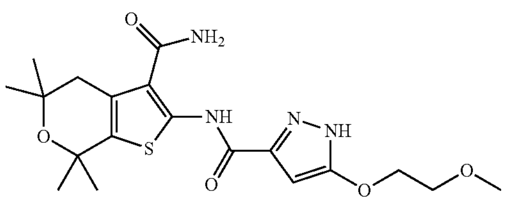 | 5-(2-Methoxy-ethoxy)-1H-pyrazole-3-carboxylic acid (3-carbamoyl-5,5,7,7-tetramethyl-4,7-dihydro-5H-thieno[2,3-c]pyran-2-yl)-amide | H1, D2, A2 | Int 3, Int 9 | 423 | 423 |
| 56 | 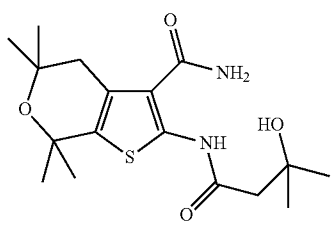 [SMILES: CC(C)(O)CC(=O)Nc1sc2c(c1C(N)=O)CC(C)(C)OC2(C)C] | 2-[(3-hydroxy-3-methyl-butanoyl)amino]-5,5,7,7-tetramethyl-4H-thieno[2,3-c]pyran-3-carboxamide | C2, A2, D4 | Int 3 | 354 | 338 |
| 57 | 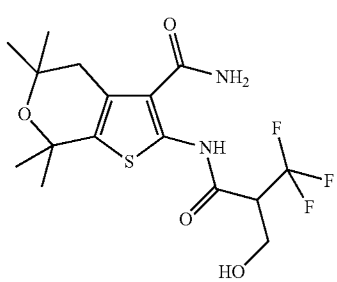 [SMILES: CC1(C)Cc2c(sc(NC(=O)C(CO)C(F)(F)F)c2C(N)=O)C(C)(C)O1] | 5,5,7,7-tetramethyl-2-[[3,3,3-trifluoro-2-(hydroxymethyl)propanoyl]amino]-4H-thieno[2,3-c]pyran-3-carboxamide | C2, A2, D4 | Int 3 | 394 | 395 |
| 58 | 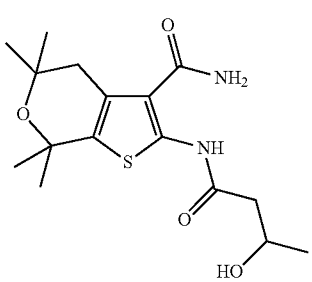 [SMILES: CC(O)CC(=O)Nc1sc2c(c1C(N)=O)CC(C)(C)OC2(C)C] | 2-(3-hydroxybutanoylamino)-5,5,7,7-tetramethyl-4H-thieno[2,3-c]pyran-3-carboxamide | C2, A2, D4 | Int 3 | 340 | 324 |

TABLE II-continued

List of final compounds

| Cpd # | Structure | Name | Mtd | Int | MW | Mes |
|---|---|---|---|---|---|---|
| 59 | 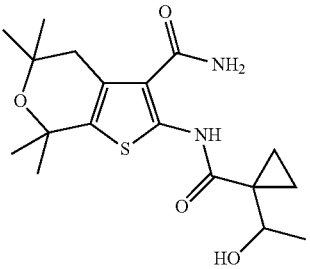 [SMILES: CC(O)C1(C(=O)Nc2sc3c(c2C(N)=O)CC(C)(C)OC3(C)C)CC1] | 2-[[1-(1-hydroxyethyl)cyclopropanecarbonyl]amino]-5,5,7,7-tetramethyl-4H-thieno[2,3-c]pyran-3-carboxamide | A2, E2 | Int 3 | 366 | 350 |
| 60 | 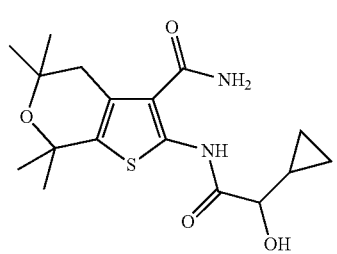 [SMILES: CC1(C)Cc2c(sc(NC(=O)C(O)C3CC3)c2C(N)=O)C(C)(C)O1] | 2-[(2-cyclopropyl-2-hydroxy-acetyl)amino]-5,5,7,7-tetramethyl-4H-thieno[2,3-c]pyran-3-carboxamide | C2, A2, D4 | Int 3 | 352 | 336 |
| 61 | 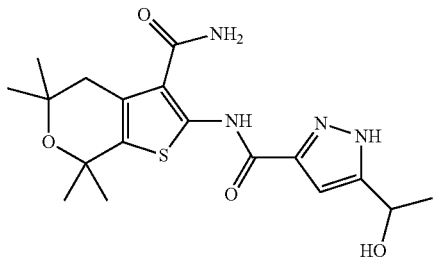 [SMILES: CC(O)c1cc(C(=O)Nc2sc3c(c2C(N)=O)CC(C)(C)OC3(C)C)n[nH]1] | 5-(1-Hydroxy-ethyl)-1H-pyrazole-3-carboxylic acid (3-carbamoyl-5,5,7,7-tetramethyl-4,7-dihydro-5H-thieno[2,3-c]pyran-2-yl)-amide | D2, A2, E2 | Int 3, Int 7 | 392 | 393 |
| 62 | 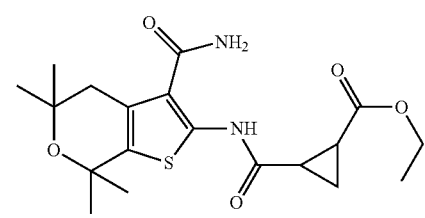 [SMILES: CCOC(=O)C1CC1C(=O)Nc1sc2c(c1C(N)=O)CC(C)(C)OC2(C)C] | 2-(3-Carbamoyl-5,5,7,7-tetramethyl-4,7-dihydro-5H-thieno[2,3-c]pyran-2-ylcarbamoyl)-cyclopropanecarboxylic acid ethyl ester | A2 | Int 3 | 394 | 395 |
| 63 | 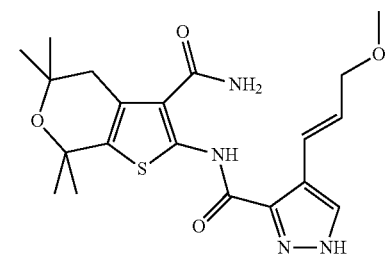 | N-(3-carbamoyl-5,5,7,7-tetramethyl-4H-thieno[2,3-c]pyran-2-yl)-4-[(E)-3-methoxyprop-1-enyl]-1H-pyrazole-3-carboxamide | D5, A2, D2, F1, C3 | Int 3, Int 4 | 419 | 419 |
| 64 | 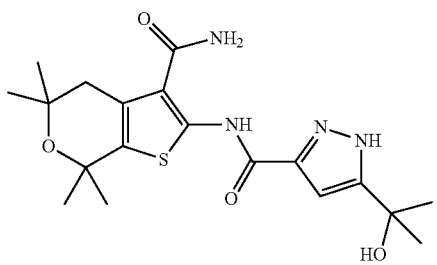 | N-(3-carbamoyl-5,5,7,7-tetramethyl-4H-thieno[2,3-c]pyran-2-yl)-5-(1-hydroxy-1-methyl-ethyl)-1H-pyrazole-3-carboxamide | D2, A2, G1 | Int 3, Int 7 | 407 | 407 |

TABLE II-continued

List of final compounds

| Cpd # | Structure | Name | Mtd | Int | MW | Mes |
|---|---|---|---|---|---|---|
| 65 | 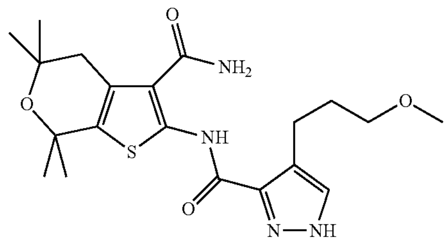 | N-(3-carbamoyl-5,5,7,7-tetramethyl-4H-thieno[2,3-c]pyran-2-yl)-4-(3-methoxypropyl)-1H-pyrazole-3-carboxamide | D5, E3, A2, D2, F1, C3 | Int 3, Int 4 | 421 | 421 |
| 66 | 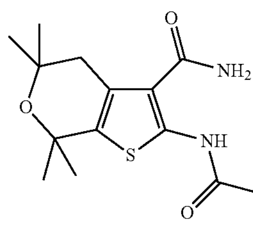 | 2-[(2-hydroxyacetyl)amino]-5,5,7,7-tetramethyl-4H-thieno[2,3-c]pyran-3-carboxamide | A1, D2 | Int 3 | 312 | 296 |
| 67 | 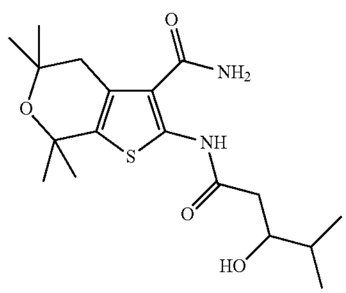 [SMILES: CC(C)C(O)CC(=O)Nc1sc2c(c1C(N)=O)CC(C)(C)OC2(C)C] | 2-[(3-hydroxy-4-methyl-pentanoyl)amino]-5,5,7,7-tetramethyl-4H-thieno[2,3-c]pyran-3-carboxamide | A4, E2 | Int 3 | 369 | 352 |
| 68 | 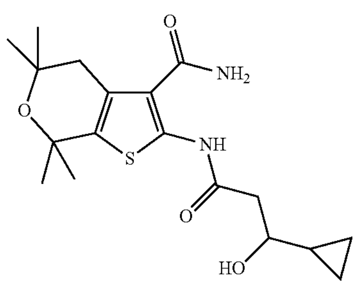 [SMILES: CC1(C)Cc2c(sc(NC(=O)CC(O)C3CC3)c2C(N)=O)C(C)(C)O1] | 2-[(3-cyclopropyl-3-hydroxy-propanoyl)amino]-5,5,7,7-tetramethyl-4H-thieno[2,3-c]pyran-3-carboxamide | A4, E2 | Int 3 | 366 | 350 |
| 69 | 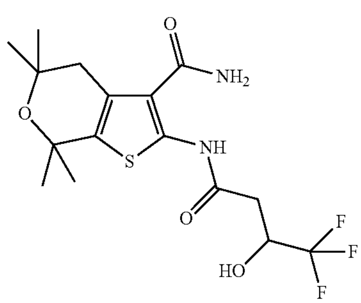 [SMILES: CC1(C)Cc2c(sc(NC(=O)CC(O)C(F)(F)F)c2C(N)=O)C(C)(C)O1] | 5,5,7,7-tetramethyl-2-[(4,4,4-trifluoro-3-hydroxy-butanoyl)amino]-4H-thieno[2,3-c]pyran-3-carboxamide | A4, E2 | Int 3 | 394 | 378 |

TABLE II-continued

List of final compounds

| Cpd # | Structure | Name | Mtd | Int | MW | Mes |
|---|---|---|---|---|---|---|
| 70 | 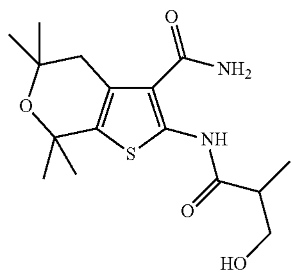 [SMILES: CC(CO)C(=O)Nc1sc2c(c1C(N)=O)CC(C)(C)OC2(C)C] | 2-[(3-hydroxy-2-methyl-propanoyl)amino]-5,5,7,7-tetramethyl-4H-thieno[2,3-c]pyran-3-carboxamide | C2, A2, D4 | Int 3 | 340 | 324 |
| 71 | 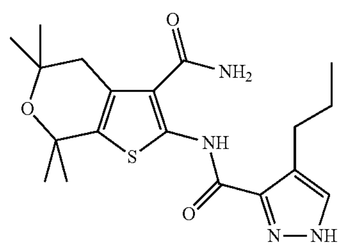 [SMILES: CCCc1c[nH]nc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-4-propyl-1H-pyrazole-3-carboxamide | D5, E3, A2, D2, F1, C3 | Int 3, Int 4 | 391 | 391 |
| 72 | 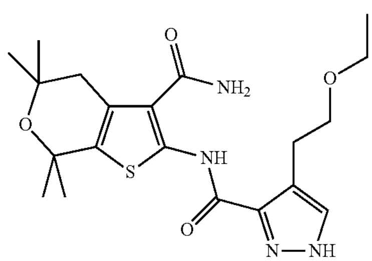 [SMILES: CCOCCc1c[nH]nc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-4-(2-ethoxyethyl)-1H-pyrazole-3-carboxamide | D5, E3, A2, D2, F1, C3 | Int 3, Int 4 | 421 | 421 |
| 73 | 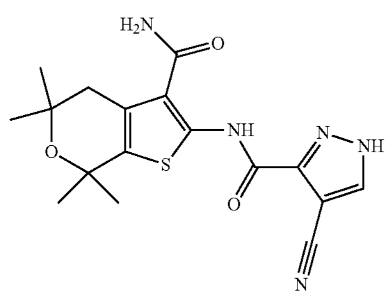 [SMILES: CC1(C)Cc2c(sc(NC(=O)c3n[nH]cc3C#N)c2C(N)=O)C(C)(C)O1] | N-(3-carbamoyl-5,5,7,7-tetramethyl-4H-thieno[2,3-c]pyran-2-yl)-4-cyano-1H-pyrazole-3-carboxamide | A2 | Int 3 | 373 | 374 |
| 74 | 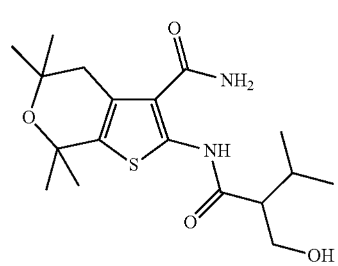 [SMILES: CC(C)C(CO)C(=O)Nc1sc2c(c1C(N)=O)CC(C)(C)OC2(C)C] | 2-[[2-(hydroxymethyl)-3-methyl-butanoyl]amino]-5,5,7,7-tetramethyl-4H-thieno[2,3-c]pyran-3-carboxamide | A4, E1 | Int 3 | 369 | 352 |

TABLE II-continued

List of final compounds

| Cpd # | Structure | Name | Mtd | Int | MW | Mes |
|---|---|---|---|---|---|---|
| 75 | 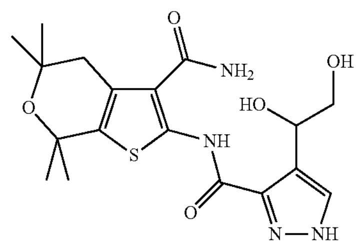 [SMILES: CC1(C)Cc2c(sc(NC(=O)c3n[nH]cc3C(O)CO)c2C(N)=O)C(C)(C)O1] | N-(3-carbamoyl-5,5,7,7-tetramethyl-4H-thieno[2,3-c]pyran-2-yl)-4-(1,2-dihydroxyethyl)-1H-pyrazole-3-carboxamide | J1, D5, A2, D2, F1, C3 | Int 3, Int 4 | 408 | 409 |
| 76 | 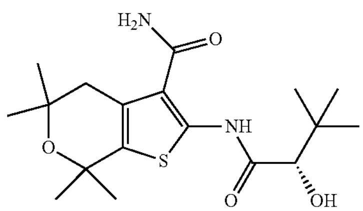 [SMILES: CC1(C)Cc2c(sc(NC(=O)[C@@H](O)C(C)(C)C)c2C(N)=O)C(C)(C)O1] | 2-[[(2S)-2-hydroxy-3,3-dimethyl-butanoyl]amino]-5,5,7,7-tetramethyl-4H-thieno[2,3-c]pyran-3-carboxamide | A2, E2 | Int 3 | 369 | 369 |
| 77 | 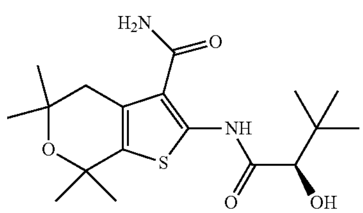 [SMILES: CC1(C)Cc2c(sc(NC(=O)[C@H](O)C(C)(C)C)c2C(N)=O)C(C)(C)O1] | 2-[[(2R)-2-hydroxy-3,3-dimethyl-butanoyl]amino]-5,5,7,7-tetramethyl-4H-thieno[2,3-c]pyran-3-carboxamide | A2, E2 | Int 3 | 369 | 369 |
| 78 | 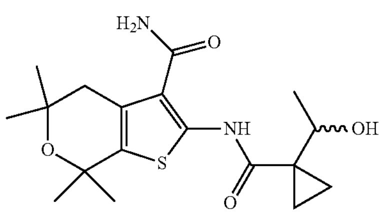 [SMILES: CC(O)C1(C(=O)Nc2sc3c(c2C(N)=O)CC(C)(C)OC3(C)C)CC1] | 2-[[1-[1-hydroxyethyl]cyclopropanecarbonyl]amino]-5,5,7,7-tetramethyl-4H-thieno[2,3-c]pyran-3-carboxamide | A2, E2 | Int 3 | 366 | 366 |
| 79 | 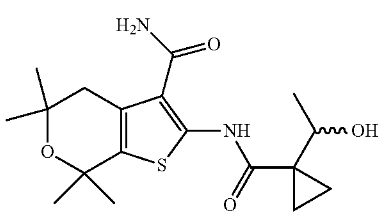 [SMILES: CC(O)C1(C(=O)Nc2sc3c(c2C(N)=O)CC(C)(C)OC3(C)C)CC1] | 2-[[1-[1-hydroxyethyl]cyclopropanecarbonyl]amino]-5,5,7,7-tetramethyl-4H-thieno[2,3-c]pyran-3-carboxamide | A2, E2 | Int 3 | 348 | 348 |
| 80 | 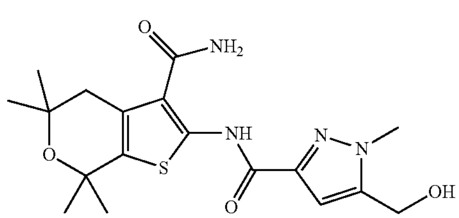 [SMILES: Cn1nc(C(=O)Nc2sc3c(c2C(N)=O)CC(C)(C)OC3(C)C)cc1CO] | N-(3-carbamoyl-5,5,7,7-tetramethyl-4H-thieno[2,3-c]pyran-2-yl)-5-(hydroxymethyl)-1-methyl-pyrazole-3-carboxamide | C4, D2, A2, D6 | Int 3 | 392 | 393 |
| 81 | 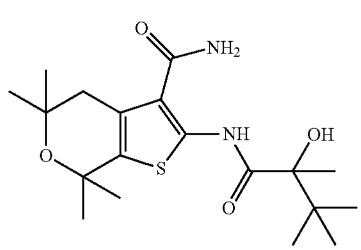 [SMILES: CC1(C)Cc2c(sc(NC(=O)C(C)(O)C(C)(C)C)c2C(N)=O)C(C)(C)O1] | 2-[(2-hydroxy-2,3,3-trimethyl-butanoyl)amino]-5,5,7,7-tetramethyl-4H-thieno[2,3-c]pyran-3-carboxamide | A2, G1 | Int 3 | 383 | 383 |

TABLE II-continued

List of final compounds

| Cpd # | Structure | Name | Mtd | Int | MW | Mes |
|---|---|---|---|---|---|---|
| 82 | 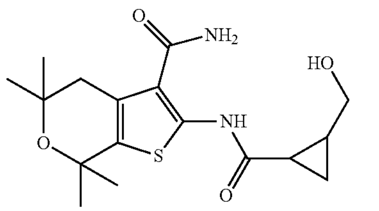 [SMILES: CC1(C)Cc2c(sc(NC(=O)C3CC3CO)c2C(N)=O)C(C)(C)O1] | 2-[[2-(hydroxymethyl)cyclopropanecarbonyl]amino]-5,5,7,7-tetramethyl-4H-thieno[2,3-c]pyran-3-carboxamide | A2, E1 | Int 3 | 352 | 353 |
| 83 | 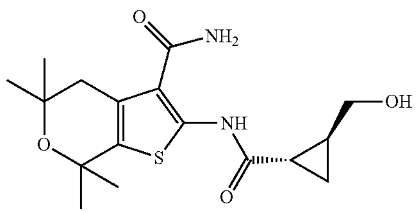 [SMILES: CC1(C)Cc2c(sc(NC(=O)[C@H]3C[C@@H]3CO)c2C(N)=O)C(C)(C)O1] | 2-[[(1S,2S)-2-(hydroxymethyl)cyclopropanecarbonyl]amino]-5,5,7,7-tetramethyl-4H-thieno[2,3-c]pyran-3-carboxamide | A2, D2 | Int 3 | 352 | 353 |
| 84 | 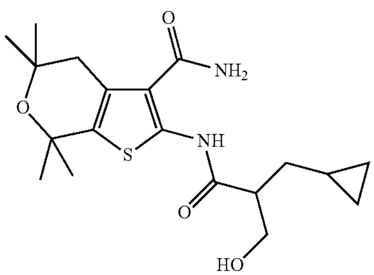 [SMILES: CC1(C)Cc2c(sc(NC(=O)C(CO)CC3CC3)c2C(N)=O)C(C)(C)O1] | 2-[[2-(cyclopropylmethyl)-3-hydroxy-propanoyl]amino]-5,5,7,7-tetramethyl-4H-thieno[2,3-c]pyran-3-carboxamide | H2, A4, E1 | Int 3 | 381 | 364 |
| 85 | 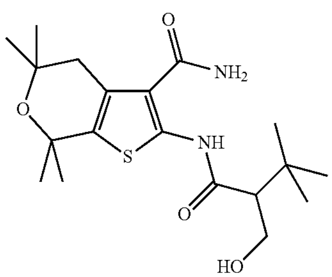 [SMILES: CC1(C)Cc2c(sc(NC(=O)C(CO)C(C)(C)C)c2C(N)=O)C(C)(C)O1] | 2-[[2-(hydroxymethyl)-3,3-dimethyl-butanoyl]amino]-5,5,7,7-tetramethyl-4H-thieno[2,3-c]pyran-3-carboxamide | D2, A2, E1 | Int 3 | 383 | 383 |
| 86 | 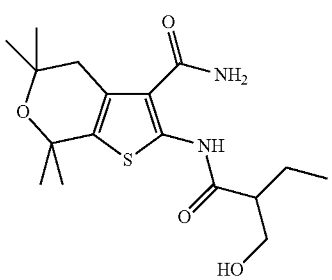 [SMILES: CCC(CO)C(=O)Nc1sc2c(c1C(N)=O)CC(C)(C)OC2(C)C] | 2-[2-(hydroxymethyl)butanoylamino]-5,5,7,7-tetramethyl-4H-thieno[2,3-c]pyran-3-carboxamide | A4, E1 | Int 3 | 354 | 338 |
| 87 | 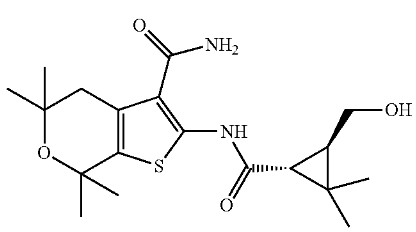 [SMILES: CC1(C)Cc2c(sc(NC(=O)[C@@H]3[C@@H](CO)C3(C)C)c2C(N)=O)C(C)(C)O1] | 2-[[(1R,3R)-3-(hydroxymethyl)-2,2-dimethyl-cyclopropanecarbonyl]amino]-5,5,7,7-tetramethyl-4H-thieno[2,3-c]pyran-3-carboxamide | A2, D2 | Int 3 | 381 | 381 |

TABLE II-continued

List of final compounds

| Cpd # | Structure | Name | Mtd | Int | MW | Mes |
|---|---|---|---|---|---|---|
| 88 | 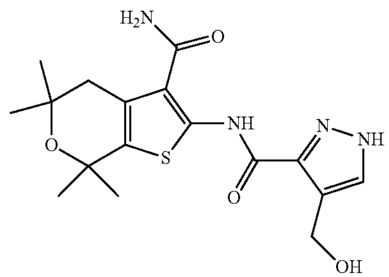 [SMILES: CC1(C)Cc2c(sc(NC(=O)c3n[nH]cc3CO)c2C(N)=O)C(C)(C)O1] | N-(3-carbamoyl-5,5,7,7-tetramethyl-4H-thieno[2,3-c]pyran-2-yl)-4-(hydroxymethyl)-1H-pyrazole-3-carboxamide | E2, E4, A2 | Int 3 | 378 | 379 |
| 89 | 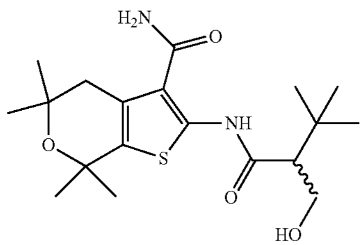 [SMILES: CC1(C)Cc2c(sc(NC(=O)C(CO)C(C)(C)C)c2C(N)=O)C(C)(C)O1] | 2-[[2-(hydroxymethyl)-3,3-dimethyl-butanoyl]amino]-5,5,7,7-tetramethyl-4H-thieno[2,3-c]pyran-3-carboxamide | D2, A2, E1 | Int 3 | 383 | 383 |
| 90 | 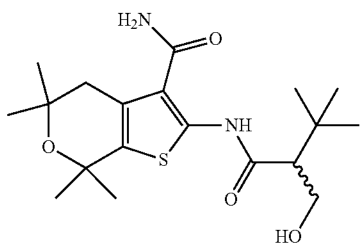 [SMILES: CC1(C)Cc2c(sc(NC(=O)C(CO)C(C)(C)C)c2C(N)=O)C(C)(C)O1] | 2-[[2-(hydroxymethyl)-3,3-dimethyl-butanoyl]amino]-5,5,7,7-tetramethyl-4H-thieno[2,3-c]pyran-3-carboxamide | D2, A2, E1 | Int 3 | 383 | 383 |
| 91 | 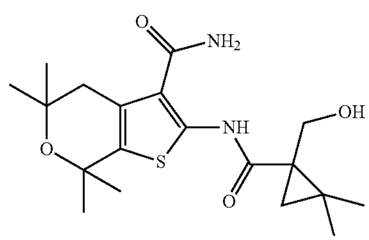 | 2-[[1-(hydroxymethyl)-2,2-dimethyl-cyclopropanecarbonyl]amino]-5,5,7,7-tetramethyl-4H-thieno[2,3-c]pyran-3-carboxamide | A2, E1 | Int 3 | 381 | 381 |
| 92 | 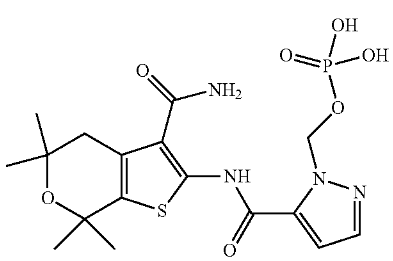 [SMILES: CC1(C)Cc2c(sc(NC(=O)c3ccnn3COP(=O)(O)O)c2C(N)=O)C(C)(C)O1] | [5-[(3-carbamoyl-5,5,7,7-tetramethyl-4H-thieno[2,3-c]pyran-2-yl)carbamoyl]pyrazol-1-yl]methyl dihydrogen phosphate | H3, D7, A2, D8 | Int 3 | 458 | 459 |
| 93 | 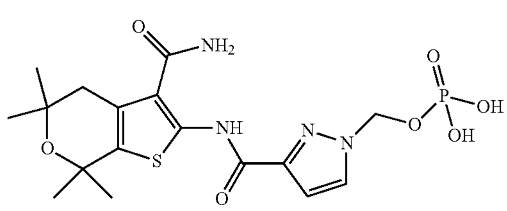 [SMILES: CC1(C)Cc2c(sc(NC(=O)c3ccn(COP(=O)(O)O)n3)c2C(N)=O)C(C)(C)O1] | [3-[(3-carbamoyl-5,5,7,7-tetramethyl-4H-thieno[2,3-c]pyran-2-yl)carbamoyl]pyrazol-1-yl]methyl dihydrogen phosphate | H3, D7, A2, D8 | Int 3 | 458 | 459 |

TABLE II-continued

List of final compounds

| Cpd # | Structure | Name | Mtd | Int | MW | Mes |
|---|---|---|---|---|---|---|
| 94 | 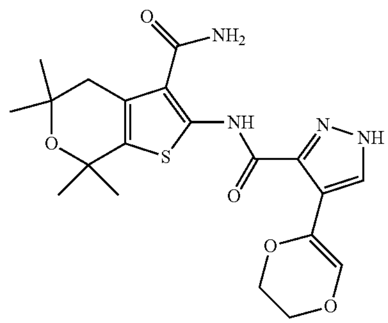 [SMILES: CC1(C)Cc2c(sc(NC(=O)c3n[nH]cc3C3=COCCO3)c2C(N)=O)C(C)(C)O1] | N-(3-carbamoyl-5,5,7,7-tetramethyl-4H-thieno[2,3-c]pyran-2-yl)-4-(2,3-dihydro-1,4-dioxin-5-yl)-1H-pyrazole-3-carboxamide | F1, D2, A2 | Int 3 | 432 | 433 |
| 95 | 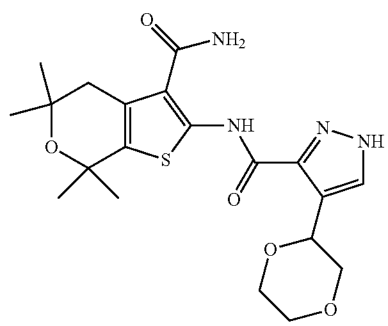 [SMILES: CC1(C)Cc2c(sc(NC(=O)c3n[nH]cc3C3COCCO3)c2C(N)=O)C(C)(C)O1] | N-(3-carbamoyl-5,5,7,7-tetramethyl-4H-thieno[2,3-c]pyran-2-yl)-4-(1,4-dioxan-2-yl)-1H-pyrazole-3-carboxamide | F1, D2, A2, E3 | Int 3 | 434 | 435 |
| 96 | 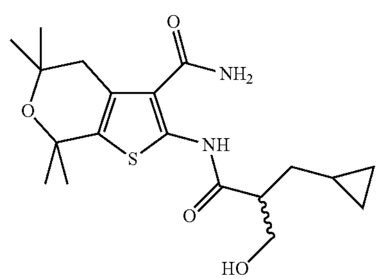 [SMILES: CC1(C)Cc2c(sc(NC(=O)C(CO)CC3CC3)c2C(N)=O)C(C)(C)O1] | 2-[[2-(cyclopropylmethyl)-3-hydroxy-propanoyl]amino]-5,5,7,7-tetramethyl-4H-thieno[2,3-c]pyran-3-carboxamide, enantiomer 1 | A4, E1, chir sep | Int 3 | 381 | 381 |
| 97 | 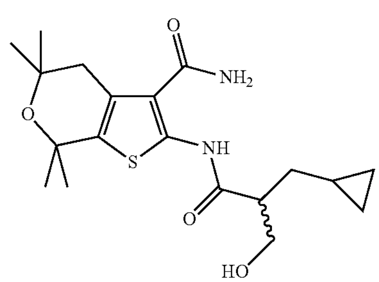 [SMILES: CC1(C)Cc2c(sc(NC(=O)C(CO)CC3CC3)c2C(N)=O)C(C)(C)O1] | 2-[[2-(cyclopropylmethyl)-3-hydroxy-propanoyl]amino]-5,5,7,7-tetramethyl-4H-thieno[2,3-c]pyran-3-carboxamide, enantiomer 2 | A4, E1, chir sep | Int 3 | 381 | 381 |
| 98 | 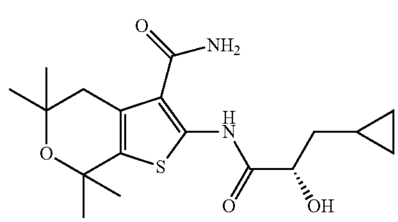 [SMILES: CC1(C)Cc2c(sc(NC(=O)[C@@H](O)CC3CC3)c2C(N)=O)C(C)(C)O1] | 2-[[(2S)-3-cyclopropyl-2-hydroxy-propanoyl]amino]-5,5,7,7-tetramethyl-4H-thieno[2,3-c]pyran-3-carboxamide | C1, A2, D2 | Int 3 | 366 | 367 |

TABLE II-continued

List of final compounds

| Cpd # | Structure | Name | Mtd | Int | MW | Mes |
|---|---|---|---|---|---|---|
| 99 | 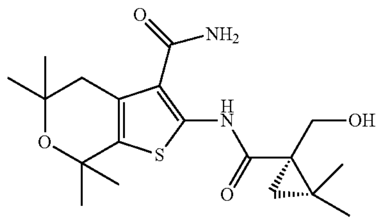 | 2-[[(1R)-1-(hydroxymethyl)-2,2-dimethyl-cyclopropanecarbonyl]amino]-5,5,7,7-tetramethyl-4H-thieno[2,3-c]pyran-3-carboxamide | D2, A2, E1, chir sep | Int 3 | 381 | 381 |
| 100 | 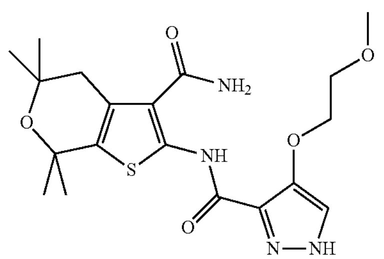 | N-(3-carbamoyl-5,5,7,7-tetramethyl-4H-thieno[2,3-c]pyran-2-yl)-4-(2-methoxyethoxy)-1H-pyrazole-3-carboxamide | C3, F2, A2, D5 | Int 3, Int 4 | 423 | 423 |
| 101 | 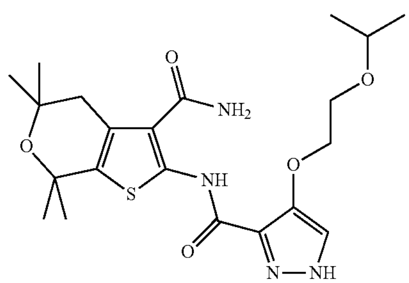 [SMILES: CC(C)OCCOc1c[nH]nc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-4-(2-isopropoxyethoxy)-1H-pyrazole-3-carboxamide | C3, F2, A2, D5 | Int 3, Int 4 | 451 | 451 |
| 102 | 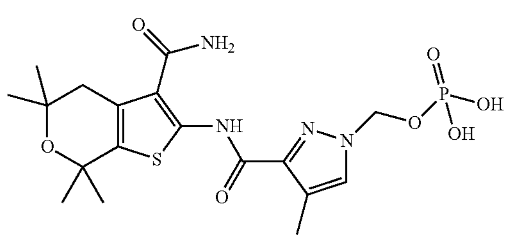 [SMILES: Cc1cn(COP(=O)(O)O)nc1C(=O)Nc1sc2c(c1C(N)=O)CC(C)(C)OC2(C)C] | [3-[(3-carbamoyl-5,5,7,7-tetramethyl-4H-thieno[2,3-c]pyran-2-yl)carbamoyl]-4-methyl-pyrazol-1-yl]methyl dihydrogen phosphate | A2, D7, D8, H3 | Int 3 | 472 | 473 |
| 103 | 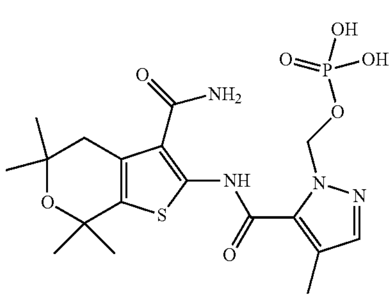 [SMILES: Cc1cnn(COP(=O)(O)O)c1C(=O)Nc1sc2c(c1C(N)=O)CC(C)(C)OC2(C)C] | [5-[(3-carbamoyl-5,5,7,7-tetramethyl-4H-thieno[2,3-c]pyran-2-yl)carbamoyl]-4-methyl-pyrazol-1-yl]methyl dihydrogen phosphate | A2, D7, D8, H3 | Int 3 | 472 | 473 |

TABLE II-continued

List of final compounds

| Cpd # | Structure | Name | Mtd | Int | MW | Mes |
|---|---|---|---|---|---|---|
| 104 | 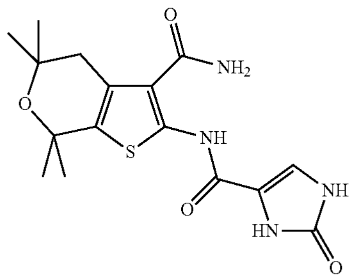 [SMILES: CC1(C)Cc2c(sc(NC(=O)c3c[nH]c(=O)[nH]3)c2C(N)=O)C(C)(C)O1] | N-(3-carbamoyl-5,5,7,7-tetramethyl-4H-thieno[2,3-c]pyran-2-yl)-2-oxo-1,3-dihydroimidazole-4-carboxamide | B2, A1 | Int 3 | 364 | 365 |
| 105 | 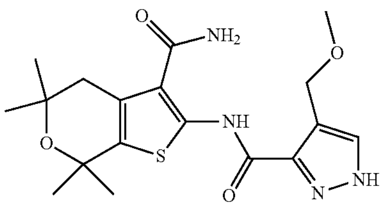 [SMILES: COCc1c[nH]nc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-4-(methoxymethyl)-1H-pyrazole-3-carboxamide | A2, C3, D10, E5, H4, F3 | Int 3 | 392 | 393 |
| 106 | 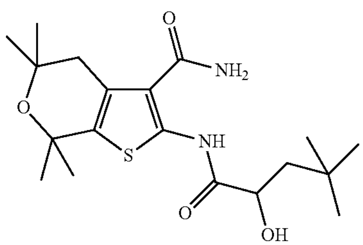 [SMILES: CC(C)(C)CC(O)C(=O)Nc1sc2c(c1C(N)=O)CC(C)(C)OC2(C)C] | 2-[(2-hydroxy-4,4-dimethyl-pentanoyl)amino]-5,5,7,7-tetramethyl-4H-thieno[2,3-c]pyran-3-carboxamide | A2, E2 | Int 3 | 383 | 383 |
| 107 | 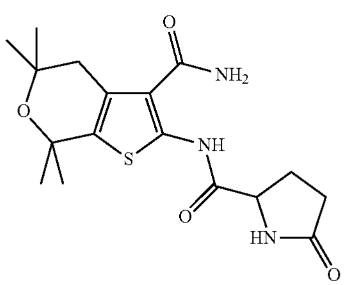 [SMILES: CC1(C)Cc2c(sc(NC(=O)C3CCC(=O)N3)c2C(N)=O)C(C)(C)O1] | N-(3-carbamoyl-5,5,7,7-tetramethyl-4H-thieno[2,3-c]pyran-2-yl)-5-oxo-pyrrolidine-2-carboxamide | A2 | Int 3 | 365 | 366 |
| 108 | 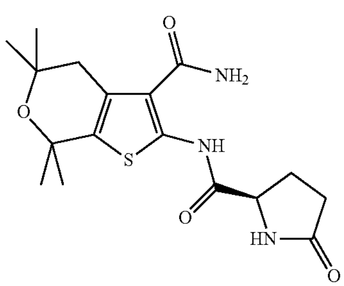 [SMILES: CC1(C)Cc2c(sc(NC(=O)[C@H]3CCC(=O)N3)c2C(N)=O)C(C)(C)O1] | (2R)-N-(3-carbamoyl-5,5,7,7-tetramethyl-4H-thieno[2,3-c]pyran-2-yl)-5-oxo-pyrrolidine-2-carboxamide | A2 | Int 3 | 365 | 366 |
| 109 | 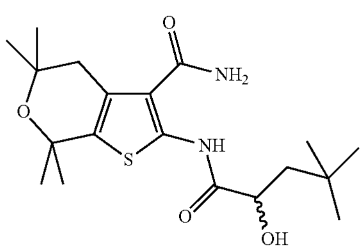 [SMILES: CC(C)(C)CC(O)C(=O)Nc1sc2c(c1C(N)=O)CC(C)(C)OC2(C)C] | 2-[[2-hydroxy-4,4-dimethyl-pentanoyl]amino]-5,5,7,7-tetramethyl-4H-thieno[2,3-c]pyran-3-carboxamide, enantiomer 1 | A2, E2, Chir sep | Int 3 | 383 | 383 |

TABLE II-continued

List of final compounds

| Cpd # | Structure | Name | Mtd | Int | MW | Mes |
|---|---|---|---|---|---|---|
| 110 | 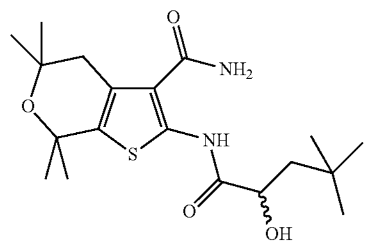 [SMILES: CC(C)(C)CC(O)C(=O)Nc1sc2c(c1C(N)=O)CC(C)(C)OC2(C)C] | 2-[[2-hydroxy-4,4-dimethyl-pentanoyl]amino]-5,5,7,7-tetramethyl-4H-thieno[2,3-c]pyran-3-carboxamide, enantiomer 2 | A2, E2, Chir sep | Int 3 | 383 | 383 |
| 111 | 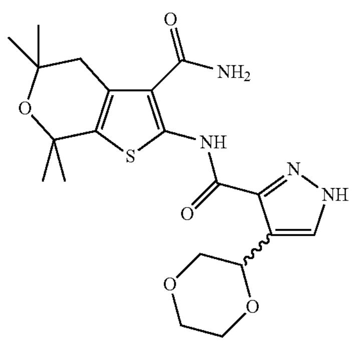 [SMILES: CC1(C)Cc2c(sc(NC(=O)c3n[nH]cc3C3COCCO3)c2C(N)=O)C(C)(C)O1] | N-(3-carbamoyl-5,5,7,7-tetramethyl-4H-thieno[2,3-c]pyran-2-yl)-4-[1,4-dioxan-2-yl]-1H-pyrazole-3-carboxamide, enantiomer 1 | F1, D2, A2, E3, chir sep | Int 3, Int 4 | 435 | 435 |
| 112 | 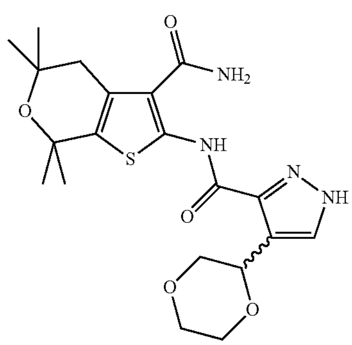 [SMILES: CC1(C)Cc2c(sc(NC(=O)c3n[nH]cc3C3COCCO3)c2C(N)=O)C(C)(C)O1] | N-(3-carbamoyl-5,5,7,7-tetramethyl-4H-thieno[2,3-c]pyran-2-yl)-4-[1,4-dioxan-2-yl]-1H-pyrazole-3-carboxamide, enantiomer 2 | F1, D2, A2, E3, chir sep | Int 3, Int 4 | 435 | 435 |
| 113 | 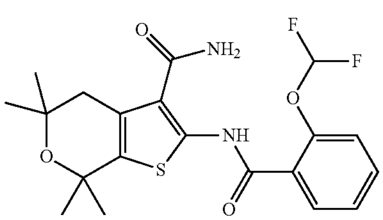 [SMILES: CC1(C)Cc2c(sc(NC(=O)c3ccccc3OC(F)F)c2C(N)=O)C(C)(C)O1] | 2-[[2-(difluoromethoxy)benzoyl]amino]-5,5,7,7-tetramethyl-4H-thieno[2,3-c]pyran-3-carboxamide | A2 | Int 3 | 424 | 425 |
| 114 | 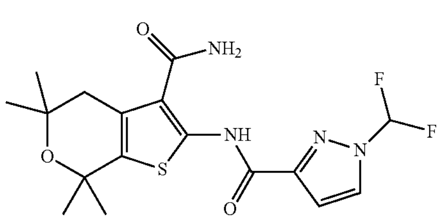 [SMILES: CC1(C)Cc2c(sc(NC(=O)c3ccn(C(F)F)n3)c2C(N)=O)C(C)(C)O1] | N-(3-carbamoyl-5,5,7,7-tetramethyl-4H-thieno[2,3-c]pyran-2-yl)-1-(difluoromethyl)pyrazole-3-carboxamide | A2 | Int 3 | 398 | 399 |

TABLE II-continued

List of final compounds

| Cpd # | Structure | Name | Mtd | Int | MW | Mes |
|---|---|---|---|---|---|---|
| 115 | 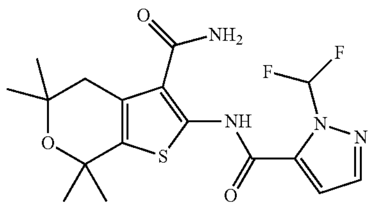 [SMILES: CC1(C)Cc2c(sc(NC(=O)c3ccnn3C(F)F)c2C(N)=O)C(C)(C)O1] | N-(3-carbamoyl-5,5,7,7-tetramethyl-4H-thieno[2,3-c]pyran-2-yl)-2-(difluoromethyl)pyrazole-3-carboxamide | A2 | Int 3 | 398 | 399 |
| 116 | 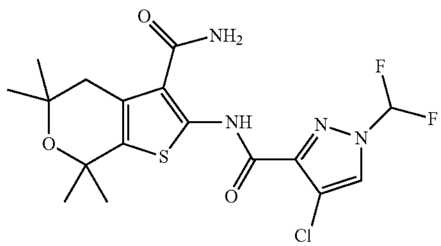 [SMILES: CC1(C)Cc2c(sc(NC(=O)c3nn(C(F)F)cc3Cl)c2C(N)=O)C(C)(C)O1] | N-(3-carbamoyl-5,5,7,7-tetramethyl-4H-thieno[2,3-c]pyran-2-yl)-4-chloro-1-(difluoromethyl)pyrazole-3-carboxamide | A2, I1 | Int 3 | 433 | 433 |
| 117 | 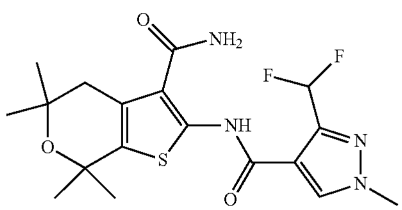 | N-(3-carbamoyl-5,5,7,7-tetramethyl-4H-thieno[2,3-c]pyran-2-yl)-3-(difluoromethyl)-1-methyl-pyrazole-4-carboxamide | A2 | Int 3 | 412 | 413 |
| 118 | 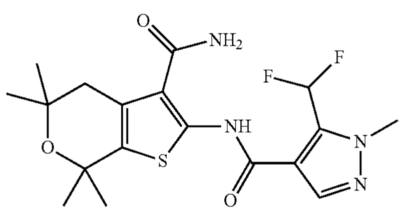 | N-(3-carbamoyl-5,5,7,7-tetramethyl-4H-thieno[2,3-c]pyran-2-yl)-5-(difluoromethyl)-1-methyl-pyrazole-4-carboxamide | A2 | int 3 | 412 | 413 |
| 119 | 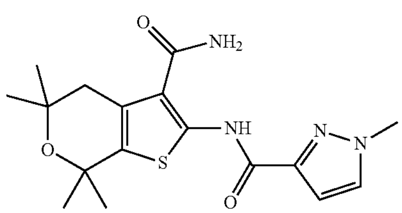 | N-(3-carbamoyl-5,5,7,7-tetramethyl-4H-thieno[2,3-c]pyran-2-yl)-1-methyl-pyrazole-3-carboxamide | A2 | Int 3 | 362 | 363 |
| 120 | 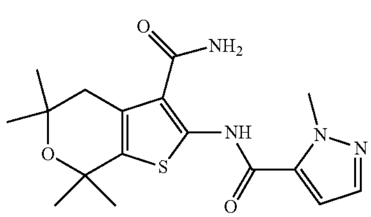 [SMILES: Cn1nccc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-2-methyl-pyrazole-3-carboxamide | A2 | Int 3 | 362 | 363 |
| 121 | 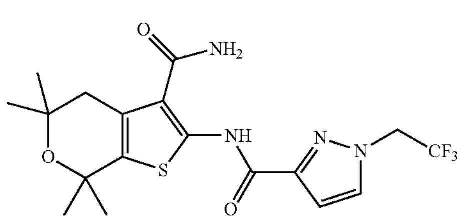 [SMILES: CC1(C)Cc2c(sc(NC(=O)c3ccn(CC(F)(F)F)n3)c2C(N)=O)C(C)(C)O1] | N-(3-carbamoyl-5,5,7,7-tetramethyl-4H-thieno[2,3-c]pyran-2-yl)-1-(2,2,2-trifluoroethyl)pyrazole-3-carboxamide | A2 | Int 3 | 430 | 431 |

TABLE II-continued

List of final compounds

| Cpd # | Name | Mtd | Int | MW | Mes |
|---|---|---|---|---|---|
| 122 | 2-[[3-(difluoromethyl)benzoyl]amino]-5,5,7,7-tetramethyl-4H-thieno[2,3-c]pyran-3-carboxamide | A2 | Int 3 | 408 | 409 |
| 123 | 2-[[2-(difluoromethyl)benzoyl]amino]-5,5,7,7-tetramethyl-4H-thieno[2,3-c]pyran-3-carboxamide | A2 | Int 3 | 408 | 409 |
| 124 | 2-[(3,3-difluoro-1-methyl-cyclobutanecarbonyl)amino]-5,5,7,7-tetramethyl-4H-thieno[2,3-c]pyran-3-carboxamide | A2 | Int 3 | 386 | 387 |
| 125 | N-(3-carbamoyl-5,5,7,7-tetramethyl-4H-thieno[2,3-c]pyran-2-yl)-2-methyl-oxazole-4-carboxamide | A2 | Int 3 | 363 | 363 |
| 126 | N-(3-carbamoyl-5,5,7,7-tetramethyl-4H-thieno[2,3-c]pyran-2-yl)-1-(2,2-difluoroethyl)pyrazole-3-carboxamide | A2 | Int 3 | 412 | 413 |
| 127 | N-(3-carbamoyl-5,5,7,7-tetramethyl-4H-thieno[2,3-c]pyran-2-yl)-2-(trifluoromethyl)thiazole-4-carboxamide | A2 | Int 3 | 433 | 434 |

TABLE II-continued

List of final compounds

| Cpd # | Structure | Name | Mtd | Int | MW | Mes |
|---|---|---|---|---|---|---|
| 128 | 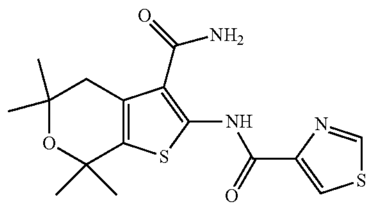 [SMILES: CC1(C)Cc2c(sc(NC(=O)c3cscn3)c2C(N)=O)C(C)(C)O1] | N-(3-carbamoyl-5,5,7,7-tetramethyl-4H-thieno[2,3-c]pyran-2-yl)thiazole-4-carboxamide | A2 | Int 3 | 365 | 366 |
| 129 | 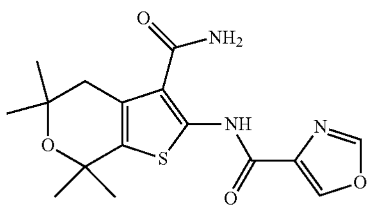 [SMILES: CC1(C)Cc2c(sc(NC(=O)c3cocn3)c2C(N)=O)C(C)(C)O1] | N-(3-carbamoyl-5,5,7,7-tetramethyl-4H-thieno[2,3-c]pyran-2-yl)oxazole-4-carboxamide | A2 | Int 3 | 349 | 350 |
| 130 | 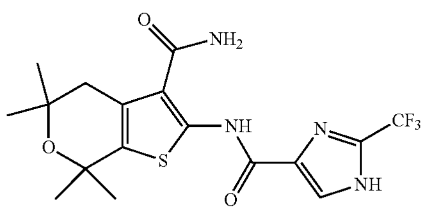 | N-(3-carbamoyl-5,5,7,7-tetramethyl-4H-thieno[2,3-c]pyran-2-yl)-2-(trifluoromethyl)-1H-imidazole-4-carboxamide | A2 | Int 3 | 416 | 417 |
| 131 | 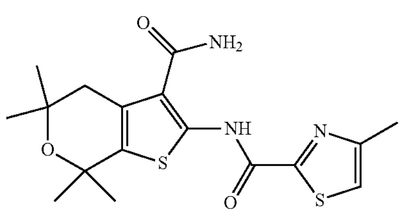 | N-(3-carbamoyl-5,5,7,7-tetramethyl-4H-thieno[2,3-c]pyran-2-yl)-4-methyl-thiazole-2-carboxamide | A2 | Int 3 | 380 | 380 |
| 132 | 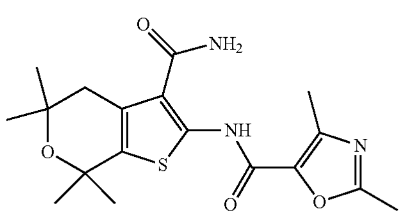 | N-(3-carbamoyl-5,5,7,7-tetramethyl-4H-thieno[2,3-c]pyran-2-yl)-2,4-dimethyl-oxazole-5-carboxamide | A2 | Int 3 | 377 | 378 |
| 133 | 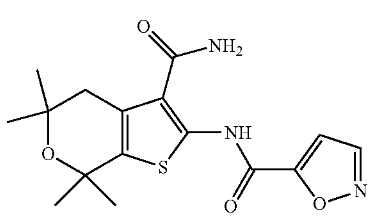 [SMILES: CC1(C)Cc2c(sc(NC(=O)c3ccno3)c2C(N)=O)C(C)(C)O1] | N-(3-carbamoyl-5,5,7,7-tetramethyl-4H-thieno[2,3-c]pyran-2-yl)isoxazole-5-carboxamide | A2 | Int 3 | 349 | 350 |
| 134 | 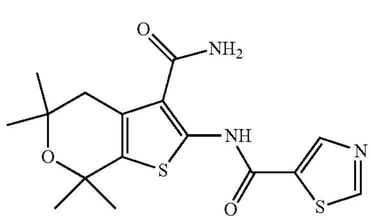 | N-(3-carbamoyl-5,5,7,7-tetramethyl-4H-thieno[2,3-c]pyran-2-yl)thiazole-5-carboxamide | A2 | Int 3 | 365 | 366 |

TABLE II-continued

List of final compounds

| Cpd # | Structure | Name | Mtd | Int | MW | Mes |
|---|---|---|---|---|---|---|
| 135 | 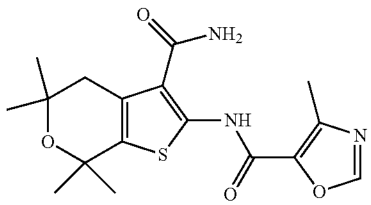 [SMILES: Cc1ncoc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-4-methyl-oxazole-5-carboxamide | A2 | Int 3 | 363 | 364 |
| 136 | 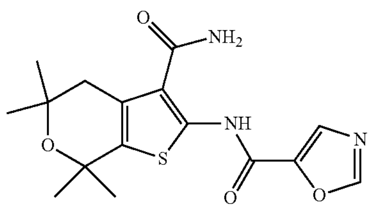 [SMILES: CC1(C)Cc2c(sc(NC(=O)c3cnco3)c2C(N)=O)C(C)(C)O1] | N-(3-carbamoyl-5,5,7,7-tetramethyl-4H-thieno[2,3-c]pyran-2-yl)oxazole-5-carboxamide | A2 | Int 3 | 349 | 350 |
| 137 | 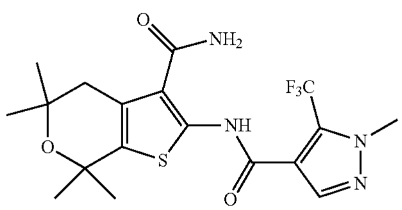 | N-(3-carbamoyl-5,5,7,7-tetramethyl-4H-thieno[2,3-c]pyran-2-yl)-1-methyl-5-(trifluoromethyl)pyrazole-4-carboxamide | A2 | Int 3 | 430 | 431 |
| 138 | 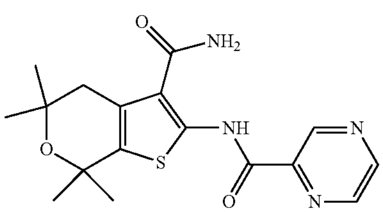 [SMILES: CC1(C)Cc2c(sc(NC(=O)c3cnccn3)c2C(N)=O)C(C)(C)O1] | N-(3-carbamoyl-5,5,7,7-tetramethyl-4H-thieno[2,3-c]pyran-2-yl)pyrazine-2-carboxamide | A2 | Int 3 | 360 | 361 |
| 139 | 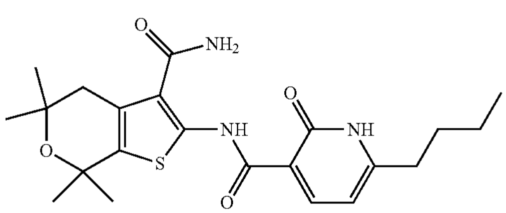 [SMILES: CCCCc1ccc(C(=O)Nc2sc3c(c2C(N)=O)CC(C)(C)OC3(C)C)c(=O)[nH]1] | 6-butyl-N-(3-carbamoyl-5,5,7,7-tetramethyl-4H-thieno[2,3-c]pyran-2-yl)-2-oxo-1H-pyridine-3-carboxamide | A2 | Int 3 | 432 | 432 |
| 140 | 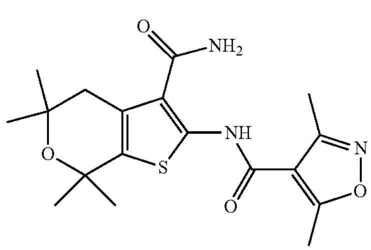 [SMILES: Cc1noc(C)c1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-3,5-dimethyl-isoxazole-4-carboxamide | A2 | Int 3 | 377 | 378 |
| 141 | 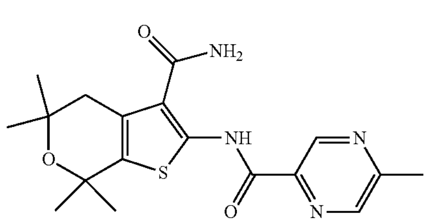 | N-(3-carbamoyl-5,5,7,7-tetramethyl-4H-thieno[2,3-c]pyran-2-yl)-5-methyl-pyrazine-2-carboxamide | A2 | Int 3 | 374 | 375 |

US 9,351,955 B2

TABLE II-continued

List of final compounds

| Cpd # | Structure | Name | Mtd | Int | MW | Mes |
|---|---|---|---|---|---|---|
| 142 | 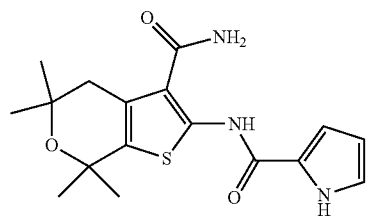 [SMILES: CC1(C)Cc2c(sc(NC(=O)c3ccc[nH]3)c2C(N)=O)C(C)(C)O1] | N-(3-carbamoyl-5,5,7,7-tetramethyl-4H-thieno[2,3-c]pyran-2-yl)-1H-pyrrole-2-carboxamide | A2 | Int 3 | 347 | 348 |
| 143 | 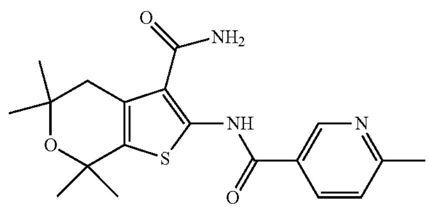 | N-(3-carbamoyl-5,5,7,7-tetramethyl-4H-thieno[2,3-c]pyran-2-yl)-6-methyl-pyridine-3-carboxamide | A2 | Int 3 | 373 | 374 |
| 144 | 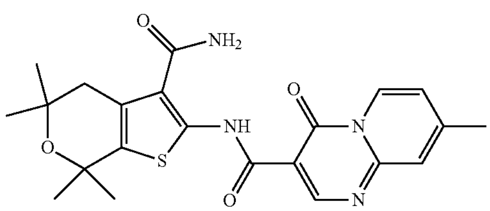 | N-(3-carbamoyl-5,5,7,7-tetramethyl-4H-thieno[2,3-c]pyran-2-yl)-8-methyl-4-oxo-pyrido[1,2-a]pyrimidine-3-carboxamide | A2 | Int 3 | 441 | 441 |
| 145 | 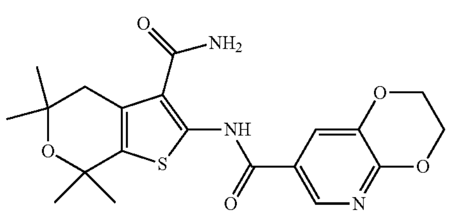 [SMILES: CC1(C)Cc2c(sc(NC(=O)c3cnc4c(c3)OCCO4)c2C(N)=O)C(C)(C)O1] | N-(3-carbamoyl-5,5,7,7-tetramethyl-4H-thieno[2,3-c]pyran-2-yl)-2,3-dihydro-[1,4]dioxino[2,3-b]pyridine-7-carboxamide | A2 | Int 3 | 417 | 418 |
| 146 | 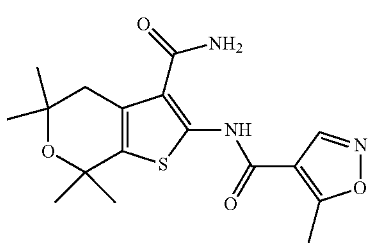 [SMILES: Cc1oncc1C(=O)Nc1sc2c(c1C(N)=O)CC(C)(C)OC2(C)C] | N-(3-carbamoyl-5,5,7,7-tetramethyl-4H-thieno[2,3-c]pyran-2-yl)-5-methyl-isoxazole-4-carboxamide | A2 | Int 3 | 363 | 364 |
| 147 | 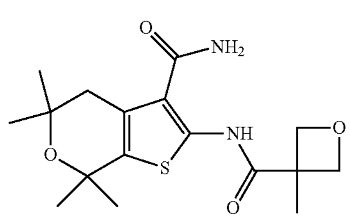 [SMILES: CC1(C)Cc2c(sc(NC(=O)C3(C)COC3)c2C(N)=O)C(C)(C)O1] | 5,5,7,7-tetramethyl-2-[(3-methyloxetane-3-carbonyl)amino]-4H-thieno[2,3-c]pyran-3-carboxamide | A2 | Int 3 | 352 | 353 |
| 148 | 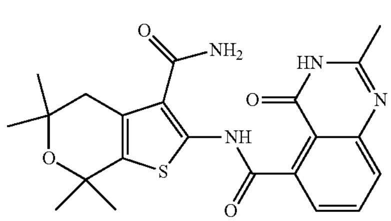 | N-(3-carbamoyl-5,5,7,7-tetramethyl-4H-thieno[2,3-c]pyran-2-yl)-2-methyl-4-oxo-3H-quinazoline-5-carboxamide | A2 | Int 3 | 441 | 441 |

TABLE II-continued

List of final compounds

| Cpd # | Structure | Name | Mtd | Int | MW | Mes |
|---|---|---|---|---|---|---|
| 149 | 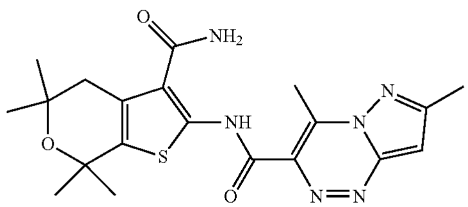 | N-(3-carbamoyl-5,5,7,7-tetramethyl-4H-thieno[2,3-c]pyran-2-yl)-4,7-dimethyl-pyrazolo[5,1-c][1,2,4]triazine-3-carboxamide | A2 | Int 3 | 429 | 429 |
| 150 | 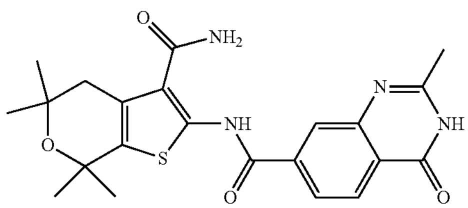 [SMILES: Cc1nc2cc(C(=O)Nc3sc4c(c3C(N)=O)CC(C)(C)OC4(C)C)ccc2c(=O)[nH]1] | N-(3-carbamoyl-5,5,7,7-tetramethyl-4H-thieno[2,3-c]pyran-2-yl)-2-methyl-4-oxo-3H-quinazoline-7-carboxamide | A2 | int 3 | 441 | 441 |
| 151 | 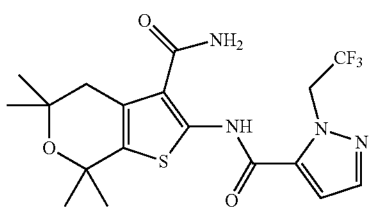 [SMILES: CC1(C)Cc2c(sc(NC(=O)c3ccnn3CC(F)(F)F)c2C(N)=O)C(C)(C)O1] | N-(3-carbamoyl-5,5,7,7-tetramethyl-4H-thieno[2,3-c]pyran-2-yl)-2-(2,2,2-trifluoroethyl)pyrazole-3-carboxamide | A2 | Int 3 | 430 | 431 |
| 152 | 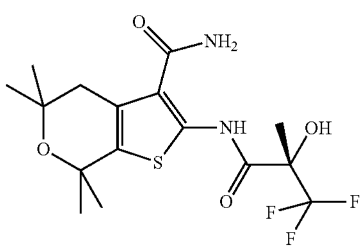 [SMILES: CC1(C)Cc2c(sc(NC(=O)[C@](C)(O)C(F)(F)F)c2C(N)=O)C(C)(C)O1] | 5,5,7,7-tetramethyl-2-[[(2S)-3,3,3-trifluoro-2-hydroxy-2-methyl-propanoyl]amino]-4H-thieno[2,3-c]pyran-3-carboxamide | C1, A2, D1 | Int 3 | 394 | 393 (M − H) |
| 153 | 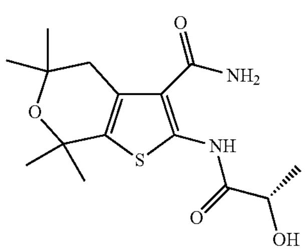 [SMILES: C[C@H](O)C(=O)Nc1sc2c(c1C(N)=O)CC(C)(C)OC2(C)C] | 2-[[(2S)-2-hydroxypropanoyl]amino]-5,5,7,7-tetramethyl-4H-thieno[2,3-c]pyran-3-carboxamide | A2, D9 | Int 3 | 326 | 325 (M − H) |
| 154 | 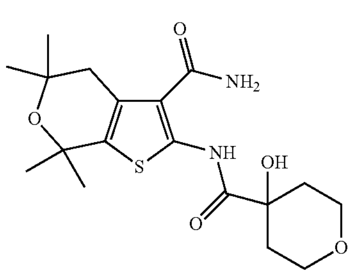 [SMILES: CC1(C)Cc2c(sc(NC(=O)C3(O)CCOCC3)c2C(N)=O)C(C)(C)O1] | 2-[(4-hydroxytetrahydropyran-4-carbonyl)amino]-5,5,7,7-tetramethyl-4H-thieno[2,3-c]pyran-3-carboxamide | C1, A2, D9 | Int 3 | 382 | 383.2 |

TABLE II-continued

List of final compounds

| Cpd # | Structure | Name | Mtd | Int | MW | Mes |
|---|---|---|---|---|---|---|
| 155 | 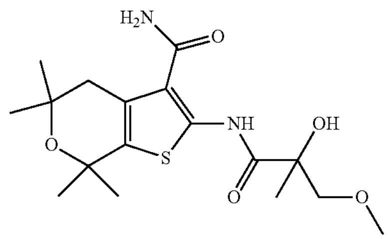 | 2-[(2-hydroxy-3-methoxy-2-methyl-propanoyl)amino]-5,5,7,7-tetramethyl-4H-thieno[2,3-c]pyran-3-carboxamide | C1, A2, D9 | Int 3 | 370 | 371.18 |
| 156 | 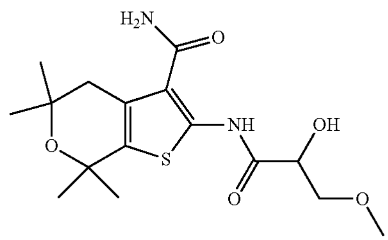 | 2-[(2-hydroxy-3-methoxy-propanoyl)amino]-5,5,7,7-tetramethyl-4H-thieno[2,3-c]pyran-3-carboxamide | C1, A2, D1 | Int 3 | 356 | 357.18 |
| 157 | 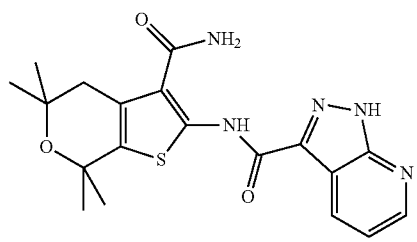 [SMILES: CC1(C)Cc2c(sc(NC(=O)c3n[nH]c4ncccc34)c2C(N)=O)C(C)(C)O1] | N-(3-carbamoyl-5,5,7,7-tetramethyl-4H-thieno[2,3-c]pyran-2-yl)-1H-pyrazolo[3,4-b]pyridine-3-carboxamide | B, A1 | Int 3 | 399 | 398.28 (M − H) |
| 158 | 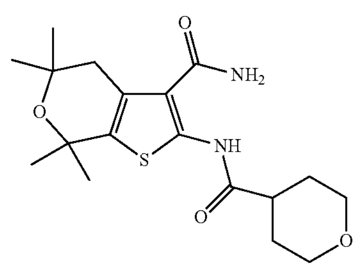 [SMILES: CC1(C)Cc2c(sc(NC(=O)C3CCOCC3)c2C(N)=O)C(C)(C)O1] | 5,5,7,7-tetramethyl-2-(tetrahydropyran-4-carbonylamino)-4H-thieno[2,3-c]pyran-3-carboxamide | A2 | Int 3 | 366 | 367.23 |
| 159 | 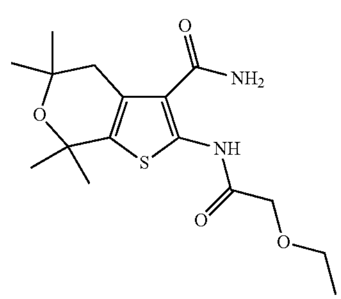 [SMILES: CCOCC(=O)Nc1sc2c(c1C(N)=O)CC(C)(C)OC2(C)C] | 2-[(2-ethoxyacetyl)amino]-5,5,7,7-tetramethyl-4H-thieno[2,3-c]pyran-3-carboxamide | A2 | Int 3 | 340 | 339.11 (M − H) |
| 160 | 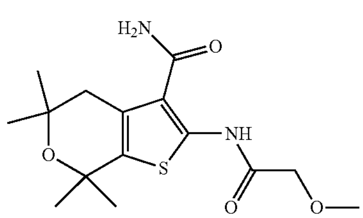 | 2-[(2-methoxyacetyl)amino]-5,5,7,7-tetramethyl-4H-thieno[2,3-c]pyran-3-carboxamide | A1 | Int 3 | 326 | 327.13 |

TABLE II-continued

List of final compounds

| Cpd # | Structure | Name | Mtd | Int | MW | Mes |
|---|---|---|---|---|---|---|
| 161 | 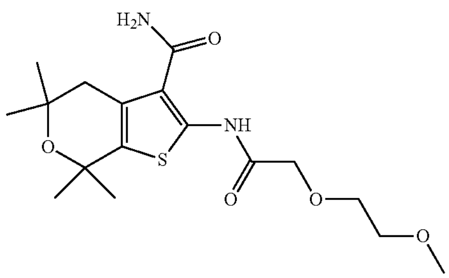 | 2-[[2-(2-methoxyethoxy)acetyl]amino]-5,5,7,7-tetramethyl-4H-thieno[2,3-c]pyran-3-carboxamide | A2 | Int 3 | 370 | 371.17 |
| 162 | 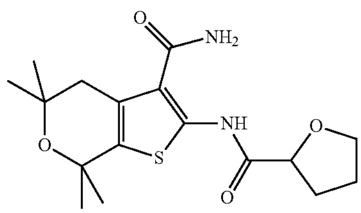 [SMILES: CC1(C)Cc2c(sc(NC(=O)C3CCCO3)c2C(N)=O)C(C)(C)O1] | 5,5,7,7-tetramethyl-2-(tetrahydrofuran-2-carbonylamino)-4H-thieno[2,3-c]pyran-3-carboxamide | A2 | Int 3 | 352 | 351.24 (M − H) |
| 163 | 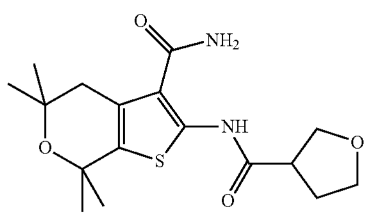 [SMILES: CC1(C)Cc2c(sc(NC(=O)C3CCOC3)c2C(N)=O)C(C)(C)O1] | 5,5,7,7-tetramethyl-2-(tetrahydrofuran-3-carbonylamino)-4H-thieno[2,3-c]pyran-3-carboxamide | A2 | Int 3 | 352 | 351.20 (M − H) |
| 164 | 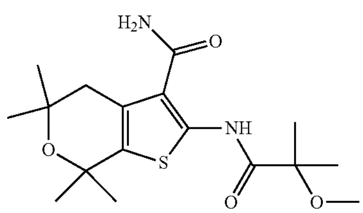 | 2-[(2-methoxy-2-methyl-propanoyl)amino]-5,5,7,7-tetramethyl-4H-thieno[2,3-c]pyran-3-carboxamide | A2 | Int 3 | 354 | 355 |
| 165 | 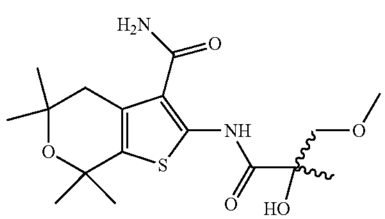 | 2-[[2-hydroxy-3-methoxy-2-methyl-propanoyl]amino]-5,5,7,7-tetramethyl-4H-thieno[2,3-c]pyran-3-carboxamide, enantiomer 1 | Chir sep | Int 3 | 370 | 371 |
| 166 | 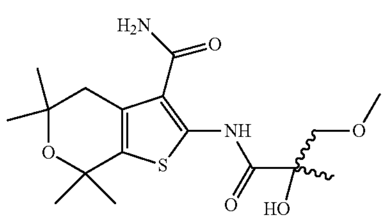 | 2-[[(2S)-2-hydroxy-3-methoxy-2-methyl-propanoyl]amino]-5,5,7,7-tetramethyl-4H-thieno[2,3-c]pyran-3-carboxamide, enantiomer 2 | Chir sep | Int 3 | 370 | 371 |

TABLE II-continued

List of final compounds

| Cpd # | Structure | Name | Mtd | Int | MW | Mes |
|---|---|---|---|---|---|---|
| 167 | 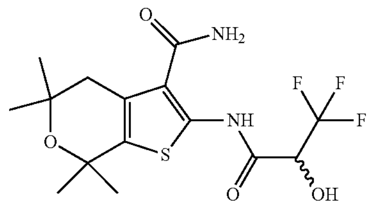 [SMILES: CC1(C)Cc2c(sc(NC(=O)C(O)C(F)(F)F)c2C(N)=O)C(C)(C)O1] | 5,5,7,7-tetramethyl-2-[(3,3,3-trifluoro-2-hydroxy-propanoyl)amino]-4H-thieno[2,3-c]pyran-3-carboxamide | C1, A2, D1 | Int 3 | 380 | 379.24 (M − H) |
| 168 | 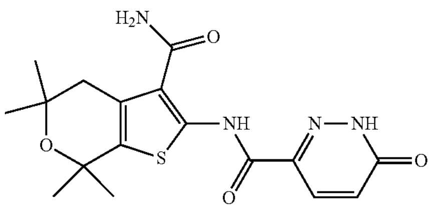 [SMILES: CC1(C)Cc2c(sc(NC(=O)c3ccc(=O)[nH]n3)c2C(N)=O)C(C)(C)O1] | 6-Oxo-1,6-dihydro-pyridazine-3-carboxylic acid (3-carbamoyl-5,5,7,7-tetramethyl-4,7-dihydro-5H-thieno[2,3-c]pyran-2-yl)-amide | A2 | Int 3 | 376 | 375 (M − H) |
| 169 | 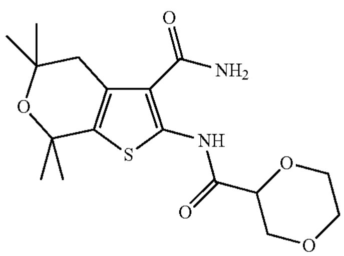 [SMILES: CC1(C)Cc2c(sc(NC(=O)C3COCCO3)c2C(N)=O)C(C)(C)O1] | 2-(1,4-dioxane-2-carboxamido)-5,5,7,7-tetramethyl-5,7-dihydro-4H-thieno[2,3-c]pyran-3-carboxamide | A2 | Int 3 | 368 | 369 |

TABLE III

Comparative compounds

| Cpd # | Structure | Name | MW |
|---|---|---|---|
| A | 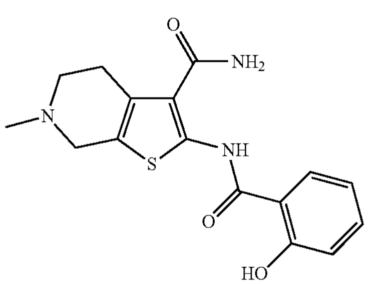 [SMILES: CN1CCc2c(sc(NC(=O)c3ccccc3O)c2C(N)=O)C1] | 2-(2-hydroxybenzamido)-6-methyl-4,5,6,7-tetrahydrothieno[2,3-c]pyridine-3-carboxamide | 331.4 |
| B | 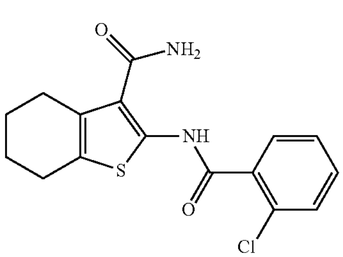 [SMILES: NC(=O)c1c(NC(=O)c2ccccc2Cl)sc2c1CCCC2] | 2-(2-chlorobenzamido)-4,5,6,7-tetrahydrobenzo[b]thiophene-3-carboxamide | 334.8 |

TABLE III-continued

Comparative compounds

| Cpd # | Structure | Name | MW |
|---|---|---|---|
| C | 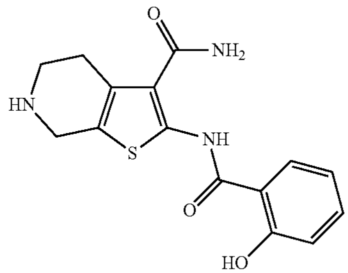 [SMILES: NC(=O)c1c(NC(=O)c2ccccc2O)sc2c1CCNC2] | 2-(2 hydroxybenzamido)-4,5,6,7-tetrahydrothieno[2,3-c]pyridine-3-carboxamide | 317.4 |
| D | 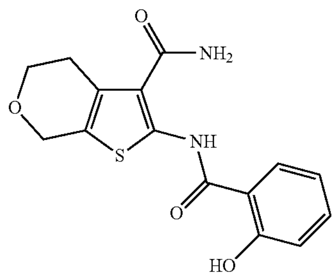 [SMILES: NC(=O)c1c(NC(=O)c2ccccc2O)sc2c1CCOC2] | 2-(2-hydroxybenzamido)-5,7-dihydro-4H-thieno[2,3-c]pyran-3-carboxamide | 318.4 |
| E | 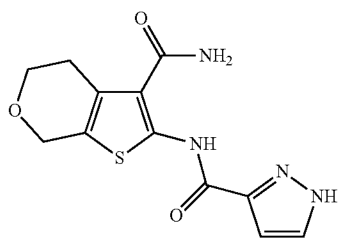 [SMILES: NC(=O)c1c(NC(=O)c2cc[nH]n2)sc2c1CCOC2] | N-(3-carbamoyl-5,7-dihydro-4H-thieno[2,3-c]pyran-2-yl)-1H-pyrazole-3-carboxamide | 292.3 |

TABLE IV

NMR Data of Representative Compounds of the Invention

Cpd # (δ) NMR data

1. $^1$H NMR δ (ppm)(DMSO-d$_6$): 12.67 (1 H, d), 8.01 (1 H, t), 7.68 (1 H, m), 7.74 (1 H, m), 7.40 (2 H, m), 7.26 (1 H, s), 2.75 (2 H, s), 1.47 (6 H, s), 1.21 (6 H, s).
2. $^1$H NMR δ (ppm)(DMSO-d$_6$) : 13.55 (1 H, s br), 12.53 (1 H, s br), 7.94 (1 H, s br), 7.54 (1 H, s br), 7.10 (1 H, s br), 6.79 (1 H, s), 2.73 (2 H, s), 1.45 (6 H, s), 1.20 (6 H, s), 1.45 (6 H, s).
3. $^1$H NMR δ (ppm)(DMSO-d$_6$): 12.91 (1 H, s), 11.66 (1 H, s), 7.95 (1 H, dd), 7.46 (1 H, s br), 7.39-7.45 (1 H, m), 7.06 (1 H, s br), 6.93-7.02 (2 H, m), 2.72 (2 H, s), 1.46 (6 H, s), 1.20 (6 H, s).
4. $^1$H NMR δ (ppm)(DMSO-d$_6$): 12.30 (1 H, s), 7.56 (1H, s br), 6.96 (1 H, s br), 6.83 (1 H, s), 2.72 (2 H, s), 1.42 (6 H, s), 1.19 (6 H, s), 1.15 (2 H, m), 1.03 (2 H, m).
5. $^1$H NMR δ (ppm)(DMSO-d$_6$): 12.04 (1 H, s), 7.89 (1 H, d), 7.79 (3H, m), 7.60 (1 H, m), 7.16 (1 H, s br), 2.69 (2 H, s), 1.46 (6 H, s), 1.20 (6 H, s).
6. $^1$H NMR δ (ppm)(DMSO-d$_6$): 12.05 (1 H, s), 7.53 (1 H, s br), 6.95 (1 H, s br), 5.97 (1 H, s), 2.70 (2 H, s), 1.42 (6 H, s), 1.33 (6 H, s), 1.19 (6 H, s).
7. $^1$H NMR δ (ppm)(DMSO-d$_6$): 12.03 (1 H, s), 7.90 (1 H, dd), 7.84 (1 H, dd), 7.73 (1 H, m), 7.62 (1 H, s br), 7.20 (1 H, s br), 2.70 (2 H, s), 1.46 (6 H, s), 1.21 (6 H, s).
8. $^1$H NMR δ (ppm)(DMSO-d$_6$): 12.65 (1 H, d), 8.06 (1 H, m), 7.69 (1 H, s br), 7.52 (1 H, m), 7.32 (1 H, m), 7.07 (1 H, s br), 2.74 (2 H, s), 1.46 (6 H, s), 1.20 (6 H, s).
9. $^1$H NMR δ (ppm)(DMSO-d$_6$): 12.06 (1 H, s), 7.12 (2 H, m), 5.30 (1 H, t), 3.58 (2 H, d), 2.67 (2 H, s), 1.40 (6 H, s), 1.17 (6 H, s), 1.05 (2 H, m), 0.82 (2 H, m).
10. $^1$H NMR δ (ppm)(DMSO-d$_6$): 12.00 (1 H, s), 7.50 (1 H, s br), 6.94 (1 H, s br), 5.16 (1 H, t), 3.41 ( 2 H, d), 2.69 (2 H, s), 1.41 (6 H, s), 1.18 (6H, s), 1.13 (6 H, s).
17. $^1$H NMR δ (ppm)(DMSO-d$_6$): 13.26 (1 H, s), 12.39 (1 H, s), 7.60 (1 H, s br), 7.00 (1 H, s br), 6.56 (1 H, s), 2.73 (2 H, s), 2.66 (2 H, q), 1.45 (6 H, s), 1.24 (6 H, s), 1.22 (3 H, t).
22. $^1$H NMRδ (ppm)(DMSO-d$_6$): 11.99 (1 H, s), 7.60 (1 H, s br), 7.00 (1 H, s br), 6.16 (1 H, d), 4.22 (1 H, m), 2.70 (2 H, s), 1.42 (6 H, s), 1.29 (3 H, d), 1.18 (6 H, s).

TABLE IV-continued

NMR Data of Representative Compounds of the Invention

| Cpd # | (δ) NMR data |
|---|---|
| 38 | $^1$H NMR δ (ppm)(DMSO-d$_6$): 11.97 (1 H, s), 7.51 (1 H, s br), 6.94 (1 H, s br), 6.20 (1 H, d), 3.73 (1 H, d), 2.70 (2 H, s), 1.43 (6 H, s), 1.18 (6 H, d), 0.92 (9 H, s). |
| 39 | $^1$H NMR δ (ppm)(DMSO-d$_6$): 11.99 (1 H, s), 7.53 (1 H, s br), 6.96 (1 H, s br), 6.10 (1 H, d), 3.97 (1 H, dd), 2.70 (2 H, s), 2.08 (1 H, m), 1.43 (6 H, s), 1.19 (6 H, d), 0.95 (6 H, d), 0.76 (6H, d). |
| 40 | $^1$H NMR δ (ppm)(DMSO-d$_6$): 11.75 (1 H, s), 7.46 (1 H, s br), 6.98 (1 H, s br), 5.30 (1 H, t), 3.66 (2 H, d), 2.69 (2 H, s), 2.26 (2 H, m), 1.95 (3 H, m), 1.80 (1 H, m), 1.42 (6H, s), 1.19 (6H, s). |
| 41 | $^1$H NMRδ (ppm)(DMSO-d$_6$): 12.31 (1 H, s), 7.37 (2 H, m), 3.77 (2 H, m), 3.60 (2 H, m), 2.70 (2 H, s), 2.16 (3 H, s), 2.04 (2 H, m), 1.98 (2 H, m), 1.42 (6 H, s), 1.18 (6 H, s). |
| 42 | $^1$H NMR δ (ppm)(DMSO-d$_6$): 13.63 (1 H, s), 12.44 (1 H, s), 7.59 (1 H, s br), 7.05 (1 H, s br), 6.73 (1 H, s), 4.47 (2 H, s), 3.28 (3 H, s), 2.73 (2 H, s), 1.45 (6 H, s), 1.20 (6 H, s). |
| 65 | $^1$H NMR δ (ppm)(DMSO-d$_6$): 13.32 (1 H, s), 12.40 (1H, s), 7.76 (1H, s), 7.60 (1 H, br), 6.95 (1 H, br), 3.33 (2 H, t), 3.23 (3 H, s), 2.76 (2 H, t), 2.72 (2 H, s), 1.79 (2 H, m), 1.45 (6 H, s), 1.20 (6 H, s). |
| 71 | $^1$H NMR δ (ppm)(DMSO-d$_6$): 13.34 (1 H, s), 12.42 (1H, s), 7.73 (1H, s), 7.55 (1 H, br), 6.95 (1 H, br), 2.73 (2 H, s), 2.70 (2 H, t), 1.54 (2 H, qt), 1.45 (6 H, s), 1.20 (6 H, s), 0.90 (3 H, t). |
| 86 | $^1$H NMR δ (ppm)(DMSO-d$_6$): 11.58 (1 H, s), 7.59 (1H, br. s), 7.00 (1H, br. s), 4.91 (1H, t), 3.53 (2H, t), 2.69 (2H, s), 2.42 (1H, m), 1.50 (2H, m), 1.41 (6H, s), 1.18 (6H, s), 1.02 (1H, d), 0.83 (3H, t). |
| 60 | $^1$H NMR δ (ppm)(DMSO-d$_6$): 11.99 (1 H, s), 7.59 (1H, br. s), 6.98 (1H, br. s), 6.07 (1H, m), 3.82 (1H, t), 2.72 (2H, s), 1.41 (6H, s), 1.19 (6H, s), 1.06 (1H, m), 0.40 (4H, m). |
| 64 | $^1$H NMR δ (ppm)(DMSO-d$_6$): 13.34 (1 H, s), 12.39 (1 H, s), 7.55 (1 H, s br), 7.00 (1 H, s br), 6.59 (1 H, d), 5.44 (1 H, s), 2.73 (1 H, s), 1.48 (6 H, s), 1.45 (6 H, s), 1.20 (6 H, s). |
| 81 | $^1$H NMR δ (ppm)(DMSO-d$_6$): 13.34 (1 H, s), 7.55 (1H, br.s), 7.00 (1H, br.s), 5.78 (1H, s br), 2.73 (1H, s), 1.45 (6H, s), 1.30 (3H, s), 1.81 (6H, d), 0.93 (9H, s). |
| 91 | $^1$H NMR δ (ppm) (DMSO-d$_6$): 13.34 (1 H, s), 7.55 (1H, s br), 7.00 (1H, s br), 5.78 (1H, s br), 3.85 (2H, q), 3.58 (2H, q), 2.67 (2H, s), 1.41 (6H, d), 1.23 (3H, s), 1.18 (6H, s), 1.00 (3H, s). |

Biological Examples

Example 6

In Vitro Assays 6.1. YFP-Halide Influx Assay for the CFTR-ΔF508 Mutation

The YFP halide influx assay measures the functionality of the cystic fibrosis Transmembrane Conductance regulator (CFTR) channels in the cystic fibrosis bronchial epithelium cell line CFBE41o-. The assay is used to evaluate the capacity of compounds to increase the open probability of existing CFTR channels in the membrane. It makes use of the observation that the yellow fluorescent protein (YFP) variant YFP H148Q, I152L has its fluorescence substantially quenched by halide ions like Cl$^-$ and I$^-$. (Galietta et al., 2001; Nagai et al., 2002)

For this purpose, CFBE410-cells are seeded in 96 well plates (6000 CFBE cells/well). One day after seeding, the CFBE cells are transduced with adenoviral vectors that direct the expression of the CFTR ΔF508 mutant and of the YFP reporter. Cells are incubated at 27° C., 5% CO$_2$ for 24 hours so as to allow for the proper folding and migration to the membrane of the CFTR channel or treated with a CFTR modulator during 24 h at 37° C.

The next day the CFTR channels are activated by treatment with the cAMP inducer forskolin (10.67 μM) and test compound in 1×D-PBS (from Gibco, Cat n#14090-041) for 10 minutes prior to addition of an I$^-$ solution (137 mM NaI, 2.7 mM KI, 1.76 mM KH$_2$PO$_4$, 10.1 mM Na$_2$HPO$_4$, 5 mM glucose). The I$^-$ induced quenching of fluorescence is recorded immediately after injection of I$^-$ for 7 seconds. The capacity of a compound to increase the channel opening is directly correlated with the decrease in fluorescence, and is expressed as (1-(fluorescence after 7 seconds (F)/fluorescence before injection (F0))) and an EC$_{50}$ can be derived from a (1−F/F0) vs compound concentration plot.

TABLE V

Illustrative EC$_{50}$ measured by YFP-halide influx assay for the CFTR-ΔF508 of the compounds of the invention.

| Cpd # | EC$_{50}$ (nM) |
|---|---|
| 1 | 12.16 |
| 2 | 10.00 |
| 3 | 4.40 |
| 4 | 32.00 |
| 5 | 63.43 |
| 6 | 75.77 |
| 7 | 60.16 |
| 8 | 22.81 |
| 9 | 28.00 |
| 10 | 121.05 |
| 11 | 27.18 |
| 12 | 951.90 |
| 13 | 17.86 |
| 14 | 32.23 |
| 15 | 7.56 |
| 16 | 25.26 |
| 17 | 15.51 |
| 18 | 829.10 |
| 19 | 41.85 |
| 20 | 305.40 |
| 21 | 6.46 |

TABLE V-continued

Illustrative $EC_{50}$ measured by YFP-halide influx assay for the CFTR-ΔF508 of the compounds of the invention.

| Cpd # | $EC_{50}$ (nM) |
|---|---|
| 22 | 219.00 |
| 23 | 102.40 |
| 24 | 313.80 |
| 25 | 4.14 |
| 26 | 1269.00 |
| 27 | 440.00 |
| 28 | 378.40 |
| 29 | 10000.00 |
| 30 | 141.10 |
| 31 | 354.00 |
| 32 | 23.00 |
| 33 | 4.00 |
| 34 | 10.00 |
| 35 | 3.00 |
| 36 | 13.00 |
| 37 | 16.00 |
| 38 | 5.00 |
| 39 | 6.00 |
| 40 | 32.00 |
| 41 | 1739.00 |
| 42 | 12.16 |

TABLE VI $EC_{50}$ measured by YFP-halide influx assay for the CFTR-ΔF508 of comparative compounds.

| Cpd # | $EC_{50}$ (nM) |
|---|---|
| A | >10000 |
| B | <370 |
| C | >10000 |
| D | 156.4 |
| E | 478.7 |

6.2. YFP-Halide Influx Assay for the CFTR-ΔF508 Mutation

The YFP halide influx assay measures the functionality of the cystic fibrosis Transmembrane Conductance regulator (CFTR) channels in the cystic fibrosis bronchial epithelium cell line CFBE41o-. The assay is used to evaluate the capacity of compounds to increase the open probability of existing CFTR channels in the membrane. It makes use of the observation that the yellow fluorescent protein (YFP) variant YFP H148Q, I152L has its fluorescence substantially quenched by halide ions like Cl— and I— (Galietta et al., 2001; Nagai et al., 2002).

For this purpose, CFBE410-cells are seeded in 384 well plates (3000 CFBE cells/well). One day after seeding, the CFBE cells are transduced with adenoviral vectors that direct the expression of the CFTR ΔF508 mutant and of the YFP reporter. Cells are incubated at 27° C., 5% $CO_2$ for 24 hours so as to allow for the proper folding and migration to the membrane of the CFTR channel or treated with a CFTR modulator during 24 h at 37° C.

The next day the CFTR channels are activated by treatment with the cAMP inducer forskolin (10.67 µM) and test compound in 1×D-PBS in a total volume of 30 µL (from Gibco, Cat n#14090-041) for 10 min prior to addition of 30 µl of following I— solution (375 mM NaI, 7.5 mM KI, 1.76 mM $KH_2PO_4$, 10.1 mM $Na_2HPO_4$, 13.75 mM glucose). The I— induced quenching of fluorescence is recorded on an immediately after injection of I— for 2 min on an FDSS/µCell (Hamamatsu). The capacity of a compound to increase the channel opening is directly correlated with the decrease in fluorescence, and is expressed as (1−(fluorescence after 36 seconds (F)/fluorescence before injection (F0))) and an EC50 can be derived from a (1−F/F0) vs compound concentration plot.

TABLE VII

Illustrative $EC_{50}$ measured by YFP-halide influx assay for the CFTR-ΔF508 of the compounds of the invention.

| Cpd # | $EC_{50}$ (nM) |
|---|---|
| 1 | 65.56 |
| 2 | 3.40 |
| 3 | 6.46 |
| 4 | 22.58 |
| 5 | 47.84 |
| 6 | 16.24 |
| 7 | 70.30 |
| 8 | 27.32 |
| 9 | 15.12 |
| 10 | 74.62 |
| 11 | 12.56 |
| 12 | 196.90 |
| 13 | 6.13 |
| 14 | 9.44 |
| 15 | 2.72 |
| 16 | 90.78 |
| 17 | 10.33 |
| 18 | 467.20 |
| 19 | 7.33 |
| 20 | 422.30 |
| 21 | 0.71 |
| 22 | 83.00 |
| 23 | 190.10 |
| 24 | 234.40 |
| 25 | 2.25 |
| 26 | 667.00 |
| 27 | 189.00 |
| 28 | 146.80 |
| 29 | 10000.00 |
| 30 | 101.24 |
| 31 | 354.10 |
| 32 | 39.60 |
| 33 | 6.93 |
| 34 | 10.08 |
| 35 | 2.44 |
| 36 | 12.40 |
| 37 | 25.42 |
| 38 | 5.99 |
| 39 | 4.51 |
| 40 | 35.58 |
| 41 | 602.10 |
| 42 | 15.34 |
| 43 | 495.50 |
| 44 | 275.80 |
| 45 | 29.59 |
| 46 | 2.84 |
| 47 | 117.60 |
| 48 | 66.64 |
| 49 | 125.30 |
| 50 | 10.61 |
| 51 | 92.55 |
| 52 | 1.97 |
| 53 | 9.91 |
| 54 | 8.51 |
| 55 | 24.52 |
| 56 | 79.29 |
| 57 | 2000.00 |
| 58 | 177.80 |
| 59 | 8.74 |
| 60 | 18.42 |
| 61 | 188.30 |
| 62 | 301.00 |
| 63 | 66.35 |
| 64 | 167.20 |
| 65 | 26.98 |
| 66 | 83.96 |

TABLE VII-continued

Illustrative $EC_{50}$ measured by YFP-halide influx assay for the CFTR-ΔF508 of the compounds of the invention.

| Cpd # | $EC_{50}$ (nM) |
|---|---|
| 67 | 42.75 |
| 68 | 60.02 |
| 69 | 34.19 |
| 70 | 176.00 |
| 71 | 14.41 |
| 72 | 17.86 |
| 73 | 20.84 |
| 74 | 82.60 |
| 75 | 667.00 |
| 76 | 2.17 |
| 77 | 126.95 |
| 78 | 6.39 |
| 79 | 23.64 |
| 80 | 667.00 |
| 81 | 3.23 |
| 82 | 2000.00 |
| 83 | 643.65 |
| 84 | 25.35 |
| 85 | 93.48 |
| 86 | 160.30 |
| 87 | 667.00 |
| 88 | 144.80 |
| 89 | 312.70 |
| 90 | 120.40 |
| 91 | 64.05 |
| 93 | 478.9 |
| 94 | 30.09 |
| 95 | 24.48 |
| 96 | 97.40 |
| 97 | 113.10 |
| 98 | 2.62 |
| 99 | 28.31 |
| 100 | 189.70 |
| 101 | 26.82 |
| 102 | 667.00 |
| 104 | 2000.00 |
| 105 | 6.67 |
| 106 | 0.54 |
| 107 | 386.90 |
| 108 | 2000.00 |
| 109 | 4.32 |
| 110 | 0.66 |
| 111 | 23.90 |
| 112 | 34.37 |
| 113 | 77.45 |
| 114 | 40.86 |
| 115 | 62.08 |
| 116 | 88.04 |
| 117 | 239.10 |
| 118 | 303.30 |
| 119 | 158.75 |
| 120 | 121.25 |
| 121 | 18.67 |
| 122 | 41.72 |
| 123 | 87.94 |
| 124 | 40.61 |
| 125 | 193.90 |
| 126 | 555.20 |
| 127 | 2000.00 |
| 128 | 34.18 |
| 129 | 77.30 |
| 130 | 2000.00 |
| 131 | 167.90 |
| 132 | 2000.00 |
| 133 | 552.00 |
| 134 | 78.58 |
| 135 | 138.30 |
| 136 | 81.50 |
| 137 | 128.20 |
| 138 | 52.22 |
| 139 | 56.97 |
| 140 | 143.50 |
| 141 | 99.46 |
| 143 | 153.40 |
| 144 | 471.60 |
| 145 | 153.50 |
| 146 | 202.30 |
| 147 | 169.00 |
| 148 | 2000.00 |
| 149 | 345.80 |
| 150 | 667.00 |
| 151 | 20.13 |
| 152 | 12.04 |
| 153 | 33.94 |
| 154 | 62.48 |
| 155 | 71.50 |
| 157 | 33.14 |
| 158 | 300.50 |
| 159 | 667.00 |
| 160 | 640.70 |
| 161 | 667.00 |
| 162 | 602.50 |
| 163 | 636.25 |
| 164 | 646.20 |
| 165 | 145.14 |
| 166 | 116.20 |
| 167 | 7.58 |
| 169 | 667 |

6.3. YFP-Halide Influx Assay for the CFTR-G551D Mutation

The YFP halide influx assay measures the functionality of the cystic fibrosis Transmembrane Conductance regulator (CFTR) channels. The assay is used to evaluate the capacity of compounds to increase the channel opening of existing mutant CFTR channels in the membrane. It makes use of the observation that the yellow fluorescent protein (YFP) variant YFP H148Q, I152L, F47L has its fluorescence substantially quenched by halide ions like $Cl^-$ and $I^-$. (Galietta et al., 2001)

For this purpose, HEK293-cells are seeded in 96 well plates. During seeding, the cells are reverse-transfected with plasmid vectors that direct the expression of the CFTR G551D mutant and of the YFP reporter. Cells are incubated at 37° C., 5% $CO_2$ for 24 hours so as to allow for sufficient expression of the CFTR protein.

The next day the CFTR channels are activated by treatment with the cAMP inducer forskolin (10.67 µM) and test compound in D-PBS (Gibco) for 10 minutes prior to addition of an $I^-$ solution (137 mM NaI, 2.7 mM KI, 1.76 mM $KH_2PO_4$, 10.1 mM $Na_2HPO_4$, 5 mM glucose). The $I^-$-induced quenching of fluorescence is recorded immediately after injection of $I^-$ for 7 seconds. The capacity of a compound to increase the channel opening is directly correlated with the decrease in fluorescence, and is expressed as (1−(fluorescence after 7 seconds (F)/fluorescence before injection (F0))) and an $EC_{50}$ can be derived from a (1−F/F0) vs compound concentration plot.

Similar YHA assays were developed for other channel gating defective or channel conductance defective CFTR mutants to determine effect of compound on channel activity. Examples of mutants are G178R, G1349D, S549N, R117H, R334W. This assay is also used for additional class I CFTR mutants, including G542X, W1282X; class II mutants including N1303K, and for class III mutants including S1251N; or wild-type CFTR.

TABLE VIII

Illustrative $EC_{50}$ measured by YFP-halide influx assay for the CFTR-G551D of the compounds of the invention.

| Cpd # | $EC_{50}$ (nM) |
|---|---|
| 1 | 281.90 |
| 2 | 500.00 |
| 3 | 162.20 |
| 4 | 1340.00 |
| 5 | 764.00 |
| 6 | 10000.00 |
| 7 | 1087.80 |
| 8 | 308.30 |
| 9 | 1000.00 |
| 10 | 2651.50 |
| 11 | 589.83 |
| 12 | 3330.00 |
| 13 | 197.90 |
| 14 | 376.60 |
| 15 | 77.48 |
| 16 | 5252.70 |
| 17 | 192.73 |
| 18 | 3330.00 |
| 19 | 356.60 |
| 20 | 3290.50 |
| 21 | 57.54 |
| 22 | 10000.00 |
| 23 | 1270.50 |
| 24 | 10000.00 |
| 25 | 80.58 |
| 26 | 10000.00 |
| 27 | 1666.00 |
| 28 | 2003.00 |
| 29 | 10000.00 |
| 30 | 6665.00 |
| 31 | 10000.00 |
| 32 | 853.90 |
| 33 | 92.05 |
| 34 | 270.30 |
| 35 | 182.70 |
| 36 | 716.30 |
| 37 | 892.00 |
| 41 | 10000.00 |
| 43 | 10000.00 |
| 44 | 10000.00 |
| 45 | 1136.70 |
| 46 | 1425.50 |
| 47 | 4706.00 |
| 48 | 4565.00 |
| 49 | 5672.00 |
| 50 | 288.34 |
| 51 | 5553.30 |
| 53 | 3330.00 |
| 54 | 10000.00 |
| 55 | 599.83 |
| 56 | 10000.00 |
| 57 | 10000.00 |
| 58 | 10000.00 |
| 59 | 3330.00 |
| 60 | 6665.00 |
| 61 | 4164.00 |
| 62 | 3330.00 |
| 63 | 1186.00 |
| 64 | 2905.00 |
| 65 | 1556.70 |
| 66 | 3330.00 |
| 67 | 3330.00 |
| 68 | 3330.00 |
| 69 | 3330.00 |
| 70 | 3330.00 |
| 71 | 1170.60 |
| 72 | 367.80 |
| 73 | 569.60 |
| 74 | 3330.00 |
| 75 | 10000.00 |
| 76 | 412.00 |
| 77 | 7776.70 |
| 78 | 3354.00 |
| 79 | 3330.00 |
| 80 | 10000.00 |
| 81 | 6665.00 |
| 82 | 10000.00 |
| 83 | 10000.00 |
| 84 | 3330.00 |
| 85 | 3330.00 |
| 86 | 10000.00 |
| 88 | 1175.00 |
| 89 | 10000.00 |
| 90 | 3200.00 |
| 93 | 3330 |
| 94 | 540.95 |
| 95 | 1063 |
| 96 | 3330.00 |
| 97 | 2777.50 |
| 98 | 5107.70 |
| 99 | 1337.20 |
| 100 | 2865.00 |
| 101 | 1364.00 |
| 102 | 10000.00 |
| 104 | 10000.00 |
| 105 | 730.10 |
| 106 | 981.45 |
| 107 | 10000.00 |
| 108 | 10000.00 |
| 109 | 3260.50 |
| 110 | 209.30 |
| 111 | 3100.50 |
| 112 | 1829.50 |
| 113 | 2786.00 |
| 114 | 1706.30 |
| 115 | 586.20 |
| 116 | 1521.00 |
| 117 | 6665.00 |
| 118 | 10000.00 |
| 119 | 2172.50 |
| 120 | 2405.00 |
| 121 | 1004.30 |
| 122 | 2380.00 |
| 123 | 824.90 |
| 124 | 685.20 |
| 125 | 3330.00 |
| 126 | 3330.00 |
| 127 | 10000.00 |
| 128 | 877.70 |
| 129 | 2290.00 |
| 130 | 10000.00 |
| 131 | 10000.00 |
| 132 | 10000.00 |
| 133 | 3330.00 |
| 134 | 2021.00 |
| 135 | 2026.00 |
| 136 | 2532.70 |
| 137 | 2657.00 |
| 138 | 10000.00 |
| 139 | 577.05 |
| 140 | 10000.00 |
| 141 | 1621.00 |
| 143 | 2706.00 |
| 144 | 10000.00 |
| 145 | 10000.00 |
| 146 | 10000.00 |
| 147 | 10000.00 |
| 148 | 10000.00 |
| 149 | 10000.00 |
| 150 | 10000.00 |
| 151 | 970.83 |
| 152 | 2163.00 |
| 153 | 10000.00 |
| 154 | 10000.00 |
| 155 | 10000.00 |
| 157 | 10000.00 |
| 158 | 10000.00 |
| 159 | 10000.00 |
| 160 | 10000.00 |
| 161 | 10000.00 |

TABLE VIII-continued

Illustrative EC$_{50}$ measured by YFP-halide influx assay for the CFTR-G551D of the compounds of the invention.

| Cpd # | EC$_{50}$ (nM) |
|---|---|
| 162 | 10000.00 |
| 163 | 10000.00 |
| 164 | 10000.00 |
| 165 | 10000.00 |
| 166 | 10000.00 |
| 167 | 10000.00 |
| 169 | 10000.00 |

TABLE IX

EC$_{50}$ measured by YFP-halide influx assay for the CFTR-G551D of comparative compounds.

| Cpd # | EC$_{50}$ |
|---|---|
| A | >10000 |
| D | >10000 |
| E | 2895 |

TABLE X

Illustrative EC$_{50}$ measured by YFP-halide influx assay for the CFTR-G178R of the compounds of the invention.

| Cpd # | EC$_{50}$ (nM) | Cpd # | EC$_{50}$ (nM) |
|---|---|---|---|
| 2 | 56.9 | 77 | 2210 |
| 9 | 699 | 92 | 82.24 |
| 13 | 98.8 | 94 | 67.61 |
| 14 | 169 | 98 | 41.51 |
| 15 | 87.5 | 101 | 346.6 |
| 33 | 88.6 | 105 | 54.41 |
| 34 | 42.2 | 106 | 26 |
| 35 | 44.1 | 110 | 22.49 |
| 38 | 96.8 | 121 | 465.7 |
| 39 | 1360 | 136 | 785.9 |
| 40 | >3330 | 151 | 221.45 |
| 42 | 156 | 154 | 3330 |
| 45 | 368 | 92 | 82.24 |
| 46 | 19 | 94 | 67.61 |
| 50 | 47.4 | 98 | 41.51 |
| 52 | 39.7 | 101 | 346.6 |
| 55 | 58.3 | 105 | 54.41 |
| 71 | 89.3 | 106 | 26 |
| 72 | 31.4 | 110 | 22.49 |
| 76 | 14.1 | 121 | 465.7 |
|   |   | 136 | 785.9 |
|   |   | 151 | 221.45 |
|   |   | 154 | 3330 |

TABLE XI

Illustrative EC$_{50}$ measured by YFP-halide influx assay for the CFTR-G1349D of the compounds of the invention.

| Cpd # | EC$_{50}$ (nM) |
|---|---|
| 2 | 63.3 |
| 9 | 578 |
| 13 | 75.3 |
| 14 | 371 |
| 15 | 75.3 |
| 33 | 116 |
| 34 | 47.4 |
| 35 | 118 |
| 38 | 517 |
| 39 | 1340 |
| 40 | 1910 |

TABLE XI-continued

Illustrative EC$_{50}$ measured by YFP-halide influx assay for the CFTR-G1349D of the compounds of the invention.

| Cpd # | EC$_{50}$ (nM) |
|---|---|
| 42 | 678 |
| 45 | 325 |
| 46 | 58.4 |
| 50 | 70.5 |
| 52 | 60.9 |
| 55 | 74 |
| 71 | 97.7 |
| 72 | 64 |
| 76 | 24.4 |
| 77 | 1310 |
| 94 | 672.30 |
| 95 | 81.43 |
| 98 | 54.67 |
| 101 | 888.00 |
| 105 | 120.00 |
| 106 | 199.90 |
| 110 | 141.70 |
| 121 | 536.30 |
| 136 | 1192.00 |
| 151 | 463.70 |
| 154 | 3330.00 |

TABLE XII

Illustrative EC$_{50}$ measured by YFP-halide influx assay for the CFTR-S549N of the compounds of the invention.

| Cpd # | EC$_{50}$ (nM) |
|---|---|
| 2 | 211 |
| 9 | 902 |
| 13 | 158 |
| 14 | 253 |
| 15 | 208 |
| 33 | 164 |
| 34 | 444 |
| 35 | 120 |
| 38 | 690 |
| 39 | 1100 |
| 40 | 1930 |
| 42 | 508 |
| 45 | 1520 |
| 46 | 140 |
| 50 | 105 |
| 52 | 86.5 |
| 55 | 108 |
| 71 | 196 |
| 72 | 122 |
| 76 | 31.5 |
| 77 | 1450 |
| 94 | 344.50 |
| 95 | 290.80 |
| 98 | 73.02 |
| 101 | 947.00 |
| 105 | 292.70 |
| 106 | 21.80 |
| 110 | 261.40 |
| 121 | 598.90 |
| 136 | 2605.00 |
| 151 | 3330.00 |
| 154 | 2374.00 |

TABLE XIII

Illustrative $EC_{50}$ measured by YFP-halide influx assay for the CFTR-R117H of the compounds of the invention.

| Cpd # | $EC_{50}$ (nM) | Cpd # | $EC_{50}$ (nM) |
|---|---|---|---|
| 2 | 166 | 35 | 180 |
| 9 | 433 | 38 | 64.3 |
| 13 | 177 | 39 | 145 |
| 14 | 207 | 40 | 2900 |
| 15 | 158 | 42 | 193 |
| 33 | 165 | 45 | 1200 |
| 34 | 301 | 46 | 24.4 |
| 50 | 76.3 | 136 | 806.70 |
| 52 | 11.4 | 151 | 780.00 |
| 55 | 38.9 | 154 | 1577.00 |
| 71 | 116 | 94 | 147.50 |
| 72 | 147 | 95 | 106.10 |
| 76 | 15.3 | 98 | 26.69 |
| 77 | 1010 | 101 | 1123.00 |
| 94 | 147.50 | 105 | 434.80 |
| 95 | 106.10 | 106 | 11.74 |
| 98 | 26.69 | 110 | 49.88 |
| 101 | 1123.00 | 121 | 723.80 |
| 105 | 434.80 | 136 | 806.70 |
| 106 | 11.74 | 151 | 780.00 |
| 110 | 49.88 | 154 | 1577.00 |
| 121 | 723.80 | | |

6.4. YFP-Halide Influx Assay for the CFTR-ΔF508 Mutation—Gluconate Buffer

The YFP halide influx assay measures the functionality of the cystic fibrosis Transmembrane Conductance regulator (CFTR) channels in the cystic fibrosis bronchial epithelium cell line CFBE41o-. The assay is used to evaluate the capacity of compounds to increase the open probability of existing CFTR channels in the membrane. It makes use of the observation that the yellow fluorescent protein (YFP) variant YFP H148Q, I152L has its fluorescence substantially quenched by halide ions like and $I^-$. (Galietta et al., 2001; Nagai et al., 2002)

For this purpose, CFBE41O-cells are seeded in 96 well plates (6000 CFBE cells/well). One day after seeding, the CFBE cells are transduced with adenoviral vectors that direct the expression of the CFTR ΔF508 mutant and of the YFP reporter. Cells are incubated at 27° C., 5% $CO_2$ for 24 hours so as to allow for the proper folding and migration to the membrane of the CFTR channel or treated with a CFTR modulator during 24 hours at 37° C.

The next day the CFTR channels are activated by treatment with the cAMP inducer forskolin (10.67 μM) and test compound in gluconate buffer (137 mM disodiumgluconate, 2.7 mM KCl, 1.76 mM $KH_2PO_4$, 10.1 mM $Na_2HPO_4$, 5 mM glucose) for 10 minutes prior to addition of an $I^-$ solution (137 mM NaI, 2.7 mM KI, 1.76 mM $KH_2PO_4$, 10.1 mM $Na_2HPO_4$, 5 mM glucose). The $I^-$-induced quenching of fluorescence is recorded immediately after injection of $I^-$ for 7 seconds. The capacity of a compound to increase the channel opening is directly correlated with the decrease in fluorescence, and is expressed as (1−(fluorescence after 7 seconds (F)/fluorescence before injection (F0))) and an $EC_{50}$ can be derived from a (1−F/F0) vs compound concentration plot.

Example 7

Cellular Assays

Electrophysiological measurements on primary human bronchial epithelial cell cultures are a useful preclinical surrogate of clinical efficacy (Rowe and Verkman, 2013), therefore compounds are evaluated in an Ussing chamber and/or TECC assay which are electrophysiological measurement assays.

7.1. Ussing Chambers Assay

7.1.1. Protocol

The Ussing chambers assay measures the functionality of the cystic fibrosis Transmembrane Conductance regulator (CFTR) by measuring the short circuit current ($I_{SC}$) generated over the basolateral and apical membrane of lung epithelial cells.

In order to measure the $I_{SC}$, the epithelium is short circuited by injecting a current that is adjusted by a feed-back amplifier to keep the transepithelial potential ($V_t$) at 0 mV. The amount of current required is adjusted by a feedback circuit and continuously measured. Intermittently the voltage is clamped to values different from 0 mV thus enabling an estimate of the transepithelial resistance ($R_e$).

For this purpose, bronchial epithelial cells isolated from CF patients homozygous for the CFTR ΔF508 mutation (hAEC-CF, Epithelix) or heterozygous for CFTR G551D and ΔF508 mutations (University of Chapel Hill, N.C.) are plated on type IV collagen-coated Snapwell supports (Corning-Costar). Human airway epithelia are generated by provision of an air-liquid interface for 21 days to form well-differentiated polarized cultures that resemble in vivo pseudo-stratified ciliated epithelium (Fulcher et al., 2005). In the case of the homozygous ΔF508 CFTR samples, the differentiated cells are treated with 3 μM VX809 (2626 South Loop West, Suite 225, Houston, Tex. 77054 USA, Cat n#51565) to allow sufficient expression of properly folded CFTR protein on the membrane (48 hours basolateral treatment and 24 hours apical treatment), prior to electrophysiological recordings. For heterozygous G551D/ΔF508, differentiated cells are used as such for the recordings.

For electrophysiological recording, the human airway epithelia are mounted in Ussing chambers for measurement of short-circuit current ($I_{SC}$). The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the basolateral side and a glutamate-ringer solution (120 mM sodium glutamate, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the apical side to generate a $Cl^-$ gradient. Both chambers are gassed with 95% $O_2$, 5% $CO_2$, and maintained at 27° C. Apical amiloride is used to inhibit the endogenous ENaC currents while forkolin is applied on both apical and basolateral side to stimulate CFTR. After forskolin triggering, compounds are added on both side to test their potential for increasing CFTR gating. The increase in $I_{SC}$ is used as a measure for the increased CFTR activity, $EC_{50}$ values can be generated by measuring impact of different concentrations of compound on Short circuit current on primary cells, for this purpose the same snapwell is used for the addition of increasing amounts of compound and the increase in $I_{sc}$ signal at each step is then transformed into a dose response curve. Inh-172, an inhibitor specific for CFTR, is used to test the specificity of the tested compounds.

7.2. TECC Assay

7.2.1. Primary Bronchial Epithelial Cells Protocol

The TECC (Tranepithelial Clamp Circuit, EP-design) assay measures the functionality of the cystic fibrosis Transmembrane Conductance regulator (CFTR) by measuring the short circuit current ($I_{SC}$) generated over the basolateral and apical membrane of lung epithelial cells. In TECC the transepithelial potential PD and transepithelial resistance ($R_t$) are measured in an open circuit and transformed to $I_{SC}$ using Ohm's law. 24 wells can be measured simultaneously allowing a higher throughput compared to Ussing chambers.

For this purpose, bronchial epithelial cells isolated from CF patients homozygous for the CFTR ΔF508 mutation (hAEC-CF, Epithelix) are plated on type IV collagen-coated Transwell supports (Costar). Human airway epithelia are generated by provision of an air-liquid interface for 21 days to form well-differentiated polarized cultures that resemble in vivo pseudo-stratified ciliated epithelium (Fulcher et al., 2005). In the case of the homozygous ΔF508 CFTR samples, the differentiated cells are treated with 3 μM VX809 (2626 South Loop West, Suite 225, Houston, Tex. 77054 USA, Cat n#51565) to allow sufficient expression of properly folded CFTR protein on the membrane (48 hours basolateral treatment and 24 hours apical treatment), prior to electrophysiological recordings. Human airway epithelia are generated by provision of an air-liquid interface for 21 days to form well-differentiated polarized cultures that resemble in vivo pseudo-stratified ciliated epithelium (Fulcher et al., 2005). In the case of the homozygous ΔF508 CFTR samples, the differentiated cells are treated with 3 μM VX809 (2626 South Loop West, Suite 225, Houston, Tex. 77054 USA, Cat n#51565) to allow sufficient expression of properly folded CFTR protein on the membrane (48 hours basolateral treatment and 24 hours apical treatment), prior to electrophysiological recordings. For heterozygous G551D/ΔF508, differentiated cells are used as such for the recordings.

Information on the compounds can be retrieved on the homozygous ΔF508 CFTR samples looking at increased CFTR activity when compounds are added in an acute mode or in a chronic mode. On G551D/ΔF508 CFTR heterozygous samples compounds are added in an acute mode to the differentiated cells.

For the acute mode, for electrophysiological recording, the human airway epithelia are mounted in the TECC heating plate for electrophysiological measurement and kept at 37° C. The epithelia are bathed in a NaCl-Ringer solution (120 mM NaCl, 25 mM NaHCO$_3$, 1.2 mM CaCl$_2$, 1.2 mM MgCl$_2$, 0.8 mM KH$_2$PO$_4$, 0.8 mM K$_2$HPO$_4$, pH 7.4, 5 mM glucose) on both the basolateral and apical sides. Apical amiloride is used to inhibit the endogenous ENaC currents while forkolin is applied on both apical and basolateral side to stimulate CFTR. After forskolin triggering, compounds are added on both sides to test their potential for increasing CFTR gating. Measurements are done during a 20 minute timeframe with recordings every 2 minutes. The increase in $I_{SC}$ is used as a measure for the increased CFTR activity, EC$_{50}$ values can be generated by measuring impact of different concentrations of compound on $I_{SC}$ on primary cells, for this purpose each transwell is treated with a different compound concentration. Inh-172, an inhibitor specific for CFTR, is used to test the specificity of the tested compounds.

For the chronic mode, the differentiated cells are treated with 3 μM VX809 (2626 South Loop West, Suite 225, Houston, Tex. 77054 USA, Cat n#51565) and potentiator compounds at different concentrations (48 hours basolateral treatment and 24 hours apical treatment), prior to electrophysiological recordings. For electrophysiological recording, the human airway epithelia are mounted in the TECC heating plate for electrophysiological measurement and kept at 37° C. The epithelia are bathed in a NaCl-Ringer solution (120 mM NaCl, 25 mM NaHCO$_3$, 1.2 mM CaCl$_2$, 1.2 mM MgCl$_2$, 0.8 mM KH$_2$PO$_4$, 0.8 mM K$_2$HPO$_4$, pH 7.4, 5 mM glucose) on both the basolateral and apical sides. Apical amiloride is used to inhibit the endogenous ENaC currents while forkolin is applied on both apical and basolateral side to stimulate CFTR. Measurements are done during a 20 minute timeframe with recordings every 2 minutes. The increase in $I_{SC}$ is used as a measure for the increased CFTR activity, EC$_{50}$ values can be generated by measuring impact of different concentrations of compound on $I_{SC}$ on primary cells, for this purpose each transwell is treated with a different compound concentration. Inh-172, an inhibitor specific for CFTR, is used to test the specificity of the tested compounds.

Similar TECC recordings are performed using primary cells for other channel gating defective or channel conductance defective CFTR mutants to determine effect of compound on channel activity. Examples of mutants include R117H, G178R. Similarly primary cells containing class I CFTR mutants, including G542X, W1282X; and additional class II mutants including N1303K can be used for electrophysiological recordings.

7.2.2. Results

When subjected to this protocol, the following values were obtained. The difference between Δ$I_{SC}$ measured as DMSO (baseline), and the Δ$I_{SC}$ measured with the compound tested.

7.2.2.1. Short Circuit Current ($I_{SC}$) Measurements

TABLE XIV

TECC assay results for illustrative compounds of the invention at 3 μM

| Cpd # | ΔIsc (μA/cm$^2$) | ΔIsc (μA/cm$^2$), DMSO | Current increase (μA/cm$^2$) |
|---|---|---|---|
| 2 | 10.9207 | −0.7427 | 11.6634 |
| 4 | 4.6728 | −0.5211 | 5.1939 |
| 10 | 3.9356 | −0.5211 | 4.4567 |

TABLE XV

TECC assay results for illustrative compounds of the invention and comparative compounds at 50 nM

| Cpd # | ΔIsc (μA/cm$^2$) | ΔIsc (μA/cm$^2$), DMSO | Current increase (μA/cm$^2$) |
|---|---|---|---|
| 2 | 4.5996 | −0.3248 | 4.9244 |
| A | −0.3248 | | −0.0559 |
| B | 0.1807 | | 0.5055 |
| E | 0.1663 | | 0.4911 |

TABLE XVI

TECC assay results for illustrative compounds of the invention and comparative compounds at 50, 100, and 200 nM

| Concentration | DMSO | Cpd A ΔIsc (μA/cm$^2$) | Cpd B ΔIsc (μA/cm$^2$) | Cpd E ΔIsc (μA/cm$^2$) | Cpd 2 ΔIsc (μA/cm$^2$) |
|---|---|---|---|---|---|
| 50 nM | | −0.3807 | 0.1807 | 0.1663 | 4.5996 |
| 100 nM | −0.3734 | −0.5401 | 0.4762 | −0.0318 | 4.9327 |
| 200 nM | | −0.6598 | 0.8022 | 0.5241 | 5.0457 |

As shown in Table XIV, Table XV, and Table XVI above, and in FIG. 1, the compounds of the invention demonstrate an activity on the CFTR protein, at 3 μM, or 50 nM, or 50/100/200 nM whereas no such activity is measured for structural analogues (comparative compounds A, B, and E), which remain at the baseline level.

7.2.2.2. CFTR ΔF508 TECC Assay $EC_{50}$ Measurements

TABLE XVII

TECC assay in CFTR ΔF508 $EC_{50}$ for illustrative compounds of the invention and comparative compounds.

| Cpd# | $EC_{50}$ |
|---|---|
| 2 | 36.96 |
| 6 | 165.4, 60.93 |
| 9 | 237.1, 65.02 |
| 21 | 16.27 |
| 105 | 54.43 |
| 154 | 502.1 |

7.2.3. FRT-CFTR G551D Protocol

For G551D recordings, Fish Rat Thyroid (FRT) cells stably transfected with G551D CFTR (a low CFTR-G551D expressing cell line and a high expressing CFTR-G551D cell line from Rosalind Franklin University of medicine and science, Chicago, Ill.) are plated on Transwell supports (Costar 6.5 mm Diameter, 0.4 µM pore size). The cells are grown for 8-10 d under liquid-liquid interface conditions prior to electrophysiological readings. For electrophysiological recording, the FRT-G551D cells are mounted in the TECC heating plate for electrophysiological measurement and kept at 37° C. The epithelia are bathed in hepes buffered culturing medium without FBS on both the basolateral and apical sides. Apical amiloride is used to inhibit the endogenous ENaC currents while forkolin is applied on both apical and basolateral side to stimulate CFTR. After forskolin triggering, compounds are added on both sides to test their potential for increasing CFTR gating. Measurements are done during a 10 minute timeframe with recordings every 2 min. The increase in $I_{SC}$ is used as a measure for the increased CFTR activity, EC50 values can be generated by measuring impact of different concentrations of compound on $I_{SC}$ on the cells, for this purpose each transwell is treated with a different compound concentration. Inh-172, an inhibitor specific for CFTR, is used to test the specificity of the tested compounds.

7.2.4. CFTR G551D TECC Assay $EC_{50}$ Measurements

When subjected to this protocol, the following $EC_{50}$ are measured.

TABLE XVIII

TECC assay in CFTR G551D $EC_{50}$ for illustrative compounds of the invention and comparative compounds in high expression cells.

| Cpd# | $EC_{50}$ |
|---|---|
| 2 | 66.16, 90.25, 85, 61.52, 57.84, 87.43 |
| 9 | 360.7, 527,694.8, 400.1, 510.7 |
| 25 | 70 |
| 35 | 43.7 |
| 110 | 192.7 |
| 136 | 62470 |

7.3. Patch-Clamp Assays

Patch clamp is a very versatile and powerful technique which can be used to study individual ion channel activity in an isolated patch of cell membrane. Patch-clamp experiments can be performed to quantify the effects of compounds on CFTR channel activity in inside-out patches excised from cells overexpressing Wild type CFTR, ΔF508 CFTR or G551D CFTR channels. Specifically, the open probability of ΔF508, wild-type or G551D CFTR can be calculated from different patches for statistical analysis. The impact of the compound on the open probability of the CFTR channel will be compared with the open probability in absence of compound as measured or as described in literature. Modulators of CFTR will increase the open probability of the mutant CFTR.

Whole cell patch clamp experiments to determine potency of compounds. For this, cells containing G551D CFTR (FRT background) are held at −40 mV and ramped from −100 to +10 mV once every 5 seconds. CFTR current is measured at −100 mV and current is monitored at −50 mV (close to the reversal for Cl−) to monitor cell stability. For each cell, a baseline current is recorded, 10 µM FSK was applied for 8-10 min followed by different concentrations of compound (4-5 min each) and then by 10 µM compound which served as 100% activation for normalization. Lastly, an inhibitor cocktail (10 µM CFTRinh-172 and 20 µM GlyH101) is added to confirm current originates from CFTR.

Example 8

Pharmacokinetic, DMPK and Toxicity Assays

8.1. Thermodynamic Solubility

A solution of 1 mg/mL of the test compound is prepared in a 0.2M phosphate buffer pH 7.4 or a 0.1M citrate buffer pH 3.0 at room temperature in a glass vial.

The samples are rotated in a Rotator drive STR 4 (Stuart Scientific, Bibby) at speed 3.0 at room temperature for 24 h.

After 24 h, 800 µL of the sample is transferred to an eppendorf tube and centrifuged 5 min at 14000 rpm. 200 µL of the supernatant of the sample is then transferred to a MultiscreenR Solubility Plate (Millipore, MSSLBPC50) and the supernatant is filtered (10-12" Hg) with the aid of a vacuum manifold into a clean Greiner polypropylene V-bottom 96 well plate (Cat no. 651201). 5 µL of the filtrate is diluted into 95 µL (F20) of the same buffer used to incubate in the plate containing the standard curve (Greiner, Cat no. 651201).

The standard curve for the compound is prepared freshly in DMSO starting from a 10 mM DMSO stock solution diluted factor 2 in DMSO (5000 µM) and then further diluted in DMSO up to 19.5 µM. 3 µL of the dilution series as from 5000 µM is then transferred to a 97 µL acetonitrile-buffer mixture (50/50). The final concentration range is 2.5 to 150 µM.

The plate is sealed with sealing mats (MA96RD-045, www.kinesis.co.uk) and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 min and ranges from 5% B to 95% B.

Peak areas are analyzed with the aid of Masslynx software package and peak areas of the samples are plotted against the standard curve to obtain the solubility of the compound.

Solubility Values are Reported in µM or µg/mL.

8.2. Aqueous Solubility

Starting from a 10 mM stock in DMSO, a serial dilution of the compound is prepared in DMSO. The dilution series is transferred to a 96 NUNC Maxisorb plate F-bottom (Cat no. 442404) and 0.1M phosphate buffer pH7.4 or 0.1M citrate buffer pH3.0 at room temperature is added.

The final concentration ranges from 300 µM to 18.75 µM in 5 equal dilution steps. The final DMSO concentration does not exceed 3%. 200 µM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number with a software tool which can be plotted onto a graph. The first concentration at which the compound appears completely dissolved is the concentration reported; however the true concentration lies somewhere between this concentration and one dilution step higher.

Solubility values measured according to this protocol are reported in µg/mL.

8.3. Plasma Protein Binding (Equilibrium Dialysis)

A 10 mM stock solution of the compound in DMSO is diluted with a factor 5 in DMSO. This solution is further diluted in freshly thawed human, rat, mouse or dog plasma (BioReclamation INC) with a final concentration of 10 µM and final DMSO concentration of 0.5% (5.5 µL in 1094.5 µL plasma in a PP-Masterblock 96well (Greiner, Cat no. 780285))

A Pierce Red Device plate with inserts (ThermoScientific, Cat no. 89809) is prepared and filled with 7500 µL PBS in the buffer chamber and 5000 µL of the spiked plasma in the plasma chamber. The plate is incubated for 4 h at 37° C. while shaking at 230 rpm. After incubation, 1200 µL of both chambers is transferred to 360 µL acetonitrile in a 96-well round bottom, PP deep-well plates (Nunc, Cat no. 278743) and sealed with an aluminum foil lid. The samples are mixed and placed on ice for 30 min. This plate is then centrifuged 30 min at 1200 ref at 4° C. and the supernatant is transferred to a 96 v-bottom PP plate (Greiner, 651201) for analysis on LCMS.

The plate is sealed with sealing mats (MA96RD-04S) of www.kinesis.co.uk and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 min and ranges from 5% B to 95% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

8.4. Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Fisher TKT-545-020B).

$2\times10^5$ cells/well are seeded in plating medium consisting of DMEM+GlutaMAXI+1% NEAA+10% FBS (FetalClone II)+1% Pen/Strep. The medium is changed every 2-3 days.

Test and reference compounds (propranolol and rhodamine123 or vinblastine, all purchased from Sigma) are prepared in Hanks' Balanced Salt Solution containing 25 mM HEPES (pH7.4) and added to either the apical (125 µL) or basolateral (600 µL) chambers of the Transwell plate assembly at a concentration of 10 µM with a final DMSO concentration of 0.25%.

50 µM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 h incubation at 37° C. while shaking at an orbital shaker at 150 rpm, 70 µL aliquots are taken from both apical (A) and basal (B) chambers and added to 100 µL1 50:50 acetonitrile:water solution containing analytical internal standard (0.5 µM carbamazepine) in a 96 well plate.

Lucifer yellow is measured with a Spectramax Gemini XS (Ex 426 nm and Em 538 nm) in a clean 96 well plate containing 150 µL of liquid from basolateral and apical side.

Concentrations of compound in the samples are measured by high performance liquid-chromatography/mass spectroscopy (LC-MS/MS).

Apparent permeability ($P_{app}$) values are calculated from the relationship:

$$P_{app} = \frac{[compound]_{acceptor\,final} \times V_{acceptor}}{([compound]_{donor\,initial} \times V_{donor})/T_{inc} \times V_{donor}} $$
$$\text{Surface area} \times 60 \times 10^{-6} \text{cm/s}$$

V=chamber volume
$T_{inc}$=incubation time.
Surface area=0.33 $cm^2$

The Efflux ratios, as an indication of active efflux from the apical cell surface, are calculated using the ratio of $P_{app}$ B>A/$P_{app}$ A>B.

The following assay acceptance criteria are used:
Propranolol: $P_{app}$ (A>B) value≥20($\times 10^{-6}$ cm/s)
Rhodamine 123 or Vinblastine: $P_{app}$ (A>B) value<5 ($\times 10^{-6}$ cm/s) with Efflux ratio>5.

Lucifer yellow permeability: 5100 nm/s 8.5. MDCKII-MDR1 Permeability

MDCKII-MDR1 cells are Madin-Darby canine kidney epithelial cells, over-expressing human multi-drug resistance (MDR1) gene, coding for P-glycoprotein (P-gp). Cells are obtained from Netherlands Cancer Institute and used after a 3-4 day cell culture in 24-well Millicell cell culture insert plates (Millipore, PSRP010R5). Bi-directional MDCKII-MDR1 permeability assay is performed as described below.

$3\times10^5$ cells/mL ($1.2\times10^5$ cells/well) are seeded in plating medium consisting of DMEM+1% Glutamax-100+1% Antibiotic/Antimycotic+10% FBS (Biowest, 51810). Cells are left in $CO_2$ incubator for 3-4 days. The medium is changed 24 h after seeding and on the day of experiment.

Test and reference compounds (amprenavir and propranolol) are prepared in Dulbecco's phosphate buffer saline (D-PBS, pH7.4) and added to either the apical (400 µL) or basolateral (800 µL) chambers of the Millicell cell culture insert plates assembly at a final concentration of 10 µM (0.5 µM in case of amprenavir) with a final DMSO concentration of 1%.

100 µM Lucifer Yellow (Sigma) is added to the all donor buffer solutions, in order to assess integrity of the cell monolayers by monitoring Lucifer Yellow permeation. Lucifer yellow is a fluorescent marker for the paracellular pathway and it is used as an internal control in every monolayer to verify tight junction integrity during the assay.

After a 1 h incubation at 37° C. while shaking at an orbital shaker at 150 rpm, 750 µL aliquots are taken from both apical (A) and basal (B) chambers and added to 225 µL acetonitrile: water solution (2:1) containing analytical internal standard (10 ng/mL warfarin) in a 96 well plate. Aliquoting is also performed at the beginning of the experiment from donor solutions to obtain initial (Co) concentration.

Concentration of compound in the samples is measured by high performance liquid-chromatography/mass spectroscopy (LC-MS/MS).

Lucifer yellow is measured with a Fluoroscan Ascent FL Thermo Scientific (Ex 485 nm and Em 530 nm) in a 96 well plate containing 150 µL of liquid from all receiver wells (basolateral or apical side).

8.6. Microsomal Stability

A 10 mM stock solution of compound in DMSO is diluted to 6 µM in a 105 mM phosphate buffer, pH7.4 in a 96 deep well plate (Greiner, Cat no. 780285) and pre-warmed at 37° C.

A Glucose-6-phosphate-dehydrogenase (G6PDH, Roche, 10127671001) working stock solution of 700 U/mL is diluted with a factor 1:700 in a 105 mM phosphate buffer, pH7.4. A co-factor mix containing 0.528M $MgCl_2.6H_2O$ (Sigma, M2670), 0.528M glucose-6-phosphate (Sigma, G-7879) and 0.208M NADP+ (Sigma, N-0505) is diluted with a factor 1:8 in a 105 mM phosphate buffer, pH7.4.

A working solution is made containing 1 mg/mL liver microsomes (Provider, Xenotech) of the species of interest (human, mouse, rat, dog . . . ), 0.8 U/mL G6PDH and co-factor mix (6.6 mM $MgCl_2$, 6.6 mM glucose-6-phosphate, 2.6 mM NADP+). This mix is pre-incubated for 15 min, but never more than 20 min, at room temperature.

After pre-incubation, compound dilution and the mix containing the microsomes, are added together in equal amount and incubated for 30 min at 300 rpm. For the time point of 0 min, two volumes of MeOH are added to the compound dilution before the microsome mix is added. The final concentration during incubation are: 3 µM test compound or control compound, 0.5 mg/mL microsomes, 0.4 U/mL G6PDH, 3.3 mM $MgCl_2$, 3.3 mM glucose-6-phosphate and 1.3 mM NaDP+.

After 30 min of incubation, the reaction is stopped with 2 volumes of MeOH.

Of both time points, samples are mixed, centrifuged and the supernatant is harvested for analysis on LC-MS/MS. The instrument responses (i.e. peak heights) are referenced to the zero time-point samples (as 100%) in order to determine the percentage of compound remaining. Standard compounds Propanolol and Verapamil are included in the assay design.

The data on microsomal stability are expressed as a percentage of the total amount of compound remaining after 30 min.

8.7. Pharmacokinetic Study in Rodents

8.7.1. Animals

Sprague-Dawley rats (male, 5-6 weeks old) are obtained from Janvier (France). Rats are acclimatized for at least 5 days before treatment and are kept on a 12 h light/dark cycle. Temperature is maintained at approximately 22° C., and food and water are provided ad libitum. Two days before administration of the test compounds, rats may undergo surgery to place a catheter in the jugular vein under isoflurane anesthesia. After the surgery, rats are housed individually. Rats are deprived of food for at least 16 h before oral dosing and 6 h after. Water is provided ad libitum.

8.7.2. Plasma Pharmacokinetic Studies

Compounds are formulated in PEG200/physiological saline (25/75) for the intravenous route and in 0.5% methylcellulose and EtOH/PEG 200/Methylcellulose 0.5% (10/25/65 v/v/v) for the oral route. Test compounds are orally dosed as a single esophageal gavage at 5 mg/kg under a dosing volume of 5 mL/kg and intravenously dosed as a bolus via the caudal vein at 1 mg/kg under a dosing volume of 5 mL/kg. Each group consist of 3 rats. Blood samples are collected via the jugular vein with lithium heparin as anti-coagulant at the following time points: 0.05 (intravenous route), 0.25 (oral route), 0.5, 1, 3, 5, 8 and 24 h. Alternatively, blood samples are collected at the retro-orbital sinus with lithium heparin as anti-coagulant at the following time points 0.25, 1, 3 and 6 h (oral route). Whole blood samples are centrifuged at 1500 g for 10 min and the resulting plasma samples are stored at −20° C. pending analysis.

8.7.3. Lung Distribution Studies

Compounds are formulated in 0.5% methylcellulose and EtOH/PEG 200/Methylcellulose 0.5% (10/25/65 v/v/v) by the oral route. Test compounds are orally dosed as a single esophageal gavage at 10 mg/kg under a dosing volume of 5 mL/kg. Each group consists of 12 rats. At each time point, typically 1, 3, 6 and 24 h, animals are euthanized and blood and lung samples are collected. Whole blood samples are centrifuged at 1500 g for 10 min and the resulting plasma samples, along with the lung samples, are stored at −20° C. pending analysis.

8.7.4. Quantification of Compound Levels in Plasma and Lung Samples

Lung samples are milled in the presence of ceramic beads and proteins present in plasma and lung samples are precipitated with an organic solvent. Concentrations of each test compound are determined by an LC-MS/MS method in which the mass spectrometer is operated in positive or negative electrospray mode.

8.7.5. Determination of Pharmacokinetic Parameters

Pharmacokinetic parameters are calculated using Winnonlin® or Phoenix® (Pharsight®, United States).

8.7.6. Data Analysis

For each animal, the lung-to-plasma ratio is determined as the ratio between compound concentration in lung and in plasma. At each sampling time point, mean, standard error of the mean (sem) and coefficient of variation (CV %) are calculated using data from three animals.

8.7.7. Results

When subjected to this protocol, the following exposure values were obtained.

TABLE XIX

Exposure values of illustrative compounds of the invention

| Cpd# | AUC(0-t) (ng.h/mL) |
|---|---|
| 2 | 3659, 1540, 1214 |
| 9 | 38930 |
| 15 | 1509 |
| 15 | 467 |
| 17 | 290 |
| 25 | 439 |

8.7.8. PXR Cellular Activation Assay

The assay allows determining the CYP induction activity of a compound, using Human Pregnane X Receptor (PXR), which primary function is to up regulate the synthesis of the cytochrome P450 in the presence of toxic agents.

This Activation Assay is outsourced to Cyprotex. (15 Beech Lane, Macclesfield, Cheshire. SK10 2DR United Kingdom. Tel: +44 (0)1625 505100).

Transcriptional activation is monitored by luminescence. Data are expressed as fold activation relative to the vehicle control. The use of 5 or more doses of test compound and positive control allows for the derivation of $EC_{50}$ and Emax values from nonlinear regression analysis of the log dose-response curves.

Test compound values are compared to those obtained for the positive control (10 µM rifampicin).

The significant response threshold for set at 35% of the maximal response obtained with the positive control.

8.7.9. Direct CYP450 Inhibition in Human Liver Microsomes

The assay measures the inhibition potency of a compound of the major CYP450 isoenzymes.

A 5 mM stock solution of test compound is prepared in methanol. This stock is serially diluted 1:3 in methanol followed by a 50 fold dilution in 50 mM potassium phosphate buffer pH 7.4, resulting in seven concentrations of test compound (0.14-100 µM, 2% methanol).

The obtained compound dilution is added to human hepatic microsomes at 20 mg protein/mL (BD Biosciences, either Cat. No. 452161, or alternatively Cat. No. 452117) and probe substrate (see table below).

After pre-warming the solution for 5 min at 37° C., the reaction is started by adding cofactor mix (7.65 mg/mL glucose-6-phosphate, 1.7 mg/mL NADP, 6 U/mL of glucose-6-phosphate dehydrogenase).

After incubation at 37° C. (Table below), the reaction (50 µL) is terminated by adding 150 µL of an acetonitrile:methanol (2:1) solution with internal standard (warfarin). Samples are centrifuged (535 g, 25 min, +4° C.) and the supernatant fractions analyzed by LC-MS/MS.

The Percentage of Control is Calculated as:

$$\% \text{ control} = \frac{[Met]_{test}}{[Met]_{solvent}} * 100$$

$[Met]_{test}$=concentration of probe metabolite in the test compound control well
$[Met]_{solvent}$=concentration of probe metabolite in the solvent control well Percent of control activity vs concentration plots are generated and fitted using GraphPad Prism software to generate $IC_{50}$.

added to cDNA-expressed human cytochrome P450 isoenzymes (BD Biosciences, Cat No. CYP1A2: 456203; CYP2C19: 456259; CYP2C9: 456258; CYP3A4: 456202; CYP2D6: 456217), specific conditions depended on the isoform studies: see Table below.

After pre-warming 10 min at 37° C., the reaction is started by adding cofactor mix (final reaction concentrations in the assay were: 0.6 U/ml Glucose-6-phosphate-dehydrogenase (G6PDH), 3.3 mM $MgCl_2$, 3.3 mM glucose-6-phosphate and 1.3 mM NADP+ for CYP3A4, CYP2C9, CYP2C19 and CYP1A2. And 0.6 U/mL G6PDH, 0.41 mM $MgCl_2$, 0.41 mM glucose-6-phosphate and 8.2 µM NADP+ for CYP2D6).

In parallel, a stability control is performed by incubating the test compound with denaturated (by heat) enzymes and cofactor mix to evaluate the stability of thereof during the incubation time.

For each time points, after incubation at 37° C. (see Table XXI), samples (50 µL) are terminated with 100 µL acetonitrile solution with internal standard (warfarin). Samples are centrifuged (805 g, 20 minutes, +4° C.) and the supernatant fractions are filtered (Varian Captiva Cat No.: A5960002), diluted in water/acetonitrile (85/15) and analyzed by LC-MS/MS (see Table 3). The instrument responses (ratio of test compound and internal standard peak areas) are referenced to the zero time-point samples (100%) in order to determine the percentage of compound remaining. Plots of the % of test compound remaining are used to determine the profile of metabolism of the test compound using Graph Pad Prism software.

TABLE XX

Isoforms and test conditions

| P450 Isoform | Microsomes (mg/mL) | Probe Substrate | Probe metabolite | Incubation (min) | Positive Control | Negative Control |
|---|---|---|---|---|---|---|
| 1A2 | 0.1 | Phenacetin (35 µM) | Acetaminophen | 10 | Furafylline | Sulphaphenazole |
| 2C9 | 0.1 | Diclofenac (10 µM) | 4'-OH-diclofenac | 5 | Sulphaphenazole | Furafylline |
| 2C19 | 0.25 | S-(+)-Mephenytoin (30 µM) | 4'-OH-mephenytoin | 15 | Tranylcypromine | Phenacetin |
| 2D6 | 0.1 | Bufuralol (10 µM) | OH-bufuralol | 10 | Quinidine | Sulphaphenazole |
| 3A4 | 0.1 | Midazolam (3 µM) | 1'-OH-midazolam | 5 | Ketoconazole | Sulphaphenazole |
| 3A4 | 0.25 | Testosterone (100 µM) | 6β-OH-testosterone | 15 | Ketoconazole | Sulphaphenazole |
| 3A4 | 0.1 | Nifedipine (5 µM) | Oxidized nifedipine | 5 | Ketoconazole | Sulphaphenazole |
| 3A4 | 0.1 | Atorvastatin (10 µM) | 2-OH Atorvastatin | 10 | Ketoconazole | Sulphaphenazole |

8.7.10. CYP450 Reaction Phenotyping
8.7.10.1. Protocol

The aim of this assay is to evaluate which of the major CYP450 isoenzyme(s) may be involved in the metabolism of a test compound.

A 1 mM stock solution of test compound is prepared in DMSO. This stock is diluted in 50 mM potassium phosphate buffer pH 7.4, resulting in a final assay concentration of test compound of 1 µM, 0.1% DMSO. This compound dilution is

TABLE XXI

Assay conditions for CYP reaction phenotyping

| Cytochrome P450 Isoform | Enzyme (mg/mL) | Incubation (min) | Positive Control |
|---|---|---|---|
| 1A2 | 0.1 | 0-30-60 | Phenacetin (1 µM) |

TABLE XXI-continued

Assay conditions for CYP reaction phenotyping

| Cytochrome P450 Isoform | Enzyme (mg/mL) | Incubation (min) | Positive Control |
|---|---|---|---|
| 2C9 | 0.1 | 0-30-60 | Diclofenac (1 μM) |
| 2C19 | 0.1 | 0-30-60 | Omeprazol (1 μM) |
| 2D6 | 0.1 | 0-30-60 | Dextromethorphan (1 μM) |
| 3A4 | 0.1 | 0-30-60 | Testosterone (1 μM) |

8.7.11. Time Dependent Inhibition (TDI)
8.7.11.1. Protocol

The mechanism-based inhibition assay for CYP3A4 is carried out to evaluate the presence of any TDI.

A 5 mM stock solution of test compound is prepared in methanol. This stock is serially diluted 1:3 in methanol and then added in duplicates to mixture containing 50 mM potassium phosphate buffer pH 7.4 and human liver microsomes (BD Gentest). Final reaction conditions are as follows: seven test compound concentrations (0.14-100 μM), prepared in duplicates and 2% methanol.

A summary of the specific conditions is shown below.

| Cytochrome P450 Isoform | Microsomes (mg/ml) | Probe compound | Probe metabolite | Incubation (min) | Positive Control | Negative Control |
|---|---|---|---|---|---|---|
| 3A4 | 0.1 | Midazolam (3 μM) | 1'-OH-midazolam | 5 | Troleandomycin | Ketoconazole |
| 3A4 | 0.25 | Testosterone (100 μM) | 6β-OH-testosterone | 15 | Troleandomycin | Ketoconazole |

After pre-warming 5 minutes at 37° C., the 20 min pre-incubation is started by adding a probe substrate to the first concentration range (first replica) and a co-factor mix (7.65 mg/mL glucose-6-phosphate, 1.7 mg/mL NADP, 6 U/mL of glucose-6-phosphate dehydrogenase) to the second replica.

After finishing the pre-incubation, the reaction is finally started by adding the co-factor mix to the first replica and probe substrate to second replica (opposite from pre-incubation).

After incubation at 37° C., the reaction (aliquot of 50 μL) is terminated with 150 μL acetonitrile:methanol (2:1) solution with internal standard (warfarin). Samples are centrifuged and the supernatant fractions analyzed by LC-MS/MS.

The instrument responses (ratio of test compound and internal standard peak areas) are referenced to those for solvent controls (assumed as 100%) in order to determine the percentage reduction in probe metabolism.

Percent of control activity vs concentration plots are generated and fitted using GraphPad Prism software to determine $IC_{50}$ for both substrate- and co-factor pre-incubations, as well as the $IC_{50}$ fold shift.

8.7.11.2. Results

For example, when subjected to this protocol, $IC_{50}$ for Compound 2 is >100 μM, both without and with preincubation using Midazolam or testosterone as probe substrate, indicating no evidence for time-dependent inhibition of CYP3A4.

General Conclusions

The data provided in the present application demonstrate that the compounds of the invention demonstrate significant activity in vitro, and may be useful in vivo in the treatment of CF and improvement over comparative compounds.

In particular, the compounds of the invention surprisingly exhibit significant improvement in vitro in potency in the CFTR-ΔF508 and CFTR-G551D mutation YFP halide influx assay over close analogues: for example Compound 3 (Compound of the invention) vs comparative Compound D, or Compound 2 (Compound of the invention) vs comparative Compound E.

Moreover, as demonstrated by the TECC assay, for example Compound 2 surprisingly shows an activity not observed for closely related analogues comparative Compounds A, B, or E.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041

Bundgaard, H., 1985. Design of prodrugs. Elsevier.

Fulcher, M. L., Gabriel, S., Burns, K. A., Yankaskas, J. R., Randell, S. H., 2005. Well-differentiated human airway epithelial cell cultures. Methods Mol. Med. 107, 183-206.

Galietta, L. J. V., Haggie, P. M., Verkman, A. S., 2001. Green fluorescent protein-based halide indicators with improved chloride and iodide affinities. FEBS Lett. 499, 220-224. doi:10.1016/S0014-5793(01)02561-3

Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080.

Morello, J.-P., Bouvier, M., Petäjä-Repo, U. E., Bichet, D. G., 2000. Pharmacological chaperones: a new twist on receptor folding. Trends Pharmacol. Sci. 21, 466-469. doi: 10.1016/S0165-6147(00)01575-3

Nagai, T., Ibata, K., Park, E. S., Kubota, M., Mikoshiba, K., Miyawaki, A., 2002. A variant of yellow fluorescent protein with fast and efficient maturation for cell-biological applications. Nat. Biotechnol. 20, 87-90. doi:10.1038/nbt0102-87

Pasyk, E. A., Foskett, J. K., 1995. Mutant (6F508) Cystic Fibrosis Transmembrane Conductance Regulator Cl—Channel Is Functional When Retained in Endoplasmic Reticulum of Mammalian Cells. J. Biol. Chem. 270, 12347-12350.

Quinton, P. M., 1990. Cystic fibrosis: a disease in electrolyte transport. FASEB J. 4, 2709-2717.

Remington, J. P., 1985. Pharmaceutical Preparations and Their Manufacture, in: Gennaro, A. R. (Ed.), Remington's Pharmaceutical Sciences. Mack Pub. Co., Easton, Pa. 18042.

Rowe, S. M., Verkman, A. S., 2013. Cystic Fibrosis Transmembrane Regulator Correctors and Potentiators. Cold Spring Harb. Perspect. Med. 3, a009761. doi:10.1101/cshperspect.a009761

Shastry, B. S., 2003. Neurodegenerative disorders of protein aggregation. Neurochem. Int. 43, 1-7. doi:10.1016/S0197-0186(02)00196-1

Wuts, P. G. M., Greene, T. W., 2012. Greene's Protective Groups in Organic Synthesis, 4 edition. ed. Wiley-Interscience.

Zhang, W., Fujii, N., Naren, A. P., 2012. Recent advances and new perspectives in targeting CFTR for therapy of cystic fibrosis and enterotoxin-induced secretory diarrheas. Future Med. Chem. 4, 329-345. doi:10.4155/fmc.12.1

The invention claimed is:

1. A method for the treatment of cystic fibrosis, comprising administering to a subject an effective amount of a compound according to Formula I

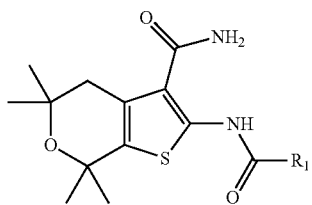

wherein
$R^1$ is
  $C_{3-7}$ mono or spirocyclic cycloalkyl, optionally substituted with one or more independently selected $R^2$ groups,
  4-7 membered mono or spirocyclic heterocycloalkyl comprising one or more heteroatoms independently selected from O, N, and S, substituted with one or more independently selected $R^2$ groups,
  $C_{6-10}$ monocyclic or bicyclic aryl optionally substituted with one or more independently selected $R^3$ groups,
  5-10 membered monocyclic or fused bicyclic heteroaryl comprising one or more heteroatoms independently selected from N, O, and S, and optionally substituted with one or more independently selected $R^3$ groups, or
  $C_{1-6}$ alkyl optionally substituted with one or more independently selected $R^4$ groups,
each $R^2$ is selected from
  halo,
  OH,
  —CN,
  —OC(=O)$C_{1-4}$ alkyl,
  —C(=O)—$C_{1-4}$ alkoxy,
  oxo,
  $C_{1-4}$ alkyl (optionally substituted with one or more independently selected $R^{5a}$), and
  $C_{1-4}$ alkoxy (optionally substituted with one or more independently selected $R^{5a}$),
each $R^3$ is selected from
  halo,
  —OH,
  —CN,
  $C_{1-4}$ alkyl (optionally substituted with one or more independently selected $R^{5b}$),
  $C_{1-4}$ alkoxy (optionally substituted with one or more independently selected $R^{5b}$),
  $C_{2-4}$ alkenyl (optionally substituted with one or more independently selected $R^{5b}$),
  $C_{3-7}$ cycloalkyl,
  4-7 membered monocyclic heterocycloalkyl comprising one or more heteroatoms independently selected from N, O, and S,
  4-7 membered monocyclic heterocycloalkenyl comprising one or more heteroatoms independently selected from N, O, and S,
  5-10 membered monocyclic or fused bicyclic heteroaryl comprising one or more heteroatoms independently selected from N, O, and S, and
  —NHSO$_2$—$C_{1-4}$ alkyl;
each $R^4$ is selected from
  halo,
  OH,
  $C_{3-7}$ monocyclic cycloalkyl,
  —CN, and
  $C_{1-4}$ alkoxy (optionally substituted with one or more independently selected $R^{5c}$),
each $R^{5a}$, $R^{5b}$, and $R^{5a}$ is independently selected from
  halo,
  OH,
  —OP(=O)$_2$OH,
  —CN,
  —NR$^{6a}$R$^{6b}$, and
  $C_{1-4}$ alkoxy; and
each $R^{5a}$, or $R^{5b}$ is independently selected from H, and $C_{1-4}$ alkyl;
or a pharmaceutically acceptable salt, or a solvate, or a pharmaceutically acceptable salt of a solvate thereof.

2. A method according to claim 1, wherein $R^1$ is mono or spirocyclic $C_{3-7}$ cycloalkyl substituted with one or more independently selected $R^2$ groups.

3. A method according to claim 1, wherein $R^1$ is cyclopropyl, cyclobutyl, cyclopentyl, or cyclohexyl, each of which is substituted with one or more independently selected $R^2$ groups.

4. A method according to claim 1, wherein $R^2$ is —CH$_3$, —CH$_2$CH$_3$, —CH(CH$_3$)$_2$, —C(CH$_3$)$_3$, —CH$_2$—OH, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

5. A method according to claim 1, wherein $R^1$ is phenyl, substituted with one or more independently selected $R^3$ groups.

6. A method according to claim 1, wherein $R^1$ is furanyl, thiophenyl, pyrazolyl, imidazolyl, thiazolyl, oxazolyl, pyridinyl, pyridazinyl, pyrimidyl, or pyrazinyl.

7. A method according to claim 1, wherein $R^1$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^3$ groups.

8. A method according to claim 1, wherein $R^3$ is F, Cl, OH, or CN.

9. A method according to claim 1, wherein $R^3$ is —CH$_3$, —CH$_2$—CH$_3$, —CH(CH$_3$)$_2$, —OCH$_3$, —OCH$_2$CH$_3$, or —OCH(CH$_3$)$_2$, each of which is optionally substituted with one or more independently selected $R^{5b}$.

10. A method according to claim 9, wherein $R^{5b}$ is F, Cl, OH, —OP(=O)$_2$OH, CN, or —OCH$_3$.

11. A method according to claim 1, wherein $R^1$ is —CH$_3$, —CH$_2$—CH$_3$, —CH(CH$_3$)$_2$, —C(CH$_3$)$_3$, —C(CH$_3$)$_2$—CH$_3$, or —C(CH$_3$)H—CH(CH$_3$)$_2$, each of which is substituted with one or more independently selected $R^4$ groups.

12. A method according to claim 11, wherein $R^4$ is F, Cl, OH, or CN.

13. A method according to claim 1, wherein the compound is selected from:
- 2-(2-fluorobenzamido)-5,5,7,7-tetramethyl-5,7-dihydro-4H-thieno[2,3-c]pyran-3-carboxamide,
- N-(3-carbamoyl-5,5,7,7-tetramethyl-5,7-dihydro-4H-thieno[2,3-c]pyran-2-yl)-1H-pyrazole-5-carboxamide,
- 2-(2-hydroxybenzamido)-5,5,7,7-tetramethyl-5,7-dihydro-4H-thieno[2,3-c]pyran-3-carboxamide,
- 2-(1-hydroxycyclopropanecarboxamido)-5,5,7,7-tetramethyl-5,7-dihydro-4H-thieno[2,3-c]pyran-3-carboxamide,
- 5,5,7,7-tetramethyl-2-(2-(trifluoromethyl)benzamido)-5,7-dihydro-4H-thieno[2,3-c]pyran-3-carboxamide,
- 2-(2-hydroxy-2-methylpropanamido)-5,5,7,7-tetramethyl-5,7-dihydro-4H-thieno[2,3-c]pyran-3-carboxamide,
- 2-(4-fluoro-2-(trifluoromethyl)benzamido)-5,5,7,7-tetramethyl-5,7-dihydro-4H-thieno[2,3-c]pyran-3-carboxamide,
- 2-(2,4-difluorobenzamido)-5,5,7,7-tetramethyl-5,7-dihydro-4H-thieno[2,3-c]pyran-3-carboxamide,
- 2-(1-(hydroxymethyl)cyclopropanecarboxamido)-5,5,7,7-tetramethyl-5,7-dihydro-4H-thieno[2,3-c]pyran-3-carboxamide,
- 2-(3-hydroxy-2,2-dimethylpropanamido)-5,5,7,7-tetramethyl-5,7-dihydro-4H-thieno[2,3-c]pyran-3-carboxamide,
- N-(3-carbamoyl-5,5,7,7-tetramethyl-5,7-dihydro-4H-thieno[2,3-c]pyran-2-yl)-5-methyl-1H-pyrazole-3-carboxamide,
- methyl 1-(3-carbamoyl-5,5,7,7-tetramethyl-5,7-dihydro-4H-thieno[2,3-c]pyran-2-ylcarbamoyl)-cyclopropanecarboxylate,
- N-(3-carbamoyl-5,5,7,7-tetramethyl-5,7-dihydro-4H-thieno[2,3-c]pyran-2-yl)-5-cyclopropyl-1H-pyrazole-3-carboxamide,
- N-(3-carbamoyl-5,5,7,7-tetramethyl-5,7-dihydro-4H-thieno[2,3-c]pyran-2-yl)-5-isopropyl-1H-pyrazole-3-carboxamide,
- N-(3-carbamoyl-5,5,7,7-tetramethyl-5,7-dihydro-4H-thieno[2,3-c]pyran-2-yl)-5-(trifluoromethyl)-1H-pyrazole-3-carboxamide,
- 5-tert-butyl-N-(3-carbamoyl-5,5,7,7-tetramethyl-5,7-dihydro-4H-thieno[2,3-c]pyran-2-yl)-1H-pyrazole-3-carboxamide,
- N-(3-carbamoyl-5,5,7,7-tetramethyl-5,7-dihydro-4H-thieno[2,3-c]pyran-2-yl)-5-ethyl-1H-pyrazole-3-carboxamide,
- N-(3-carbamoyl-5,5,7,7-tetramethyl-5,7-dihydro-4H-thieno[2,3-c]pyran-2-yl)-1H-1,2,4-triazole-3-carboxamide,
- N-(3-carbamoyl-5,5,7,7-tetramethyl-5,7-dihydro-4H-thieno[2,3-c]pyran-2-yl)-3-ethyl-4-methyl-1H-pyrazole-5-carboxamide,
- N-(3-carbamoyl-5,5,7,7-tetramethyl-5,7-dihydro-4H-thieno[2,3-c]pyran-2-yl)-2-fluoronicotinamide,
- 2-(4-fluoro-2-hydroxybenzamido)-5,5,7,7-tetramethyl-5,7-dihydro-4H-thieno[2,3-c]pyran-3-carboxamide,
- 2-(2-hydroxypropanamido)-5,5,7,7-tetramethyl-5,7-dihydro-4H-thieno[2,3-c]pyran-3-carboxamide,
- N-(3-carbamoyl-5,5,7,7-tetramethyl-5,7-dihydro-4H-thieno[2,3-c]pyran-2-yl)-2-oxo-1,2-dihydropyridine-3-carboxamide,
- N-(3-carbamoyl-5,5,7,7-tetramethyl-5,7-dihydro-4H-thieno[2,3-c]pyran-2-yl)-6-fluoropicolinamide,
- N-(3-carbamoyl-5,5,7,7-tetramethyl-5,7-dihydro-4H-thieno[2,3-c]pyran-2-yl)-4-chloro-1H-pyrazole-3-carboxamide,
- 2-(2-(1H-1,2,4-triazol-5-yl)benzamido)-5,5,7,7-tetramethyl-5,7-dihydro-4H-thieno[2,3-c]pyran-3-carboxamide,
- 2-(2-(1H-imidazol-2-yl)benzamido)-5,5,7,7-tetramethyl-5,7-dihydro-4H-thieno[2,3-c]pyran-3-carboxamide,
- 5,5,7,7-tetramethyl-2-(2-(methylsulfonamido)benzamido)-5,7-dihydro-4H-thieno[2,3-c]pyran-3-carboxamide,
- N-(3-carbamoyl-5,5,7,7-tetramethyl-5,7-dihydro-4H-thieno[2,3-c]pyran-2-yl)-5-oxopyrrolidine-3-carboxamide,
- N-(3-carbamoyl-5,5,7,7-tetramethyl-5,7-dihydro-4H-thieno[2,3-c]pyran-2-yl)-2-oxopyrrolidine-3-carboxamide,
- N-(3-carbamoyl-5,5,7,7-tetramethyl-5,7-dihydro-4H-thieno[2,3-c]pyran-2-yl)-5-methyl-4,5,6,7-tetrahydro-1H-pyrazolo[4,3-c]pyridine-3-carboxamide,
- N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide,
- 4-bromo-N-(3-carbamoyl-5,5,7,7-tetramethyl-5,7-dihydro-4H-thieno[2,3-c]pyran-2-yl)-1H-pyrazole-3-carboxamide,
- N-(3-carbamoyl-5,5,7,7-tetramethyl-5,7-dihydro-4H-thieno[2,3-c]pyran-2-yl)-4-chloro-5-methyl-1H-pyrazole-3-carboxamide,
- N-(3-carbamoyl-5,5,7,7-tetramethyl-5,7-dihydro-4H-thieno[2,3-c]pyran-2-yl)-4-methyl-1H-pyrazole-3-carboxamide,
- N-(3-carbamoyl-5,5,7,7-tetramethyl-5,7-dihydro-4H-thieno[2,3-c]pyran-2-yl)-4-chloro-5-ethyl-1H-pyrazole-3-carboxamide,
- N-(3-carbamoyl-5,5,7,7-tetramethyl-5,7-dihydro-4H-thieno[2,3-c]pyran-2-yl)-4,6-dihydro-1H-furo[3,4-c]pyrazole-3-carboxamide, 2-(2-hydroxy-3,3-dimethylbutanamido)-5,5,7,7-tetramethyl-5,7-dihydro-4H-thieno[2,3-c]pyran-3-carboxamide,
2-(2-hydroxy-3-methylbutanamido)-5,5,7,7-tetramethyl-5,7-dihydro-4H-thieno[2,3-c]pyran-3-carboxamide,
2-(1-(hydroxymethyl)cyclobutanecarboxamido)-5,5,7,7-tetramethyl-5,7-dihydro-4H-thieno[2,3-c]pyran-3-carboxamide,
4-(3-carbamoyl-5,5,7,7-tetramethyl-5,7-dihydro-4H-thieno[2,3-c]pyran-2-ylcarbamoyl)tetrahydro-2H-pyran-4-yl acetate,
N-(3-carbamoyl-5,5,7,7-tetramethyl-5,7-dihydro-4H-thieno[2,3-c]pyran-2-yl)-5-(methoxymethyl)-1H-pyrazole-3-carboxamide,
Cis-2-[[2-fluorocyclopropanecarbonyl]amino]-5,5,7,7-tetramethyl-4H-thieno[2,3-c]pyran-3-carboxamide, Enantiomer 1,
Cis-2-[[2-fluorocyclopropanecarbonyl]amino]-5,5,7,7-tetramethyl-4H-thieno[2,3-c]pyran-3-carboxamide, Enantiomer 2,
N-(3-carbamoyl-5,5,7,7-tetramethyl-4H-thieno[2,3-c]pyran-2-yl)-4-(3,6-dihydro-2H-pyran-4-yl)-1H-pyrazole-3-carboxamide,
2-[(2-hydroxy-4-methyl-pentanoyl)amino]-5,5,7,7-tetramethyl-4H-thieno[2,3-c]pyran-3-carboxamide,
2-[(3,3-difluorocyclobutanecarbonyl)amino]-5,5,7,7-tetramethyl-4H-thieno[2,3-c]pyran-3-carboxamide,
2-[(2,2-difluorocyclopropanecarbonyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-1H-pyrazole-4-carboxamide,
N-(3-carbamoyl-5,5,7,7-tetramethyl-4H-thieno[2,3-c]pyran-2-yl)-4-chloro-5-(methoxymethyl)-1H-pyrazole-3-carboxamide,
2-[[2-hydroxy-3-methyl-butanoyl]amino]-5,5,7,7-tetramethyl-4H-thieno[2,3-c]pyran-3-carboxamide, Enantiomer 1,
2-[[2-hydroxy-3-methyl-butanoyl]amino]-5,5,7,7-tetramethyl-4H-thieno[2,3-c]pyran-3-carboxamide, Enantiomer 2,
2-(2-hydroxybutanoylamino)-5,5,7,7-tetramethyl-4H-thieno[2,3-c]pyran-3-carboxamide,
5-Ethoxy-1H-pyrazole-3-carboxylic acid (3-carbamoyl-5,5,7,7-tetramethyl-4,7-dihydro-5H-thieno[2,3-c]pyran-2-yl)-amide,
5-(2-Methoxy-ethoxy)-1H-pyrazole-3-carboxylic acid (3-carbamoyl-5,5,7,7-tetramethyl-4,7-dihydro-5H-thieno[2,3-c]pyran-2-yl)-amide,
2-[(3-hydroxy-3-methyl-butanoyl)amino]-5,5,7,7-tetramethyl-4H-thieno[2,3-c]pyran-3-carboxamide,
5,5,7,7-tetramethyl-2-[[3,3,3-trifluoro-2-(hydroxymethyl)propanoyl]amino]-4H-thieno[2,3-c]pyran-3-carboxamide,
2-(3-hydroxybutanoylamino)-5,5,7,7-tetramethyl-4H-thieno[2,3-c]pyran-3-carboxamide,
2-[[1-(1-hydroxyethyl)cyclopropanecarbonyl]amino]-5,5,7,7-tetramethyl-4H-thieno[2,3-c]pyran-3-carboxamide,
2-[(2-cyclopropyl-2-hydroxy-acetyl)amino]-5,5,7,7-tetramethyl-4H-thieno[2,3-c]pyran-3-carboxamide,
5-(1-Hydroxy-ethyl)-1H-pyrazole-3-carboxylic acid (3-carbamoyl-5,5,7,7-tetramethyl-4,7-dihydro-5H-thieno[2,3-c]pyran-2-yl)-amide,
2-(3-Carbamoyl-5,5,7,7-tetramethyl-4,7-dihydro-5H-thieno[2,3-c]pyran-2-ylcarbamoyl)-cyclopropanecarboxylic acid ethyl ester,
N-(3-carbamoyl-5,5,7,7-tetramethyl-4H-thieno[2,3-c]pyran-2-yl)-4-[(E)-3-methoxyprop-1-enyl]-1H-pyrazole-3-carboxamide,
N-(3-carbamoyl-5,5,7,7-tetramethyl-4H-thieno[2,3-c]pyran-2-yl)-5-(1-hydroxy-1-methyl-ethyl)-1H-pyrazole-3-carboxamide,
N-(3-carbamoyl-5,5,7,7-tetramethyl-4H-thieno[2,3-c]pyran-2-yl)-4-(3-methoxypropyl)-1H-pyrazole-3-carboxamide,
2-[(2-hydroxyacetyl)amino]-5,5,7,7-tetramethyl-4H-thieno[2,3-c]pyran-3-carboxamide,
2-[(3-hydroxy-4-methyl-pentanoyl)amino]-5,5,7,7-tetramethyl-4H-thieno[2,3-c]pyran-3-carboxamide,
2-[(3-cyclopropyl-3-hydroxy-propanoyl)amino]-5,5,7,7-tetramethyl-4H-thieno[2,3-c]pyran-3-carboxamide,
5,5,7,7-tetramethyl-2-[(4,4,4-trifluoro-3-hydroxy-butanoyl)amino]-4H-thieno[2,3-c]pyran-3-carboxamide,
2-[(3-hydroxy-2-methyl-propanoyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-4-propyl-1H-pyrazole-3-carboxamide,
N-(3-carbamoyl-5,5,7,7-tetramethyl-4H-thieno[2,3-c]pyran-2-yl)-4-(2-ethoxyethyl)-1H-pyrazole-3-carboxamide,
N-(3-carbamoyl-5,5,7,7-tetramethyl-4H-thieno[2,3-c]pyran-2-yl)-4-cyano-1H-pyrazole-3-carboxamide,
2-[[2-(hydroxymethyl)-3-methyl-butanoyl]amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-4-(1,2-dihydroxyethyl)-1H-pyrazole-3-carboxamide,
2-[[(2S)-2-hydroxy-3,3-dimethyl-butanoyl]amino]-5,5,7,7-tetramethyl-4H-thieno[2,3-c]pyran-3-carboxamide,
2-[[(2R)-2-hydroxy-3,3-dimethyl-butanoyl]amino]-5,5,7,7-tetramethyl-4H-thieno[2,3-c]pyran-3-carboxamide,
2-[[1-[1-hydroxyethyl]cyclopropanecarbonyl]amino]-5,5,7,7-tetramethyl-4H-thieno[2,3-c]pyran-3-carboxamide,
2-[[1-[1-hydroxyethyl]cyclopropanecarbonyl]amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-5-(hydroxymethyl)-1-methyl-pyrazole-3-carboxamide,
2-[(2-hydroxy-2,3,3-trimethyl-butanoyl)amino]-5,5,7,7-tetramethyl-4H-thieno[2,3-c]pyran-3-carboxamide,
2-[[2-(hydroxymethyl)cyclopropanecarbonyl]amino]-5,5,7,7-tetramethyl-4H-thieno[2,3-c]pyran-3-carboxamide,
2-[[(1S,2S)-2-(hydroxymethyl)cyclopropanecarbonyl]amino]-5,5,7,7-tetramethyl-4H-thieno[2,3-c]pyran-3-carboxamide,
2-[[2-(cyclopropylmethyl)-3-hydroxy-propanoyl]amino]-5,5,7,7-tetramethyl-4H-thieno[2,3-c]pyran-3-carboxamide,
2-[[2-(hydroxymethyl)-3,3-dimethyl-butanoyl]amino]-5,5,7,7-tetramethyl-4H-thieno[2,3-c]pyran-3-carboxamide,
2-[2-(hydroxymethyl)butanoylamino]-5,5,7,7-tetramethyl-4H-thieno[2,3-c]pyran-3-carboxamide,
2-[[(1R,3R)-3-(hydroxymethyl)-2,2-dimethyl-cyclopropanecarbonyl]amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-4-(hydroxymethyl)-1H-pyrazole-3-carboxamide, 2-[[2-(hydroxymethyl)-3,3-dimethyl-butanoyl]amino]-5,5,7,7-tetramethyl-4H-thieno[2,3-c]pyran-3-carboxamide,
2-[[2-(hydroxymethyl)-3,3-dimethyl-butanoyl]amino]-5,5,7,7-tetramethyl-4H-thieno[2,3-c]pyran-3-carboxamide,
2-[[1-(hydroxymethyl)-2,2-dimethyl-cyclopropanecarbonyl]amino]-5,5,7,7-tetramethyl-4H-thieno[2,3-c]pyran-3-carboxamide,
[5-[(3-carbamoyl-5,5,7,7-tetramethyl-4H-thieno[2,3-c]pyran-2-yl)carbamoyl]pyrazol-1-yl]methyl dihydrogen phosphate,
[3-[(3-carbamoyl-5,5,7,7-tetramethyl-4H-thieno[2,3-c]pyran-2-yl)carbamoyl]pyrazol-1-yl]methyl dihydrogen phosphate,
N-(3-carbamoyl-5,5,7,7-tetramethyl-4H-thieno[2,3-c]pyran-2-yl)-4-(2,3-dihydro-1,4-dioxin-5-yl)-1H-pyrazole-3-carboxamide,
N-(3-carbamoyl-5,5,7,7-tetramethyl-4H-thieno[2,3-c]pyran-2-yl)-4-(1,4-dioxan-2-yl)-1H-pyrazole-3-carboxamide,
2-[[2-(cyclopropylmethyl)-3-hydroxy-propanoyl]amino]-5,5,7,7-tetramethyl-4H-thieno[2,3-c]pyran-3-carboxamide, enantiomer 1,
2-[[2-(cyclopropylmethyl)-3-hydroxy-propanoyl]amino]-5,5,7,7-tetramethyl-4H-thieno[2,3-c]pyran-3-carboxamide, enantiomer 2,
2-[[(2S)-3-cyclopropyl-2-hydroxy-propanoyl]amino]-5,5,7,7-tetramethyl-4H-thieno[2,3-c]pyran-3-carboxamide,
2-[[(1R)-1-(hydroxymethyl)-2,2-dimethyl-cyclopropanecarbonyl]amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-4-(2-methoxyethoxy)-1H-pyrazole-3-carboxamide,
N-(3-carbamoyl-5,5,7,7-tetramethyl-4H-thieno[2,3-c]pyran-2-yl)-4-(2-isopropoxyethoxy)-1H-pyrazole-3-carboxamide,
[3-[(3-carbamoyl-5,5,7,7-tetramethyl-4H-thieno[2,3-c]pyran-2-yl)carbamoyl]-4-methyl-pyrazol-1-yl]methyl dihydrogen phosphate,
[5-[(3-carbamoyl-5,5,7,7-tetramethyl-4H-thieno[2,3-c]pyran-2-yl)carbamoyl]-4-methyl-pyrazol-1-yl]methyl dihydrogen phosphate,
N-(3-carbamoyl-5,5,7,7-tetramethyl-4H-thieno[2,3-c]pyran-2-yl)-2-oxo-1,3-dihydroimidazole-4-carboxamide,
N-(3-carbamoyl-5,5,7,7-tetramethyl-4H-thieno[2,3-c]pyran-2-yl)-4-(methoxymethyl)-1H-pyrazole-3-carboxamide,
2-[(2-hydroxy-4,4-dimethyl-pentanoyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-5-oxo-pyrrolidine-2-carboxamide,
(2R)—N-(3-carbamoyl-5,5,7,7-tetramethyl-4H-thieno[2,3-c]pyran-2-yl)-5-oxo-pyrrolidine-2-carboxamide,
2-[[2-hydroxy-4,4-dimethyl-pentanoyl]amino]-5,5,7,7-tetramethyl-4H-thieno[2,3-c]pyran-3-carboxamide, enantiomer 1,
2-[[2-hydroxy-4,4-dimethyl-pentanoyl]amino]-5,5,7,7-tetramethyl-4H-thieno[2,3-c]pyran-3-carboxamide, enantiomer 2,
N-(3-carbamoyl-5,5,7,7-tetramethyl-4H-thieno[2,3-c]pyran-2-yl)-4-[1,4-dioxan-2-yl]-1H-pyrazole-3-carboxamide, enantiomer 1,
N-(3-carbamoyl-5,5,7,7-tetramethyl-4H-thieno[2,3-c]pyran-2-yl)-4-[1,4-dioxan-2-yl]-1H-pyrazole-3-carboxamide, enantiomer 2,
2-[[2-(difluoromethoxy)benzoyl]amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-1-(difluoromethyl)pyrazole-3-carboxamide,
N-(3-carbamoyl-5,5,7,7-tetramethyl-4H-thieno[2,3-c]pyran-2-yl)-2-(difluoromethyl)pyrazole-3-carboxamide,
N-(3-carbamoyl-5,5,7,7-tetramethyl-4H-thieno[2,3-c]pyran-2-yl)-4-chloro-1-(difluoromethyl)pyrazole-3-carboxamide,
N-(3-carbamoyl-5,5,7,7-tetramethyl-4H-thieno[2,3-c]pyran-2-yl)-3-(difluoromethyl)-1-methyl-pyrazole-4-carboxamide,
N-(3-carbamoyl-5,5,7,7-tetramethyl-4H-thieno[2,3-c]pyran-2-yl)-5-(difluoromethyl)-1-methyl-pyrazole-4-carboxamide,
N-(3-carbamoyl-5,5,7,7-tetramethyl-4H-thieno[2,3-c]pyran-2-yl)-1-methyl-pyrazole-3-carboxamide,
N-(3-carbamoyl-5,5,7,7-tetramethyl-4H-thieno[2,3-c]pyran-2-yl)-2-methyl-pyrazole-3-carboxamide,
N-(3-carbamoyl-5,5,7,7-tetramethyl-4H-thieno[2,3-c]pyran-2-yl)-1-(2,2,2-trifluoroethyl)pyrazole-3-carboxamide,
2-[[3-(difluoromethyl)benzoyl]amino]-5,5,7,7-tetramethyl-4H-thieno[2,3-c]pyran-3-carboxamide,
2-[[2-(difluoromethyl)benzoyl]amino]-5,5,7,7-tetramethyl-4H-thieno[2,3-c]pyran-3-carboxamide,
2-[(3,3-difluoro-1-methyl-cyclobutanecarbonyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-2-methyl-oxazole-4-carboxamide,
N-(3-carbamoyl-5,5,7,7-tetramethyl-4H-thieno[2,3-c]pyran-2-yl)-1-(2,2-difluoroethyl)pyrazole-3-carboxamide,
N-(3-carbamoyl-5,5,7,7-tetramethyl-4H-thieno[2,3-c]pyran-2-yl)-2-(trifluoromethyl)thiazole-4-carboxamide,
N-(3-carbamoyl-5,5,7,7-tetramethyl-4H-thieno[2,3-c]pyran-2-yl)thiazole-4-carboxamide,
N-(3-carbamoyl-5,5,7,7-tetramethyl-4H-thieno[2,3-c]pyran-2-yl)oxazole-4-carboxamide,
N-(3-carbamoyl-5,5,7,7-tetramethyl-4H-thieno[2,3-c]pyran-2-yl)-2-(trifluoromethyl)-1H-imidazole-4-carboxamide,
N-(3-carbamoyl-5,5,7,7-tetramethyl-4H-thieno[2,3-c]pyran-2-yl)-4-methyl-thiazole-2-carboxamide,
N-(3-carbamoyl-5,5,7,7-tetramethyl-4H-thieno[2,3-c]pyran-2-yl)-2,4-dimethyl-oxazole-5-carboxamide,
N-(3-carbamoyl-5,5,7,7-tetramethyl-4H-thieno[2,3-c]pyran-2-yl)isoxazole-5-carboxamide,
N-(3-carbamoyl-5,5,7,7-tetramethyl-4H-thieno[2,3-c]pyran-2-yl)thiazole-5-carboxamide,
N-(3-carbamoyl-5,5,7,7-tetramethyl-4H-thieno[2,3-c]pyran-2-yl)-4-methyl-oxazole-5-carboxamide,
N-(3-carbamoyl-5,5,7,7-tetramethyl-4H-thieno[2,3-c]pyran-2-yl)oxazole-5-carboxamide,
N-(3-carbamoyl-5,5,7,7-tetramethyl-4H-thieno[2,3-c]pyran-2-yl)-1-methyl-5-(trifluoromethyl)pyrazole-4-carboxamide,
N-(3-carbamoyl-5,5,7,7-tetramethyl-4H-thieno[2,3-c]pyran-2-yl)pyrazine-2-carboxamide,
6-butyl-N-(3-carbamoyl-5,5,7,7-tetramethyl-4H-thieno[2,3-c]pyran-2-yl)-2-oxo-1H-pyridine-3-carboxamide,
N-(3-carbamoyl-5,5,7,7-tetramethyl-4H-thieno[2,3-c]pyran-2-yl)-3,5-dimethyl-isoxazole-4-carboxamide, N-(3-carbamoyl-5,5,7,7-tetramethyl-4H-thieno[2,3-c]pyran-2-yl)-5-methyl-pyrazine-2-carboxamide,
N-(3-carbamoyl-5,5,7,7-tetramethyl-4H-thieno[2,3-c]pyran-2-yl)-1H-pyrrole-2-carboxamide,
N-(3-carbamoyl-5,5,7,7-tetramethyl-4H-thieno[2,3-c]pyran-2-yl)-6-methyl-pyridine-3-carboxamide,
N-(3-carbamoyl-5,5,7,7-tetramethyl-4H-thieno[2,3-c]pyran-2-yl)-8-methyl-4-oxo-pyrido[1,2-a]pyrimidine-3-carboxamide,
N-(3-carbamoyl-5,5,7,7-tetramethyl-4H-thieno[2,3-c]pyran-2-yl)-2,3-dihydro-[1,4]dioxino[2,3-b]pyridine-7-carboxamide,
N-(3-carbamoyl-5,5,7,7-tetramethyl-4H-thieno[2,3-c]pyran-2-yl)-5-methyl-isoxazole-4-carboxamide,
5,5,7,7-tetramethyl-2-[(3-methyloxetane-3-carbonyl)amino]-4H-thieno[2,3-c]pyran-3-carboxamide,
N-(3-carbamoyl-5,5,7,7-tetramethyl-4H-thieno[2,3-c]pyran-2-yl)-2-methyl-4-oxo-3H-quinazoline-5-carboxamide,
N-(3-carbamoyl-5,5,7,7-tetramethyl-4H-thieno[2,3-c]pyran-2-yl)-4,7-dimethyl-pyrazolo[5,1-c][1,2,4]triazine-3-carboxamide,
N-(3-carbamoyl-5,5,7,7-tetramethyl-4H-thieno[2,3-c]pyran-2-yl)-2-methyl-4-oxo-3H-quinazoline-7-carboxamide,
N-(3-carbamoyl-5,5,7,7-tetramethyl-4H-thieno[2,3-c]pyran-2-yl)-2-(2,2,2-trifluoroethyl)pyrazole-3-carboxamide,
5,5,7,7-tetramethyl-2-[[(2S)-3,3,3-trifluoro-2-hydroxy-2-methyl-propanoyl]amino]-4H-thieno[2,3-c]pyran-3-carboxamide,
2-[[(2S)-2-hydroxypropanoyl]amino]-5,5,7,7-tetramethyl-4H-thieno[2,3-c]pyran-3-carboxamide,
2-[(4-hydroxytetrahydropyran-4-carbonyl)amino]-5,5,7,7-tetramethyl-4H-thieno[2,3-c]pyran-3-carboxamide,
2-[(2-hydroxy-3-methoxy-2-methyl-propanoyl)amino]-5,5,7,7-tetramethyl-4H-thieno[2,3-c]pyran-3-carboxamide,
2-[(2-hydroxy-3-methoxy-propanoyl)amino]-5,5,7,7-tetramethyl-4H-thieno[2,3-c]pyran-3-carboxamide,
N-(3-carbamoyl-5,5,7,7-tetramethyl-4H-thieno[2,3-c]pyran-2-yl)-1H-pyrazolo[3,4-b]pyridine-3-carboxamide,
5,5,7,7-tetramethyl-2-(tetrahydropyran-4-carbonylamino)-4H-thieno[2,3-c]pyran-3-carboxamide,
2-[(2-ethoxyacetyl)amino]-5,5,7,7-tetramethyl-4H-thieno[2,3-c]pyran-3-carboxamide,
2-[(2-methoxyacetyl)amino]-5,5,7,7-tetramethyl-4H-thieno[2,3-c]pyran-3-carboxamide,
2-[[2-(2-methoxyethoxy)acetyl]amino]-5,5,7,7-tetramethyl-4H-thieno[2,3-c]pyran-3-carboxamide,
5,5,7,7-tetramethyl-2-(tetrahydrofuran-2-carbonylamino)-4H-thieno[2,3-c]pyran-3-carboxamide,
5,5,7,7-tetramethyl-2-(tetrahydrofuran-3-carbonylamino)-4H-thieno[2,3-c]pyran-3-carboxamide,
2-[(2-methoxy-2-methyl-propanoyl)amino]-5,5,7,7-tetramethyl-4H-thieno[2,3-c]pyran-3-carboxamide,
2-[[2-hydroxy-3-methoxy-2-methyl-propanoyl]amino]-5,5,7,7-tetramethyl-4H-thieno[2,3-c]pyran-3-carboxamide, enantiomer 1,
2-[[(2S)-2-hydroxy-3-methoxy-2-methyl-propanoyl]amino]-5,5,7,7-tetramethyl-4H-thieno[2,3-c]pyran-3-carboxamide, enantiomer 2,
5,5,7,7-tetramethyl-2-[(3,3,3-trifluoro-2-hydroxy-propanoyl)amino]-4H-thieno[2,3-c]pyran-3-carboxamide,
6-Oxo-1,6-dihydro-pyridazine-3-carboxylic acid (3-carbamoyl-5,5,7,7-tetramethyl-4,7-dihydro-5H-thieno[2,3-c]pyran-2-yl)-amide, and
2-(1,4-dioxane-2-carboxamido)-5,5,7,7-tetramethyl-5,7-dihydro-4H-thieno[2,3-c]pyran-3-carboxamide.

14. A method for the treatment of cystic fibrosis, comprising administering to a subject a pharmaceutical composition comprising a pharmaceutically acceptable carrier and a pharmaceutically effective amount of a compound according to Formula I

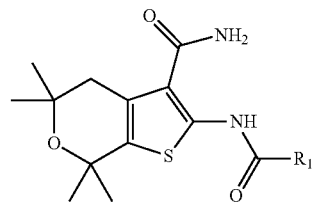

wherein
R$^1$ is
C$_{3-7}$ mono or spirocyclic cycloalkyl, optionally substituted with one or more independently selected R$^2$ groups,
4-7 membered mono or spirocyclic heterocycloalkyl comprising one or more heteroatoms independently selected from O, N, and S, substituted with one or more independently selected R$^2$ groups,
C$_{6-10}$ monocyclic or bicyclic aryl optionally substituted with one or more independently selected R$^3$ groups,
5-10 membered monocyclic or fused bicyclic heteroaryl comprising one or more heteroatoms independently selected from N, O, and S, and optionally substituted with one or more independently selected R$^3$ groups, or
C$_{1-6}$ alkyl optionally substituted with one or more independently selected R$^4$ groups,
each R$^2$ is selected from
halo,
OH,
—CN,
—OC(=O)C$_{1-4}$ alkyl,
—C(=O)—C$_{1-4}$ alkoxy,
oxo,
C$_{1-4}$ alkyl (optionally substituted with one or more independently selected R$^{5a}$), and
C$_{1-4}$ alkoxy (optionally substituted with one or more independently selected R$^{5a}$),
each R$^3$ is selected from
halo,
—OH,
—CN,
C$_{1-4}$ alkyl (optionally substituted with one or more independently selected R$^{5b}$),
C$_{1-4}$ alkoxy (optionally substituted with one or more independently selected R$^{5b}$),
C$_{2-4}$ alkenyl (optionally substituted with one or more independently selected R$^{5b}$),
C$_{3-7}$ cycloalkyl,
4-7 membered monocyclic heterocycloalkyl comprising one or more heteroatoms independently selected from N, O, and S,
4-7 membered monocyclic heterocycloalkenyl comprising one or more heteroatoms independently selected from N, O, and S, 5-10 membered monocyclic or fused bicyclic heteroaryl comprising one or more heteroatoms independently selected from N, O, and S, and
—NHSO$_2$—C$_{1-4}$ alkyl;

each R$^4$ is selected from
halo,
OH,
C$_{3-7}$ monocyclic cycloalkyl,
—CN, and
C$_{1-4}$ alkoxy (optionally substituted with one or more independently selected R$^{5c}$), each R$^{5a}$, R$^{5b}$, and R$^{5c}$ is independently selected from
halo,
OH,
—OP(=O)$_2$OH,
—CN,
—NR$^{6a}$R$^{6b}$, and
C$_{1-4}$ alkoxy; and each R$^{5a}$, or R$^{5b}$ is independently selected from H, and C$_{1-4}$ alkyl;

or a pharmaceutically acceptable salt, or a solvate, or a pharmaceutically acceptable salt of a solvate thereof.

* * * * *